US010822422B2

(12) United States Patent
Poulton et al.

(10) Patent No.: US 10,822,422 B2
(45) Date of Patent: Nov. 3, 2020

(54) ANTIBODIES AGAINST TL1A AND USES THEREOF

(71) Applicant: Teva Pharmaceuticals Australia Pty Ltd, Macquarie Park, NSW (AU)

(72) Inventors: Lynn Dorothy Poulton, Macquarie Park (AU); Adam Clarke, Five Dock (AU); Andrew James Pow, Pascoe Vale (AU); Debra Tamvakis, Camberwell (AU); George Kopsidas, Preston (AU); Anthony Gerard Doyle, Drummoyne (AU); Philip Anthony Jennings, Warrawee (AU); Matthew Pollard, Dural (AU)

(73) Assignee: Teva Pharmaceuticals Australia Pty Ltd, Macquarie Park (AU)

( * ) Notice: Subject to any disclaimer, the term of this patent is extended or adjusted under 35 U.S.C. 154(b) by 409 days.

(21) Appl. No.: 15/206,493

(22) Filed: Jul. 11, 2016

(65) Prior Publication Data

US 2016/0333104 A1 Nov. 17, 2016

Related U.S. Application Data

(63) Continuation of application No. 14/228,367, filed on Mar. 28, 2014, now abandoned, which is a (Continued)

(30) Foreign Application Priority Data

Sep. 30, 2011 (AU) ................................ 2011904042

(51) Int. Cl.
*C07K 16/24* (2006.01)
*C07K 16/28* (2006.01)
(Continued)

(52) U.S. Cl.
CPC ........ *C07K 16/2875* (2013.01); *C07K 16/241* (2013.01); *G01N 33/6863* (2013.01);
(Continued)

(58) Field of Classification Search
None
See application file for complete search history.

(56) References Cited

U.S. PATENT DOCUMENTS 7,597,886 B2 10/2009 Yu et al.
7,820,798 B2 10/2010 Yu et al.
(Continued)

FOREIGN PATENT DOCUMENTS

WO 2005018571 3/2005
WO WO 2005/092927 A1 10/2005
(Continued)

OTHER PUBLICATIONS

Chen et al., Enhancement and destruction of antibody function by somatic mutation: unequal occurrence is controlled by V gene combinatorial association, EMBO J. 14(12):2784-2794, 1995.*
(Continued)

*Primary Examiner* — Claire Kaufman
(74) *Attorney, Agent, or Firm* — Sterne, Kessler, Goldstein & Fox P.L.L.C.

(57) ABSTRACT

The disclosure provides TNF-like ligand 1a (TL1a)-binding proteins comprising an antigen binding domain of an antibody which binds specifically to TL1a and inhibits interaction of TL1a and Death Receptor 3 (DR3) and which does not inhibit the interaction of TL1a and Decoy Receptor 3 (DcR3). The disclosure also provides uses of the TL1a-binding proteins.

13 Claims, 34 Drawing Sheets

Specification includes a Sequence Listing.

Related U.S. Application Data continuation of application No. PCT/AU2012/001161, filed on Sep. 28, 2012.

(60) Provisional application No. 61/541,590, filed on Sep. 30, 2011.

(51) Int. Cl.
*G01N 33/68* (2006.01)
*A61K 39/00* (2006.01)

(52) U.S. Cl.
CPC .... *A61K 2039/505* (2013.01); *C07K 2317/21* (2013.01); *C07K 2317/34* (2013.01); *C07K 2317/55* (2013.01); *C07K 2317/62* (2013.01); *C07K 2317/622* (2013.01); *C07K 2317/76* (2013.01); *C07K 2317/92* (2013.01); *C07K 2317/94* (2013.01)

(56) References Cited

U.S. PATENT DOCUMENTS

| | | | |
|---|---|---|---|
| 8,263,743 | B2 | 9/2012 | Smith et al. |
| 8,642,741 | B2 | 2/2014 | Classon et al. |
| 8,728,482 | B2 | 5/2014 | Smith et al. |
| 9,017,679 | B2 | 4/2015 | Podack et al. |
| 9,068,003 | B2 | 6/2015 | Siegel et al. |
| 9,290,576 | B2 | 3/2016 | Attinger et al. |
| 9,416,185 | B2 | 8/2016 | Smith et al. |
| 9,556,277 | B2 | 1/2017 | Classon et al. |
| 9,683,998 | B2 | 6/2017 | Arch et al. |
| 2011/0217310 | A1 | 9/2011 | Siegel et al. |
| 2012/0328559 | A1 | 12/2012 | Podack et al. |
| 2014/0255302 | A1 | 9/2014 | Poulton et al. |
| 2014/0315250 | A1 | 10/2014 | Smith et al. |
| 2016/0060335 | A1 | 3/2016 | Shih et al. |
| 2016/0333104 | A1 | 11/2016 | Poulton et al. |
| 2017/0081400 | A1 | 3/2017 | Poulton et al. |

FOREIGN PATENT DOCUMENTS

| | | |
|---|---|---|
| WO | 2006127900 | 11/2006 |
| WO | 2007076465 | 7/2007 |
| WO | WO2008/106451 A2 | 9/2008 |
| WO | 09064854 | 5/2009 |
| WO | 2009064854 | 5/2009 |
| WO | WO2010/118210 A1 | 10/2010 |
| WO | 2011080314 | 7/2011 |
| WO | 2012064682 | 5/2012 |
| WO | 2012161856 | 11/2012 |
| WO | WO2013/044298 A1 | 4/2013 |
| WO | 2014106602 | 7/2014 |
| WO | WO2014/160883 A1 | 10/2014 |
| WO | WO2014/186665 A2 | 11/2014 |
| WO | WO2015/010108 A1 | 1/2015 |
| WO | WO2015/035261 A1 | 3/2015 |
| WO | 2015073580 | 5/2015 |
| WO | WO 2017106383 A1 | 6/2017 |

OTHER PUBLICATIONS

MacCallum et al.,Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. BIol. Chem. 276:36687-94, 2001.*
Migone, et al., "TL1A is a TNF-like Ligand for DR3 and TR6/DcR3 and Functions as a T Cell Costimulator", Immunity, vol. 16, Mar. 2002, pp. 479-492.
Rajpal, et al., "A general method for greatly improving the affinity of antibodies by using combinatorial libraries", Proceedings of the National Academy of Sciences, vol. 102, No. 24, Jun. 1, 2005, pp. 8466-8471.
Daugherty, et al., "Quantitative analysis of the effect of the mutation frequency on the affinity maturation of single chain Fv antibodies", Proceedings ofthe National Academy of Sciences, vol. 97, No. 5, Feb. 29, 2000, pp. 2029-2034.
Steidl, et al., "In vitro affinity maturation of human GM-CSF antibodies by targeted CDR-diversification", Molecular Immunology, vol. 46, No. 1, Nov. 1, 2008, pp. 135-144.
Yang, et al. "CDR Walking Mutagenesis for the Affinity Maturation of a Potent Human Anti-HIV-1 Antibody into the Picomolar Range", Journal of Molecular Biology, vol. 254, Jan. 1, 1995, pp. 392-403.
Thie, "Affinity Maturation by Random Mutagenesis and Phage Display", Antibody Entineering, vol. 1, Jan. 1, 2010, pp. 397-409.
Chang, et al., "Affinity Maturation of an Epidermal Growth Factor Receptor Targeting Human Monoclonal Antibody by CDR Mutation", Immune Network, vol. 12, No. 4, Jan. 1, 2012, p. 155.
International Search Report and Written Opinion from PCT/AU2012/001161.
International Search Report and Written Opinion for International Application No. PCT/AU2011/001662, Australian Patent Office, Australia dated Feb. 20, 2012, 8 pages.
International Search Report and written Opinion for International Application No. PCT/US2016/052040, European Patent Office, Rijswijk dated Dec. 5, 2016, 12 pages.
Office Action dated Mar. 23, 2018, in U.S. Appl. 15/267,213, Poulton et al., filed Sep. 16, 2016, 8 pges.
Aiba, Y., et al. "Systemic and local expression levels of TNF-like ligand 1A and its decoy receptor 3 are increased in primary biliary cirrhosis," Liver Int. 34(5):679-88 (2014).
Bamias, G , et al., High intestinal and systemic levels of decoy receptor 3 (DcR3) and its ligand TL1A in active ulcerative colitis, Clin Immunol 137(2):242-9 (2010).
Bamias, G., et al., "Expression, Localization, and Functional Activity of TL 1A, a novel Th1-Polarizing Cytokine in Inflammatory Bowel Disease," J Immunol 171 (9):4868-74 (2003).
Bamias, G., et al., "Role of TL1A and its receptor DR3 in two models of chronic murine ileitis," Proc Natl Acad Sci USA 103(22):8441-6 (2006).
Bamias, G., et al., "Circulating levels of TNF-like cytokine 1A (TL1A) and its decoy receptor 3 (DcR3) in rheumatoid arthritis," Clin Immunol. 129(2):249-55 (2008).
Connelly, TM., et al., "The TNFSF15 Gene Single Nucleotide Polymorphism rs7848647 is Associated with Surgical Diverticulitis," Ann Surg 259(6):1132-7 (2014).
Czogalla, B., et al., "A meta-analysis of immunogenetic Case-Control Association Studies in irritable bowel syndrome," Neurogastroenterol Motil 27 (5):717-27 (May 2015).
Fang, L., et al., "Essential role of TNF receptor superfamily 25 (TNFRSF25) in the development of allergic lung inflammation," J Exp Med 205(5):1037-48 (2008).
Haritunians, T., et al., "Genetic predictors of medically refractory ulcerative colitis," Inflamm Bowel Dis 16(11):1830-40 (2010).
Hirano, A., et al., "Association study of 71 European Crohn's disease susceptibility loci in a Japanese population," Inflamm Bowel Dis 19 (3):526-33 (2013).
Jia, Y., et al., "IL-$13^+$ Type 2 innate lymphoid cells correlate with asthma control status and treatment response," Am J Respir Cell Mol Biol 55(5):675-683 (Jun. 2016).
Jones, GW., et al., "Naive and activated T cells display differential responsiveness to TL1A that affects Th17 generation, maintenance, and proliferation," FASEB J. 25(1):409-19 (2011).
Kakuta, Y., et al., "TNFSF15 transcripts from risk haplotype for Crohn's disease are overexpressed in stimulated T cells," Hum Mol Genet 18 (6):1089-98 (2009).
Kamada, N., et al., TL1A produced by lamina propria macrophages induces TH1 and Th17 immune responses in cooperation with IL-23 in patients with Crohn's disease, Inflamm Bowel Dis 16(4):568-75 (2010).
Kayamuro, H., et al., "TNF superfamily member, TL1A, is a potential mucosal vaccine adjuvant," Biochem Biophys Res Commun 384 (3):296-300 (2009).
Wolterink, R.G., et al., "Pulmonary innate lymphoid cells are major producers of IL-5 and IL-13 in murine models of allergic asthma," Eur J Immunol 42(5):1106-16 (2012).

(56) References Cited

OTHER PUBLICATIONS

Konsta, M., et al., "Increased levels of soluble TNF-like cytokine 1A in ankylosing spondylitis," Rheumatology (Oxford) 52(3):448-51 (2013).
Liu, JZ., et al., "Association analyses identify 38 susceptibility loci for inflammatory bowel disease and highlight shared genetic risk across populations," Nat Genet 47(9):979-86 (May 2015).
Meylan, F., et al., "The TNF-family receptor DR3 is essential for diverse T cell-mediated inflammatory diseases," Immunity 29(1):79-89 (2008).
Meylan, F., et al., "The TNF-family cytokine TL1A promotes allergic immunopathology through group 2 innate lymphoid cells," Mucosal Immunol 7(4):958-68 (2014).
Meylan, F., et al.,"TNF superfamily cytokines in the promotion of Th9 differentiation and immunopathology," Semin Immunopathol 39(1):21-2 (2017).
Meylan, F., et al., "The TNF-family cytokine TL1A drives IL-13-dependent small intestinal inflammation," Mucosal Immunol 4 (2):172-85 (2011).
Michelsen, K.S., et al., "IBD-associated TL1A gene (TNFSF15) haplotypes determine increased expression of TL1A protein," PLoS One 4 (3):e4719 (2009).
Mjosberg, J.M., et al., "Human IL-25- and IL-33-responsive type 2 innate lymphoid cells are defined by expression of CRTH2 and CD161," Nat Immunol 12 (11):1055-62 (2011).
Moffatt, M.F., et al.,"A large-scale, consortium-based genomewide association study of asthma," N Engl J Med 363 (13):1211-21 (2010).
Neill, D.R., et al., "Nuocytes represent a new innate effector leukocyte that mediates type-2 immunity," Nature 464 (7293):1367-70 (2010).
Papadakis, K.A., et al., "TL1A synergizes with IL-12 and IL-18 to enhance IFN-gamma production in human T cells and NK cells," J Immunol 172 (11):7002-7 (2004).
Pappu, B.P., et al., "TL1A-DR3 interaction regulates Th17 cell function and Th17-mediated autoimmune disease," J Exp Med 205(5):1049-62 (2008).
Pedersen, A.E., et al., "Secretion, blood levels and cutaneous expression of TL1A in psoriasis patients," APMIS 123(7):547-55 (Feb. 2015).
Prehn, J.L., et al., "Potential role for TL1A, the new TNF-family member and potent costimulator of IFN-gamma, in mucosal inflammation," Clin Immunol 112 (1):66-77 (2004).
Richard, A.C., et al., "The TNF-family ligand TL1A and its receptor DR3 promote T cell-mediated allergic immunopathology by enhancing differentiation and pathogenicity of IL-9-producing T cells," J Immunol 194(8):3567-82 (Feb. 2015).
Sampson, H.A., et al., "Second symposium on the definition and management of anaphylaxis: summary report—Second National Institute of Allergy and Infectious Disease/Food Allergy and Anaphylaxis Network symposium," J Allergy Clin Immunol. 117(2):391-7 (2006).
Screaton, G.R., et al., "LARD: a new lymphoid-specific death domain containing receptor regulated by alternative pre-mRNA splicing," Proc Natl Acad Sci USA 94(9):4615-9 (1997).
Shih, D.Q., et al., "Inhibition of a novel fibrogenic factor T11a reverses established colonic fibrosis," Mucosal Immunol 7(6):1492-503 (2014).
Soroosh, P.,et al., "Th9 and allergic disease," Immunology 127(4):450-8 (2009).
Swan, C., et al., "Identifying and testing candidate genetic polymorphisms in the irritable bowel syndrome (IBS): association with TNFSF15 and TNFα," Gut 62 (7):985-94 (2013).
Takedatsu, H., et al., "TL1A (TNFSF15) regulates the development of chronic colitis by modulating both T-helper ($T_H$) 1 and $T_H$ 17 activation," Gastroenterology 135(2):552-67 (2008).
Thiebaut, R., et al., "TNFSF15 polymorphisms are associated with susceptibility to inflammatory bowel disease in a new European cohort," Am J Gastroenterol 104(2):384-91 (2009).
Wen, L., et al.,"TL1A-induced NF-kB activation and c-IAP2 production Prevent DR3-mediated apoptosis in TF-1 Cells," Journal of Biological Chemistry 278 (40):39251-39258 (2003).
Xu, W.D., et al., "Elevated plasma levels of TL1A in newly diagnosed systemic lupus erythematosus patients," Rheumatol Int. 35(8):1435-7 (May 2015).
Yamazaki, K., et al., "Single nucleotide polymorphisms in TNFSF15 confer susceptibility to Crohn's disease," Hum Mol Genet 14 (22):3499-506 (2005).
Yu, X., et al., "TNF superfamily member TL1A elicits type 2 innate lymphoid cells at mucosal barriers," Mucosal Immunol 7(3):730-40 (2014).
Zhang, J., et al., "Associations between TNFSF15 polymorphisms and susceptibility to ulcerative colitis and Crohn's disease: A meta-analysis," Autoimmunity 47(8):512-8 (2014).
Zucchelli, M., et al., "Association of TNFSF15 polymorphism with irritable bowel syndrome," Gut 60(12):1671-7 (2011).
Clarke AW, Poulton L, Shim D, Mabon D, Butt D, Pollard M, et al. An anti-TL1A antibody for the treatment of asthma and inflammatory bowel disease. mAbs 2018; 10(4):664-677. doi:10.1080/19420862.2018.1440164.
Singh RK, Perks WV, Twohig JP, Kidd EJJ, Broadley K, Farrow SN, et al. Death receptor 3 regulates distinct pathological attributes of acute versus chronic murine allergic lung inflammation. Cell Immunol. 2017;320:62-70. doi:10.1016/j.cellimm.2017.09.005.
Huang, S-M., et al., "Therapeutic protein-drug interactions and implications for drug development," Clinical Pharmacology and Therapeutics 87:497-503 (2010).
Jin, T., et al., "X-ray crystal structure of TNF ligand family member TL1A at 2.1A," Biochem Biophys Res Comm 364:1-6 (2007).
Vugmeyster, Y., et al.,"Pharmacokinetics and toxicology of therapeutic proteins: Advances and challenges," World J Biol Chem. 26;3(4):73-92 (2012).
Zhan, C., et al., "Decoy strategies: The structure of TL1A:DcR3 complex," Structure 19(2):162-171 (2011).
Agoram, BM., "Use of pharmacokinetic/ pharmacodynamic modelling for starting dose selection in first-in-human trials of high-risk biologics," Br J Clin Pharmacol. 67(2):153-60 (2008).
Sharma, V., et al., "To scale or not to scale: the principles of dose extrapolation," Br J Pharmacol. 157(6):907-21 (2009).
Zhao, L., et al., "Clinical pharmacology considerations in biologics development," Acta Pharmacol Sin. 33(11):1339-47 (2012).
Baker, DL., et al., "Evaluation of IgE Antibodies to Omalizumab (Xolair®) and Their Potential Correlation to Anaphylaxis," AAPS J.18(1):115-23 (Jan. 2016).
Galant, SP., "The Evaluable Subject," Ann Allergy Asthma Immunol 79:173-5 (1997).
Leckie, M.J., et al., "Effects of an interleukin-5 blocking monoclonal antibody on eosinophils, airway hyper-responsiveness, and the late asthmatic response," Lancet 356: 2144-8 (2000).
Ma, L., et al., "Case fatality and population mortality associated with anaphylaxis in the United States," J Allergy Clin Immunol. 133(4):1075-83 (2014).
Woodcock, A., et al., "Efficacy and safety of fluticasone furoate/vilanterol compared with fluticasone propionate/salmeterol combination in adult and adolescent patients with persistent asthma: a randomized trial," Chest 144 (4);1222-9 (2013).
Bamias, G., et al., "Upregulation and nuclear localization of TNF-like Cytokine 1A (TL1A) and its receptors DR3 and DcR3 in psoriatic skin lesions," Experimental Dermatology 20:725-731 (2011).
Wang, W., et al., "Monoclonal antibody pharmacokinetics and pharmacodynamics," Clin Pharmacol Ther. 84(5):548-58 (2008).
Abdel-Razzak Z., et al. Cytokines down-regulate expression of major cytochrome P-450 enzymes in adult human hepatocytes in primary culture. Mol Pharmacol. 44(4):707-15 (1993).
Bamias, G., et al., "Differential expression of the TL1A/DcR3 system of TNF/TNFR-like proteins in large vs. small intestinal Crohn's disease," Dig Liver Dis. 44(1):30-6 (2012).
Diamant, Z., et al., "Setipiprant, a selective CRTH2 antagonist, reduces allergen-induced airway responses in allergic asthmatics," Clin Exp Allergy 44(8):1044-52 (2014).

(56) References Cited

OTHER PUBLICATIONS

Xue, L., et al.,"Evaluation of pre-existing antibody presence as a risk factor for posttreatment antidrug antibody induction: analysis of human clinical study data for multiple biotherapeutics," AAPS J 15(3):893-6 (2013).
Franciosi, LG., et al., "Efficacy and safety of RPL554, a dual PDE3 and PDE4 inhibitor, in healthy volunteers and in patients with asthma or chronic obstructive pulmonary disease: findings from four clinical trials," Lancet Respir Med.l(9):714-27 (2013).
Girish, S., et al., "AAPS workshop report: strategies to address therapeutic protein-drug interactions during clinical development," AAPS J. 13(3):405-16 (2011).
Jover, R., et al., "Down-regulation of human CYP3A4 by the inflammatory signal interleukin-6: molecular mechanism and transcription factors involved," FASEB J. 16(13):1799-801 (2002).
Kim, H., et al., "Omalizumab: Practical considerations regarding the risk of anaphylaxis," Allergy Asthma Clin Immunol. 6(1):32 (2010).
Muntané-Relat, J., et al., "Differential effects of cytokines on the inducible expression of CYP1A1, CYP1A2, and CYP3A4 in human hepatocytes in primary culture," Hepatology 22(4 Pt 1):1143-53 (1995).
Shah, D.K., et al.,"Towards a platform PBPK model to characterize the plasma and tissue disposition of monoclonal antibodies in preclinical species and human," J Pharmacokinet Pharmacodyn. 39(1):67-86 (2012).
Shah RR, Morganroth J, Kleiman RB. ICH E14 Q&A(R2) document: commentary on the further updated recommendations on thorough QT studies. Br J Clin Pharmacol. 79(3):456-64 (Mar. 2015).
Tranter, E., et al.,"Giving monoclonal antibodies to healthy volunteers in phase 1 trials: is it safe?" Br J Clin Pharmacol. 76(2):164-72 (2013).
Vargas, HM, et al., Scientific review and recommendations on preclinical cardiovascular safety evaluation of biologics, J Pharmacol Toxicol Methods. 58(2):72-6 (2008).
Wenzel, S., et al., "Dupilumab in persistent asthma with elevated eosinophil levels," N Engl J Med. 27;368(26):2455-66 (2013).
Zhao, J., et al., "Across-Species Scaling of Monoclonal Antibody Pharmacokinetics Using a Minimal PBPK Model," Pharm Res. 32(10):3269-81 (Oct. 2015).
Zidek, Z., et al., "Current status and challenges of cytokine pharmacology," Br J Pharmacol.157(3):342-61 (2009).
Bayry, "TL1A in the inflammatory network in autoimmune diseases", Nature Reviews, vol. 6, Feb. 2010, pp. 67-68.
Bull, et al., "The Death Receptor 3-TNF-like protein 1A pathway drives adverse bone pathology in inflammatory arthritis", J. Exp. Med., vol. 205, No. 11, 2008, pp. 2457-2464.
Chen, et al., "Enhancement and destruction of antibody function by somatic mutation: unequal occurrence is controlled by V gene combinatorial associations", The EMBO Journal, vol. 14, No. 12, 1995, pp. 2784-2794.
Yang, et al., "Soluble decoy receptor 3 induces angiogenesis by neutralization of TL1A, a cytokine belonging to tumor necrosis factor superfamily and exhibiting angiostatic action", Cancer Research, vol. 64, Feb. 1, 2004, pp. 1122-1129.
Takedatsu, et al., "TL1A (TNFSF15) Regulates the Development of Chronic Colitis by Modulating Both T-Helper 1 and T-Helper17 Activation", Gastroenterology 2008, vol. 135, pp. 552-567.
Zhan, et al., "Decoy Strategies: The Structure of TL1A:DcR3 Complex", Structure, vol. 19, Feb. 9, 2011, pp. 162-171.
Zhan, et al., "Biochemical and Structural Characterization of the Human TL1A Ectodomain", Biochemistry, vol. 48, 2009, pp. 7636-7645.

* cited by examiner

| | | CDR1 | | CDR2 |
|---|---|---|---|---|
| C336 | EVQLVQSGAEVKKPGASVKVSCKAS | GYTFTGYYMH | WVRQAPGQGLEWMG | WINPNSGGTNYA |
| C334 | QMQLVQSGAEVKKPGSSVKVSCKAS | GGTFSSYTIS | WVRQAPGQGLEWMG | GIIPIFGTANHA |
| C333 | QVQLVQSGAEVKKPGSSVKVSCKAS | GGTFSSYTIS | WVRQAPGQGLEWMG | GIIPIFGTTNYA |
| C323 | QMQLVQSGAEVKKPGSSVKVSCKAS | GGTFSSYTIS | WVRQAPGQGLEWMG | GIIPIFGTTNYA |
| C321 | QVQLVQSGAEVKKPGASVKVSCKAS | GYTFTSYGIS | WVRQAPGQGLEWMG | WISAYNGNTNYA |
| C320 | QVQLVQSGAEVKKPGASVKVSCKAS | GYTFTSYDIN | WVRQATGQGLEWMG | WMNPNSGNTGYA |
| C319 | QLQLQESGPGLVKPSGTLSLTCAVS | GGSISSRNWWS | WVRQSPGKGLEWIG | EIY HSDITNYN |

| | CDR2 | | CDR3 | | |
|---|---|---|---|---|---|
| C336 | QKFQG | RVTMTRDTSISTAYMELSRLRSDDTAVYYCAS | GGQTHL DV | WGQGTTVTVSS | SEQ ID NO: 2 |
| C334 | QSFQG | RVTITADESTSTAYMELSSLRSEDTAVYYCST | NSYSSSWYDAF DI | WGQGTMVTVSS | SEQ ID NO: 10 |
| C333 | QRFQG | RVTITADESTSTAYMELSSLRSEDTAIYYCST | NSYSSSWYDAF DI | WGQGTMVTVSS | SEQ ID NO: 18 |
| C323 | QRFQG | RVTITADESTSTAYMELSSLRSEDTAIYYCST | NSYSSSWYDAF DI | WGQGTMVTVSS | SEQ ID NOT 26 |
| C321 | QKLQG | RVTMTTDTSTSTAYMELRSLRSDDTAVYYCAR | DSHIYDILTGY DY | WGQGTLVTVSS | SEQ ID NO: 34 |
| C320 | QKFQG | RVTMTRNTSISTAYMELSSLRSEDTAVYYCAR | EVPDTASF EY | WGQGTLVTVSS | SEQ ID NO: 42 |
| C319 | PSLKS | RVTISVDKSKNQFSLKLSSVTAADTAVYYCAK | DGEAGGTYIDAFDV | WGQGTMVTVSS | SEQ ID NO: 50 |

FIGURE 1A

| | | CDR1 | | CDR2 |
|---|---|---|---|---|
| C336 | DIQMTQSPSSLSASVGDRVTITC | QASQ DITDYLN | WYQQRPGKAPKLLIY | DASNLET |
| C334 | DVVMTQSPAFLSVSPGERATLSC | RASQ SISNNLA | WYQQMPGQAPRLLLY | DASTRAT |
| C333 | EIVLTQSPATLSVSPGERATLSC | RASQ SITNNLA | WYQQLPGQAPRLLIY | DASTRAT |
| C323 | AIQLTQSPSSLSASVGDRVTITC | RASQ GIGSALA | WYQQKPGKAPKLLIY | DASSLQS |
| C321 | DVVMTQTPLSSPVTLGQPASISC | HSSQSLVHSDGNTYLS | WLQQRPGQPPRLLIY | KISNRFS |
| C320 | QSVLTQPPSVSGA PGQRVTISC | AGSSSDIG AGLGVH | WYQQLPGTAPKLLIY | GYYNRPS |
| C319 | QSALTQPRSVSGS PGQSVTISC | TGTSSDVG IYNYVS | WYQQHPGKAPKLIIY | DVSERPS |

| | | CDR3 | | |
|---|---|---|---|---|
| C336 | GVPSRFSGSGSGTYFTFTISSLQPEDFATYYC | QQYDNLP IT | FGQGTRLEIKR | SEQ ID NO: 6 |
| C334 | DIPARFSGSGSGSEFTLTISGLQSADFAVYYC | QQYNNWP LT | FGGGTKLEIKR | SEQ ID NO: 14 |
| C333 | DIPARFSGTGSGSEFTLTISGLQSADFAVYYC | QQYNNWP LT | FGGGTKVDIKR | SEQ ID NO: 22 |
| C323 | GVPSRYSGSGSGTDFTLTISGLQPEDFATYYC | QQFSYYP LT | FGGGTKLEIKR | SEQ ID NO: 30 |
| C321 | GVPDRFSGSGAGTDFTLKISRVEAEDVGVYYC | MQDTQFP QT | FGQGTKVEIKR | SEQ ID NO: 38 |
| C320 | GVPDRFSGSKSGTSASLAITGLLPEDEGDYYC | QSYDGTLSAL | FGGGTKLTVLG | SEQ ID NO: 46 |
| C319 | GVPDRFSGSKSDNTASLTISGLQAEDEADYYC | YSYAGTYTSL | FGGGTKVTVLG | SEQ ID NO: 54 |

FIGURE 1B

| | | CDR1 | | CDR2 |
|---|---|---|---|---|
| C320 | QVQLVQSGAEVKKPGASVKVSCKAS | GYTFTSYDIN | WVRQATGQGLEWMG | WMNPNSGNTGYAQKFQG |
| C320-3 | QVQLVQSGAEVKKPGASVKVSCKAS | GYTFTSYDIN | WVRQAPGQGLEWMG | WMNPNSGNTGYAQKFQG |
| C320-90 | QVQLVQSGAEVKKPGASVKVSCKAS | GYTFTSYDIN | WVRQATGQGLEWMG | WMNPNSGNTGYAQKFQG |
| C320-103 | QVQLVQSGAEVKKPGASVKVSCKAS | GYTFTSYDIN | WVRQATGQGLEWMG | WMNPNSGNTGYAQKFQG |
| C320-114 | QVQLVQSGAEVKKPGASVKVSCKAS | GYTFTSYDIN | WVRQATGQGLEWMG | WMNPNSGNTGYAQKFQG |
| C320-115 | QVQLVQSGAEVKKPGASVKVSCKAS | GYTFTSYDIN | WVRQATGQGLEWMG | WMNPNSGNTGYAQKFQG |
| C320-129 | QVQLVQSGAEVKKPGASVKVSCKAS | GYTFTSYDIN | WVRQATGQGLEWMG | WMNPNSGNTGYAQKFQG |
| C320-130 | QVQLVQSGAEVKKPGASVKVSCKAS | GYTFTSYDIN | WVRQATGQGLEWMG | WLNPNSGNTGYAQKFQG |
| CONSENSUS | QVQLVQSGAEVKKPGASVKVSCKAS | GYTFTSYDIN | WVRQAXGQGLEWMG | WXNPNSGNTGYAQKFQG |
| | | | T | M |
| | | | P | L |

| | | CDR3 | | |
|---|---|---|---|---|
| C320 | RVTMTRNTSISTAYMELSSLRSEDTAVYYCAR | EVPDTASFEY | WGQGTLVTVSS | SEQ ID NO: 42 |
| C320-3 | RVTMTRNTSISTAYMELSSLRSEDTAVYYCAR | EVPDTASFEY | WGQGTLVTVSS | SEQ ID NO: 58 |
| C320-90 | RVTMTRNTSISTAYMELSSLRSEDTAVYYCAR | EVPDDASFEY | WGQGTLVTVSS | SEQ ID NO: 66 |
| C320-103 | RVTMTRNTSISTAYMELSSLRSEDTAVYYCAR | EVPDTAAFEY | WGQGTLVTVSS | SEQ ID NO: 70 |
| C320-114 | RVTMTRNTSISTAYMELSSLRSEDTAVYYCAR | EVPDTASFLY | WGQGTLVTVSS | SEQ ID NO: 74 |
| C320-115 | RVTMTRNTSISTAYMELSSLRSEDTAVYYCAR | EVPDTASFDY | WGQGTLVTVSS | SEQ ID NO: 78 |
| C320-129 | RVTMTRNTSISTAYMELSSLRSEDTAVYYCAR | EVPETASFEY | WGQGTLVTVSS | SEQ ID NO: 86 |
| C320-130 | RVTMTRNTSISTAYMELSSLRSEDTAVYYCAR | EVPDTASFEY | WGQGTLVTVSS | SEQ ID NO: 90 |
| CONSENSUS | RVTMTRNTSISTAYMELSSLRSEDTAVYYCAR | EVPXXAXFXY | WGQGTLVTVSS | SEQ ID NO: 94 |
| | | ET S L | | |
| | | DD A D | | |
| | | E | | |

FIGURE 1C

```
                                                    CDR1                               CDR2
C320       QVQLV-QSGAEVKKPGASVKVSCKAS  GYTFTSYDIN  WVRQATGQGLEWMG  WMNPNSGNTGYAQKFQG
1TZG       .....-.......R..S..T......  ..........  .....P.R......  .................
1RHH       E...LE.........S..Q.......  ..........  .....P.H......  .................
2DD8       ....Q-.........S..........  ..........  .....P........  .................
2JB5       .....-.........S..........  ..........  .....P........  .................
3FKU       .....-.........S......TS.   ..........  .....P......L.  .................
3GBM       E....-E........S..........  ..........  .....P...P....  .................
3LMJ       ...V.-......R..........V.   ..........  .....P.K......  ................K
3P30       .....-........A.S..R......  ..........  .....P...PQ...  .................
3IYW       E....-......R.....T.......  ..........  .....P........  .................

Consensus  XVQXXXXSGAEVXXPGXSXXVSCXXS  GYTFTSYDIN  WVRQAXGXGXXWXG  WMNPNSGNTGYAQKFQG
           Q  LV-Q     KK  A VK   KA                    T Q LE M
           E  VLLE     RR  S TT   TS                    P R PQ L
                Q       A     Q    V                      H
                              R                           K

                                                   CDR3
C320       RVTMTRNTSISTAYMELSSLRSEDTAVYYCAR  EVPDTASFEY  WGQGTLVTVSS  SEQ ID NO: 42
1TZG       .I.I.ADR.T....L..N...P..........  ..........  ...........  SEQ ID NO: 154
1RHH       ...F.ADQAT.......TN...D.........  ..........  ...........  SEQ ID NO: 155
2DD8       ...I.TDE.T......................  ..........  .....T.....  SEQ ID NO: 156
2JB5       ...I.ADE.T......................  ..........  ...........  SEQ ID NO: 157
3FKU       ...I.ADQ.TR....D.R..............  ..........  ...........  SEQ ID NO: 158
3GBM       ...I.ADDFAG.V.............M....K  ..........  ..K..T.....  SEQ ID NO: 159
3LMJ       ..S..ED..TN....................T  ..........  ...........  SEQ ID NO: 160
3P30       .L.I.AD..TN...L......YD.......T.  ..........  ...........  SEQ ID NO: 161
3IYW       ......D..T..V...................  ..........  ...........  SEQ ID NO: 234

Consensus  RXXXTXXXXXXTXYXXLXXLRXXDTAXYYCXX  EVPDTASFEY  WGXGTXVTVSS  SEQ ID NO: 162
            VTM RNTSIS A ME SS  SE   V   AR                 Q  L
            ISI ADRATR V LD NN  PD   M   TK                 K  T
            L F T QFAG      T   Y        T
                 E E  N     R
                   D
```

FIGURE 1D

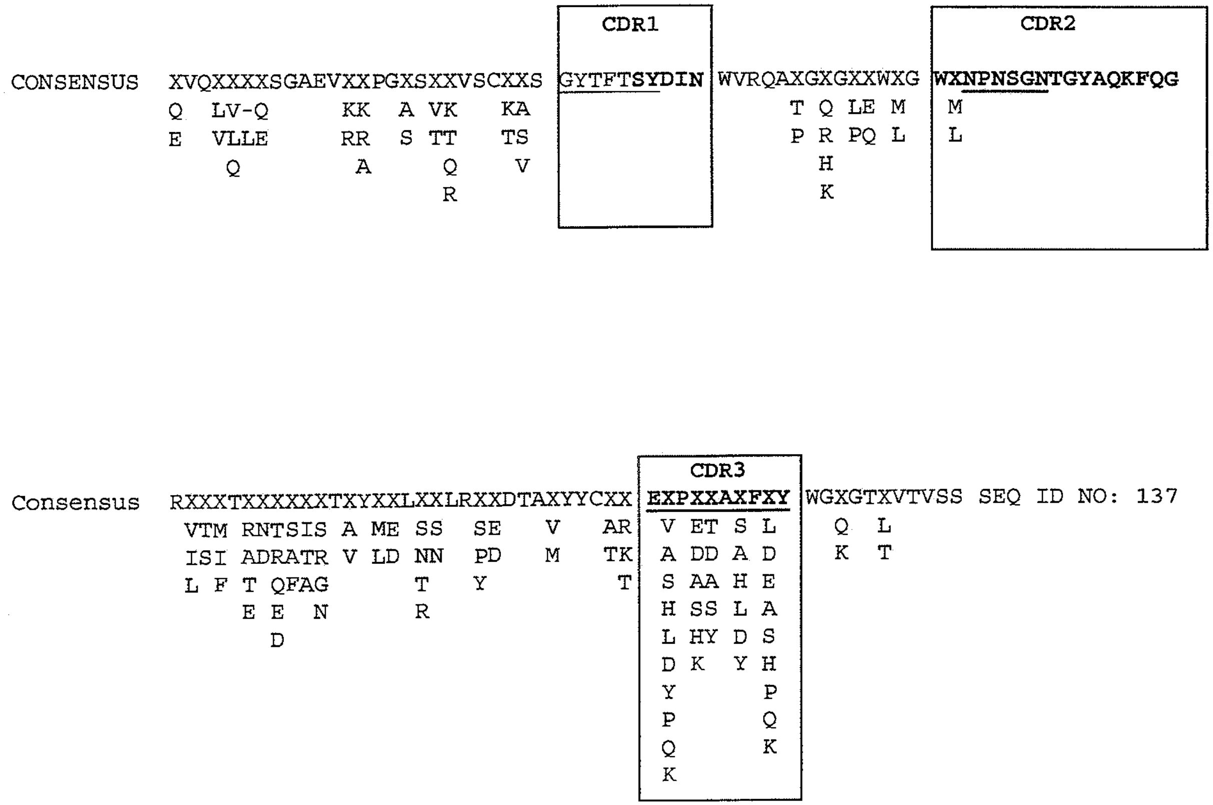

FIGURE 1E

```
                                                          ┌──────────────┐                            ┌────────────────────┐
                                                          │     CDR1     │                            │       CDR2         │
CONSENSUS  XVQXXXXSGAEVXKPGXSXXVSCXXS                     │GYTFTSYDIN    │ WVRQAXGXGXXWXG             │WXNPNSGNTGYAQKFQG   │
           Q  LV-Q         KK  A  VK   KA                 └──────────────┘       T Q LE M             │M                   │
           E  VLLE         RR  S  TT   TS                                        P R PQ L             │L                   │
              Q               A    Q    V                                            H                └────────────────────┘
                                   R                                                 K

                                                          ┌────────────────┐
                                                          │     CDR3       │
Consensus  RXXXTXXXXXXTXYXXLXXLRXXDTAXYYCXX               │EXPXXAXFXY      │ WGXGTXVTVSS   SEQ ID NO: 137
           VTM RNTSIS A ME SS  SE    V  AR                │  V ET S L      │                Q L
           ISI ADRATR V LD NN  PD    M  TK                │  A DD A D      │                K T
           L F T QFAG    T  Y         T                   │  S AA H E      │
             E E N       R                                │  H SS L A      │
                 D                                        │  L HY D S      │
                                                          │  D K  Y H      │
                                                          │    Y  P        │
                                                          │    P  Q        │
                                                          │    Q                                      
                                                          │    K           │
                                                          └────────────────┘

```

| | | CDR1 | | CDR2 |
|---|---|---|---|---|
| C320 | QSVLTQPPSVSGAPGQRVTISC | **AGSSSDIGAGLGVH** | WYQQLPGTAPKLLIY | **GYYNRPS** |
| C320-5 | QSVLTQPPSVSGAPGQRVTISC | **AGSSSDIGAGLGVH** | WYQQLPGTAPKLLIY | **GYYNRPS** |
| C320-120 | QSVLTQPPSVSGAPGQRVTISC | **TGSSSDIGAGLGVH** | WYQQLPGTAPKLLIY | **GYYNRPS** |
| CONSENSUS | QSVLTQPPSVSGAPGQRVTISC | **XGSSSDIGAGLGVH**<br>A<br>T | WYQQLPGTAPKLLIY | **GYYNRPS** |

| | | CDR3 | | |
|---|---|---|---|---|
| C320 | GVPDRFSGSKSGTSASLAITGLLPEDEGDYYC | **QSYDGTLSAL** | FGGGTKLTVLG | SEQ ID NO: 46 |
| C320-5 | GVPDRFSGSKSGTSASLTITGLLPEDEGDYYC | **QSYDGTLSAL** | FGGGTKLTVLG | SEQ ID NO: 62 |
| C320-120 | GVPDRFSGSKSGTSASLAITGLLPEDEGDYYC | **QSYDGTLSAL** | FGGGTKLTVLG | SEQ ID NO: 82 |
| CONSENSUS | GVPDRFSGSKSGTSASLXITGLLPEDEGDYYC<br>A<br>T | **QSYDGTLSAL** | FGGGTKLTVLG | SEQ ID NO: 95 |

FIGURE 1F

```
                                                 CDR1                               CDR2
C320        QSVLTQPP-SVSGAPGQRVTISC AGSSSDIGAGLGVH WYQQLPGTAPKLLIY GYYNRPS
1RHH        EL....S.GTL.LSA.E.A.L.. .............. ....K..Q..R.... .......
1TZGL       EI....S.GTQ.LS..E.A.L.. .............. ....R..Q..R.... .......
2DD8        SYE.....-...V...KTAR.T. .............. ....K..Q..V.VV. .......
2JB5        DIA....A-....S...SI.... .............. ....H..K....M.. .......
3FKU        .PG.....-...KGLR.TA.LT. .............. .L..HQ.HP....S. .......
3GBM        ........-...A....K..... .............. ............... .......
3LMJ        .......S-....T......... .............. ............... .......
3P30        ........-....T......... .............. ............... .......
3IYW        .......S-....T......... .............. ............... .......

CONSENSUS   XXXLTQXXXXXSXXXXXXXXXXC AGSSSDIGAGLGVH WXQQXXGXXPXLXXY GYYNRPS
            QSV   PP-SV GAPGQRVTIS                 Y  LP TA K LI
            ELE   SAGTL LSARETARLT                 L  KQ QP R VV
            SIA     S  Q VGL KSI                      R  K  V MS
            DYG          KT   K                       H  H
             P           A

                                                         CDR3
C320        GVPDRFSGSKSGTSASLAITGLLPEDEGDYYC QSYDGTLSAL FGGGTKLTVLG SEQ ID NO: 46
1RHH        I......C.G...DFT.T.GR.E...LAV... .......... .Q....EIKR. SEQ ID NO: 164
1TZGL       .A......G...DFT.T.SR.E...FAV.... .......... .Q...VE.KR. SEQ ID NO: 165
2DD8        I.E.....N..NT.T.T.SRVEAG..A..... .......... .T...V..... SEQ ID NO: 166
2JB5        .SN........NT...T.S..QA...A..... .......... ........... SEQ ID NO: 167
3FKU        ISE...A.R..NT...T....Q....A..... .......... ........... SEQ ID NO: 168
3GBM        I............T.G....QTG..AN..... .......... ........... SEQ ID NO: 169
3LMJ        ..................S..QS...A..... .......... ........... SEQ ID NO: 170
3P30        ..................S..RS...A..... .......... .A......... SEQ ID NO: 171
3IYW        ..................S..RS...A..... .......... .A......... SEQ ID NO: 172

CONSENSUS   XXPDRFXGXKSXXXXSXAXXXXXXEXXXDYYC QSYDGTLSAL FXGGTXXXXXG SEQ ID NO: 173
            GVP   S S  GTSA L ITGLLP DEG                G    KLTVL
            IAE   A G  NDFT T GRVEAG LAV                Q    VEIKR
             SN     N       G S  QT   F N               T
                    R            RS                     A
```

FIGURE 1G

```
                                                     CDR1                            CDR2
CONSENSUS  XXXLTQXXXXXSXXXXXXXXXXC XXSSSDIGAGLGVH WXQQXXGXXPXLXXX GYYNRPS
           QSV    PP-SV GAPGQRVTIS AG              Y  LP TA K LIP
                                   TS              L  KQ QP R VVE
           QSV    PP-SV GAPGQRVTIS                    R  K  V MSG
           SIA    SSGTQ VGLRKSIRLT                    H  H      Y
           DYG     A  L KTA EKA
           EPE          AS   T
            L           L

                                                              CDR3
CONSENSUS  XXXDRFXGXKSXXXXSXXXXXXXXEXXXDYYC QSYDGTLSAL FXGGTXXXXXG SEQ ID NO: 138
           GVP   S S  GTSA LAITGLLP DEG                  G    KLTVL
           IAE   A G  NDFT TTGRVEAG LAV                  Q    VEIKR
            SN     N       G S  QTA F N                  T
                   R            RS   A                   A
                                 Q
```

FIGURE 1H

| | | CDR1 | | CDR2 | |
|---|---|---|---|---|---|
| C320 variable light chain | QSVLTQPPSVSGAPGQRVTISC | **AGSSSDIGAGLGVH** | WYQQLPGTAPKLLIY | **GYYNRPS** | GVPDRFSGSKSGTSASLAITGL |
| IGLV1-40*01 | ...................... | T....N....YD.. | ............... | .NS.... | ...................... |

| | | CDR3 | |
|---|---|---|---|
| C320 variable light chain | LPEDEGDYYC | **QSYDGTLSAL** | FGGGTKLTVLG |
| IGLV1-40*01 | QA...A.... | ....SS..GX | XXXXXXXXXXX |

FIGURE 9A

```
                                         CDR1                                CDR2
C320        QVQLVQSGAEVKKPGASVKVSCKAS GYTFTSYDIN WVRQATGQGLEWMG WMNPNSGNTGYAQKFQG RVTMTRNTSISTAY
C320-162    ......................... .......... ....P......... .L............... .........A....
C320-163    ......................... .......... ....P......... ................. .....ADR.T....
C320-164    ......................... .......... ....P......... .L............... ..............
C320-165    ......................... .......... ....P......... .L............... ..............
C320-166    ......................... .......... ....P......... .L............... ..............
C320-167    ......................... .......... ....P......... .L............... ..............
C320-168    ......................... .......... ....P......... .L............... ..............
C320-169    ......................... .......... ....P......... .L............... ..............
C320-170    ......................... .......... ....P......... ................. .....ADR.T....
C320-171    ......................... .......... ....P......... ................. .....ADR.T....
C320-172    ......................... .......... ....P......... ................. .....ADR.T....
C320-179    ......................... .......... ....P......... .L............... .....ADR.T....
C320-183    ......................... .......... ....P......... .L............... .....ADR.T....

Consensus   ......................... .......... ....X......... .X............... .....XXXXX....
                                                   T             M                     RNTSI
                                                   P             L                     ADRAT

                                  CDR3
C320        MELSSLRSEDTAVYYCAR EVPDTASFEY WGQGTLVTVSS
C320-162    .................. ...E...... ...........   SEQ ID NO: 175
C320-163    .................. .......... ...........   SEQ ID NO: 176
C320-164    .................. ...E...... ...........   SEQ ID NO: 177
C320-165    .................. ...E...... ...........   SEQ ID NO: 178
C320-166    .................. ...E...... ...........   SEQ ID NO: 179
C320-167    .................. ...E...... ...........   SEQ ID NO: 180
C320-168    .................. ...E..A... ...........   SEQ ID NO: 181
C320-169    .................. ...E..A... ...........   SEQ ID NO: 182
C320-170    .................. .......... ...........   SEQ ID NO: 183
C320-171    .................. .......... ...........   SEQ ID NO: 184
C320-172    .................. .......... ...........   SEQ ID NO: 185
C320-179    .................. ...E..A... ...........   SEQ ID NO: 186
C320-183    .................. ...E..A... ...........   SEQ ID NO: 187

Consensus   .................. ...X..X... ...........   SEQ ID NO: 173
                                  D  S
                                  E  A
```

FIGURE 9B

```
                                     CDR1                                  CDR2
C320       QSVLTQPPSVSGAPGQRVTISC AGSSSDIGAGLGVH WYQQLPGTAPKLLIY GYYNRPS GVPDRFSGSKSGTSASLAITGL
C320-162   ...................... .............. ............... ....... .................T....
C320-163   ...................... .............. ............... ....... .................T....
C320-164   ...................... .S............ ............... ....... .................T....
C320-165   ...................... TS............ ............... ....... .................T....
C320-166   ...................... T............. ............... ....... .................T....
C320-167   ...................... .............. ............... ....... .................T....
C320-168   ...................... TS............ ............... ....... .................T....
C320-169   ...................... .............. ............... ....... .................T....
C320-170   ...................... TS............ ............... ....... .................T....
C320-171   ...................... TS............ ..............P ....... .................T....
C320-172   ...................... TS............ ..............E ....... .................T....
C320-179   ...................... TS............ ..............E ....... .................T....
C320-183   ...................... TS............ ..............G ....... .................T....

Consensus  ...................... XX............ ..............X ....... .................X....
                                  AG                          Y                           A
                                  TS                          P                           T
                                                              E
                                                              G

                       CDR3
C320       LPEDEGDYYC QSYDGTLSAL FGGGTKLTVLG
C320-162   .......... .......... ...........   SEQ ID NO: 188
C320-163   .......... .......... ...........   SEQ ID NO: 189
C320-164   .......... .......... ...........   SEQ ID NO: 190
C320-165   .......... .......... ...........   SEQ ID NO: 191
C320-166   .......... .......... ...........   SEQ ID NO: 192
C320-167   .......... .......... ...........   SEQ ID NO: 193
C320-168   .......... .......... ...........   SEQ ID NO: 194
C320-169   .......... .......... ...........   SEQ ID NO: 195
C320-170   .......... .......... ...........   SEQ ID NO: 196
C320-171   .......... .......... ...........   SEQ ID NO: 197
C320-172   .......... .......... ...........   SEQ ID NO: 198
C320-179   .......... .......... ...........   SEQ ID NO: 199
C320-183   .......... .......... ...........   SEQ ID NO: 200

Consensus  .......... .......... ...........   SEQ ID NO: 174
```

FIGURE 9C

ANTIBODIES AGAINST TL1A AND USES THEREOF

CROSS REFERENCE TO RELATED APPLICATIONS

This application is a continuation of U.S. patent application Ser. No. 14/228,367 filed on Mar. 28, 2014, which is a continuation of International Application No. PCT/AU2012/001161 filed on Sep. 28, 2012, and claims priority to U.S. Provisional Application No. 61/541,590 filed on Sep. 30, 2011 and Australian Patent Application No. 2011904042 filed on Sep. 30, 2011. Each of these applications is incorporated by reference herein, in its entirety and for all purposes.

REFERENCE TO A SEQUENCE LISTING

This application includes a Sequence Listing submitted electronically as a text file named 512500 Sequence Listing 27 Sep. 2012_ST25.txt, created on Sep. 27, 2012, with a size of 173,000 bytes. The Sequence Listing is incorporated by reference herein.

FIELD OF THE INVENTION

The disclosure relates to proteins that bind to TL1a and uses thereof, e.g., in therapy, prophylaxis, diagnosis or prognosis.

BACKGROUND OF THE INVENTION

TNF-like ligand 1a (TL1a, syn. TNF superfamily member 15 (TNFSF15); TL1 and VEGI) is a member of the tumor necrosis factor superfamily, which is expressed by antigen presenting cells (including dendritic cells, B cells and macrophages), $CD4^+$ and $CD8^+$ T cells and endothelial cells and can be expressed on the cell surface or secreted as a soluble cytokine. The receptor for TL1a, Death Receptor 3 (DR3) is expressed by a variety of cells, including $CD4^+$ and $CD8^+$ T cells, NK cells, NKT cells and $FOXP3^+$ regulatory T (Treg) cells.

TL1a can also bind a decoy receptor (DcR3), which is a competitive inhibitor of DR3. DcR3 also acts as a decoy receptor for Fas-ligand (Fas-L) and lymphotoxin-like inducible protein that competes with glycoprotein D for binding herpesvirus entry mediator on T-cells (LIGHT). Accordingly, DcR3 is an important regulator of several signal transduction pathways.

The TL1a/DR3 signaling pathway has been implicated in several biological systems, which are associated with human diseases. For example, TL1a has been shown to play a role in immunity and in angiogenesis.

Using mice deficient in TL1a and/or DR3, researchers have also shown that inhibiting this pathway can provide prophylactic or therapeutic benefit in several immune-mediated conditions, such as, experimental autoimmune encephalomyelitis (EAE; a model of multiple sclerosis), colitis, inflammatory bowel disease, asthma and arthritis. TL1a has also been shown to promote formation of foam cells and atherosclerotic plaques.

It will be apparent to the skilled artisan from the foregoing that TL1a plays an important role in biological processes involved in several important human diseases. Accordingly, compounds that inhibit TL1a activity are desirable, e.g., for their therapeutic, prophylactic, diagnostic and prognostic uses.

SUMMARY OF THE INVENTION

The inventors have produced TL1a-binding proteins comprising antigen binding domains of antibodies which are capable of specifically binding to TL1a and inhibiting interaction of TL1a and DR3 (thereby neutralizing TL1a activity(ies)) without inhibiting interaction of TL1a and DcR3. Without being bound by any theory or mode of action, the inventors reasoned that such TL1a-binding proteins may be capable of reducing or preventing signaling of TL1a through DR3 without significantly disturbing the homeostatic interaction of DcR3 and TL1a. This preserves the natural antagonistic effects of DcR3 on TL1a-DR3 interactions, which may be advantageous because DcR3 also regulates the amount of free Fas-L and LIGHT available for binding to their receptors (Fas and H-VEM, respectively). Since Fas-mediated killing plays a role in cancer surveillance, potential downstream consequences of increasing the amount of DcR3 to bind to Fas-L could include increased susceptibility to cancer. Again, without being bound by theory or mode of action, proteins that specifically inhibit interaction of TL1a and DR3, but not DcR3, could be advantageous in treating disease but without compromising safety.

A subclass of the TL1a-binding proteins identified by the inventors was also found to inhibit or prevent apoptosis of TF-1 cells induced by human TL1a at low concentrations, i.e., the antibodies had a low effective concentration or $EC_{50}$. TL1a-binding proteins capable of inhibiting or preventing TL1a activity (e.g., TL1a-induced apoptosis of TF-1 cells) are sometimes referred to herein as highly potent TL1a-binding proteins.

The inventors have also identified a region of TL1a which is bound by a highly potent TL1a-binding protein which binds specifically to TL1a and inhibits interaction of TL1a with DR3 without inhibiting the ability of TL1a to interact with DcR3.

The TL1a-binding proteins identified by the inventors form the basis for various therapeutic/prophylactic/diagnostic/prognostic uses. This is demonstrated by the inventors' use of a TL1a-binding protein of the disclosure to treat accepted models of colitis, with the protein showing efficacy at least equal to the current standard of care for this condition.

Accordingly, the disclosure provides an isolated or recombinant TL1a-binding protein comprising an antigen binding domain of an antibody, wherein the antigen binding domain specifically binds to TL1a and, wherein the TL1a-binding protein inhibits interaction of TL1a and DR3 and does not inhibit interaction of TL1a and DcR3.

In one example, the TL1a-binding protein does not detectably reduce interaction of TL1a and DcR3. For example, the effect of the TL1a-binding protein on interaction of TL1a and DcR3 is assessed using a competition enzyme linked immunosorbent assay (ELISA). For example, the TL1a-binding protein is incubated with TL1a (e.g., human TL1a) and then contacted with a polypeptide comprising DcR3 (e.g., human DcR3 (hDcR3)) fused to an Fc region of an antibody ("DcR3/Fc") and the level of bound TL1a is detected. In one example, the level of bound TL1a in the presence or absence of the protein is not significantly different and/or is insufficiently different to permit calculation of an $EC_{50}$.

In one example, the level of inhibition of interaction of TL1a and DcR3 (or DcR3/Fc) in the presence of the TL1a-binding protein expressed as a percentage of the level of binding in the absence of the protein is 25% or less, or 22% or less, or 20% or less, or 18% or less, or 15% or less, or 12% or less, or 10% or less, or 7% or less, or 5% or less.

In one example, the ability of a TL1a-binding protein to inhibit interaction of TL1a and DR3 or DcR3 is assessed by immobilizing DcR3/Fc or a polypeptide comprising DR3 (e.g., human DR3 (hDR3)) fused to a Fc region of an antibody (DR3/Fc) on a solid or semi-solid surface (e.g., an ELISA plate) at a concentration of about 2 μg/ml. The TL1a-binding protein is then contacted with biotinylated human TL1a (at a concentration of about 1 μg/ml) for about 30 minutes then added to the immobilized DcR3/Fc or DR3/Fc. Following washing, bound TL1a is detected. To determine percentage binding or inhibition, data are normalized by expression as a percentage of maximum binding of TL1a to the immobilized DcR3/Fc or DR3/Fc in the absence of a TL1a-binding protein. By calculating the level of inhibition at multiple concentrations of the TL1a-binding protein, an $EC_{50}$ can be determined.

In one example, the TL1a-binding protein inhibits interaction of TL1a and DR3 (or DR3/Fc) but not TL1a and DcR3 (or DcR3/Fc).

For example, the TL1a-binding protein inhibits interaction of DR3/Fc and TL1a with an $EC_{50}$ of from about 20 nM to about 10 fM, or an $EC_{50}$ of 20 nM or less, such as, 15 nM or less, for example, 11 nM or less, for example 5 nM or less. In one example, the $EC_{50}$ is 5 nM or less. For example, the $EC_{50}$ is 3 nM or less. For example, the $EC_{50}$ is 2.5 nM or less. For example, the $EC_{50}$ is 1 nM or less. For example, the $EC_{50}$ is 0.5 nM or less. In one example, the $EC_{50}$ is assessed using a competition enzyme linked immunosorbent assay (ELISA). For example, various concentrations of the TL1a-binding protein are incubated with TL1a (e.g., human TL1a) (e.g., about 1 μg/ml of TL1a) and then contacted with the DR3/Fc (e.g., about 2 μg/ml of the DR3/Fc) and the level of bound TL1a is detected. The concentration of protein at which half maximal inhibition of binding to TL1a is detected is considered the $EC_{50}$.

In one example, the TL1a-binding protein neutralizes TL1a activity in or on a cell by interfering with TL1a and DR3 interactions.

In one example, the TL1a-binding protein binds to the extracellular domain of TL1a, such as the extracellular domain of human TL1a.

In one example, the TL1a-binding protein binds to human TL1a produced by mammalian cells, such as human cells.

Exemplary TL1a-binding proteins of the disclosure reduce the level of apoptosis of TF-1 cells cultured in the presence of human TL1a, such as human TL1a produced by mammalian cells (e.g., human cells) (e.g., about 100 ng human TL1a per mL of culture) and cycloheximide. For example, about $7\times10^4$ to $8\times10^4$ TF-1 cells (e.g., $7.5\times10^4$ cells) are contacted with about 1 μg human TL1a per mL of culture and cycloheximide. For example, the TL1a-binding protein reduces the level of apoptosis of the TF-1 cells with an $EC_{50}$ (i.e., a concentration of the TL1a-binding protein that achieves 50% of the maximum inhibition of TL1a-induced apoptosis of TF-1 cells achieved by the TL1a-binding protein) of 25 nM or less. In one example, the $EC_{50}$ is 5 nM or less. In one example, the $EC_{50}$ is 2 nM or less. In one example, the $EC_{50}$ is 1.5 nM or less or 1.2 nM or less or 1.1 nM or less. In one example, the $EC_{50}$ is 1 nM or less. In one example, the $EC_{50}$ is 0.75 nM or less. In one example, the $EC_{50}$ is 0.3 nM or less. In one example, the $EC_{50}$ is 0.1 nM or less. In one example, the $EC_{50}$ is from about 1.5 nM to about 10 fM, such as from about 1 nM to about 50 fM, for example, from about 1 nM to about 100 fM.

In one example, the TL1a-binding protein binds to TL1a on the surface of a cell with an $EC_{50}$ (i.e., a concentration of the TL1a-binding protein that achieves 50% of the maximum binding to the cell achieved by the TL1a-binding protein) of about 10 nM or less, e.g., as determined using flow cytometry. In one example, the flow cytometry is performed with about $2\times10^5$ to $3\times10^5$ cells (e.g., $2.5\times10^5$ cells). In one example, the $EC_{50}$ is 5 nM or less. In one example, the $EC_{50}$ is 2 nM or less. In one example, the $EC_{50}$ is from about 10.0 nM or 5.0 nM or 1.0 nM or 0.5 nM or 0.1 nM to about 10 fM.

The disclosure also provides an isolated or recombinant TL1a-binding protein comprising an antigen binding domain of an antibody, wherein the antigen binding domain binds specifically to TL1a and inhibits the interaction of biotinylated TL1a and DR3/Fc with an $EC_{50}$ of about 2.5 nM or less, such as 1 nM or less or from about 2.5 nM, or about 1.0 nM, or about 0.5 nM, or about 0.1 nM to about 10 fM in a competition ELISA, wherein the DR3/Fc is immobilized on a solid or semi-solid substrate (e.g., a solid substrate such as an ELISA plate) at a concentration of about 2 μg/mL, and wherein the biotinylated TL1a is contacted for about 30 minutes at a concentration of about 1 μg/mL with the TL1a binding protein at a concentration range of from about 10 μg/mL to about 0.01 μg/mL and is then contacted to the immobilized DR3/Fc, and wherein the TL1a-binding protein does not detectably reduce interaction of biotinylated TL1a and DcR3/Fc in a competition ELISA compared to the level of the binding of biotinylated TL1a to DcR3/Fc in the absence of the TL1a-binding protein, wherein the DcR3/Fc is immobilized on a solid or semi-solid substrate (e.g., a solid substrate such as an ELISA plate) at a concentration of about 2 μg/mL, wherein the biotinylated TL1a is contacted for about 30 minutes at a concentration of about 1 μg/mL with the TL1a-binding protein at a concentration of from about 10 μg/mL to 0.1 μg/mL and is then contacted to the immobilized DcR3/Fc.

The disclosure also provides an isolated or recombinant TL1a-binding protein comprising an antigen binding domain of an antibody, wherein the antigen binding domain binds specifically to TL1a and inhibits the interaction of biotinylated TL1a and DR3/Fc with an $EC_{50}$ of about 2.5 nM or less, such as 1 nM or less or from about 2.5 nM, or about 1.0 nM, or about 0.5 nM, or about 0.1 nM to about 10 fM in a competition ELISA, wherein the DR3/Fc is immobilized on a solid or semi-solid substrate (e.g., a solid substrate such as an ELISA plate) at a concentration of about 2 μg/mL, and wherein the biotinylated TL1a is contacted for about 30 minutes at a concentration of about 1 μg/mL with the TL1-a binding protein at a concentration range of from about 10 μg/mL to about 0.01 μg/mL and is then contacted to the immobilized DR3/Fc, and wherein the TL1a-binding protein does not detectably reduce interaction of biotinylated TL1a and DcR3/Fc in a competition ELISA compared to the level of the binding of biotinylated TL1a to DcR3/Fc in the absence of the TL1a-binding protein, and wherein the DcR3/Fc is immobilized on a solid or semi-solid substrate (e.g., a solid substrate such as an ELISA plate) at a concentration of about 2 μg/mL, wherein the biotinylated TL1a is contacted for about 30 minutes at a concentration of about 1 μg/mL with the TL1a-binding protein at a concentration of from about 10 μg/mL to 0.1 μg/mL and is then contacted to the immobilized DcR3/Fc, and wherein the TL1a-binding protein reduces the level of apoptosis of TF-1 cells cultured in the presence of human TL1a produced by human cells and cycloheximide with an $EC_{50}$ (i.e., a concentration of the TL1a-binding protein that achieves 50% of the maximum inhibition of TL1a-induced apoptosis of TF-1 cells achieved by the TL1a-binding protein) of 25 nM or less, or from about 1.5 nM or 1.0 nM or 0.5 nM or 0.1 nM or 0.05 nM to about 10 fM wherein about $7.5\times10^4$ TF-1 cells are contacted with about 100 ng human TL1a per mL of culture and about 10 μg/ml cycloheximide with the TL1a-binding protein at a concentration of about 5 μg/mL or less for about 4 to 5 hours.

In one example, the TL1a is biotinylated at one site, i.e., the biotin is linked to only one amino acid in TL1a.

In one example, the TL1a-binding protein does not detectably reduce interaction of the biotinylated TL1a and DcR3/Fc in the competition ELISA compared to the level of the binding of biotinylated TL1a to DcR3/Fc in the absence of the TL1a-binding protein, wherein the biotinylated TL1a is contacted for about 30 minutes at a concentration of about 1 μg/mL with the TL1a-binding protein at a concentration of about 100 μg/mL and is then contacted to the immobilized DcR3/Fc.

In one example, the TL1a-binding protein does not detectably reduce interaction of the biotinylated TL1a and DcR3/Fc in the competition ELISA compared to the level of the binding of biotinylated TL1a to DcR3/Fc in the absence of the TL1a-binding protein, wherein the biotinylated TL1a is contacted for about 30 minutes at a concentration of about 1 μg/mL with the TL1a-binding protein at a concentration of about 10 μg/mL and is then contacted to the immobilized DcR3/Fc.

In one example, the TL1a-binding protein reduces the level of apoptosis of the TF-1 cells with an $EC_{50}$ of 22 nM or less. In one example, the $EC_{50}$ is 10 nM or less. In one example, the $EC_{50}$ is 5 nM or less. In one example, the $EC_{50}$ is 2 nM or less. In one example, the $EC_{50}$ is 1.5 nM or less or 1.2 nM or less or 1.1 nM or less. In one example, the $EC_{50}$ is 1 nM or less. In one example, the $EC_{50}$ is 0.75 nM or less. In one example, the $EC_{50}$ is 0.3 nM or less. In one example, the $EC_{50}$ is 0.1 nM or less.

The disclosure additionally, or alternatively, provides an isolated or recombinant TL1a-binding protein comprising an antigen binding domain of an antibody, wherein the antigen binding domain specifically binds to TL1a and, wherein the TL1a-binding protein inhibits interaction of TL1a and DR3 and does not inhibit interaction of TL1a and DcR3, and wherein the TL1a-binding protein binds a mutant form of soluble human TL1a comprising a sequence set forth in SEQ ID NO: 202 in which the arginine at position 32 has been substituted with alanine and/or the arginine at position 85 has been substituted with alanine at a level that is at least 75% lower than the level with which the TL1a-binding protein binds to soluble human TL1a comprising a sequence set forth in SEQ ID NO: 202.

In one example, the mutant form of soluble human TL1a is immobilized on a solid or semi-solid substrate (e.g., a solid substrate such as an ELISA plate) at a concentration of about 1 μg/mL, and wherein the TL1a binding protein at a concentration range of from about 10 μg/mL to about 0.01 μg/mL is then contacted to the immobilized mutant TL1a.

In one example, the TL1a-binding protein binds a mutant form of soluble human TL1a comprising a sequence set forth in SEQ ID NO: 202 in which the arginine at position 32 has been substituted with alanine and/or the arginine at position 85 has been substituted with alanine at a level that is no greater than 25% of the level with which the protein binds to soluble human TL1a comprising a sequence set forth in SEQ ID NO: 202. For example, the level of binding of the TL1a-binding protein to the mutant form of soluble human TL1a is no greater than 25% of the level with which the protein binds to soluble human TL1a, when the TL1a-binding protein is tested at a concentration of 10 μg/mL.

The disclosure additionally, or alternatively, provides an isolated or recombinant TL1a-binding protein comprising an antigen binding domain of an antibody, wherein the antigen binding domain specifically binds to TL1a and, wherein the TL1a-binding protein inhibits interaction of TL1a and DR3 and does not inhibit interaction of TL1a and DcR3, and wherein the TL1a-binding protein binds a mutant form of soluble human TL1a comprising a sequence set forth in SEQ ID NO: 202 in which the arginine at position 32 has been substituted with alanine and/or the arginine at position 85 has been substituted with alanine at a level that is at least 75% lower than the level with which the protein binds to soluble human TL1a comprising a sequence set forth in SEQ ID NO: 202, wherein the mutant form of TL1a is immobilized on a solid or semi-solid substrate at a concentration of about 1 μg/mL, and wherein the TL1a binding protein at a concentration of 10 μg/mL is then contacted to the immobilized mutant TL1a.

In one example, the mutant form of soluble human TL1a comprises a sequence set forth in SEQ ID NO: 202 in which the arginine at position 32 has been substituted with alanine.

In one example, the mutant form of soluble human TL1a comprises a sequence set forth in SEQ ID NO: 202 in which the arginine at position 85 has been substituted with alanine.

In one example, the mutant form of soluble human TL1a comprises a sequence set forth in SEQ ID NO: 202 in which the arginine at position 32 has been substituted with alanine and in which the arginine at position 85 has been substituted with alanine.

In one example, the level of binding of the TL1a-binding protein to the mutant form of soluble human TL1a is at least 80% or 85% or 90% or 95% lower than the level with which the protein binds to soluble human TL1a comprising a sequence set forth in SEQ ID NO: 202.

In one example, the TL1a-binding protein does not detectably bind to the mutant form of soluble human TL1a.

In one example, the binding of the TL1a-binding protein to soluble human TL1a or a mutant form thereof is assessed using Surface Plasmon Resonance. For example, the soluble human TL1a or a mutant form thereof is immobilized (e.g., at a concentration of about 1 μg/mL) and the TL1a-binding protein (e.g., at a concentration of about 500 ng/mL) contacted to the immobilized soluble human TL1a or a mutant form thereof and binding detected by Surface Plasmon Resonance. By comparing the level of binding to the soluble human TL1a or a mutant form thereof a comparison can be made to determine a TL1a-binding protein that binds at a level that is at least 75% lower than the level with which the protein binds to soluble human TL1a.

In one example, the binding of the TL1a-binding protein to soluble human TL1a or a mutant form thereof is assessed using ELISA. For example, the soluble human TL1a or a mutant form thereof is immobilized (e.g., at a concentration of about 1 μg/mL) and the TL1a-binding protein (e.g., at a concentration of about 10 μg/mL) contacted to the immobilized soluble human TL1a or a mutant form thereof and binding detected by ELISA (e.g., using standard methods in the art).

In one example, the TL1a-binding protein binds to an epitope within TL1a comprising residues corresponding to arginine at position 32 of SEQ ID NO: 202 and the arginine at position 85 of SEQ ID NO: 202. In one example, the epitope is a conformational epitope.

In one example, the TL1a-binding protein binds at least at amino acid residues arginine at position 32 and arginine at position 85 of a human TL1a which comprises an amino acid sequence as set forth in SEQ ID NO:202.

Exemplary TL1a-binding proteins having the binding characteristics set forth in the foregoing paragraphs will be apparent to the skilled artisan from the description herein and include those comprising the following pairs of $V_H$ and $V_L$:

(i) a $V_H$ comprising a sequence set forth in SEQ ID NO: 94 and a $V_L$ comprising a sequence set forth in SEQ ID NO: 95;
(ii) a $V_H$ comprising a sequence set forth in SEQ ID NO: 137 and a $V_L$ comprising a sequence set forth in SEQ ID NO: 138;
(iii) a $V_H$ comprising a sequence set forth in SEQ ID NO: 162 and a $V_L$ comprising a sequence set forth in SEQ ID NO: 172; or
(iv) a $V_H$ comprising a sequence set forth in SEQ ID NO: 173 and a $V_L$ comprising a sequence set forth in SEQ ID NO: 174.

$V_H$ and $V_L$ falling within the foregoing sequences will be apparent to the skilled person from the description herein and are to be taken to apply mutatis mutandis to the present example of the disclosure.

In one example, a TL1a-binding protein of the disclosure inhibits interaction of TL1a from human, cynomolgus monkey or rhesus monkey and DR3. Such TL1a-binding proteins are useful for characterization in animal models of human disease.

In one example, a TL1a-binding protein of the disclosure does not detectably inhibit interaction of TL1a from mouse, pig, rabbit or guinea pig and DR3, e.g., the TL1a-binding protein does not detectably inhibit the level of apoptosis of TF-1 cells cultured in the presence of the relevant TL1a, e.g. as determined using an assay described herein.

In one example, a TL1a-binding protein of the disclosure detectably inhibits interaction of TL1a from rat and DR3. For example, the TL1a-binding protein detectably inhibits the level of apoptosis of TF-1 cells cultured in the presence of the relevant TL1a, e.g. as determined using an assay described herein.

In one example, a TL1a-binding protein of the disclosure detectably binds to an isoform of TL1a consisting of amino acids 72-251 of SEQ ID NO: 123 and/or to an isoform of TL1a consisting of amino acids 84-251 of SEQ ID NO: 123.

For example, binding is assessed by an ELISA in which the isoform of TL1a is immobilized at a concentration of 1 μg/ml and the TL1a-binding protein is contacted to the isoform and the level of binding assessed.

The disclosure additionally or alternatively provides an isolated or recombinant TL1a-binding protein comprising an antigen binding domain of an antibody comprising any one or more of the following:

(i) a$V_H$ comprising a sequence set forth in SEQ ID NO: 94 and a $V_L$ comprising a sequence set forth in SEQ ID NO: 95;
(ii) a$V_H$ comprising a sequence set forth in SEQ ID NO: 137 and a $V_L$ comprising a sequence set forth in SEQ ID NO: 138;
(iii) a$V_H$ comprising a sequence set forth in SEQ ID NO: 162 and a $V_L$ comprising a sequence set forth in SEQ ID NO: 172; or
(iv) a$V_H$ comprising a sequence set forth in SEQ ID NO: 173 and a $V_L$ comprising a sequence set forth in SEQ ID NO: 174.

The disclosure additionally or alternatively provides an isolated or recombinant TL1a-binding protein comprising an antigen binding domain of an antibody comprising any one or more of the following:

(i) a$V_H$ comprising a sequence set forth in SEQ ID NO: 2 and a $V_L$ comprising a sequence set forth in SEQ ID NO: 6;
(ii) a $V_H$ comprising a sequence set forth in SEQ ID NO: 10 and a $V_L$ comprising a sequence set forth in SEQ ID NO: 14;
(iii) a $V_H$ comprising a sequence set forth in SEQ ID NO: 18 and a $V_L$ comprising a sequence set forth in SEQ ID NO: 22;
(iv) a $V_H$ comprising a sequence set forth in SEQ ID NO: 26 and a $V_L$ comprising a sequence set forth in SEQ ID NO: 30;
(v) a $V_H$ comprising a sequence set forth in SEQ ID NO: 34 and a $V_L$ comprising a sequence set forth in SEQ ID NO:38;
(vi) a $V_H$ comprising a sequence set forth in SEQ ID NO: 42 and a $V_L$ comprising a sequence set forth in SEQ ID NO: 46;
(vii) a $V_H$ comprising a sequence set forth in SEQ ID NO: 50 and a $V_L$ comprising a sequence set forth in SEQ ID NO: 54;
(viii) a $V_H$ comprising a sequence set forth in SEQ ID NO: 58 and a $V_L$ comprising a sequence set forth in SEQ ID NO: 46;
(ix) a $V_H$ comprising a sequence set forth in SEQ ID NO: 42 and a $V_L$ comprising a sequence set forth in SEQ ID NO: 62;
(x) a $V_H$ comprising a sequence set forth in SEQ ID NO: 66 and a $V_L$ comprising a sequence set forth in SEQ ID NO: 62;
(xi) a $V_H$ comprising a sequence set forth in SEQ ID NO: 70 and a $V_L$ comprising a sequence set forth in SEQ ID NO: 62;
(xii) a $V_H$ comprising a sequence set forth in SEQ ID NO: 74 and a $V_L$ comprising a sequence set forth in SEQ ID NO: 62;
(xiii) a $V_H$ comprising a sequence set forth in SEQ ID NO: 78 and a $V_L$ comprising a sequence set forth in SEQ ID NO: 62;
(xiv) a $V_H$ comprising a sequence set forth in SEQ ID NO: 58 and a $V_L$ comprising a sequence set forth in SEQ ID NO: 82;
(xv) a $V_H$ comprising a sequence set forth in SEQ ID NO: 86 and a $V_L$ comprising a sequence set forth in SEQ ID NO: 46;
(xvi) a $V_H$ comprising a sequence set forth in SEQ ID NO: 90 and a $V_L$ comprising a sequence set forth in SEQ ID NO: 46;
(xvii) a $V_H$ comprising a sequence set forth in SEQ ID NO: 58 and a $V_L$ comprising a sequence set forth in SEQ ID NO: 62;
(xviii) a $V_H$ comprising a sequence set forth in SEQ ID NO: 154 and a $V_L$ comprising a sequence set forth in SEQ ID NO: 164;
(xix) a $V_H$ comprising a sequence set forth in SEQ ID NO: 155 and a $V_L$ comprising a sequence set forth in SEQ ID NO: 163;
(xx) a $V_H$ comprising a sequence set forth in SEQ ID NO: 156 and a $V_L$ comprising a sequence set forth in SEQ ID NO: 165;
(xxi) a $V_H$ comprising a sequence set forth in SEQ ID NO: 157 and a $V_L$ comprising a sequence set forth in SEQ ID NO: 166;
(xxii) a $V_H$ comprising a sequence set forth in SEQ ID NO: 158 and a $V_L$ comprising a sequence set forth in SEQ ID NO: 167;
(xxiii) a $V_H$ comprising a sequence set forth in SEQ ID NO: 159 and a $V_L$ comprising a sequence set forth in SEQ ID NO: 168;
(xxiv) a $V_H$ comprising a sequence set forth in SEQ ID NO: 160 and a $V_L$ comprising a sequence set forth in SEQ ID NO: 169;

(xxv) a $V_H$ comprising a sequence set forth in SEQ ID NO: 161 and a $V_L$ comprising a sequence set forth in SEQ ID NO: 170;

(xxvi) a $V_H$ comprising a sequence set forth in SEQ ID NO: 234 and a $V_L$ comprising a sequence set forth in SEQ ID NO: 169;

(xxvii) a $V_H$ comprising a sequence set forth in SEQ ID NO: 154 and a $V_L$ comprising a sequence set forth in SEQ ID NO: 46;

(xxviii) a $V_H$ comprising a sequence set forth in SEQ ID NO: 155 and a $V_L$ comprising a sequence set forth in SEQ ID NO: 46;

(xxix) a $V_H$ comprising a sequence set forth in SEQ ID NO: 156 and a $V_L$ comprising a sequence set forth in SEQ ID NO: 46;

(xxx) a $V_H$ comprising a sequence set forth in SEQ ID NO: 157 and a $V_L$ comprising a sequence set forth in SEQ ID NO: 46;

(xxxi) a $V_H$ comprising a sequence set forth in SEQ ID NO: 158 and a $V_L$ comprising a sequence set forth in SEQ ID NO: 46;

(xxxii) a $V_H$ comprising a sequence set forth in SEQ ID NO: 159 and a $V_L$ comprising a sequence set forth in SEQ ID NO: 46;

(xxxiii) a $V_H$ comprising a sequence set forth in SEQ ID NO: 160 and a $V_L$ comprising a sequence set forth in SEQ ID NO: 46;

(xxxiv) a $V_H$ comprising a sequence set forth in SEQ ID NO: 161 and a $V_L$ comprising a sequence set forth in SEQ ID NO: 46;

(xxxv) a $V_H$ comprising a sequence set forth in SEQ ID NO: 234 and a $V_L$ comprising a sequence set forth in SEQ ID NO: 46;

(xxxvi) a $V_H$ comprising a sequence set forth in SEQ ID NO: 42 and a $V_L$ comprising a sequence set forth in SEQ ID NO: 164;

(xxxvii) a $V_H$ comprising a sequence set forth in SEQ ID NO: 42 and a $V_L$ comprising a sequence set forth in SEQ ID NO: 165;

(xxxviii) a $V_H$ comprising a sequence set forth in SEQ ID NO: 42 and a $V_L$ comprising a sequence set forth in SEQ ID NO: 166;

(xxxix) a $V_H$ comprising a sequence set forth in SEQ ID NO: 42 and a $V_L$ comprising a sequence set forth in SEQ ID NO: 167;

(xl) a $V_H$ comprising a sequence set forth in SEQ ID NO: 42 and a $V_L$ comprising a sequence set forth in SEQ ID NO: 168;

(xli) a $V_H$ comprising a sequence set forth in SEQ ID NO: 42 and a $V_L$ comprising a sequence set forth in SEQ ID NO: 169;

(xlii) a $V_H$ comprising a sequence set forth in SEQ ID NO: 42 and a $V_L$ comprising a sequence set forth in SEQ ID NO: 170;

(xliii) a $V_H$ comprising a sequence set forth in SEQ ID NO: 42 and a $V_L$ comprising a sequence set forth in SEQ ID NO: 171;

(xliv) a $V_H$ comprising a sequence set forth in SEQ ID NO: 42 and a $V_L$ comprising a sequence set forth in SEQ ID NO: 172;

(xlv) a $V_H$ comprising a sequence set forth in SEQ ID NO: 175 and a $V_L$ comprising a sequence set forth in SEQ ID NO: 188;

(xlvi) a $V_H$ comprising a sequence set forth in SEQ ID NO: 176 and a $V_L$ comprising a sequence set forth in SEQ ID NO: 189;

(xlvii) a $V_H$ comprising a sequence set forth in SEQ ID NO: 177 and a $V_L$ comprising a sequence set forth in SEQ ID NO: 190;

(xlviii) a $V_H$ comprising a sequence set forth in SEQ ID NO: 178 and a $V_L$ comprising a sequence set forth in SEQ ID NO: 191;

(xlix) a $V_H$ comprising a sequence set forth in SEQ ID NO: 179 and a $V_L$ comprising a sequence set forth in SEQ ID NO: 192;

(l) a $V_H$ comprising a sequence set forth in SEQ ID NO: 180 and a $V_L$ comprising a sequence set forth in SEQ ID NO: 193;

(li) a $V_H$ comprising a sequence set forth in SEQ ID NO: 181 and a $V_L$ comprising a sequence set forth in SEQ ID NO: 194;

(lii) a $V_H$ comprising a sequence set forth in SEQ ID NO: 182 and a $V_L$ comprising a sequence set forth in SEQ ID NO: 195;

(liii) a $V_H$ comprising a sequence set forth in SEQ ID NO: 183 and a $V_L$ comprising a sequence set forth in SEQ ID NO: 196;

(liv) a $V_H$ comprising a sequence set forth in SEQ ID NO: 184 and a $V_L$ comprising a sequence set forth in SEQ ID NO: 197;

(lv) a $V_H$ comprising a sequence set forth in SEQ ID NO: 185 and a $V_L$ comprising a sequence set forth in SEQ ID NO: 198;

(lvi) a $V_H$ comprising a sequence set forth in SEQ ID NO: 186 and a $V_L$ comprising a sequence set forth in SEQ ID NO: 199; or (lvii) a $V_H$ comprising a sequence set forth in SEQ ID NO: 187 and a $V_L$ comprising a sequence set forth in SEQ ID NO: 200.

In a particular example, there is provided an isolated or recombinant TL1a-binding protein comprising an antigen binding domain of an antibody comprising a $V_H$ and a $V_L$, wherein the $V_H$ and $V_L$ respectively comprise sequences selected from the group consisting of (i) a $V_H$ comprising a sequence set forth in SEQ ID NO: 42 and a $V_L$ comprising a sequence set forth in SEQ ID NO: 46;

(ii) a $V_H$ encoded by a nucleic acid comprising a sequence at least about 95% identical to the sequence set forth in SEQ ID NO: 106 or a nucleic acid that hybridizes thereto under moderate to high stringency conditions and a $V_L$ encoded by a nucleic acid comprising a sequence at least about 95% identical to the sequence set forth in SEQ ID NO: 107 or a nucleic acid that hybridizes thereto under moderate to high stringency conditions;

(iii) a $V_H$ comprising a sequence set forth in SEQ ID NO: 175 and a $V_L$ comprising a sequence set forth in SEQ ID NO: 188;

(iv) a $V_H$ encoded by a nucleic acid comprising a sequence at least about 95% identical to the sequence set forth in SEQ ID NO: 222 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(v) a $V_H$ comprising a sequence set forth in SEQ ID NO: 176 and a $V_L$ comprising a sequence set forth in SEQ ID NO: 189;

(vi) a $V_H$ encoded by a nucleic acid comprising a sequence at least about 95% identical to the sequence set forth in SEQ ID NO: 223 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(vii) a $V_H$ comprising a sequence set forth in SEQ ID NO: 177 and a $V_L$ comprising a sequence set forth in SEQ ID NO: 190;

(viii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 229 or a nucleic acid that hybridizes thereto under moderate to high stringency conditions;

(ix) a $V_H$ comprising a sequence set forth in SEQ ID NO: 178 and a $V_L$ comprising a sequence set forth in SEQ ID NO: 191;

(x) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xi) a $V_H$ comprising a sequence set forth in SEQ ID NO: 179 and a $V_L$ comprising a sequence set forth in SEQ ID NO: 192;

(xii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 231 or a nucleic acid that hybridizes thereto under moderate to high stringency conditions;

(xiii) a $V_H$ comprising a sequence set forth in SEQ ID NO: 180 and a $V_L$ comprising a sequence set forth in SEQ ID NO: 193;

(xiv) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(xv) a $V_H$ comprising a sequence set forth in SEQ ID NO: 181 and a $V_L$ comprising a sequence set forth in SEQ ID NO: 194;

(xvi) a $V_H$ encoded by a nucleic acid comprising a sequence at least about 95% identical to the sequence set forth in SEQ ID NO: 225 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xvii) a $V_H$ comprising a sequence set forth in SEQ ID NO: 183 and a $V_L$ comprising a sequence set forth in SEQ ID NO: 196;

(xviii) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xix) a $V_H$ comprising a sequence set forth in SEQ ID NO: 185 and a $V_L$ comprising a sequence set forth in SEQ ID NO: 198;

(xx) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxi) a $V_H$ comprising a sequence set forth in SEQ ID NO: 186 and a $V_L$ comprising a sequence set forth in SEQ ID NO: 199;

(xxii) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxiii) a $V_H$ comprising a sequence set forth in SEQ ID NO: 187 and a $V_L$ comprising a sequence set forth in SEQ ID NO: 200; and (xxiv) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 233 or a nucleic acid that hybridizes thereto under moderate to high stringency conditions.

The disclosure additionally or alternatively provides an isolated or recombinant TL1a-binding protein comprising an antigen binding domain of an antibody comprising a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:

(i) the $V_H$ comprises an alanine at position 16 of SEQ ID NO: 42;

(ii) the $V_H$ comprises an alanine at position 100 of SEQ ID NO: 42 and the $V_L$ comprises a threonine at position 76 of SEQ ID NO: 46;

(iii) the $V_H$ comprises a serine at position 100 of SEQ ID NO: 42 and the $V_L$ comprises a threonine at position 76 of SEQ ID NO: 46;

(iv) the $V_H$ comprises a histidine at position 100 of SEQ ID NO: 42 and the $V_L$ comprises a threonine at position 76 of SEQ ID NO: 46;

(v) the $V_H$ comprises a leucine at position 100 of SEQ ID NO: 42 and the $V_L$ comprises a threonine at position 76 of SEQ ID NO: 46;

(vi) the $V_H$ comprises an aspartic acid at position 100 of SEQ ID NO: 42 and the $V_L$ comprises a threonine at position 76 of SEQ ID NO: 46;

(vii) the $V_H$ comprises a tyrosine at position 100 of SEQ ID NO: 42 and the $V_L$ comprises a threonine at position 76 of SEQ ID NO: 46;

(viii) the $V_H$ comprises a proline at position 100 of SEQ ID NO: 42 and the $V_L$ comprises a threonine at position 76 of SEQ ID NO: 46;

(ix) the $V_H$ comprises a glutamine at position 100 of SEQ ID NO: 42 and the $V_L$ comprises a threonine at position 76 of SEQ ID NO: 46;

(x) the $V_H$ comprises a lysine at position 100 of SEQ ID NO: 42 and the $V_L$ comprises a threonine at position 76 of SEQ ID NO: 46;

(xi) the $V_H$ comprises an alanine at position 101 of SEQ ID NO: 42 and the $V_L$ comprises a threonine at position 76 of SEQ ID NO: 46;

(xii) the $V_H$ comprises a serine at position 101 of SEQ ID NO: 42 and the $V_L$ comprises a threonine at position 76 of SEQ ID NO: 46;

(xiii) the $V_H$ comprises a histidine at position 101 of SEQ ID NO: 42 and the $V_L$ comprises a threonine at position 76 of SEQ ID NO: 46;

(xiv) the $V_H$ comprises a leucine at position 101 of SEQ ID NO: 42 and the $V_L$ comprises a threonine at position 76 of SEQ ID NO: 46;

(xv) the $V_H$ comprises an aspartic acid at position 101 of SEQ ID NO: 42 and the $V_L$ comprises a threonine at position 76 of SEQ ID NO: 46;

(xvi) the $V_H$ comprises a tyrosine at position 101 of SEQ ID NO: 42 and the $V_L$ comprises a threonine at position 76 of SEQ ID NO: 46;

(xvii) the $V_H$ comprises a glutamine at position 101 of SEQ ID NO: 42 and the $V_L$ comprises a threonine at position 76 of SEQ ID NO: 46;

(xviii) the $V_H$ comprises a lysine at position 101 of SEQ ID NO: 42 and the $V_L$ comprises a threonine at position 76 of SEQ ID NO: 46;

(xix) the $V_H$ comprises an alanine at position 102 of SEQ ID NO: 42 and the $V_L$ comprises a threonine at position 76 of SEQ ID NO: 46;

(xx) the $V_H$ comprises a serine at position 102 of SEQ ID NO: 42 and the $V_L$ comprises a threonine at position 76 of SEQ ID NO: 46;

(xxi) the $V_H$ comprises a histidine at position 102 of SEQ ID NO: 42 and the $V_L$ comprises a threonine at position 76 of SEQ ID NO: 46;

(xxii) the $V_H$ comprises a leucine at position 102 of SEQ ID NO: 42 and the $V_L$ comprises a threonine at position 76 of SEQ ID NO: 46;

(xxiii) the $V_H$ comprises a tyrosine at position 102 of SEQ ID NO: 42 and the $V_L$ comprises a threonine at position 76 of SEQ ID NO: 46;

(xxiv) the $V_H$ comprises a proline at position 102 of SEQ ID NO: 42 and the $V_L$ comprises a threonine at position 76 of SEQ ID NO: 46;

(xxv) the $V_H$ comprises a glutamine at position 102 of SEQ ID NO: 42 and the $V_L$ comprises a threonine at position 76 of SEQ ID NO: 46;

(xxvi) the $V_H$ comprises a lysine at position 102 of SEQ ID NO: 42 and the $V_L$ comprises a threonine at position 76 of SEQ ID NO: 46;

(xxvii) the $V_H$ comprises an alanine at position 103 of SEQ ID NO: 42 and the $V_L$ comprises a threonine at position 76 of SEQ ID NO: 46;

(xxviii) the $V_H$ comprises a serine at position 103 of SEQ ID NO: 42 and the $V_L$ comprises a threonine at position 76 of SEQ ID NO: 46;

(xxix) the $V_H$ comprises a histidine at position 103 of SEQ ID NO: 42 and the $V_L$ comprises a threonine at position 76 of SEQ ID NO: 46;

(xxx) the $V_H$ comprises a leucine at position 103 of SEQ ID NO: 42 and the $V_L$ comprises a threonine at position 76 of SEQ ID NO: 46;

(xxxi) the $V_H$ comprises an aspartic acid at position 103 of SEQ ID NO: 42 and the $V_L$ comprises a threonine at position 76 of SEQ ID NO: 46;

(xxxii) the $V_H$ comprises a tyrosine at position 103 of SEQ ID NO: 42 and the $V_L$ comprises a threonine at position 76 of SEQ ID NO: 46;

(xxxiii) the $V_H$ comprises a proline at position 103 of SEQ ID NO: 42 and the $V_L$ comprises a threonine at position 76 of SEQ ID NO: 46;

(xxxiv) the $V_H$ comprises a glutamine at position 103 of SEQ ID NO: 42 and the $V_L$ comprises a threonine at position 76 of SEQ ID NO: 46;

(xxxv) the $V_H$ comprises a lysine at position 103 of SEQ ID NO: 42 and the $V_L$ comprises a threonine at position 76 of SEQ ID NO: 46;

(xxxvi) the $V_H$ comprises a serine at position 104 of SEQ ID NO: 42 and the $V_L$ comprises a threonine at position 76 of SEQ ID NO: 46;

(xxxvii) the $V_H$ comprises a histidine at position 104 of SEQ ID NO: 42 and the $V_L$ comprises a threonine at position 76 of SEQ ID NO: 46;

(xxxviii) the $V_H$ comprises a leucine at position 104 of SEQ ID NO: 42 and the $V_L$ comprises a threonine at position 76 of SEQ ID NO: 46;

(xxxix) the $V_H$ comprises an aspartic acid at position 104 of SEQ ID NO: 42 and the $V_L$ comprises a threonine at position 76 of SEQ ID NO: 46;

(xl) the $V_H$ comprises a tyrosine at position 104 of SEQ ID NO: 42 and the $V_L$ comprises a threonine at position 76 of SEQ ID NO: 46;

(xli) the $V_H$ comprises a proline at position 104 of SEQ ID NO: 42 and the $V_L$ comprises a threonine at position 76 of SEQ ID NO: 46;

(xlii) the $V_H$ comprises a glutamine at position 104 of SEQ ID NO: 42 and the $V_L$ comprises a threonine at position 76 of SEQ ID NO: 46;

(xliii) the $V_H$ comprises a lysine at position 104 of SEQ ID NO: 42 and the $V_L$ comprises a threonine at position 76 of SEQ ID NO: 46;

(xliv) the $V_H$ comprises an alanine at position 105 of SEQ ID NO: 42 and the $V_L$ comprises a threonine at position 76 of SEQ ID NO: 46;

(xlv) the $V_H$ comprises a histidine at position 105 of SEQ ID NO: 42 and the $V_L$ comprises a threonine at position 76 of SEQ ID NO: 46;

(xlvi) the $V_H$ comprises a leucine at position 105 of SEQ ID NO: 42 and the $V_L$ comprises a threonine at position 76 of SEQ ID NO: 46;

(xlvii) the $V_H$ comprises an aspartic acid at position 105 of SEQ ID NO: 42 and the $V_L$ comprises a threonine at position 76 of SEQ ID NO: 46;

(xlviii) the $V_H$ comprises a tyrosine at position 105 of SEQ ID NO: 42 and the $V_L$ comprises a threonine at position 76 of SEQ ID NO: 46;

(xlix) the $V_H$ comprises a proline at position 105 of SEQ ID NO: 42 and the $V_L$ comprises a threonine at position 76 of SEQ ID NO: 46;

(l) the $V_H$ comprises a glutamine at position 105 of SEQ ID NO: 42 and the $V_L$ comprises a threonine at position 76 of SEQ ID NO: 46;

(li) the $V_H$ comprises a lysine at position 105 of SEQ ID NO: 42 and the $V_L$ comprises a threonine at position 76 of SEQ ID NO: 46;

(lii) the $V_H$ comprises an alanine at position 107 of SEQ ID NO: 42 and the $V_L$ comprises a threonine at position 76 of SEQ ID NO: 46;

(liii) the $V_H$ comprises a serine at position 107 of SEQ ID NO: 42 and the $V_L$ comprises a threonine at position 76 of SEQ ID NO: 46;

(liv) the $V_H$ comprises a histidine at position 107 of SEQ ID NO: 42 and the $V_L$ comprises a threonine at position 76 of SEQ ID NO: 46;

(lv) the $V_H$ comprises a leucine at position 107 of SEQ ID NO: 42 and the $V_L$ comprises a threonine at position 76 of SEQ ID NO: 46;

(lvi) the $V_H$ comprises an aspartic acid at position 107 of SEQ ID NO: 42 and the $V_L$ comprises a threonine at position 76 of SEQ ID NO: 46;

(lvii) the $V_H$ comprises a tyrosine at position 107 of SEQ ID NO: 42 and the $V_L$ comprises a threonine at position 76 of SEQ ID NO: 46;

(lviii) the $V_H$ comprises a proline at position 107 of SEQ ID NO: 42 and the $V_L$ comprises a threonine at position 76 of SEQ ID NO: 46;

(lix) the $V_H$ comprises a glutamine at position 107 of SEQ ID NO: 42 and the $V_L$ comprises a threonine at position 76 of SEQ ID NO: 46;

(lx) the $V_H$ comprises a lysine at position 107 of SEQ ID NO: 42 and the $V_L$ comprises a threonine at position 76 of SEQ ID NO: 46;

(lxi) the $V_H$ comprises a threonine at position 41 of SEQ ID NO: 42 and the $V_L$ comprises an alanine at position 23 of SEQ ID NO: 46;

(lxii) the $V_H$ comprises a threonine at position 41 of SEQ ID NO: 42 and the $V_L$ comprises an aspartic acid at position 28 of SEQ ID NO: 46;

(lxiii) the $V_H$ comprises a threonine at position 41 of SEQ ID NO: 42 and the $V_L$ comprises a tyrosine at position 33 of SEQ ID NO: 46;

(lxiv) the $V_H$ comprises a threonine at position 41 of SEQ ID NO: 42 and the $V_L$ comprises an aspartic acid at position 34 of SEQ ID NO: 46;

(lxv) the $V_H$ comprises a threonine at position 41 of SEQ ID NO: 42 and the $V_L$ comprises an asparagine at position 53 of SEQ ID NO: 46;

(lxvi) the $V_H$ comprises a threonine at position 41 of SEQ ID NO: 42 and the $V_L$ comprises a serine at position 54 of SEQ ID NO: 46;

(lxvii) the $V_H$ comprises a threonine at position 41 of SEQ ID NO: 42 and the $V_L$ comprises an alanine at position 82 of SEQ ID NO: 46;

(lxviii) the $V_H$ comprises a threonine at position 41 of SEQ ID NO: 42 and the $V_L$ comprises a serine at position 95 of SEQ ID NO: 46;

(lxix) the $V_H$ comprises a threonine at position 41 of SEQ ID NO: 42 and the $V_L$ comprises a serine at position 96 of SEQ ID NO: 46;

(lxx) the $V_H$ comprises a threonine at position 41 of SEQ ID NO: 42 and the $V_L$ comprises a threonine at position 76 of SEQ ID NO: 46;

(lxxi) the $V_H$ comprises a serine at position 47 of SEQ ID NO: 42 and the $V_L$ comprises a threonine at position 23 of SEQ ID NO: 46;

(lxxii) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 76 of SEQ ID NO: 46;

(lxxiii) the $V_H$ comprises a proline at position 41, a leucine at position 51 and a glutamic acid at position 102 each relative to SEQ ID NO: 42 and the $V_L$ comprises a serine at position 24 and a threonine at position 76 each relative to SEQ ID NO: 46;

(lxxiv) the $V_H$ comprises a proline at position 41, a leucine at position 51 and a glutamic acid at position 102 each relative to SEQ ID NO: 42 and the $V_L$ comprises a threonine at position 23, a serine at position 24 and a threonine at position 76 each relative to SEQ ID NO: 46;

(lxxv) the $V_H$ comprises a proline at position 41, a leucine at position 51 and a glutamic acid at position 102 each relative to SEQ ID NO: 42 and the $V_L$ comprises a threonine at position 23 and a threonine at position 76 each relative to SEQ ID NO: 46;

(lxxvi) the $V_H$ comprises a proline at position 41, a leucine at position 51 and a glutamic acid at position 102 each relative to SEQ ID NO: 42 and the $V_L$ comprises a threonine at position 76 of SEQ ID NO: 46;

(lxxvii) the $V_H$ comprises a proline at position 41, a leucine at position 51, a glutamic acid at position 102 and an alanine at position 105 each relative to SEQ ID NO: 42 and the $V_L$ comprises a threonine at position 23, a serine at position 24 and a threonine at position 76 each relative to SEQ ID NO: 46;

(lxxviii) the $V_H$ comprises a proline at position 41, a leucine at position 51, a glutamic acid at position 102 and an alanine at position 105 each relative to SEQ ID NO: 42 and the $V_L$ comprises a threonine at position 76 of SEQ ID NO: 46;

(lxxix) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 23, a serine at position 24 and a threonine at position 76 each relative to SEQ ID NO: 46;

(lxxx) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 23, a serine at position 24, a threonine at position 76 and a glutamic acid at position 51 each relative to SEQ ID NO: 46;

(lxxxi) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glutamic acid at position 51 each relative to SEQ ID NO: 46; and (lxxxii) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glycine at position 51 each relative to SEQ ID NO: 46.

In one example, the TL1a-binding protein comprises an antigen binding domain of an antibody comprising any one or more of the following:

(i) a $V_H$ comprising a sequence set forth in SEQ ID NO: 26 and a $V_L$ comprising a sequence set forth in SEQ ID NO: 30;

(ii) a $V_H$ comprising a sequence set forth in SEQ ID NO: 34 and a $V_L$ comprising a sequence set forth in SEQ ID NO:38; and (iii) a $V_H$ comprising a sequence set forth in SEQ ID NO: 42 and a $V_L$ comprising a sequence set forth in SEQ ID NO: 46.

In one particular example, there is provided an isolated or recombinant TL1a-binding protein comprising an antigen binding domain of an antibody comprising a $V_H$ and a $V_L$, wherein the $V_H$ and $V_L$ respectively comprise sequences selected from the group consisting of (i) a $V_H$ comprising a sequence set forth in SEQ ID NO: 42 and a $V_L$ comprising a sequence set forth in SEQ ID NO: 46;
(ii) a $V_H$ comprising a sequence set forth in SEQ ID NO: 175 and a $V_L$ comprising a sequence set forth in SEQ ID NO: 188;
(iii) a $V_H$ comprising a sequence set forth in SEQ ID NO: 176 and a $V_L$ comprising a sequence set forth in SEQ ID NO: 189;
(iv) a $V_H$ comprising a sequence set forth in SEQ ID NO: 177 and a $V_L$ comprising a sequence set forth in SEQ ID NO: 190;
(v) a $V_H$ comprising a sequence set forth in SEQ ID NO: 178 and a $V_L$ comprising a sequence set forth in SEQ ID NO: 191;
(vi) a $V_H$ comprising a sequence set forth in SEQ ID NO: 179 and a $V_L$ comprising a sequence set forth in SEQ ID NO: 192;
(vii) a $V_H$ comprising a sequence set forth in SEQ ID NO: 180 and a $V_L$ comprising a sequence set forth in SEQ ID NO: 193;
(viii) a $V_H$ comprising a sequence set forth in SEQ ID NO: 181 and a $V_L$ comprising a sequence set forth in SEQ ID NO: 194;
(ix) a $V_H$ comprising a sequence set forth in SEQ ID NO: 183 and a $V_L$ comprising a sequence set forth in SEQ ID NO: 196;
(x) a $V_H$ comprising a sequence set forth in SEQ ID NO: 185 and a $V_L$ comprising a sequence set forth in SEQ ID NO: 198;
(xi) a $V_H$ comprising a sequence set forth in SEQ ID NO: 186 and a $V_L$ comprising a sequence set forth in SEQ ID NO: 199; and
(xii) a $V_H$ comprising a sequence set forth in SEQ ID NO: 187 and a $V_L$ comprising a sequence set forth in SEQ ID NO: 200.

In one example, a TL1a-binding protein of the disclosure comprises an antigen binding domain comprising a CDR3 of a variable region of an antibody recited above. For example, the CDR3 is defined according to the Kabat numbering system and comprises a sequence set forth in any one of SEQ ID NOs: 5, 9, 13, 17, 21, 25, 29, 33, 37, 41, 45, 49, 53, 57, 61, 65, 69, 73, 77, 81, 85, 89, 93 or a sequence labeled as "CDR3" and shown in bold text in FIG. 1A to 1H or in FIG. 9B or 9C or a sequence comprising amino acids 99 to 108 of any one of SEQ ID NOs: 175 to 187 or amino acids 91 to 100 of any one of SEQ ID NOs: 188 to 200 or 234.

For example, the CDR3 is defined according to the Kabat numbering system and comprises a sequence set forth in SEQ ID NO: 45 or 49 or a sequence comprising amino acids 99 to 108 of any one of SEQ ID NOs: 175 to 181, 183 or 185 to 187 or amino acids 91 to 100 of any one of SEQ ID NOs: 188 to 194, 196 or 198 to 200.

In another example, the CDR3 (e.g., a HCDR3) is defined according to the enhanced Chothia numbering system and comprises a sequence labeled as "CDR3" and shown in underlined text in any one of FIG. 1A, 1C, 1D or 1E or 9B.

In one example, the CDR3 comprises a sequence $EVPX_1TAX_2FEY$ (SEQ ID NO: 143), wherein $X_1$ is aspartic acid or glutamic acid and $X_2$ is serine or alanine.

In one example, the CDR3 comprises a sequence $EXIPX_2X_3AX_4FX_5Y$ (SEQ ID NO: 235), wherein:

$X_1$ is an amino acid selected from the group consisting of valine, alanine, serine, histidine, aspartic acid, leucine, tyrosine, proline, glutamine or lysine;

$X_2$ is an amino acid selected from the group consisting of alanine, serine, histidine, lysine, glutamic acid or aspartic acid;

$X_3$ is an amino acid selected from the group consisting of alanine, serine, aspartic acid, tyrosine or threonine;

$X_4$ is an amino acid selected from the group consisting of serine, alanine, histidine, leucine, aspartic acid or tyrosine; and $X_5$ is an amino acid selected from the group consisting of alanine, serine, histidine, leucine, aspartic acid, proline, glutamine, glutamic acid or lysine.

In one example, the CDR3 (e.g., a LCDR3) comprises a sequence set forth in SEQ ID NO: 141 (or sequence labeled as CDR3 in bold text of the sequence labeled "Consensus" in FIG. 1F or 9C).

For example, the antigen binding domain comprises three CDRs of a variable region of the antibody.

In some examples of the disclosure, the antigen binding domain is an antibody variable region comprising three CDRs of a variable region comprising an amino acid sequence set forth in any one of SEQ ID NOs: 2, 6, 10, 14, 18, 22, 26, 30, 34, 38, 42, 46, 50, 54, 58, 62, 66, 70, 74, 78, 82, 86, 90, 94, 95, 137, 138, 152 to 200 or 234.

In some examples, the antigen binding domain is an antibody variable region comprising three CDRs of a variable region comprising:

(a) a $V_H$ comprising a sequence set forth in SEQ ID NO: 42 and comprising one or more of the following substitutions or groups of substitutions:
(i) an alanine at position 16 of SEQ ID NO: 42;
(ii) an alanine at position 100 of SEQ ID NO: 42;
(iii) a serine at position 100 of SEQ ID NO: 42;
(iv) a histidine at position 100 of SEQ ID NO: 42;
(v) a leucine at position 100 of SEQ ID NO: 42;
(vi) an aspartic acid at position 100 of SEQ ID NO: 42;
(vii) a tyrosine at position 100 of SEQ ID NO: 42;
(viii) a proline at position 100 of SEQ ID NO: 42;
(ix) a glutamine at position 100 of SEQ ID NO: 42;
(x) a lysine at position 100 of SEQ ID NO: 42;
(xi) an alanine at position 101 of SEQ ID NO: 42;
(xii) a serine at position 101 of SEQ ID NO: 42;
(xiii) a histidine at position 101 of SEQ ID NO: 42;
(xiv) a leucine at position 101 of SEQ ID NO: 42;
(xv) an aspartic acid at position 101 of SEQ ID NO: 42;
(xvi) a tyrosine at position 101 of SEQ ID NO: 42;
(xvii) a glutamine at position 101 of SEQ ID NO: 42;
(xviii) a lysine at position 101 of SEQ ID NO: 42;
(xix) an alanine at position 102 of SEQ ID NO: 42;
(xx) a serine at position 102 of SEQ ID NO: 42;
(xxi) a histidine at position 102 of SEQ ID NO: 42;
(xxii) a leucine at position 102 of SEQ ID NO: 42;
(xxiii) a tyrosine at position 102 of SEQ ID NO: 42;
(xxiv) a proline at position 102 of SEQ ID NO: 42;
(xxv) a glutamine at position 102 of SEQ ID NO: 42;
(xxvi) a lysine at position 102 of SEQ ID NO: 42;
(xxvii) an alanine at position 103 of SEQ ID NO: 42;
(xxviii) a serine at position 103 of SEQ ID NO: 42;
(xxix) a histidine at position 103 of SEQ ID NO: 42;
(xxx) a leucine at position 103 of SEQ ID NO: 42;
(xxxi) an aspartic acid at position 103 of SEQ ID NO: 42;
(xxxii) a tyrosine at position 103 of SEQ ID NO: 42;
(xxxiii) a proline at position 103 of SEQ ID NO: 42;
(xxxiv) a glutamine at position 103 of SEQ ID NO: 42;
(xxxv) a lysine at position 103 of SEQ ID NO: 42;
(xxxvi) a serine at position 104 of SEQ ID NO: 42;
(xxxvii) a histidine at position 104 of SEQ ID NO: 42;
(xxxviii) a leucine at position 104 of SEQ ID NO: 42;
(xxxix) an aspartic acid at position 104 of SEQ ID NO: 42;
(xl) a tyrosine at position 104 of SEQ ID NO: 42;
(xli) a proline at position 104 of SEQ ID NO: 42;

(xlii) a glutamine at position 104 of SEQ ID NO: 42;
(xliii) a lysine at position 104 of SEQ ID NO: 42;
(xliv) an alanine at position 105 of SEQ ID NO: 42;
(xlv) a histidine at position 105 of SEQ ID NO: 42;
(xlvi) a leucine at position 105 of SEQ ID NO: 42;
(xlvii) an aspartic acid at position 105 of SEQ ID NO: 42;
(xlviii) a tyrosine at position 105 of SEQ ID NO: 42;
(xlix) a proline at position 105 of SEQ ID NO: 42;
(l) a glutamine at position 105 of SEQ ID NO: 42;
(li) a lysine at position 105 of SEQ ID NO: 42;
(lii) an alanine at position 107 of SEQ ID NO: 42;
(liii) a serine at position 107 of SEQ ID NO: 42;
(liv) a histidine at position 107 of SEQ ID NO: 42;
(lv) a leucine at position 107 of SEQ ID NO: 42;
(lvi) an aspartic acid at position 107 of SEQ ID NO: 42;
(lvii) a tyrosine at position 107 of SEQ ID NO: 42;
(lviii) a proline at position 107 of SEQ ID NO: 42;
(lix) a glutamine at position 107 of SEQ ID NO: 42;
(lx) a lysine at position 107 of SEQ ID NO: 42;
(lxi) a threonine at position 41 of SEQ ID NO: 42;
(lxii) a serine at position 47 of SEQ ID NO: 42;
(lxiii) a proline at position 41, an alanine at position 72, an aspartic acid at position 73 and an arginine at position 74 and a threonine at position 76 each relative to SEQ ID NO: 42;
(lxiv) a proline at position 41, a leucine at position 51 and a glutamic acid at position 102 each relative to SEQ ID NO: 42;
(lxv) a proline at position 41, a leucine at position 51, a glutamic acid at position 102 and an alanine at position 105 each relative to SEQ ID NO: 42;
(lxvi) a proline at position 41, a leucine at position 51, an alanine at position 72, an aspartic acid at position 73, an arginine at position 74, a threonine at position 76, a glutamic acid at position 102 and an alanine at position 105; or
(b) a $V_L$ comprising a sequence set forth in SEQ ID NO: 46 and comprising one or more of the following substitutions or groups of substitutions:
(i) a threonine at position 76 of SEQ ID NO: 46;
(ii) a threonine at position 23 of SEQ ID NO: 46;
(iii) an asparagine at position 28 of SEQ ID NO: 46;
(iv) a tyrosine at position 33 of SEQ ID NO: 46;
(v) an aspartic acid at position 34 of SEQ ID NO: 46;
(vi) an asparagine at position 53 of SEQ ID NO: 46;
(vii) a serine at position 54 of SEQ ID NO: 46;
(viii) an alanine at position 82 of SEQ ID NO: 46;
(ix) a serine at position 95 of SEQ ID NO: 46;
(x) a serine at position 96 of SEQ ID NO: 46;
(xi) a threonine at position 23, a serine at position 24 and a threonine at position 76 each relative to SEQ ID NO: 46;
(xii) a threonine at position 23 and a threonine at position 76 each relative to SEQ ID NO: 46;
(xiii) a threonine at position 23, a serine at position 24, a threonine at position 76 and a glutamic acid at position 51 each relative to SEQ ID NO: 46; or
(xiv) a threonine at position 23, a serine at position 24, a threonine at position 76 and a glycine at position 51 each relative to SEQ ID NO: 46.

For example, the antigen binding domain is a $V_H$ comprising three CDRs of an amino acid sequence set forth in any one of SEQ ID NOs: 2, 10, 18, 26, 34, 42, 50, 58, 66, 70, 74, 78, 86, 90, 94, 137, 152, 154 to 162, 173, 175 to 187 or 234.

In one example, the CDRs are defined according to the Kabat numbering system.

For example, the TL1a-binding protein comprises a $V_H$ including CDRs as follows:

(i) a CDR1 comprising a sequence set forth in SEQ ID NO: 3, a CDR2 comprising a sequence set forth in SEQ ID NO: 4 (wherein any one or more of the five C-terminal amino acids of the CDR2 amino acid sequence are substituted with any other naturally-occurring amino acid) and a CDR3 comprising a sequence set forth in SEQ ID NO: 5 (or sequences labeled as CDRs 1, 2 and 3 in bold text of antibody C336 in FIG. 1A);

(ii) a CDR1 comprising a sequence set forth in SEQ ID NO: 11, a CDR2 comprising a sequence set forth in SEQ ID NO: 12 (wherein any one or more of the five C-terminal amino acids of the CDR2 amino acid sequence are substituted with any other naturally-occurring amino acid) and a CDR3 comprising a sequence set forth in SEQ ID NO: 13 (or sequences labeled as CDRs 1, 2 and 3 in bold text of antibody C334 in FIG. 1A);

(iii) a CDR1 comprising a sequence set forth in SEQ ID NO: 19, a CDR2 comprising a sequence set forth in SEQ ID NO: 20 (wherein any one or more of the five C-terminal amino acids of the CDR2 amino acid sequence are substituted with any other naturally-occurring amino acid) and a CDR3 comprising a sequence set forth in SEQ ID NO: 21 (or sequences labeled as CDRs 1, 2 and 3 in bold text of antibody C333 in FIG. 1A);

(iv) a CDR1 comprising a sequence set forth in SEQ ID NO: 27, a CDR2 comprising a sequence set forth in SEQ ID NO: 28 (wherein any one or more of the five C-terminal amino acids of the CDR2 amino acid sequence are substituted with any other naturally-occurring amino acid) and a CDR3 comprising a sequence set forth in SEQ ID NO: 29 (or sequences labeled as CDRs 1, 2 and 3 in bold text of antibody C323 in FIG. 1A);

(v) a CDR1 comprising a sequence set forth in SEQ ID NO: 35, a CDR2 comprising a sequence set forth in SEQ ID NO: 36 (wherein any one or more of the five C-terminal amino acids of the CDR2 amino acid sequence are substituted with any other naturally-occurring amino acid) and a CDR3 comprising a sequence set forth in SEQ ID NO: 37 (or sequences labeled as CDRs 1, 2 and 3 in bold text of antibody C321 in FIG. 1A);

(vi) a CDR1 comprising a sequence set forth in SEQ ID NO: 43, a CDR2 comprising a sequence set forth in SEQ ID NO: 44 (wherein any one or more of the five C-terminal amino acids of the CDR2 amino acid sequence are substituted with any other naturally-occurring amino acid) and a CDR3 comprising a sequence set forth in SEQ ID NO: 45 (or sequences labeled as CDRs 1, 2 and 3 in bold text of antibody C320 in FIG. 1A);

(vii) a CDR1 comprising a sequence set forth in SEQ ID NO: 51, a CDR2 comprising a sequence set forth in SEQ ID NO: 52 (wherein any one or more of the five C-terminal amino acids of the CDR2 amino acid sequence are substituted with any other naturally-occurring amino acid) and a CDR3 comprising a sequence set forth in SEQ ID NO: 53 (or sequences labeled as CDRs 1, 2 and 3 in bold text of antibody C319 in FIG. 1A);

(viii) a CDR1 comprising a sequence set forth in SEQ ID NO: 67, a CDR2 comprising a sequence set forth in SEQ ID NO: 68 (wherein any one or more of the five C-terminal amino acids of the CDR2 amino acid sequence are substituted with any other naturally-occurring amino acid) and a CDR3 comprising a sequence set forth in SEQ ID NO: 69 (or sequences labeled as CDRs 1, 2 and 3 in bold text of antibody C320-90 in FIG. 1C);

(ix) a CDR1 comprising a sequence set forth in SEQ ID NO: 71, a CDR2 comprising a sequence set forth in SEQ ID NO: 72 (wherein any one or more of the five C-terminal amino acids of the CDR2 amino acid sequence are substituted with any other naturally-occurring amino acid) and a CDR3 comprising a sequence set forth in SEQ ID NO: 73 (or sequences labeled as CDRs 1, 2 and 3 in bold text of antibody C320-103 in FIG. 1C);

(x) a CDR1 comprising a sequence set forth in SEQ ID NO: 75, a CDR2 comprising a sequence set forth in SEQ ID NO: 76 (wherein any one or more of the five C-terminal amino acids of the CDR2 amino acid sequence are substituted with any other naturally-occurring amino acid) and a CDR3 comprising a sequence set forth in SEQ ID NO: 77 (or sequences labeled as CDRs 1, 2 and 3 in bold text of antibody C320-114 in FIG. 1C);

(xi) a CDR1 comprising a sequence set forth in SEQ ID NO: 79, a CDR2 comprising a sequence set forth in SEQ ID NO: 80 (wherein any one or more of the five C-terminal amino acids of the CDR2 amino acid sequence are substituted with any other naturally-occurring amino acid) and a CDR3 comprising a sequence set forth in SEQ ID NO: 81 (or sequences labeled as CDRs 1, 2 and 3 in bold text of antibody C320-115 in FIG. 1C);

(xii) a CDR1 comprising a sequence set forth in SEQ ID NO: 87, a CDR2 comprising a sequence set forth in SEQ ID NO: 88 (wherein any one or more of the five C-terminal amino acids of the CDR2 amino acid sequence are substituted with any other naturally-occurring amino acid) and a CDR3 comprising a sequence set forth in SEQ ID NO: 89 (or sequences labeled as CDRs 1, 2 and 3 in bold text of antibody C320-129 in FIG. 1C);

(xiii) a CDR1 comprising a sequence set forth in SEQ ID NO: 91, a CDR2 comprising a sequence set forth in SEQ ID NO: 92 (wherein any one or more of the five C-terminal amino acids of the CDR2 amino acid sequence are substituted with any other naturally-occurring amino acid) and a CDR3 comprising a sequence set forth in SEQ ID NO: 93 (or sequences labeled as CDRs 1, 2 and 3 in bold text of antibody C320-130 in FIG. 1C);

(xiv) a CDR1 comprising a sequence set forth in amino acids 31 to 35 of any one of SEQ ID NOs: 175 to 187, a CDR2 comprising amino acids 50 to 66 of any one of SEQ ID NOs: 175 to 187 (wherein any one or more of the five C-terminal amino acids of the CDR2 amino acid sequence are substituted with any other naturally-occurring amino acid) and amino acids 99 to 108 of any one of SEQ ID NOs: 175 to 187; and (xv) a CDR1 comprising a sequence set forth in amino acids 26 to 35 of any one of SEQ ID NOs: 175 to 187, a CDR2 comprising amino acids 50 to 66 of any one of SEQ ID NOs: 175 to 187 (wherein any one or more of the five C-terminal amino acids of the CDR2 amino acid sequence are substituted with any other naturally-occurring amino acid) and amino acids 99 to 108 of any one of SEQ ID NOs: 175 to 187.

For example, the TL1a-binding protein comprises a $V_H$ including CDRs as follows:

(i) a CDR1 comprising a sequence set forth in SEQ ID NO: 43, a CDR2 comprising a sequence set forth in SEQ ID NO: 44 (wherein any one or more of the five C-terminal amino acids of the CDR2 amino acid sequence are substituted with any other naturally-occurring amino acid) and a CDR3 comprising a sequence set forth in SEQ ID NO: 45 (or sequences labeled as CDRs 1, 2 and 3 in bold text of antibody C320 in FIG. 1A);

(ii) a CDR1 comprising a sequence set forth in amino acids 31 to 35 of any one of SEQ ID NOs: 175 to 181, 183 or 185 to 187, a CDR2 comprising amino acids 50 to 66 of any one of SEQ ID NOs: 175 to 181, 183 or 185 to 187 (wherein any one or more of the five C-terminal amino acids of the CDR2 amino acid sequence are substituted with any other naturally-occurring amino acid) and amino acids 99 to 108 of any one of SEQ ID NOs: 175 to 181, 183 or 185 to 187; or (iii) a CDR1 comprising a sequence set forth in amino acids 26 to 35 of any one of SEQ ID NOs: 175 to 181, 183 or 185 to 187, a CDR2 comprising amino acids 50 to 66 of any one of SEQ ID NOs: 175 to 181, 183 or 185 to 187 (wherein any one or more of the five C-terminal amino acids of the CDR2 amino acid sequence are substituted with any other naturally-occurring amino acid) and amino acids 99 to 108 of any one of SEQ ID NOs: 175 to 181, 183 or 185 to 187

In one example, the TL1a-binding protein comprises a $V_H$ including CDRs as follows:

(i) a CDR1 comprising a sequence set forth in SEQ ID NO: 43 (or sequence labeled as CDR 1 in bold text of the sequence labeled "Consensus" in FIG. 1E);

(ii) a CDR2 comprising a sequence $WX_1NPNSGNTGYAQKFQG$ (SEQ ID NO: 142), wherein $X_1$ is methionine or leucine (or sequence labeled as CDR 2 in bold text of the sequence labeled "Consensus" in FIG. 1E or FIG. 9B); and (iii) a CDR3 comprising a sequence $EVPX_1TAX_2FEY$ (SEQ ID NO: 143), wherein $X_1$ is aspartic acid or glutamic acid and $X_2$ is serine or alanine. (or sequence labeled as CDR3 in bold text of the sequence labeled "Consensus" in FIG. 1E or FIG. 9B) or comprising a sequence $EXIPX_2X_3AX_4FX_5Y$ (SEQ ID NO: 235), wherein:

$X_1$ is an amino acid selected from the group consisting of valine, alanine, serine, histidine, aspartic acid, leucine, tyrosine, proline, glutamine or lysine;

$X_2$ is an amino acid selected from the group consisting of alanine, serine, histidine, lysine, glutamic acid or aspartic acid;

$X_3$ is an amino acid selected from the group consisting of alanine, serine, aspartic acid, tyrosine or threonine;

$X_4$ is an amino acid selected from the group consisting of serine, alanine, histidine, leucine, aspartic acid or tyrosine; and $X_5$ is an amino acid selected from the group consisting of alanine, serine, histidine, leucine, aspartic acid, proline, glutamine, glutamic acid or lysine.

Additional residues suitable for inclusion in CDR3 are described herein and are to be taken to apply mutatis mutandis to the present example of the disclosure.

In one example, the CDRs are defined according to the enhanced Chothia numbering system. For example, the TL1a-binding protein comprises a $V_H$ including CDRs labeled as CDRs 1, 2 and 3 in underlined text of antibody 336, 334, 333, 323, 321, 320 or 319 in FIG. 1A or of antibody C320-90, C320-103, C320-114, C320-115, C320-129 or C320-130 in FIG. 1C or of the sequence labeled "Consensus" in FIG. 1C or FIG. 1E or FIG. 9B.

In one example, the TL1a-binding protein additionally comprises the following:

(i) a heavy chain FR1 comprising an amino acid sequence set forth in SEQ ID NO: 144;

(ii) a heavy chain FR2 comprising an amino acid sequence set forth in SEQ ID NO: 145;

(iii) a heavy chain FR3 comprising an amino acid sequence set forth in SEQ ID NO: 146; and (iv) a heavy chain FR4 comprising an amino acid sequence set forth in SEQ ID NO: 147.

In one example, the TL1a-binding protein comprises the following:

(i) a heavy chain FR1 comprising an amino acid sequence set forth in SEQ ID NO: 144;

(ii) a heavy chain CDR1 comprising a sequence set forth in SEQ ID NO: 43;

(iii) a heavy chain FR2 comprising an amino acid sequence set forth in SEQ ID NO: 145;

(iv) a heavy chain CDR2 comprising a sequence set forth in SEQ ID NO: 142;

(v) a heavy chain FR3 comprising an amino acid sequence set forth in SEQ ID NO: 146;

(vi) a heavy chain CDR3 comprising a sequence set forth in SEQ ID NO: 143 or 235; and (vii) a heavy chain FR4 comprising an amino acid sequence set forth in SEQ ID NO: 147.

For example, the antigen binding domain is a $V_L$ comprising three CDRs of an amino acid sequence set forth in any one of SEQ ID NOs: 6, 14, 22, 30, 38, 46, 54, 62, 82, 95, 153, 163 to 172, 174, or 188 to 200. In one example, the CDRs are defined according to the Kabat numbering system. For example, the TL1a-binding protein comprises a $V_L$ including CDRs as follows:

(i) a CDR1 comprising a sequence set forth in SEQ ID NO: 7, a CDR2 comprising a sequence set forth in SEQ ID NO: 8 and a CDR3 comprising a sequence set forth in SEQ ID NO: 9 (or sequences labeled as CDRs 1, 2 and 3 in bold text of antibody C336 in FIG. 1B);

(ii) a CDR1 comprising a sequence set forth in SEQ ID NO: 15, a CDR2 comprising a sequence set forth in SEQ ID NO: 16 and a CDR3 comprising a sequence set forth in SEQ ID NO: 17 (or sequences labeled as CDRs 1, 2 and 3 in bold text of antibody C334 in FIG. 1B);

(iii) a CDR1 comprising a sequence set forth in SEQ ID NO: 23, a CDR2 comprising a sequence set forth in SEQ ID NO: 24 and a CDR3 comprising a sequence set forth in SEQ ID NO: 25 (or sequences labeled as CDRs 1, 2 and 3 in bold text of antibody C333 in FIG. 1B);

(iv) a CDR1 comprising a sequence set forth in SEQ ID NO: 31, a CDR2 comprising a sequence set forth in SEQ ID NO: 32 and a CDR3 comprising a sequence set forth in SEQ ID NO: 33 (or sequences labeled as CDRs 1, 2 and 3 in bold text of antibody C323 in FIG. 1B);

(v) a CDR1 comprising a sequence set forth in SEQ ID NO: 39, a CDR2 comprising a sequence set forth in SEQ ID NO: 40 and a CDR3 comprising a sequence set forth in SEQ ID NO: 41 (or sequences labeled as CDRs 1, 2 and 3 in bold text of antibody C321 in FIG. 1B);

(vi) a CDR1 comprising a sequence set forth in SEQ ID NO: 47, a CDR2 comprising a sequence set forth in SEQ ID NO: 48 and a CDR3 comprising a sequence set forth in SEQ ID NO: 49 (or sequences labeled as CDRs 1, 2 and 3 in bold text of antibody C320 in FIG. 1B);

(vii) a CDR1 comprising a sequence set forth in SEQ ID NO: 55, a CDR2 comprising a sequence set forth in SEQ ID NO: 56 and a CDR3 comprising a sequence set forth in SEQ ID NO: 57 (or sequences labeled as CDRs 1, 2 and 3 in bold text of antibody C319 in FIG. 1B);

(viii) a CDR1 comprising a sequence set forth in SEQ ID NO: 83, a CDR2 comprising a sequence set forth in SEQ ID NO: 84 and a CDR3 comprising a sequence set forth in SEQ ID NO: 85 (or sequences labeled as CDRs 1, 2 and 3 in bold text of antibody C320-120 in FIG. 1F); or (ix) a CDR1 comprising amino acids 23 to 36 of any one of SEQ ID NOs: 188 to 200, a CDR2 comprising amino acids 52 to 58 of any one of SEQ ID NOs: 188 to 200 and a CDR3 comprising amino acids 91 to 100 of any one of SEQ ID NOs: 188 to 200.

In one example, the TL1a-binding protein comprises a $V_L$ including CDRs as follows:

(i) a CDR1 comprising a sequence $X_1X_2$SSSDIGAGLGVH (SEQ ID NO: 139), wherein $X_1$ is alanine or threonine; $X_2$ is glycine or serine (or sequence labeled as CDR 1 in bold text of the sequence labeled "Consensus" in FIG. 9C);

(ii) a CDR2 comprising a sequence set forth in SEQ ID NO: 140; and (iii) a CDR3 comprising a sequence set forth in SEQ ID NO: 141.

In one example, the TL1a-binding protein additionally comprises the following:

(i) a light chain FR1 comprising an amino acid sequence set forth in SEQ ID NO: 148;

(ii) a light chain FR2 comprising an amino acid sequence set forth in SEQ ID NO: 149;

(iii) a light chain FR3 comprising an amino acid sequence set forth in SEQ ID NO: 150; and (iv) a light chain FR4 comprising an amino acid sequence set forth in SEQ ID NO: 151.

In one example, the TL1a-binding protein comprises the following:

(i) a light chain FR1 comprising an amino acid sequence set forth in SEQ ID NO: 148;

(ii) a light chain CDR1 comprising a sequence set forth in SEQ ID NO: 139;

(iii) a light chain FR2 comprising an amino acid sequence set forth in SEQ ID NO: 149;

(iv) a light chain CDR2 comprising a sequence set forth in SEQ ID NO: 140;

(v) a light chain FR3 comprising an amino acid sequence set forth in SEQ ID NO: 150;

(vi) a light chain CDR3 comprising a sequence set forth in SEQ ID NO: 141; and (vii) a light chain FR4 comprising an amino acid sequence set forth in SEQ ID NO: 151.

In one example, the CDRs are defined according to the enhanced Chothia numbering system. For example, the TL1a-binding protein comprises a $V_L$ including CDRs labeled as CDRs 1, 2 and 3 in underlined text of antibody 336, 334, 333, 323, 321, 320 or 319 in FIG. 1B or of antibody C320-120 in FIG. 1F or of the sequence labeled "Consensus" in FIG. 1H and FIG. 9.

In one example, the antigen binding domain comprises six CDRs of one of the following pairs of variable regions:

(i) a$V_H$ comprising a sequence set forth in SEQ ID NO: 2 and a $V_L$ comprising a sequence set forth in SEQ ID NO: 6;

(ii) a $V_H$ comprising a sequence set forth in SEQ ID NO: 10 and a $V_L$ comprising a sequence set forth in SEQ ID NO: 14;

(iii) a $V_H$ comprising a sequence set forth in SEQ ID NO: 18 and a $V_L$ comprising a sequence set forth in SEQ ID NO: 22;

(iv) a $V_H$ comprising a sequence set forth in SEQ ID NO: 26 and a $V_L$ comprising a sequence set forth in SEQ ID NO: 30;

(v) a $V_H$ comprising a sequence set forth in SEQ ID NO: 34 and a $V_L$ comprising a sequence set forth in SEQ ID NO:38;

(vi) a $V_H$ comprising a sequence set forth in SEQ ID NO: 42 and a $V_L$ comprising a sequence set forth in SEQ ID NO: 46;

(vii) a $V_H$ comprising a sequence set forth in SEQ ID NO: 50 and a $V_L$ comprising a sequence set forth in SEQ ID NO: 54;

(viii) a $V_H$ comprising a sequence set forth in SEQ ID NO: 58 and a $V_L$ comprising a sequence set forth in SEQ ID NO: 46;

(ix) a $V_H$ comprising a sequence set forth in SEQ ID NO: 42 and a $V_L$ comprising a sequence set forth in SEQ ID NO: 62;

(x) a $V_H$ comprising a sequence set forth in SEQ ID NO: 66 and a $V_L$ comprising a sequence set forth in SEQ ID NO: 62;

(xi) a $V_H$ comprising a sequence set forth in SEQ ID NO: 70 and a $V_L$ comprising a sequence set forth in SEQ ID NO: 62;

(xii) a $V_H$ comprising a sequence set forth in SEQ ID NO: 74 and a $V_L$ comprising a sequence set forth in SEQ ID NO: 62;

(xiii) a $V_H$ comprising a sequence set forth in SEQ ID NO: 78 and a $V_L$ comprising a sequence set forth in SEQ ID NO: 62;

(xiv) a $V_H$ comprising a sequence set forth in SEQ ID NO: 58 and a $V_L$ comprising a sequence set forth in SEQ ID NO: 82;

(xv) a $V_H$ comprising a sequence set forth in SEQ ID NO: 86 and a $V_L$ comprising a sequence set forth in SEQ ID NO: 46;

(xvi) a $V_H$ comprising a sequence set forth in SEQ ID NO: 90 and a $V_L$ comprising a sequence set forth in SEQ ID NO: 46;

(xvii) a $V_H$ comprising a sequence set forth in SEQ ID NO: 58 and a $V_L$ comprising a sequence set forth in SEQ ID NO: 62;

(xviii) a $V_H$ comprising a sequence set forth in SEQ ID NO: 154 and a $V_L$ comprising a sequence set forth in SEQ ID NO: 164;

(xix) a $V_H$ comprising a sequence set forth in SEQ ID NO: 155 and a $V_L$ comprising a sequence set forth in SEQ ID NO: 163;

(xx) a $V_H$ comprising a sequence set forth in SEQ ID NO: 156 and a $V_L$ comprising a sequence set forth in SEQ ID NO: 165;

(xxi) a $V_H$ comprising a sequence set forth in SEQ ID NO: 157 and a $V_L$ comprising a sequence set forth in SEQ ID NO: 166;

(xxii) a $V_H$ comprising a sequence set forth in SEQ ID NO: 158 and a $V_L$ comprising a sequence set forth in SEQ ID NO: 167;

(xxiii) a $V_H$ comprising a sequence set forth in SEQ ID NO: 159 and a $V_L$ comprising a sequence set forth in SEQ ID NO: 168;

(xxiv) a $V_H$ comprising a sequence set forth in SEQ ID NO: 160 and a $V_L$ comprising a sequence set forth in SEQ ID NO: 169;

(xxv) a $V_H$ comprising a sequence set forth in SEQ ID NO: 161 and a $V_L$ comprising a sequence set forth in SEQ ID NO: 170;

(xxvi) a $V_H$ comprising a sequence set forth in SEQ ID NO: 234 and a $V_L$ comprising a sequence set forth in SEQ ID NO: 169;

(xxvii) a $V_H$ comprising a sequence set forth in SEQ ID NO: 154 and a $V_L$ comprising a sequence set forth in SEQ ID NO: 46;

(xxviii) a $V_H$ comprising a sequence set forth in SEQ ID NO: 155 and a $V_L$ comprising a sequence set forth in SEQ ID NO: 46;

(xxix) a $V_H$ comprising a sequence set forth in SEQ ID NO: 156 and a $V_L$ comprising a sequence set forth in SEQ ID NO: 46;

(xxx) a $V_H$ comprising a sequence set forth in SEQ ID NO: 157 and a $V_L$ comprising a sequence set forth in SEQ ID NO: 46;

(xxxi) a $V_H$ comprising a sequence set forth in SEQ ID NO: 158 and a $V_L$ comprising a sequence set forth in SEQ ID NO: 46;

(xxxii) a $V_H$ comprising a sequence set forth in SEQ ID NO: 159 and a $V_L$ comprising a sequence set forth in SEQ ID NO: 46;

(xxxiii) a $V_H$ comprising a sequence set forth in SEQ ID NO: 160 and a $V_L$ comprising a sequence set forth in SEQ ID NO: 46;

(xxxiv) a $V_H$ comprising a sequence set forth in SEQ ID NO: 161 and a $V_L$ comprising a sequence set forth in SEQ ID NO: 46;

(xxxv) a $V_H$ comprising a sequence set forth in SEQ ID NO: 234 and a $V_L$ comprising a sequence set forth in SEQ ID NO: 46;

(xxxvi) a $V_H$ comprising a sequence set forth in SEQ ID NO: 42 and a $V_L$ comprising a sequence set forth in SEQ ID NO: 164;

(xxxvii) a $V_H$ comprising a sequence set forth in SEQ ID NO: 42 and a $V_L$ comprising a sequence set forth in SEQ ID NO: 165;

(xxxviii) a $V_H$ comprising a sequence set forth in SEQ ID NO: 42 and a $V_L$ comprising a sequence set forth in SEQ ID NO: 166;

(xxxix) a $V_H$ comprising a sequence set forth in SEQ ID NO: 42 and a $V_L$ comprising a sequence set forth in SEQ ID NO: 167;

(xl) a $V_H$ comprising a sequence set forth in SEQ ID NO: 42 and a $V_L$ comprising a sequence set forth in SEQ ID NO: 168;

(xli) a $V_H$ comprising a sequence set forth in SEQ ID NO: 42 and a $V_L$ comprising a sequence set forth in SEQ ID NO: 169;

(xlii) a $V_H$ comprising a sequence set forth in SEQ ID NO: 42 and a $V_L$ comprising a sequence set forth in SEQ ID NO: 170;

(xliii) a $V_H$ comprising a sequence set forth in SEQ ID NO: 42 and a $V_L$ comprising a sequence set forth in SEQ ID NO: 171;

(xliv) a $V_H$ comprising a sequence set forth in SEQ ID NO: 42 and a $V_L$ comprising a sequence set forth in SEQ ID NO: 172;

(xlv) a $V_H$ comprising a sequence set forth in SEQ ID NO: 175 and a $V_L$ comprising a sequence set forth in SEQ ID NO: 188;

(xlvi) a $V_H$ comprising a sequence set forth in SEQ ID NO: 176 and a $V_L$ comprising a sequence set forth in SEQ ID NO: 189;

(xlvii) a $V_H$ comprising a sequence set forth in SEQ ID NO: 177 and a $V_L$ comprising a sequence set forth in SEQ ID NO: 190;

(xlviii) a $V_H$ comprising a sequence set forth in SEQ ID NO: 178 and a $V_L$ comprising a sequence set forth in SEQ ID NO: 191;

(xlix) a $V_H$ comprising a sequence set forth in SEQ ID NO: 179 and a $V_L$ comprising a sequence set forth in SEQ ID NO: 192;

(l) a $V_H$ comprising a sequence set forth in SEQ ID NO: 180 and a $V_L$ comprising a sequence set forth in SEQ ID NO: 193;

(li) a $V_H$ comprising a sequence set forth in SEQ ID NO: 181 and a $V_L$ comprising a sequence set forth in SEQ ID NO: 194;

(lii) a $V_H$ comprising a sequence set forth in SEQ ID NO: 182 and a $V_L$ comprising a sequence set forth in SEQ ID NO: 195;

(liii) a $V_H$ comprising a sequence set forth in SEQ ID NO: 183 and a $V_L$ comprising a sequence set forth in SEQ ID NO: 196;

(liv) a $V_H$ comprising a sequence set forth in SEQ ID NO: 184 and a $V_L$ comprising a sequence set forth in SEQ ID NO: 197;

(lv) a $V_H$ comprising a sequence set forth in SEQ ID NO: 185 and a $V_L$ comprising a sequence set forth in SEQ ID NO: 198;

(lvi) a $V_H$ comprising a sequence set forth in SEQ ID NO: 186 and a $V_L$ comprising a sequence set forth in SEQ ID NO: 199; or (lvii) a $V_H$ comprising a sequence set forth in SEQ ID NO: 187 and a $V_L$ comprising a sequence set forth in SEQ ID NO: 200.

In one example, the antigen binding domain comprises six CDRs of an antibody comprising a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:

(i) the $V_H$ comprises an alanine at position 16 of SEQ ID NO: 42;

(ii) the $V_H$ comprises an alanine at position 100 of SEQ ID NO: 42 and the $V_L$ comprises a threonine at position 76 of SEQ ID NO: 46;

(iii) the $V_H$ comprises a serine at position 100 of SEQ ID NO: 42 and the $V_L$ comprises a threonine at position 76 of SEQ ID NO: 46;

(iv) the $V_H$ comprises a histidine at position 100 of SEQ ID NO: 42 and the $V_L$ comprises a threonine at position 76 of SEQ ID NO: 46;

(v) the $V_H$ comprises a leucine at position 100 of SEQ ID NO: 42 and the $V_L$ comprises a threonine at position 76 of SEQ ID NO: 46;

(vi) the $V_H$ comprises an aspartic acid at position 100 of SEQ ID NO: 42 and the $V_L$ comprises a threonine at position 76 of SEQ ID NO: 46;

(vii) the $V_H$ comprises a tyrosine at position 100 of SEQ ID NO: 42 and the $V_L$ comprises a threonine at position 76 of SEQ ID NO: 46;

(viii) the $V_H$ comprises a proline at position 100 of SEQ ID NO: 42 and the $V_L$ comprises a threonine at position 76 of SEQ ID NO: 46;

(ix) the $V_H$ comprises a glutamine at position 100 of SEQ ID NO: 42 and the $V_L$ comprises a threonine at position 76 of SEQ ID NO: 46;

(x) the $V_H$ comprises a lysine at position 100 of SEQ ID NO: 42 and the $V_L$ comprises a threonine at position 76 of SEQ ID NO: 46;

(xi) the $V_H$ comprises an alanine at position 101 of SEQ ID NO: 42 and the $V_L$ comprises a threonine at position 76 of SEQ ID NO: 46;

(xii) the $V_H$ comprises a serine at position 101 of SEQ ID NO: 42 and the $V_L$ comprises a threonine at position 76 of SEQ ID NO: 46;

(xiii) the $V_H$ comprises a histidine at position 101 of SEQ ID NO: 42 and the $V_L$ comprises a threonine at position 76 of SEQ ID NO: 46;

(xiv) the $V_H$ comprises a leucine at position 101 of SEQ ID NO: 42 and the $V_L$ comprises a threonine at position 76 of SEQ ID NO: 46;

(xv) the $V_H$ comprises an aspartic acid at position 101 of SEQ ID NO: 42 and the $V_L$ comprises a threonine at position 76 of SEQ ID NO: 46;

(xvi) the $V_H$ comprises a tyrosine at position 101 of SEQ ID NO: 42 and the $V_L$ comprises a threonine at position 76 of SEQ ID NO: 46;

(xvii) the $V_H$ comprises a glutamine at position 101 of SEQ ID NO: 42 and the $V_L$ comprises a threonine at position 76 of SEQ ID NO: 46;

(xviii) the $V_H$ comprises a lysine at position 101 of SEQ ID NO: 42 and the $V_L$ comprises a threonine at position 76 of SEQ ID NO: 46;

(xix) the $V_H$ comprises an alanine at position 102 of SEQ ID NO: 42 and the $V_L$ comprises a threonine at position 76 of SEQ ID NO: 46;

(xx) the $V_H$ comprises a serine at position 102 of SEQ ID NO: 42 and the $V_L$ comprises a threonine at position 76 of SEQ ID NO: 46;

(xxi) the $V_H$ comprises a histidine at position 102 of SEQ ID NO: 42 and the $V_L$ comprises a threonine at position 76 of SEQ ID NO: 46;

(xxii) the $V_H$ comprises a leucine at position 102 of SEQ ID NO: 42 and the $V_L$ comprises a threonine at position 76 of SEQ ID NO: 46;

(xxiii) the $V_H$ comprises a tyrosine at position 102 of SEQ ID NO: 42 and the $V_L$ comprises a threonine at position 76 of SEQ ID NO: 46;

(xxiv) the $V_H$ comprises a proline at position 102 of SEQ ID NO: 42 and the $V_L$ comprises a threonine at position 76 of SEQ ID NO: 46;

(xxv) the $V_H$ comprises a glutamine at position 102 of SEQ ID NO: 42 and the $V_L$ comprises a threonine at position 76 of SEQ ID NO: 46;

(xxvi) the $V_H$ comprises a lysine at position 102 of SEQ ID NO: 42 and the $V_L$ comprises a threonine at position 76 of SEQ ID NO: 46;

(xxvii) the $V_H$ comprises an alanine at position 103 of SEQ ID NO: 42 and the $V_L$ comprises a threonine at position 76 of SEQ ID NO: 46;

(xxviii) the $V_H$ comprises a serine at position 103 of SEQ ID NO: 42 and the $V_L$ comprises a threonine at position 76 of SEQ ID NO: 46;

(xxix) the $V_H$ comprises a histidine at position 103 of SEQ ID NO: 42 and the $V_L$ comprises a threonine at position 76 of SEQ ID NO: 46;

(xxx) the $V_H$ comprises a leucine at position 103 of SEQ ID NO: 42 and the $V_L$ comprises a threonine at position 76 of SEQ ID NO: 46;

(xxxi) the $V_H$ comprises an aspartic acid at position 103 of SEQ ID NO: 42 and the $V_L$ comprises a threonine at position 76 of SEQ ID NO: 46;

(xxxii) the $V_H$ comprises a tyrosine at position 103 of SEQ ID NO: 42 and the $V_L$ comprises a threonine at position 76 of SEQ ID NO: 46;

(xxxiii) the $V_H$ comprises a proline at position 103 of SEQ ID NO: 42 and the $V_L$ comprises a threonine at position 76 of SEQ ID NO: 46;

(xxxiv) the $V_H$ comprises a glutamine at position 103 of SEQ ID NO: 42 and the $V_L$ comprises a threonine at position 76 of SEQ ID NO: 46;

(xxxv) the $V_H$ comprises a lysine at position 103 of SEQ ID NO: 42 and the $V_L$ comprises a threonine at position 76 of SEQ ID NO: 46;

(xxxvi) the $V_H$ comprises a serine at position 104 of SEQ ID NO: 42 and the $V_L$ comprises a threonine at position 76 of SEQ ID NO: 46;

(xxxvii) the $V_H$ comprises a histidine at position 104 of SEQ ID NO: 42 and the $V_L$ comprises a threonine at position 76 of SEQ ID NO: 46;

(xxxviii) the $V_H$ comprises a leucine at position 104 of SEQ ID NO: 42 and the $V_L$ comprises a threonine at position 76 of SEQ ID NO: 46;

(xxxix) the $V_H$ comprises an aspartic acid at position 104 of SEQ ID NO: 42 and the $V_L$ comprises a threonine at position 76 of SEQ ID NO: 46;

(xl) the $V_H$ comprises a tyrosine at position 104 of SEQ ID NO: 42 and the $V_L$ comprises a threonine at position 76 of SEQ ID NO: 46;

(xli) the $V_H$ comprises a proline at position 104 of SEQ ID NO: 42 and the $V_L$ comprises a threonine at position 76 of SEQ ID NO: 46;

(xlii) the $V_H$ comprises a glutamine at position 104 of SEQ ID NO: 42 and the $V_L$ comprises a threonine at position 76 of SEQ ID NO: 46;

(xliii) the $V_H$ comprises a lysine at position 104 of SEQ ID NO: 42 and the $V_L$ comprises a threonine at position 76 of SEQ ID NO: 46;

(xliv) the $V_H$ comprises an alanine at position 105 of SEQ ID NO: 42 and the $V_L$ comprises a threonine at position 76 of SEQ ID NO: 46;

(xlv) the $V_H$ comprises a histidine at position 105 of SEQ ID NO: 42 and the $V_L$ comprises a threonine at position 76 of SEQ ID NO: 46;

(xlvi) the $V_H$ comprises a leucine at position 105 of SEQ ID NO: 42 and the $V_L$ comprises a threonine at position 76 of SEQ ID NO: 46;

(xlvii) the $V_H$ comprises an aspartic acid at position 105 of SEQ ID NO: 42 and the $V_L$ comprises a threonine at position 76 of SEQ ID NO: 46;

(xlviii) the $V_H$ comprises a tyrosine at position 105 of SEQ ID NO: 42 and the $V_L$ comprises a threonine at position 76 of SEQ ID NO: 46;

(xlix) the $V_H$ comprises a proline at position 105 of SEQ ID NO: 42 and the $V_L$ comprises a threonine at position 76 of SEQ ID NO: 46;

(l) the $V_H$ comprises a glutamine at position 105 of SEQ ID NO: 42 and the $V_L$ comprises a threonine at position 76 of SEQ ID NO: 46;

(li) the $V_H$ comprises a lysine at position 105 of SEQ ID NO: 42 and the $V_L$ comprises a threonine at position 76 of SEQ ID NO: 46;

(lii) the $V_H$ comprises an alanine at position 107 of SEQ ID NO: 42 and the $V_L$ comprises a threonine at position 76 of SEQ ID NO: 46;

(liii) the $V_H$ comprises a serine at position 107 of SEQ ID NO: 42 and the $V_L$ comprises a threonine at position 76 of SEQ ID NO: 46;

(liv) the $V_H$ comprises a histidine at position 107 of SEQ ID NO: 42 and the $V_L$ comprises a threonine at position 76 of SEQ ID NO: 46;

(lv) the $V_H$ comprises a leucine at position 107 of SEQ ID NO: 42 and the $V_L$ comprises a threonine at position 76 of SEQ ID NO: 46;

(lvi) the $V_H$ comprises an aspartic acid at position 107 of SEQ ID NO: 42 and the $V_L$ comprises a threonine at position 76 of SEQ ID NO: 46;

(lvii) the $V_H$ comprises a tyrosine at position 107 of SEQ ID NO: 42 and the $V_L$ comprises a threonine at position 76 of SEQ ID NO: 46;

(lviii) the $V_H$ comprises a proline at position 107 of SEQ ID NO: 42 and the $V_L$ comprises a threonine at position 76 of SEQ ID NO: 46;

(lix) the $V_H$ comprises a glutamine at position 107 of SEQ ID NO: 42 and the $V_L$ comprises a threonine at position 76 of SEQ ID NO: 46;

(lx) the $V_H$ comprises a lysine at position 107 of SEQ ID NO: 42 and the $V_L$ comprises a threonine at position 76 of SEQ ID NO: 46;

(lxi) the $V_H$ comprises a threonine at position 41 of SEQ ID NO: 42 and the $V_L$ comprises an alanine at position 23 of SEQ ID NO: 46;

(lxii) the $V_H$ comprises a threonine at position 41 of SEQ ID NO: 42 and the $V_L$ comprises an aspartic acid at position 28 of SEQ ID NO: 46;

(lxiii) the $V_H$ comprises a threonine at position 41 of SEQ ID NO: 42 and the $V_L$ comprises a tyrosine at position 33 of SEQ ID NO: 46;

(lxiv) the $V_H$ comprises a threonine at position 41 of SEQ ID NO: 42 and the $V_L$ comprises an aspartic acid at position 34 of SEQ ID NO: 46;

(lxv) the $V_H$ comprises a threonine at position 41 of SEQ ID NO: 42 and the $V_L$ comprises an asparagine at position 53 of SEQ ID NO: 46;

(lxvi) the $V_H$ comprises a threonine at position 41 of SEQ ID NO: 42 and the $V_L$ comprises a serine at position 54 of SEQ ID NO: 46;

(lxvii) the $V_H$ comprises a threonine at position 41 of SEQ ID NO: 42 and the $V_L$ comprises an alanine at position 82 of SEQ ID NO: 46;

(lxviii) the $V_H$ comprises a threonine at position 41 of SEQ ID NO: 42 and the $V_L$ comprises a serine at position 95 of SEQ ID NO: 46;

(lxix) the $V_H$ comprises a threonine at position 41 of SEQ ID NO: 42 and the $V_L$ comprises a serine at position 96 of SEQ ID NO: 46;

(lxx) the $V_H$ comprises a threonine at position 41 of SEQ ID NO: 42 and the $V_L$ comprises a threonine at position 76 of SEQ ID NO: 46;

(lxxi) the $V_H$ comprises a serine at position 47 of SEQ ID NO: 42 and the $V_L$ comprises a threonine at position 23 of SEQ ID NO: 46;

(lxxii) the $V_H$ comprises a proline at position 41, an alanine at position 72, an aspartic acid at position 73 and an arginine at position 74 and a threonine at position 76 each relative to SEQ ID NO: 42 and the $V_L$ comprises a threonine at position 76 of SEQ ID NO: 46;

(lxxiii) the $V_H$ comprises a proline at position 41, a leucine at position 51 and a glutamic acid at position 102 each relative to SEQ ID NO: 42 and the $V_L$ comprises a serine at position 24 and a threonine at position 76 each relative to SEQ ID NO: 46;

(lxxiv) the $V_H$ comprises a proline at position 41, a leucine at position 51 and a glutamic acid at position 102 each relative to SEQ ID NO: 42 and the $V_L$ comprises a threonine at position 23, a serine at position 24 and a threonine at position 76 each relative to SEQ ID NO: 46;

(lxxv) the $V_H$ comprises a proline at position 41, a leucine at position 51 and a glutamic acid at position 102 each relative to SEQ ID NO: 42 and the $V_L$ comprises a threonine at position 23 and a threonine at position 76 each relative to SEQ ID NO: 46;

(lxxvi) the $V_H$ comprises a proline at position 41, a leucine at position 51 and a glutamic acid at position 102 each relative to SEQ ID NO: 42 and the $V_L$ comprises a threonine at position 76 of SEQ ID NO: 46;

(lxxvii) the $V_H$ comprises a proline at position 41, a leucine at position 51, a glutamic acid at position 102 and an alanine at position 105 each relative to SEQ ID NO: 42 and the $V_L$ comprises a threonine at position 23, a serine at position 24 and a threonine at position 76 each relative to SEQ ID NO: 46;

(lxxviii) the $V_H$ comprises a proline at position 41, a leucine at position 51, a glutamic acid at position 102 and an alanine at position 105 each relative to SEQ ID NO: 42 and the $V_L$ comprises a threonine at position 76 of SEQ ID NO: 46;

(lxxix) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24 and a threonine at position 76 each relative to SEQ ID NO: 46;

(lxxx) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24, a threonine at position 76 and a glutamic acid at position 51 each relative to SEQ ID NO: 46;

(lxxxi) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glutamic acid at position 51 each relative to SEQ ID NO: 46; or (lxxxii) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glycine at position 51 each relative to SEQ ID NO: 46.

In one example, the antigen binding domain comprises six CDRs of one of the following pairs of variable regions:

(i) a $V_H$ comprising a sequence set forth in SEQ ID NO: 42 and a $V_L$ comprising a sequence set forth in SEQ ID NO: 46;

(ii) a $V_H$ encoded by a nucleic acid comprising a sequence at least about 95% identical to the sequence set forth in SEQ ID NO: 106 or a nucleic acid that hybridizes thereto under moderate to high stringency conditions and a $V_L$ encoded by a nucleic acid comprising a sequence at least about 95% identical to the sequence set forth in SEQ ID NO: 107 or a nucleic acid that hybridizes thereto under moderate to high stringency conditions;

(iii) a $V_H$ comprising a sequence set forth in SEQ ID NO: 175 and a $V_L$ comprising a sequence set forth in SEQ ID NO: 188;

(iv) a $V_H$ encoded by a nucleic acid comprising a sequence at least about 95% identical to the sequence set forth in SEQ ID NO: 222 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(v) a $V_H$ comprising a sequence set forth in SEQ ID NO: 176 and a $V_L$ comprising a sequence set forth in SEQ ID NO: 189;

(vi) a $V_H$ encoded by a nucleic acid comprising a sequence at least about 95% identical to the sequence set forth in SEQ ID NO: 223 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(vii) a $V_H$ comprising a sequence set forth in SEQ ID NO: 177 and a $V_L$ comprising a sequence set forth in SEQ ID NO: 190;

(viii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 229 or a nucleic acid that hybridizes thereto under moderate to high stringency conditions;

(ix) a $V_H$ comprising a sequence set forth in SEQ ID NO: 178 and a $V_L$ comprising a sequence set forth in SEQ ID NO: 191;

(x) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xi) a $V_H$ comprising a sequence set forth in SEQ ID NO: 179 and a $V_L$ comprising a sequence set forth in SEQ ID NO: 192;

(xii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 231 or a nucleic acid that hybridizes thereto under moderate to high stringency conditions;

(xiii) a $V_H$ comprising a sequence set forth in SEQ ID NO: 180 and a $V_L$ comprising a sequence set forth in SEQ ID NO: 193;

(xiv) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(xv) a $V_H$ comprising a sequence set forth in SEQ ID NO: 181 and a $V_L$ comprising a sequence set forth in SEQ ID NO: 194;

(xvi) a $V_H$ encoded by a nucleic acid comprising a sequence at least about 95% identical to the sequence set forth in SEQ ID NO: 225 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xvii) a $V_H$ comprising a sequence set forth in SEQ ID NO: 183 and a $V_L$ comprising a sequence set forth in SEQ ID NO: 196;

(xviii) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xix) a $V_H$ comprising a sequence set forth in SEQ ID NO: 185 and a $V_L$ comprising a sequence set forth in SEQ ID NO: 198;

(xx) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxi) a $V_H$ comprising a sequence set forth in SEQ ID NO: 186 and a $V_L$ comprising a sequence set forth in SEQ ID NO: 199; and (xxii) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxiii) a $V_H$ comprising a sequence set forth in SEQ ID NO: 187 and a $V_L$ comprising a sequence set forth in SEQ ID NO: 200; or (xxiv) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 233 or a nucleic acid that hybridizes thereto under moderate to high stringency conditions.

In one example, the TL1a-binding protein comprises the following six CDRs:

(i) a heavy chain CDR1 comprising a sequence set forth in SEQ ID NO: 43 (or sequence labeled as CDR 1 in bold text of the sequence labeled "Consensus" in FIG. 1E);

(ii) a heavy chain CDR2 comprising a sequence $WX_1NPNSGNTGYAQKFQG$ (SEQ ID NO: 142), wherein $X_1$ is methionine or leucine (or sequence labeled as CDR 2 in bold text of the sequence labeled "Consensus" in FIG. 1E);

(iii) a heavy chain CDR3 comprising a sequence $EVPX_1TAX_2FEY$ (SEQ ID NO: 143), wherein $X_1$ is aspartic acid or glutamic acid and $X_2$ is serine or alanine. (or the sequence labeled as CDR 3 in bold text of the sequence labeled "Consensus" in FIG. 9B) or a sequence $EX_1PX_2X_3AX_4FX_5Y$ (SEQ ID NO: 235), wherein:

$X_1$ is an amino acid selected from the group consisting of valine, alanine, serine, histidine, aspartic acid, leucine, tyrosine, proline, glutamine or lysine;

$X_2$ is an amino acid selected from the group consisting of alanine, serine, histidine, lysine, glutamic acid or aspartic acid;

$X_3$ is an amino acid selected from the group consisting of alanine, serine, aspartic acid, tyrosine or threonine;

$X_4$ is an amino acid selected from the group consisting of serine, alanine, histidine, leucine, aspartic acid or tyrosine; and $X_5$ is an amino acid selected from the group consisting of alanine, serine, histidine, leucine, aspartic acid, proline, glutamine, glutamic acid or lysine;

(iv) a CDR1 comprising a sequence $X_1X_2SSSDIGAGLGVH$ (SEQ ID NO: 139), wherein $X_1$ is alanine or threonine; $X_2$ is glycine or serine (or sequence labeled as CDR 1 in bold text of the sequence labeled "Consensus" in FIG. 9C);

(v) a CDR2 comprising a sequence set forth in SEQ ID NO: 48; and (vi) a CDR3 comprising a sequence set forth in SEQ ID NO: 49 In one example, the TL1a-binding protein comprises the following:

(a) a $V_H$ comprising:

(i) a heavy chain FR1 comprising an amino acid sequence set forth in SEQ ID NO: 144;

(ii) a heavy chain CDR1 comprising a sequence set forth in SEQ ID NO: 43;

(iii) a heavy chain FR2 comprising an amino acid sequence set forth in SEQ ID NO: 145;

(iv) a heavy chain CDR2 comprising a sequence set forth in SEQ ID NO: 142;

(v) a heavy chain FR3 comprising an amino acid sequence set forth in SEQ ID NO: 146;

(vi) a heavy chain CDR3 comprising a sequence set forth in SEQ ID NO: 143 or 235; and (vii) a heavy chain FR4 comprising an amino acid sequence set forth in SEQ ID NO: 147; and (b) a $V_L$ comprising:

(i) a light chain FR1 comprising an amino acid sequence set forth in SEQ ID NO: 148;

(ii) a light chain CDR1 comprising a sequence set forth in SEQ ID NO: 139;

(iii) a light chain FR2 comprising an amino acid sequence set forth in SEQ ID NO: 149;

(iv) a light chain CDR2 comprising a sequence set forth in SEQ ID NO: 48;

(v) a light chain FR3 comprising an amino acid sequence set forth in SEQ ID NO: 150;

(vi) a light chain CDR3 comprising a sequence set forth in SEQ ID NO: 49; and (vii) a light chain FR4 comprising an amino acid sequence set forth in SEQ ID NO: 151.

Additional residues suitable for inclusion in heavy chain CDR3 are described herein and are to be taken to apply mutatis mutandis to the present example of the disclosure.

In one example, the CDRs are defined according to the Kabat numbering system. Exemplary CDRs defined according to the Kabat numbering system are described above and/or in FIG. 1A to 1H, 9B or 9C labeled as CDRs 1 to 3 in bold text and are taken to apply mutatis mutandis to the present example of the disclosure.

In one example, the CDRs are defined according to the enhanced Chothia numbering system. Exemplary CDRs defined according to the enhanced Chothia numbering system are described above and/or in FIGS. 1A to 1H labeled as CDRs 1 to 3 in underlined text and are taken to apply mutatis mutandis to the present example of the disclosure.

In one example, the TL1a-binding protein comprises a variable region of the antibody.

In one example, the TL1a-binding protein comprises a $V_H$ comprising a sequence set forth in any one of SEQ ID NOs: 2, 10, 18, 26, 34, 42, 50, 58, 66, 70, 74, 78, 86, 90, 94, 137, 152, 154 to 162, 173, 175 to 187 or 234 or a sequence having at least about 80% identity to any one of the foregoing. In one example, the $V_H$ comprises a sequence set forth in any one of SEQ ID NOs: 26, 34, 42 or 94 or a sequence having at least about 80% identity to any one of the foregoing. In one example, the $V_H$ comprises a sequence set forth in any one of SEQ ID NOs: 42, 175 to 181, 183 or 185 to 187 or a sequence having at least about 80% identity to any one of the foregoing.

In one example, the TL1a-binding protein comprises a $V_H$ comprising a sequence set forth in SEQ ID NO: 94, 137, 152, 162 or 173. In one example, the $V_H$ comprises a sequence set forth in any one of SEQ ID NOs: 42, 58, 66, 70, 74, 78, 86 or 90. In one example, the $V_H$ comprises a sequence set forth in SEQ ID NO: 42.

In one example, the TL1a-binding protein comprises a $V_H$ comprising a sequence set forth in SEQ ID NO: 42 and comprising one or more of the following substitutions or groups of substitutions:

(i) an alanine at position 16 of SEQ ID NO: 42;

(ii) an alanine at position 100 of SEQ ID NO: 42;

(iii) a serine at position 100 of SEQ ID NO: 42;

(iv) a histidine at position 100 of SEQ ID NO: 42;
(v) a leucine at position 100 of SEQ ID NO: 42;
(vi) an aspartic acid at position 100 of SEQ ID NO: 42;
(vii) a tyrosine at position 100 of SEQ ID NO: 42;
(viii) a proline at position 100 of SEQ ID NO: 42;
(ix) a glutamine at position 100 of SEQ ID NO: 42;
(x) a lysine at position 100 of SEQ ID NO: 42;
(xi) an alanine at position 101 of SEQ ID NO: 42;
(xii) a serine at position 101 of SEQ ID NO: 42;
(xiii) a histidine at position 101 of SEQ ID NO: 42;
(xiv) a leucine at position 101 of SEQ ID NO: 42;
(xv) an aspartic acid at position 101 of SEQ ID NO: 42;
(xvi) a tyrosine at position 101 of SEQ ID NO: 42;
(xvii) a glutamine at position 101 of SEQ ID NO: 42;
(xviii) a lysine at position 101 of SEQ ID NO: 42;
(xix) an alanine at position 102 of SEQ ID NO: 42;
(xx) a serine at position 102 of SEQ ID NO: 42;
(xxi) a histidine at position 102 of SEQ ID NO: 42;
(xxii) a leucine at position 102 of SEQ ID NO: 42;
(xxiii) a tyrosine at position 102 of SEQ ID NO: 42;
(xxiv) a proline at position 102 of SEQ ID NO: 42;
(xxv) a glutamine at position 102 of SEQ ID NO: 42;
(xxvi) a lysine at position 102 of SEQ ID NO: 42;
(xxvii) an alanine at position 103 of SEQ ID NO: 42;
(xxviii) a serine at position 103 of SEQ ID NO: 42;
(xxix) a histidine at position 103 of SEQ ID NO: 42;
(xxx) a leucine at position 103 of SEQ ID NO: 42;
(xxxi) an aspartic acid at position 103 of SEQ ID NO: 42;
(xxxii) a tyrosine at position 103 of SEQ ID NO: 42;
(xxxiii) a proline at position 103 of SEQ ID NO: 42;
(xxxiv) a glutamine at position 103 of SEQ ID NO: 42;
(xxxv) a lysine at position 103 of SEQ ID NO: 42;
(xxxvi) a serine at position 104 of SEQ ID NO: 42;
(xxxvii) a histidine at position 104 of SEQ ID NO: 42;
(xxxviii) a leucine at position 104 of SEQ ID NO: 42;
(xxxix) an aspartic acid at position 104 of SEQ ID NO: 42;
(xl) a tyrosine at position 104 of SEQ ID NO: 42;
(xli) a proline at position 104 of SEQ ID NO: 42;
(xlii) a glutamine at position 104 of SEQ ID NO: 42;
(xliii) a lysine at position 104 of SEQ ID NO: 42;
(xliv) an alanine at position 105 of SEQ ID NO: 42;
(xlv) a histidine at position 105 of SEQ ID NO: 42;
(xlvi) a leucine at position 105 of SEQ ID NO: 42;
(xlvii) an aspartic acid at position 105 of SEQ ID NO: 42;
(xlviii) a tyrosine at position 105 of SEQ ID NO: 42;
(xlix) a proline at position 105 of SEQ ID NO: 42;
(l) a glutamine at position 105 of SEQ ID NO: 42;
(li) a lysine at position 105 of SEQ ID NO: 42;
(lii) an alanine at position 107 of SEQ ID NO: 42;
(liii) a serine at position 107 of SEQ ID NO: 42;
(liv) a histidine at position 107 of SEQ ID NO: 42;
(lv) a leucine at position 107 of SEQ ID NO: 42;
(lvi) an aspartic acid at position 107 of SEQ ID NO: 42;
(lvii) a tyrosine at position 107 of SEQ ID NO: 42;
(lviii) a proline at position 107 of SEQ ID NO: 42;
(lix) a glutamine at position 107 of SEQ ID NO: 42;
(lx) a lysine at position 107 of SEQ ID NO: 42;
(lxi) a threonine at position 41 of SEQ ID NO: 42;
(lxii) a serine at position 47 of SEQ ID NO: 42;
(lxiii) a proline at position 41, an alanine at position 72, a aspartic acid at position 73 an arginine at position 74 and a threonine at position 76 each relative to SEQ ID NO: 42;
(lxiv) a proline at position 41, a leucine at position 51 and a glutamic acid at position 102 each relative to SEQ ID NO: 42;
(lxv) a proline at position 41, a leucine at position 51, a glutamic acid at position 102 and an alanine at position 105 each relative to SEQ ID NO: 42;
(lxvi) a proline at position 41, a leucine at position 51, an alanine at position 72, a aspartic acid at position 73, an arginine at position 74, a threonine at position 76 a glutamic acid at position 102 and an alanine at position 105; or
(lxvii) a sequence having at least about 80% identity to any one of the foregoing.

In one example, the TL1a-binding protein comprises a $V_H$ encoded by a nucleic acid comprising a sequence set forth in any one of SEQ ID NOs: 96, 98, 100, 102, 104, 106, 108, 110, 112, 113, 114, 115, 117, 118 or 222 to 227 or a sequence at least about 80% identical thereto or a nucleic acid that hybridizes thereto under moderate to high stringency conditions.

In one example, the TL1a-binding protein comprises a $V_H$ encoded by a nucleic acid comprising a sequence set forth in SEQ ID NO: 106 or 222 to 227 or a sequence at least about 80% identical thereto or a nucleic acid that hybridizes thereto under moderate to high stringency conditions.

In one example, the TL1a-binding protein comprises a $V_L$ comprising a sequence set forth in any one of SEQ ID NOs: 6, 14, 22, 30, 38, 46, 54, 62, 82, 95, 138, 153, 163 or 174, or a sequence having at least about 80% identity to any one of the foregoing. In one example, the $V_L$ comprises a sequence set forth in any one of SEQ ID NOs: 30, 38, 46, 188 to 194, 196 or 198 to 200 or a sequence having at least about 80% identity to any one of the foregoing.

In one example, the TL1a-binding protein comprises a $V_L$ comprising a sequence set forth in SEQ ID NO: 95, 138, 153, 163 or 174. In one example, the TL1a-binding protein comprises a $V_L$ comprising a sequence set forth in any one of SEQ ID NOs: 46, 62 or 82. In one example, the TL1a-binding protein comprises a $V_L$ comprising a sequence set forth in SEQ ID NO: 46.

In one example, the TL1a-binding protein comprises a $V_L$ comprising a sequence set forth in SEQ ID NO: 46 and comprising one or more of the following substitutions or groups of substitutions:
(i) a threonine at position 76 of SEQ ID NO: 46;
(ii) an threonine at position 23 of SEQ ID NO: 46;
(iii) an asparagine at position 28 of SEQ ID NO: 46;
(iv) a tyrosine at position 33 of SEQ ID NO: 46;
(v) an aspartic acid at position 34 of SEQ ID NO: 46;
(vi) an asparagine at position 53 of SEQ ID NO: 46;
(vii) a serine at position 54 of SEQ ID NO: 46;
(viii) an alanine at position 82 of SEQ ID NO: 46;
(ix) a serine at position 95 of SEQ ID NO: 46;
(x) a serine at position 96 of SEQ ID NO: 46;
(xi) a threonine at position 23, a serine at position 24 and a threonine at position 76 each relative to SEQ ID NO: 46;
(xii) a threonine at position 23 and a threonine at position 76 each relative to SEQ ID NO: 46;
(xiii) a threonine at position 23, a serine at position 24, a threonine at position 76 and a glutamic acid at position 51 each relative to SEQ ID NO: 46;
(xiv) a threonine at position 23, a serine at position 24, a threonine at position 76 and a glycine at position 51 each relative to SEQ ID NO: 46; or
(xv) a sequence having at least about 80% identity to any one of the foregoing.

In one example, the TL1a-binding protein comprises a $V_L$ encoded by a nucleic acid comprising a sequence set forth in any one of SEQ ID NOs: 97, 99, 101, 103, 105, 107, 109, 111, 116 or 228 to 233 or a sequence at least about 80% identical thereto or a nucleic acid that hybridizes thereto under moderate to high stringency conditions.

In one example, the protein comprises a $V_L$ encoded by a nucleic acid comprising a sequence set forth in SEQ ID NO: 107 or 228 to 233 or a sequence at least about 80% identical thereto or a nucleic acid that hybridizes thereto under moderate to high stringency conditions.

In one example, the TL1a-binding protein is a domain antibody, optionally linked to a heavy chain constant region or a Fc or a heavy chain constant domain ($C_H$) 2 and/or $C_{H3}$ or a protein that binds to an immune effector cell.

In one example, a TL1a-binding protein of the disclosure comprises at least a $V_H$ and a $V_L$, wherein the $V_H$ and $V_L$ bind to form a Fv comprising the antigen binding domain. For example, the TL1a-binding protein comprises any one of the following pairs of $V_H$ and $V_L$:

(i) a$V_H$ comprising a sequence set forth in SEQ ID NO: 2 and a $V_L$ comprising a sequence set forth in SEQ ID NO: 6;
(ii) a $V_H$ comprising a sequence set forth in SEQ ID NO: 10 and a $V_L$ comprising a sequence set forth in SEQ ID NO: 14;
(iii) a $V_H$ comprising a sequence set forth in SEQ ID NO: 18 and a $V_L$ comprising a sequence set forth in SEQ ID NO: 22;
(iv) a $V_H$ comprising a sequence set forth in SEQ ID NO: 26 and a $V_L$ comprising a sequence set forth in SEQ ID NO: 30;
(v) a $V_H$ comprising a sequence set forth in SEQ ID NO: 34 and a $V_L$ comprising a sequence set forth in SEQ ID NO:38;
(vi) a $V_H$ comprising a sequence set forth in SEQ ID NO: 42 and a $V_L$ comprising a sequence set forth in SEQ ID NO: 46;
(vii) a $V_H$ comprising a sequence set forth in SEQ ID NO: 50 and a $V_L$ comprising a sequence set forth in SEQ ID NO: 54;
(viii) a $V_H$ comprising a sequence set forth in SEQ ID NO: 58 and a $V_L$ comprising a sequence set forth in SEQ ID NO: 46;
(ix) a $V_H$ comprising a sequence set forth in SEQ ID NO: 42 and a $V_L$ comprising a sequence set forth in SEQ ID NO: 62;
(x) a $V_H$ comprising a sequence set forth in SEQ ID NO: 66 and a $V_L$ comprising a sequence set forth in SEQ ID NO: 62;
(xi) a $V_H$ comprising a sequence set forth in SEQ ID NO: 70 and a $V_L$ comprising a sequence set forth in SEQ ID NO: 62;
(xii) a $V_H$ comprising a sequence set forth in SEQ ID NO: 74 and a $V_L$ comprising a sequence set forth in SEQ ID NO: 62;
(xiii) a $V_H$ comprising a sequence set forth in SEQ ID NO: 78 and a $V_L$ comprising a sequence set forth in SEQ ID NO: 62;
(xiv) a $V_H$ comprising a sequence set forth in SEQ ID NO: 58 and a $V_L$ comprising a sequence set forth in SEQ ID NO: 82;
(xv) a $V_H$ comprising a sequence set forth in SEQ ID NO: 86 and a $V_L$ comprising a sequence set forth in SEQ ID NO: 46;
(xvi) a $V_H$ comprising a sequence set forth in SEQ ID NO: 90 and a $V_L$ comprising a sequence set forth in SEQ ID NO: 46;
(xvii) a $V_H$ comprising a sequence set forth in SEQ ID NO: 58 and a $V_L$ comprising a sequence set forth in SEQ ID NO: 62;
(xviii) a $V_H$ comprising a sequence set forth in SEQ ID NO: 154 and a $V_L$ comprising a sequence set forth in SEQ ID NO: 164;
(xix) a $V_H$ comprising a sequence set forth in SEQ ID NO: 155 and a $V_L$ comprising a sequence set forth in SEQ ID NO: 163;
(xx) a $V_H$ comprising a sequence set forth in SEQ ID NO: 156 and a $V_L$ comprising a sequence set forth in SEQ ID NO: 165;
(xxi) a $V_H$ comprising a sequence set forth in SEQ ID NO: 157 and a $V_L$ comprising a sequence set forth in SEQ ID NO: 166;
(xxii) a $V_H$ comprising a sequence set forth in SEQ ID NO: 158 and a $V_L$ comprising a sequence set forth in SEQ ID NO: 167;
(xxiii) a $V_H$ comprising a sequence set forth in SEQ ID NO: 159 and a $V_L$ comprising a sequence set forth in SEQ ID NO: 168;
(xxiv) a $V_H$ comprising a sequence set forth in SEQ ID NO: 160 and a $V_L$ comprising a sequence set forth in SEQ ID NO: 169;
(xxv) a $V_H$ comprising a sequence set forth in SEQ ID NO: 161 and a $V_L$ comprising a sequence set forth in SEQ ID NO: 170;
(xxvi) a $V_H$ comprising a sequence set forth in SEQ ID NO: 234 and a $V_L$ comprising a sequence set forth in SEQ ID NO: 169;
(xxvii) a $V_H$ comprising a sequence set forth in SEQ ID NO: 154 and a $V_L$ comprising a sequence set forth in SEQ ID NO: 46;
(xxviii) a $V_H$ comprising a sequence set forth in SEQ ID NO: 155 and a $V_L$ comprising a sequence set forth in SEQ ID NO: 46;
(xxix) a $V_H$ comprising a sequence set forth in SEQ ID NO: 156 and a $V_L$ comprising a sequence set forth in SEQ ID NO: 46;
(xxx) a $V_H$ comprising a sequence set forth in SEQ ID NO: 157 and a $V_L$ comprising a sequence set forth in SEQ ID NO: 46;
(xxxi) a $V_H$ comprising a sequence set forth in SEQ ID NO: 158 and a $V_L$ comprising a sequence set forth in SEQ ID NO: 46;
(xxxii) a $V_H$ comprising a sequence set forth in SEQ ID NO: 159 and a $V_L$ comprising a sequence set forth in SEQ ID NO: 46;
(xxxiii) a $V_H$ comprising a sequence set forth in SEQ ID NO: 160 and a $V_L$ comprising a sequence set forth in SEQ ID NO: 46;
(xxxiv) a $V_H$ comprising a sequence set forth in SEQ ID NO: 161 and a $V_L$ comprising a sequence set forth in SEQ ID NO: 46;
(xxxv) a $V_H$ comprising a sequence set forth in SEQ ID NO: 234 and a $V_L$ comprising a sequence set forth in SEQ ID NO: 46;
(xxxvi) a $V_H$ comprising a sequence set forth in SEQ ID NO: 42 and a $V_L$ comprising a sequence set forth in SEQ ID NO: 164;
(xxxvii) a $V_H$ comprising a sequence set forth in SEQ ID NO: 42 and a $V_L$ comprising a sequence set forth in SEQ ID NO: 165;
(xxxviii) a $V_H$ comprising a sequence set forth in SEQ ID NO: 42 and a $V_L$ comprising a sequence set forth in SEQ ID NO: 166;
(xxxix) a $V_H$ comprising a sequence set forth in SEQ ID NO: 42 and a $V_L$ comprising a sequence set forth in SEQ ID NO: 167;
(xl) a $V_H$ comprising a sequence set forth in SEQ ID NO: 42 and a $V_L$ comprising a sequence set forth in SEQ ID NO: 168;
(xli) a $V_H$ comprising a sequence set forth in SEQ ID NO: 42 and a $V_L$ comprising a sequence set forth in SEQ ID NO: 169;
(xlii) a $V_H$ comprising a sequence set forth in SEQ ID NO: 42 and a $V_L$ comprising a sequence set forth in SEQ ID NO: 170;

(xliii) a $V_H$ comprising a sequence set forth in SEQ ID NO: 42 and a $V_L$ comprising a sequence set forth in SEQ ID NO: 171;
(xliv) a $V_H$ comprising a sequence set forth in SEQ ID NO: 42 and a $V_L$ comprising a sequence set forth in SEQ ID NO: 172;
(xlv) a $V_H$ comprising a sequence set forth in SEQ ID NO: 175 and a $V_L$ comprising a sequence set forth in SEQ ID NO: 188;
(xlvi) a $V_H$ comprising a sequence set forth in SEQ ID NO: 176 and a $V_L$ comprising a sequence set forth in SEQ ID NO: 189;
(xlvii) a $V_H$ comprising a sequence set forth in SEQ ID NO: 177 and a $V_L$ comprising a sequence set forth in SEQ ID NO: 190;
(xlviii) a $V_H$ comprising a sequence set forth in SEQ ID NO: 178 and a $V_L$ comprising a sequence set forth in SEQ ID NO: 191;
(xlix) a $V_H$ comprising a sequence set forth in SEQ ID NO: 179 and a $V_L$ comprising a sequence set forth in SEQ ID NO: 192;
(l) a $V_H$ comprising a sequence set forth in SEQ ID NO: 180 and a $V_L$ comprising a sequence set forth in SEQ ID NO: 193;
(li) a $V_H$ comprising a sequence set forth in SEQ ID NO: 181 and a $V_L$ comprising a sequence set forth in SEQ ID NO: 194;
(lii) a $V_H$ comprising a sequence set forth in SEQ ID NO: 182 and a $V_L$ comprising a sequence set forth in SEQ ID NO: 195;
(liii) a $V_H$ comprising a sequence set forth in SEQ ID NO: 183 and a $V_L$ comprising a sequence set forth in SEQ ID NO: 196;
(liv) a $V_H$ comprising a sequence set forth in SEQ ID NO: 184 and a $V_L$ comprising a sequence set forth in SEQ ID NO: 197;
(lv) a $V_H$ comprising a sequence set forth in SEQ ID NO: 185 and a $V_L$ comprising a sequence set forth in SEQ ID NO: 198;
(lvi) a $V_H$ comprising a sequence set forth in SEQ ID NO: 186 and a $V_L$ comprising a sequence set forth in SEQ ID NO: 199; or
(lvii) a $V_H$ comprising a sequence set forth in SEQ ID NO: 187 and a $V_L$ comprising a sequence set forth in SEQ ID NO: 200.

In one example, the TL1a-binding protein comprises any one of the following pairs of $V_H$ and $V_L$:
(i) a $V_H$ comprising a sequence set forth in SEQ ID NO: 26 and a $V_L$ comprising a sequence set forth in SEQ ID NO: 30;
(ii) a $V_H$ comprising a sequence set forth in SEQ ID NO: 34 and a $V_L$ comprising a sequence set forth in SEQ ID NO:38;
(iii) a $V_H$ comprising a sequence set forth in SEQ ID NO: 42 and a $V_L$ comprising a sequence set forth in SEQ ID NO: 46;
(iv) a $V_H$ comprising a sequence set forth in SEQ ID NO: 175 and a $V_L$ comprising a sequence set forth in SEQ ID NO: 188;
(v) a $V_H$ comprising a sequence set forth in SEQ ID NO: 176 and a $V_L$ comprising a sequence set forth in SEQ ID NO: 189;
(vi) a $V_H$ comprising a sequence set forth in SEQ ID NO: 177 and a $V_L$ comprising a sequence set forth in SEQ ID NO: 190;
(vii) a $V_H$ comprising a sequence set forth in SEQ ID NO: 178 and a $V_L$ comprising a sequence set forth in SEQ ID NO: 191;
(viii) a $V_H$ comprising a sequence set forth in SEQ ID NO: 179 and a $V_L$ comprising a sequence set forth in SEQ ID NO: 192;
(ix) a $V_H$ comprising a sequence set forth in SEQ ID NO: 180 and a $V_L$ comprising a sequence set forth in SEQ ID NO: 193;
(x) a $V_H$ comprising a sequence set forth in SEQ ID NO: 181 and a $V_L$ comprising a sequence set forth in SEQ ID NO: 194;
(xi) a $V_H$ comprising a sequence set forth in SEQ ID NO: 183 and a $V_L$ comprising a sequence set forth in SEQ ID NO: 196;
(xii) a $V_H$ comprising a sequence set forth in SEQ ID NO: 185 and a $V_L$ comprising a sequence set forth in SEQ ID NO: 198;
(xiii) a $V_H$ comprising a sequence set forth in SEQ ID NO: 186 and a $V_L$ comprising a sequence set forth in SEQ ID NO: 199; or
(xiv) a $V_H$ comprising a sequence set forth in SEQ ID NO: 187 and a $V_L$ comprising a sequence set forth in SEQ ID NO: 200; In one example, the TL1a-binding protein comprises a $V_H$ comprising a sequence set forth in SEQ ID NO: 94 and a $V_L$ comprising a sequence set forth in SEQ ID NO: 95.

In one example, the TL1a-binding protein comprises a $V_H$ comprising a sequence set forth in SEQ ID NO: 137 and a $V_L$ comprising a sequence set forth in SEQ ID NO: 138.

In one example, the TL1a-binding protein comprises a $V_H$ comprising a sequence set forth in SEQ ID NO: 152 and a $V_L$ comprising a sequence set forth in SEQ ID NO: 153.

In one example, the TL1a-binding protein comprises a $V_H$ comprising a sequence set forth in SEQ ID NO: 173 and a $V_L$ comprising a sequence set forth in SEQ ID NO: 174.

In one example, the TL1a-binding protein comprises any one of the following pairs of $V_H$ and $V_L$:
(i) a $V_H$ comprising a sequence set forth in SEQ ID NO: 58 and a $V_L$ comprising a sequence set forth in SEQ ID NO: 46;
(ii) a $V_H$ comprising a sequence set forth in SEQ ID NO: 42 and a $V_L$ comprising a sequence set forth in SEQ ID NO: 62;
(iii) a $V_H$ comprising a sequence set forth in SEQ ID NO: 66 and a $V_L$ comprising a sequence set forth in SEQ ID NO: 62;
(iv) a $V_H$ comprising a sequence set forth in SEQ ID NO: 70 and a $V_L$ comprising a sequence set forth in SEQ ID NO: 62;
(v) a $V_H$ comprising a sequence set forth in SEQ ID NO: 74 and a $V_L$ comprising a sequence set forth in SEQ ID NO: 62;
(vi) a $V_H$ comprising a sequence set forth in SEQ ID NO: 78 and a $V_L$ comprising a sequence set forth in SEQ ID NO: 62;
(vii) a $V_H$ comprising a sequence set forth in SEQ ID NO: 58 and a $V_L$ comprising a sequence set forth in SEQ ID NO: 82;
(viii) a $V_H$ comprising a sequence set forth in SEQ ID NO: 86 and a $V_L$ comprising a sequence set forth in SEQ ID NO: 46;
(ix) a $V_H$ comprising a sequence set forth in SEQ ID NO: 90 and a $V_L$ comprising a sequence set forth in SEQ ID NO: 46; or
(x) a $V_H$ comprising a sequence set forth in SEQ ID NO: 58 and a $V_L$ comprising a sequence set forth in SEQ ID NO: 62.

For example, the TL1a-binding protein comprises a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:
(i) the $V_H$ comprises an alanine at position 16 of SEQ ID NO: 42;
(ii) the $V_H$ comprises an alanine at position 100 of SEQ ID NO: 42 and the $V_L$ comprises a threonine at position 76 of SEQ ID NO: 46;

(iii) the $V_H$ comprises a serine at position 100 of SEQ ID NO: 42 and the $V_L$ comprises a threonine at position 76 of SEQ ID NO: 46;
(iv) the $V_H$ comprises a histidine at position 100 of SEQ ID NO: 42 and the $V_L$ comprises a threonine at position 76 of SEQ ID NO: 46;
(v) the $V_H$ comprises a leucine at position 100 of SEQ ID NO: 42 and the $V_L$ comprises a threonine at position 76 of SEQ ID NO: 46;
(vi) the $V_H$ comprises an aspartic acid at position 100 of SEQ ID NO: 42 and the $V_L$ comprises a threonine at position 76 of SEQ ID NO: 46;
(vii) the $V_H$ comprises a tyrosine at position 100 of SEQ ID NO: 42 and the $V_L$ comprises a threonine at position 76 of SEQ ID NO: 46;
(viii) the $V_H$ comprises a proline at position 100 of SEQ ID NO: 42 and the $V_L$ comprises a threonine at position 76 of SEQ ID NO: 46;
(ix) the $V_H$ comprises a glutamine at position 100 of SEQ ID NO: 42 and the $V_L$ comprises a threonine at position 76 of SEQ ID NO: 46;
(x) the $V_H$ comprises a lysine at position 100 of SEQ ID NO: 42 and the $V_L$ comprises a threonine at position 76 of SEQ ID NO: 46;
(xi) the $V_H$ comprises an alanine at position 101 of SEQ ID NO: 42 and the $V_L$ comprises a threonine at position 76 of SEQ ID NO: 46;
(xii) the $V_H$ comprises a serine at position 101 of SEQ ID NO: 42 and the $V_L$ comprises a threonine at position 76 of SEQ ID NO: 46;
(xiii) the $V_H$ comprises a histidine at position 101 of SEQ ID NO: 42 and the $V_L$ comprises a threonine at position 76 of SEQ ID NO: 46;
(xiv) the $V_H$ comprises a leucine at position 101 of SEQ ID NO: 42 and the $V_L$ comprises a threonine at position 76 of SEQ ID NO: 46;
(xv) the $V_H$ comprises an aspartic acid at position 101 of SEQ ID NO: 42 and the $V_L$ comprises a threonine at position 76 of SEQ ID NO: 46;
(xvi) the $V_H$ comprises a tyrosine at position 101 of SEQ ID NO: 42 and the $V_L$ comprises a threonine at position 76 of SEQ ID NO: 46;
(xvii) the $V_H$ comprises a glutamine at position 101 of SEQ ID NO: 42 and the $V_L$ comprises a threonine at position 76 of SEQ ID NO: 46;
(xviii) the $V_H$ comprises a lysine at position 101 of SEQ ID NO: 42 and the $V_L$ comprises a threonine at position 76 of SEQ ID NO: 46;
(xix) the $V_H$ comprises an alanine at position 102 of SEQ ID NO: 42 and the $V_L$ comprises a threonine at position 76 of SEQ ID NO: 46;
(xx) the $V_H$ comprises a serine at position 102 of SEQ ID NO: 42 and the $V_L$ comprises a threonine at position 76 of SEQ ID NO: 46;
(xxi) the $V_H$ comprises a histidine at position 102 of SEQ ID NO: 42 and the $V_L$ comprises a threonine at position 76 of SEQ ID NO: 46;
(xxii) the $V_H$ comprises a leucine at position 102 of SEQ ID NO: 42 and the $V_L$ comprises a threonine at position 76 of SEQ ID NO: 46;
(xxiii) the $V_H$ comprises a tyrosine at position 102 of SEQ ID NO: 42 and the $V_L$ comprises a threonine at position 76 of SEQ ID NO: 46;
(xxiv) the $V_H$ comprises a proline at position 102 of SEQ ID NO: 42 and the $V_L$ comprises a threonine at position 76 of SEQ ID NO: 46;
(xxv) the $V_H$ comprises a glutamine at position 102 of SEQ ID NO: 42 and the $V_L$ comprises a threonine at position 76 of SEQ ID NO: 46;
(xxvi) the $V_H$ comprises a lysine at position 102 of SEQ ID NO: 42 and the $V_L$ comprises a threonine at position 76 of SEQ ID NO: 46;
(xxvii) the $V_H$ comprises an alanine at position 103 of SEQ ID NO: 42 and the $V_L$ comprises a threonine at position 76 of SEQ ID NO: 46;
(xxviii) the $V_H$ comprises a serine at position 103 of SEQ ID NO: 42 and the $V_L$ comprises a threonine at position 76 of SEQ ID NO: 46;
(xxix) the $V_H$ comprises a histidine at position 103 of SEQ ID NO: 42 and the $V_L$ comprises a threonine at position 76 of SEQ ID NO: 46;
(xxx) the $V_H$ comprises a leucine at position 103 of SEQ ID NO: 42 and the $V_L$ comprises a threonine at position 76 of SEQ ID NO: 46;
(xxxi) the $V_H$ comprises an aspartic acid at position 103 of SEQ ID NO: 42 and the $V_L$ comprises a threonine at position 76 of SEQ ID NO: 46;
(xxxii) the $V_H$ comprises a tyrosine at position 103 of SEQ ID NO: 42 and the $V_L$ comprises a threonine at position 76 of SEQ ID NO: 46;
(xxxiii) the $V_H$ comprises a proline at position 103 of SEQ ID NO: 42 and the $V_L$ comprises a threonine at position 76 of SEQ ID NO: 46;
(xxxiv) the $V_H$ comprises a glutamine at position 103 of SEQ ID NO: 42 and the $V_L$ comprises a threonine at position 76 of SEQ ID NO: 46;
(xxxv) the $V_H$ comprises a lysine at position 103 of SEQ ID NO: 42 and the $V_L$ comprises a threonine at position 76 of SEQ ID NO: 46;
(xxxvi) the $V_H$ comprises a serine at position 104 of SEQ ID NO: 42 and the $V_L$ comprises a threonine at position 76 of SEQ ID NO: 46;
(xxxvii) the $V_H$ comprises a histidine at position 104 of SEQ ID NO: 42 and the $V_L$ comprises a threonine at position 76 of SEQ ID NO: 46;
(xxxviii) the $V_H$ comprises a leucine at position 104 of SEQ ID NO: 42 and the $V_L$ comprises a threonine at position 76 of SEQ ID NO: 46;
(xxxix) the $V_H$ comprises an aspartic acid at position 104 of SEQ ID NO: 42 and the $V_L$ comprises a threonine at position 76 of SEQ ID NO: 46;
(xl) the $V_H$ comprises a tyrosine at position 104 of SEQ ID NO: 42 and the $V_L$ comprises a threonine at position 76 of SEQ ID NO: 46;
(xli) the $V_H$ comprises a proline at position 104 of SEQ ID NO: 42 and the $V_L$ comprises a threonine at position 76 of SEQ ID NO: 46;
(xlii) the $V_H$ comprises a glutamine at position 104 of SEQ ID NO: 42 and the $V_L$ comprises a threonine at position 76 of SEQ ID NO: 46;
(xliii) the $V_H$ comprises a lysine at position 104 of SEQ ID NO: 42 and the $V_L$ comprises a threonine at position 76 of SEQ ID NO: 46;
(xliv) the $V_H$ comprises an alanine at position 105 of SEQ ID NO: 42 and the $V_L$ comprises a threonine at position 76 of SEQ ID NO: 46;
(xlv) the $V_H$ comprises a histidine at position 105 of SEQ ID NO: 42 and the $V_L$ comprises a threonine at position 76 of SEQ ID NO: 46;
(xlvi) the $V_H$ comprises a leucine at position 105 of SEQ ID NO: 42 and the $V_L$ comprises a threonine at position 76 of SEQ ID NO: 46;

(xlvii) the $V_H$ comprises an aspartic acid at position 105 of SEQ ID NO: 42 and the $V_L$ comprises a threonine at position 76 of SEQ ID NO: 46;

(xlviii) the $V_H$ comprises a tyrosine at position 105 of SEQ ID NO: 42 and the $V_L$ comprises a threonine at position 76 of SEQ ID NO: 46;

(xlix) the $V_H$ comprises a proline at position 105 of SEQ ID NO: 42 and the $V_L$ comprises a threonine at position 76 of SEQ ID NO: 46;

(l) the $V_H$ comprises a glutamine at position 105 of SEQ ID NO: 42 and the $V_L$ comprises a threonine at position 76 of SEQ ID NO: 46;

(li) the $V_H$ comprises a lysine at position 105 of SEQ ID NO: 42 and the $V_L$ comprises a threonine at position 76 of SEQ ID NO: 46;

(lii) the $V_H$ comprises an alanine at position 107 of SEQ ID NO: 42 and the $V_L$ comprises a threonine at position 76 of SEQ ID NO: 46;

(liii) the $V_H$ comprises a serine at position 107 of SEQ ID NO: 42 and the $V_L$ comprises a threonine at position 76 of SEQ ID NO: 46;

(liv) the $V_H$ comprises a histidine at position 107 of SEQ ID NO: 42 and the $V_L$ comprises a threonine at position 76 of SEQ ID NO: 46;

(lv) the $V_H$ comprises a leucine at position 107 of SEQ ID NO: 42 and the $V_L$ comprises a threonine at position 76 of SEQ ID NO: 46;

(lvi) the $V_H$ comprises an aspartic acid at position 107 of SEQ ID NO: 42 and the $V_L$ comprises a threonine at position 76 of SEQ ID NO: 46;

(lvii) the $V_H$ comprises a tyrosine at position 107 of SEQ ID NO: 42 and the $V_L$ comprises a threonine at position 76 of SEQ ID NO: 46;

(lviii) the $V_H$ comprises a proline at position 107 of SEQ ID NO: 42 and the $V_L$ comprises a threonine at position 76 of SEQ ID NO: 46;

(lix) the $V_H$ comprises a glutamine at position 107 of SEQ ID NO: 42 and the $V_L$ comprises a threonine at position 76 of SEQ ID NO: 46;

(lx) the $V_H$ comprises a lysine at position 107 of SEQ ID NO: 42 and the $V_L$ comprises a threonine at position 76 of SEQ ID NO: 46;

(lxi) the $V_H$ comprises a threonine at position 41 of SEQ ID NO: 42 and the $V_L$ comprises an alanine at position 23 of SEQ ID NO: 46;

(lxii) the $V_H$ comprises a threonine at position 41 of SEQ ID NO: 42 and the $V_L$ comprises an aspartic acid at position 28 of SEQ ID NO: 46;

(lxiii) the $V_H$ comprises a threonine at position 41 of SEQ ID NO: 42 and the $V_L$ comprises a tyrosine at position 33 of SEQ ID NO: 46;

(lxiv) the $V_H$ comprises a threonine at position 41 of SEQ ID NO: 42 and the $V_L$ comprises an aspartic acid at position 34 of SEQ ID NO: 46;

(lxv) the $V_H$ comprises a threonine at position 41 of SEQ ID NO: 42 and the $V_L$ comprises an asparagine at position 53 of SEQ ID NO: 46;

(lxvi) the $V_H$ comprises a threonine at position 41 of SEQ ID NO: 42 and the $V_L$ comprises a serine at position 54 of SEQ ID NO: 46;

(lxvii) the $V_H$ comprises a threonine at position 41 of SEQ ID NO: 42 and the $V_L$ comprises a alanine at position 82 of SEQ ID NO: 46;

(lxviii) the $V_H$ comprises a threonine at position 41 of SEQ ID NO: 42 and the $V_L$ comprises a serine at position 95 of SEQ ID NO: 46;

(lxix) the $V_H$ comprises a threonine at position 41 of SEQ ID NO: 42 and the $V_L$ comprises a serine at position 96 of SEQ ID NO: 46;

(lxx) the $V_H$ comprises a threonine at position 41 of SEQ ID NO: 42 and the $V_L$ comprises a threonine at position 76 of SEQ ID NO: 46;

(lxxi) the $V_H$ comprises a serine at position 47 of SEQ ID NO: 42 and the $V_L$ comprises an threonine at position 23 of SEQ ID NO: 46;

(lxxii) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 76 of SEQ ID NO: 46;

(lxxiii) the $V_H$ comprises a proline at position 41, a leucine at position 51 and a glutamic acid at position 102 each relative to SEQ ID NO: 42 and the $V_L$ comprises a serine at position 24 and a threonine at position 76 each relative to SEQ ID NO: 46;

(lxxiv) the $V_H$ comprises a proline at position 41, a leucine at position 51 and a glutamic acid at position 102 each relative to SEQ ID NO: 42 and the $V_L$ comprises a threonine at position 23, a serine at position 24 and a threonine at position 76 each relative to SEQ ID NO: 46;

(lxxv) the $V_H$ comprises a proline at position 41, a leucine at position 51 and a glutamic acid at position 102 each relative to SEQ ID NO: 42 and the $V_L$ comprises a threonine at position 23 and a threonine at position 76 each relative to SEQ ID NO: 46;

(lxxvi) the $V_H$ comprises a proline at position 41, a leucine at position 51 and a glutamic acid at position 102 each relative to SEQ ID NO: 42 and the $V_L$ comprises a threonine at position 76 of SEQ ID NO: 46;

(lxxvii) the $V_H$ comprises a proline at position 41, a leucine at position 51, a glutamic acid at position 102 and an alanine at position 105 each relative to SEQ ID NO: 42 and the $V_L$ comprises a threonine at position 23, a serine at position 24 and a threonine at position 76 each relative to SEQ ID NO: 46;

(lxxviii) the $V_H$ comprises a proline at position 41, a leucine at position 51, a glutamic acid at position 102 and an alanine at position 105 each relative to SEQ ID NO: 42 and the $V_L$ comprises a threonine at position 76 of SEQ ID NO: 46;

(lxxix) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24 and a threonine at position 76 each relative to SEQ ID NO: 46;

(lxxx) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24, a threonine at position 76 and a glutamic acid at position 51 each relative to SEQ ID NO: 46;

(lxxxi) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glutamic acid at position 51 each relative to SEQ ID NO: 46; or (lxxxii) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glycine at position 51 each relative to SEQ ID NO: 46.

In one example, the $V_H$ and the $V_L$ are in a single polypeptide chain. For example, the TL1a-binding protein is:

(i) a single chain Fv fragment (scFv);
(ii) a dimeric scFv (di-scFv);
(iii) one of (i) or (ii) linked to a heavy chain constant region or a Fc or a heavy chain constant domain ($C_H$) 2 and/or $C_H3$; or
(iv) one of (i) or (ii) linked to a protein that binds to an immune effector cell.

In another example, the $V_L$ and $V_H$ are in separate polypeptide chains. For example, the TL1a-binding protein is:

(i) a diabody;
(ii) a triabody;
(iii) a tetrabody;
(iv) a Fab;
(v) a $F(ab')_2$;
(vi) a Fv;
(vii) one of (i) to (vi) linked to a heavy chain constant region or a Fc or a heavy chain constant domain ($C_H$) 2 and/or $C_{H3}$; or
(viii) one of (i) to (vi) linked to a protein that binds to an immune effector cell.

In an exemplary form of the disclosure, the TL1a-binding protein is an antibody.

Exemplary TL1a-binding proteins of the disclosure are chimeric, de-immunized, humanized, human, synhumanized or primatized.

In one example, the disclosure provides an antibody comprising an antigen binding domain, wherein the antigen binding domain specifically binds to TL1a and, wherein the antibody inhibits interaction of TL1a and DR3 and does not inhibit interaction of TL1a and DcR3, the antigen binding domain comprising any one of:

(i) a $V_H$ comprising a sequence set forth in SEQ ID NO: 2 and a $V_L$ comprising a sequence set forth in SEQ ID NO: 6;
(ii) a $V_H$ comprising a sequence set forth in SEQ ID NO: 10 and a $V_L$ comprising a sequence set forth in SEQ ID NO: 14;
(iii) a $V_H$ comprising a sequence set forth in SEQ ID NO: 18 and a $V_L$ comprising a sequence set forth in SEQ ID NO: 22;
(iv) a $V_H$ comprising a sequence set forth in SEQ ID NO: 26 and a $V_L$ comprising a sequence set forth in SEQ ID NO: 30;
(v) a $V_H$ comprising a sequence set forth in SEQ ID NO: 34 and a $V_L$ comprising a sequence set forth in SEQ ID NO:38;
(vi) a $V_H$ comprising a sequence set forth in SEQ ID NO: 42 and a $V_L$ comprising a sequence set forth in SEQ ID NO: 46;
(vii) a $V_H$ comprising a sequence set forth in SEQ ID NO: 50 and a $V_L$ comprising a sequence set forth in SEQ ID NO: 54;
(viii) a $V_H$ comprising a sequence set forth in SEQ ID NO: 58 and a $V_L$ comprising a sequence set forth in SEQ ID NO: 46;
(ix) a $V_H$ comprising a sequence set forth in SEQ ID NO: 42 and a $V_L$ comprising a sequence set forth in SEQ ID NO: 62;
(x) a $V_H$ comprising a sequence set forth in SEQ ID NO: 66 and a $V_L$ comprising a sequence set forth in SEQ ID NO: 62;
(xi) a $V_H$ comprising a sequence set forth in SEQ ID NO: 70 and a $V_L$ comprising a sequence set forth in SEQ ID NO: 62;
(xii) a $V_H$ comprising a sequence set forth in SEQ ID NO: 74 and a $V_L$ comprising a sequence set forth in SEQ ID NO: 62;
(xiii) a $V_H$ comprising a sequence set forth in SEQ ID NO: 78 and a $V_L$ comprising a sequence set forth in SEQ ID NO: 62;
(xiv) a $V_H$ comprising a sequence set forth in SEQ ID NO: 58 and a $V_L$ comprising a sequence set forth in SEQ ID NO: 82;
(xv) a $V_H$ comprising a sequence set forth in SEQ ID NO: 86 and a $V_L$ comprising a sequence set forth in SEQ ID NO: 46;
(xvi) a $V_H$ comprising a sequence set forth in SEQ ID NO: 90 and a $V_L$ comprising a sequence set forth in SEQ ID NO: 46;
(xvii) a $V_H$ comprising a sequence set forth in SEQ ID NO: 58 and a $V_L$ comprising a sequence set forth in SEQ ID NO: 62;
(xviii) a $V_H$ comprising a sequence set forth in SEQ ID NO: 154 and a $V_L$ comprising a sequence set forth in SEQ ID NO: 164;
(xix) a $V_H$ comprising a sequence set forth in SEQ ID NO: 155 and a $V_L$ comprising a sequence set forth in SEQ ID NO: 163;
(xx) a $V_H$ comprising a sequence set forth in SEQ ID NO: 156 and a $V_L$ comprising a sequence set forth in SEQ ID NO: 165;
(xxi) a $V_H$ comprising a sequence set forth in SEQ ID NO: 157 and a $V_L$ comprising a sequence set forth in SEQ ID NO: 166;
(xxii) a $V_H$ comprising a sequence set forth in SEQ ID NO: 158 and a $V_L$ comprising a sequence set forth in SEQ ID NO: 167;
(xxiii) a $V_H$ comprising a sequence set forth in SEQ ID NO: 159 and a $V_L$ comprising a sequence set forth in SEQ ID NO: 168;
(xxiv) a $V_H$ comprising a sequence set forth in SEQ ID NO: 160 and a $V_L$ comprising a sequence set forth in SEQ ID NO: 169;
(xxv) a $V_H$ comprising a sequence set forth in SEQ ID NO: 161 and a $V_L$ comprising a sequence set forth in SEQ ID NO: 170;
(xxvi) a $V_H$ comprising a sequence set forth in SEQ ID NO: 234 and a $V_L$ comprising a sequence set forth in SEQ ID NO: 169;
(xxvii) a $V_H$ comprising a sequence set forth in SEQ ID NO: 154 and a $V_L$ comprising a sequence set forth in SEQ ID NO: 46;
(xxviii) a $V_H$ comprising a sequence set forth in SEQ ID NO: 155 and a $V_L$ comprising a sequence set forth in SEQ ID NO: 46;
(xxix) a $V_H$ comprising a sequence set forth in SEQ ID NO: 156 and a $V_L$ comprising a sequence set forth in SEQ ID NO: 46;
(xxx) a $V_H$ comprising a sequence set forth in SEQ ID NO: 157 and a $V_L$ comprising a sequence set forth in SEQ ID NO: 46;
(xxxi) a $V_H$ comprising a sequence set forth in SEQ ID NO: 158 and a $V_L$ comprising a sequence set forth in SEQ ID NO: 46;
(xxxii) a $V_H$ comprising a sequence set forth in SEQ ID NO: 159 and a $V_L$ comprising a sequence set forth in SEQ ID NO: 46;
(xxxiii) a $V_H$ comprising a sequence set forth in SEQ ID NO: 160 and a $V_L$ comprising a sequence set forth in SEQ ID NO: 46;
(xxxiv) a $V_H$ comprising a sequence set forth in SEQ ID NO: 161 and a $V_L$ comprising a sequence set forth in SEQ ID NO: 46;

(xxxv) a $V_H$ comprising a sequence set forth in SEQ ID NO: 234 and a $V_L$ comprising a sequence set forth in SEQ ID NO: 46;

(xxxvi) a $V_H$ comprising a sequence set forth in SEQ ID NO: 42 and a $V_L$ comprising a sequence set forth in SEQ ID NO: 164;

(xxxvii) a $V_H$ comprising a sequence set forth in SEQ ID NO: 42 and a $V_L$ comprising a sequence set forth in SEQ ID NO: 165;

(xxxviii) a $V_H$ comprising a sequence set forth in SEQ ID NO: 42 and a $V_L$ comprising a sequence set forth in SEQ ID NO: 166;

(xxxix) a $V_H$ comprising a sequence set forth in SEQ ID NO: 42 and a $V_L$ comprising a sequence set forth in SEQ ID NO: 167;

(xl) a $V_H$ comprising a sequence set forth in SEQ ID NO: 42 and a $V_L$ comprising a sequence set forth in SEQ ID NO: 168;

(xli) a $V_H$ comprising a sequence set forth in SEQ ID NO: 42 and a $V_L$ comprising a sequence set forth in SEQ ID NO: 169;

(xlii) a $V_H$ comprising a sequence set forth in SEQ ID NO: 42 and a $V_L$ comprising a sequence set forth in SEQ ID NO: 170;

(xliii) a $V_H$ comprising a sequence set forth in SEQ ID NO: 42 and a $V_L$ comprising a sequence set forth in SEQ ID NO: 171;

(xliv) a $V_H$ comprising a sequence set forth in SEQ ID NO: 42 and a $V_L$ comprising a sequence set forth in SEQ ID NO: 172;

(xlv) a $V_H$ comprising a sequence set forth in SEQ ID NO: 175 and a $V_L$ comprising a sequence set forth in SEQ ID NO: 188;

(xlvi) a $V_H$ comprising a sequence set forth in SEQ ID NO: 176 and a $V_L$ comprising a sequence set forth in SEQ ID NO: 189;

(xlvii) a $V_H$ comprising a sequence set forth in SEQ ID NO: 177 and a $V_L$ comprising a sequence set forth in SEQ ID NO: 190;

(xlviii) a $V_H$ comprising a sequence set forth in SEQ ID NO: 178 and a $V_L$ comprising a sequence set forth in SEQ ID NO: 191;

(xlix) a $V_H$ comprising a sequence set forth in SEQ ID NO: 179 and a $V_L$ comprising a sequence set forth in SEQ ID NO: 192;

(l) a $V_H$ comprising a sequence set forth in SEQ ID NO: 180 and a $V_L$ comprising a sequence set forth in SEQ ID NO: 193;

(li) a $V_H$ comprising a sequence set forth in SEQ ID NO: 181 and a $V_L$ comprising a sequence set forth in SEQ ID NO: 194;

(lii) a $V_H$ comprising a sequence set forth in SEQ ID NO: 182 and a $V_L$ comprising a sequence set forth in SEQ ID NO: 195;

(liii) a $V_H$ comprising a sequence set forth in SEQ ID NO: 183 and a $V_L$ comprising a sequence set forth in SEQ ID NO: 196;

(liv) a $V_H$ comprising a sequence set forth in SEQ ID NO: 184 and a $V_L$ comprising a sequence set forth in SEQ ID NO: 197;

(lv) a $V_H$ comprising a sequence set forth in SEQ ID NO: 185 and a $V_L$ comprising a sequence set forth in SEQ ID NO: 198;

(lvi) a $V_H$ comprising a sequence set forth in SEQ ID NO: 186 and a $V_L$ comprising a sequence set forth in SEQ ID NO: 199; or (lvii) a $V_H$ comprising a sequence set forth in SEQ ID NO: 187 and a $V_L$ comprising a sequence set forth in SEQ ID NO: 200.

In one example, the antibody comprises any one of the following pairs of $V_H$ and $V_L$:

(i) a $V_H$ comprising a sequence set forth in SEQ ID NO: 26 and a $V_L$ comprising a sequence set forth in SEQ ID NO: 30;

(ii) a $V_H$ comprising a sequence set forth in SEQ ID NO: 34 and a $V_L$ comprising a sequence set forth in SEQ ID NO:38; and (iii) a $V_H$ comprising a sequence set forth in SEQ ID NO: 42 and a $V_L$ comprising a sequence set forth in SEQ ID NO: 46.

In one example, the antibody comprises any one of the following pairs of $V_H$ and $V_L$:

(i) a $V_H$ comprising a sequence set forth in SEQ ID NO: 42 and a $V_L$ comprising a sequence set forth in SEQ ID NO: 46;

(ii) a $V_H$ encoded by a nucleic acid comprising a sequence at least about 95% identical to the sequence set forth in SEQ ID NO: 106 or a nucleic acid that hybridizes thereto under moderate to high stringency conditions and a $V_L$ encoded by a nucleic acid comprising a sequence at least about 95% identical to the sequence set forth in SEQ ID NO: 107 or a nucleic acid that hybridizes thereto under moderate to high stringency conditions;

(iii) a $V_H$ comprising a sequence set forth in SEQ ID NO: 175 and a $V_L$ comprising a sequence set forth in SEQ ID NO: 188;

(iv) a $V_H$ encoded by a nucleic acid comprising a sequence at least about 95% identical to the sequence set forth in SEQ ID NO: 222 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(v) a $V_H$ comprising a sequence set forth in SEQ ID NO: 176 and a $V_L$ comprising a sequence set forth in SEQ ID NO: 189;

(vi) a $V_H$ encoded by a nucleic acid comprising a sequence at least about 95% identical to the sequence set forth in SEQ ID NO: 223 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(vii) a $V_H$ comprising a sequence set forth in SEQ ID NO: 177 and a $V_L$ comprising a sequence set forth in SEQ ID NO: 190;

(viii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 229 or a nucleic acid that hybridizes thereto under moderate to high stringency conditions;

(ix) a $V_H$ comprising a sequence set forth in SEQ ID NO: 178 and a $V_L$ comprising a sequence set forth in SEQ ID NO: 191;

(x) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xi) a $V_H$ comprising a sequence set forth in SEQ ID NO: 179 and a $V_L$ comprising a sequence set forth in SEQ ID NO: 192;

(xii) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 231 or a nucleic acid that hybridizes thereto under moderate to high stringency conditions;

(xiii) a $V_H$ comprising a sequence set forth in SEQ ID NO: 180 and a $V_L$ comprising a sequence set forth in SEQ ID NO: 193;

(xiv) a $V_H$ encoded by a nucleic acid comprising a sequence at least about 95% identical to the sequence set forth in SEQ ID NO: 224 or a nucleic acid that hybridizes thereto under moderate to high stringency conditions and a $V_L$ encoded by a nucleic acid comprising a sequence at least about 95% identical to the sequence set forth in SEQ ID NO: 228 or a nucleic acid that hybridizes thereto under moderate to high stringency conditions;

(xv) a $V_H$ comprising a sequence set forth in SEQ ID NO: 181 and a $V_L$ comprising a sequence set forth in SEQ ID NO: 194;

(xvi) a $V_H$ encoded by a nucleic acid comprising a sequence at least about 95% identical to the sequence set forth in SEQ ID NO: 225 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xvii) a $V_H$ comprising a sequence set forth in SEQ ID NO: 183 and a $V_L$ comprising a sequence set forth in SEQ ID NO: 196;

(xviii) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 230 or a nucleic acid that hybridizes thereto under moderate to high stringency conditions;

(xix) a $V_H$ comprising a sequence set forth in SEQ ID NO: 185 and a $V_L$ comprising a sequence set forth in SEQ ID NO: 198;

(xx) a $V_H$ encoded by a nucleic acid comprising a sequence at least about 95% identical to the sequence set forth in SEQ ID NO: 226 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxi) a $V_H$ comprising a sequence set forth in SEQ ID NO: 186 and a $V_L$ comprising a sequence set forth in SEQ ID NO: 199;

(xxii) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 232 or a nucleic acid that hybridizes thereto under moderate to high stringency conditions;

(xxiii) a $V_H$ comprising a sequence set forth in SEQ ID NO: 187 and a $V_L$ comprising a sequence set forth in SEQ ID NO: 200; or (xxiv) a $V_H$ encoded by a nucleic acid comprising a sequence at least about 95% identical to the sequence set forth in SEQ ID NO: 227 or a nucleic acid that hybridizes thereto under moderate to high stringency conditions and a $V_L$ encoded by a nucleic acid comprising a sequence at least about 95% identical to the sequence set forth in SEQ ID NO: 233 or a nucleic acid that hybridizes thereto under moderate to high stringency conditions.

In one example, the antibody comprises a $V_H$ comprising a sequence set forth in SEQ ID NO: 94 and a $V_L$ comprising a sequence set forth in SEQ ID NO: 95.

In one example, the antibody comprises any one of the following pairs of $V_H$ and $V_L$:

(i) a $V_H$ comprising a sequence set forth in SEQ ID NO: 58 and a $V_L$ comprising a sequence set forth in SEQ ID NO: 46;

(ii) a $V_H$ comprising a sequence set forth in SEQ ID NO: 42 and a $V_L$ comprising a sequence set forth in SEQ ID NO: 62;

(iii) a $V_H$ comprising a sequence set forth in SEQ ID NO: 66 and a $V_L$ comprising a sequence set forth in SEQ ID NO: 62;

(iv) a $V_H$ comprising a sequence set forth in SEQ ID NO: 70 and a $V_L$ comprising a sequence set forth in SEQ ID NO: 62;

(v) a $V_H$ comprising a sequence set forth in SEQ ID NO: 74 and a $V_L$ comprising a sequence set forth in SEQ ID NO: 62;

(vi) a $V_H$ comprising a sequence set forth in SEQ ID NO: 78 and a $V_L$ comprising a sequence set forth in SEQ ID NO: 62;

(vii) a $V_H$ comprising a sequence set forth in SEQ ID NO: 58 and a $V_L$ comprising a sequence set forth in SEQ ID NO: 82;

(viii) a $V_H$ comprising a sequence set forth in SEQ ID NO: 86 and a $V_L$ comprising a sequence set forth in SEQ ID NO: 46;

(ix) a $V_H$ comprising a sequence set forth in SEQ ID NO: 90 and a $V_L$ comprising a sequence set forth in SEQ ID NO: 46; or (x) a $V_H$ comprising a sequence set forth in SEQ ID NO: 58 and a $V_L$ comprising a sequence set forth in SEQ ID NO: 62.

The disclosure also provides a TL1a-binding antibody comprising a $V_H$ of SEQ ID NO:42 and a $V_L$ of SEQ ID NO:46.

The disclosure also provides a TL1a-binding antibody comprising a $V_H$ of SEQ ID NO: 175 and a $V_L$ of SEQ ID NO: 188.

The disclosure also provides a TL1a-binding antibody comprising a $V_H$ of SEQ ID NO: 176 and a $V_L$ of SEQ ID NO: 189.

The disclosure also provides a TL1a-binding antibody comprising a $V_H$ of SEQ ID NO: 177 and a $V_L$ of SEQ ID NO: 190.

The disclosure also provides a TL1a-binding antibody comprising a $V_H$ of SEQ ID NO: 178 and a $V_L$ of SEQ ID NO: 191.

The disclosure also provides a TL1a-binding antibody comprising a $V_H$ of SEQ ID NO: 179 and a $V_L$ of SEQ ID NO: 192.

The disclosure also provides a A TL1a-binding antibody comprising a $V_H$ of SEQ ID NO: 180 and a $V_L$ of SEQ ID NO: 193.

The disclosure also provides a TL1a-binding antibody comprising a $V_H$ of SEQ ID NO: 181 and a $V_L$ of SEQ ID NO: 194.

The disclosure also provides a TL1a-binding antibody comprising a $V_H$ of SEQ ID NO: 183 and a $V_L$ of SEQ ID NO: 196.

The disclosure also provides a TL1a-binding antibody comprising a $V_H$ of SEQ ID NO: 185 and a $V_L$ of SEQ ID NO: 198.

The disclosure also provides a TL1a-binding antibody comprising a $V_H$ of SEQ ID NO: 186 and a $V_L$ of SEQ ID NO: 199.

The disclosure also provides a TL1a-binding antibody comprising a $V_H$ of SEQ ID NO: 187 and a $V_L$ of SEQ ID NO: 200.

The antibodies set out in the foregoing list provide one or more of the following advantages:

(i) inhibit TL1a interaction with DR3 and do not inhibit interaction of TL1a and DcR3 as determined by the methods described herein;

(ii) reduce the level of apoptosis of the TF-1 cells (e.g., about $7\times10^4$ cells-$8\times10^4$ cells (e.g., $7.5\times10^4$ cells)) with an $EC_{50}$ of less than about 2 nM (such as less than about 1.5 nM or 1.2 nM or 1.1 nM; or 1 nM or less) compared to the level of apoptosis in the absence of the TL1a-binding protein; or (iii) bind to TL1a on the surface of a cell with an $EC_{50}$ of less than about 10 nM, such as less than about 5 nM or 3 nM or 2 nM, e.g., as assessed using flow cytometry performed with about $2\times10^5$ to $3\times10^5$ cells (e.g., $2.5\times10^5$ cells).

In one example, the antibody comprises a $V_H$ comprising a sequence set forth in SEQ ID NO: 137 and a $V_L$ comprising a sequence set forth in SEQ ID NO: 138.

In one example, the TL1a-binding protein comprises a $V_H$ comprising a sequence set forth in SEQ ID NO: 152 and a $V_L$ comprising a sequence set forth in SEQ ID NO: 153.

In one example, the TL1a-binding protein comprises a $V_H$ comprising a sequence set forth in SEQ ID NO: 162 and a $V_L$ comprising a sequence set forth in SEQ ID NO: 172.

In one example, the TL1a-binding protein comprises a $V_H$ comprising a sequence set forth in SEQ ID NO: 163 and a $V_L$ comprising a sequence set forth in SEQ ID NO: 174.

For example, the antibody comprises a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:

(i) the $V_H$ comprises an alanine at position 16 of SEQ ID NO: 42;

(ii) the $V_H$ comprises an alanine at position 100 of SEQ ID NO: 42 and the $V_L$ comprises a threonine at position 76 of SEQ ID NO: 46;

(iii) the $V_H$ comprises a serine at position 100 of SEQ ID NO: 42 and the $V_L$ comprises a threonine at position 76 of SEQ ID NO: 46;

(iv) the $V_H$ comprises a histidine at position 100 of SEQ ID NO: 42 and the $V_L$ comprises a threonine at position 76 of SEQ ID NO: 46;

(v) the $V_H$ comprises a leucine at position 100 of SEQ ID NO: 42 and the $V_L$ comprises a threonine at position 76 of SEQ ID NO: 46;

(vi) the $V_H$ comprises an aspartic acid at position 100 of SEQ ID NO: 42 and the $V_L$ comprises a threonine at position 76 of SEQ ID NO: 46;

(vii) the $V_H$ comprises a tyrosine at position 100 of SEQ ID NO: 42 and the $V_L$ comprises a threonine at position 76 of SEQ ID NO: 46;

(viii) the $V_H$ comprises a proline at position 100 of SEQ ID NO: 42 and the $V_L$ comprises a threonine at position 76 of SEQ ID NO: 46;

(ix) the $V_H$ comprises a glutamine at position 100 of SEQ ID NO: 42 and the $V_L$ comprises a threonine at position 76 of SEQ ID NO: 46;

(x) the $V_H$ comprises a lysine at position 100 of SEQ ID NO: 42 and the $V_L$ comprises a threonine at position 76 of SEQ ID NO: 46;

(xi) the $V_H$ comprises an alanine at position 101 of SEQ ID NO: 42 and the $V_L$ comprises a threonine at position 76 of SEQ ID NO: 46;

(xii) the $V_H$ comprises a serine at position 101 of SEQ ID NO: 42 and the $V_L$ comprises a threonine at position 76 of SEQ ID NO: 46;

(xiii) the $V_H$ comprises a histidine at position 101 of SEQ ID NO: 42 and the $V_L$ comprises a threonine at position 76 of SEQ ID NO: 46;

(xiv) the $V_H$ comprises a leucine at position 101 of SEQ ID NO: 42 and the $V_L$ comprises a threonine at position 76 of SEQ ID NO: 46;

(xv) the $V_H$ comprises an aspartic acid at position 101 of SEQ ID NO: 42 and the $V_L$ comprises a threonine at position 76 of SEQ ID NO: 46;

(xvi) the $V_H$ comprises a tyrosine at position 101 of SEQ ID NO: 42 and the $V_L$ comprises a threonine at position 76 of SEQ ID NO: 46;

(xvii) the $V_H$ comprises a glutamine at position 101 of SEQ ID NO: 42 and the $V_L$ comprises a threonine at position 76 of SEQ ID NO: 46;

(xviii) the $V_H$ comprises a lysine at position 101 of SEQ ID NO: 42 and the $V_L$ comprises a threonine at position 76 of SEQ ID NO: 46;

(xix) the $V_H$ comprises an alanine at position 102 of SEQ ID NO: 42 and the $V_L$ comprises a threonine at position 76 of SEQ ID NO: 46;

(xx) the $V_H$ comprises a serine at position 102 of SEQ ID NO: 42 and the $V_L$ comprises a threonine at position 76 of SEQ ID NO: 46;

(xxi) the $V_H$ comprises a histidine at position 102 of SEQ ID NO: 42 and the $V_L$ comprises a threonine at position 76 of SEQ ID NO: 46;

(xxii) the $V_H$ comprises a leucine at position 102 of SEQ ID NO: 42 and the $V_L$ comprises a threonine at position 76 of SEQ ID NO: 46;

(xxiii) the $V_H$ comprises a tyrosine at position 102 of SEQ ID NO: 42 and the $V_L$ comprises a threonine at position 76 of SEQ ID NO: 46;

(xxiv) the $V_H$ comprises a proline at position 102 of SEQ ID NO: 42 and the $V_L$ comprises a threonine at position 76 of SEQ ID NO: 46;

(xxv) the $V_H$ comprises a glutamine at position 102 of SEQ ID NO: 42 and the $V_L$ comprises a threonine at position 76 of SEQ ID NO: 46;

(xxvi) the $V_H$ comprises a lysine at position 102 of SEQ ID NO: 42 and the $V_L$ comprises a threonine at position 76 of SEQ ID NO: 46;

(xxvii) the $V_H$ comprises an alanine at position 103 of SEQ ID NO: 42 and the $V_L$ comprises a threonine at position 76 of SEQ ID NO: 46;

(xxviii) the $V_H$ comprises a serine at position 103 of SEQ ID NO: 42 and the $V_L$ comprises a threonine at position 76 of SEQ ID NO: 46;

(xxix) the $V_H$ comprises a histidine at position 103 of SEQ ID NO: 42 and the $V_L$ comprises a threonine at position 76 of SEQ ID NO: 46;

(xxx) the $V_H$ comprises a leucine at position 103 of SEQ ID NO: 42 and the $V_L$ comprises a threonine at position 76 of SEQ ID NO: 46;

(xxxi) the $V_H$ comprises an aspartic acid at position 103 of SEQ ID NO: 42 and the $V_L$ comprises a threonine at position 76 of SEQ ID NO: 46;

(xxxii) the $V_H$ comprises a tyrosine at position 103 of SEQ ID NO: 42 and the $V_L$ comprises a threonine at position 76 of SEQ ID NO: 46;

(xxxiii) the $V_H$ comprises a proline at position 103 of SEQ ID NO: 42 and the $V_L$ comprises a threonine at position 76 of SEQ ID NO: 46;

(xxxiv) the $V_H$ comprises a glutamine at position 103 of SEQ ID NO: 42 and the $V_L$ comprises a threonine at position 76 of SEQ ID NO: 46;

(xxxv) the $V_H$ comprises a lysine at position 103 of SEQ ID NO: 42 and the $V_L$ comprises a threonine at position 76 of SEQ ID NO: 46;

(xxxvi) the $V_H$ comprises a serine at position 104 of SEQ ID NO: 42 and the $V_L$ comprises a threonine at position 76 of SEQ ID NO: 46;

(xxxvii) the $V_H$ comprises a histidine at position 104 of SEQ ID NO: 42 and the $V_L$ comprises a threonine at position 76 of SEQ ID NO: 46;

(xxxviii) the $V_H$ comprises a leucine at position 104 of SEQ ID NO: 42 and the $V_L$ comprises a threonine at position 76 of SEQ ID NO: 46;

(xxxix) the $V_H$ comprises an aspartic acid at position 104 of SEQ ID NO: 42 and the $V_L$ comprises a threonine at position 76 of SEQ ID NO: 46;

(xl) the $V_H$ comprises a tyrosine at position 104 of SEQ ID NO: 42 and the $V_L$ comprises a threonine at position 76 of SEQ ID NO: 46;

(xli) the $V_H$ comprises a proline at position 104 of SEQ ID NO: 42 and the $V_L$ comprises a threonine at position 76 of SEQ ID NO: 46;

(xlii) the $V_H$ comprises a glutamine at position 104 of SEQ ID NO: 42 and the $V_L$ comprises a threonine at position 76 of SEQ ID NO: 46;

(xliii) the $V_H$ comprises a lysine at position 104 of SEQ ID NO: 42 and the $V_L$ comprises a threonine at position 76 of SEQ ID NO: 46;

(xliv) the $V_H$ comprises an alanine at position 105 of SEQ ID NO: 42 and the $V_L$ comprises a threonine at position 76 of SEQ ID NO: 46;

(xlv) the $V_H$ comprises a histidine at position 105 of SEQ ID NO: 42 and the $V_L$ comprises a threonine at position 76 of SEQ ID NO: 46;

(xlvi) the $V_H$ comprises a leucine at position 105 of SEQ ID NO: 42 and the $V_L$ comprises a threonine at position 76 of SEQ ID NO: 46;

(xlvii) the $V_H$ comprises an aspartic acid at position 105 of SEQ ID NO: 42 and the $V_L$ comprises a threonine at position 76 of SEQ ID NO: 46;

(xlviii) the $V_H$ comprises a tyrosine at position 105 of SEQ ID NO: 42 and the $V_L$ comprises a threonine at position 76 of SEQ ID NO: 46;

(xlix) the $V_H$ comprises a proline at position 105 of SEQ ID NO: 42 and the $V_L$ comprises a threonine at position 76 of SEQ ID NO: 46;

(l) the $V_H$ comprises a glutamine at position 105 of SEQ ID NO: 42 and the $V_L$ comprises a threonine at position 76 of SEQ ID NO: 46;

(li) the $V_H$ comprises a lysine at position 105 of SEQ ID NO: 42 and the $V_L$ comprises a threonine at position 76 of SEQ ID NO: 46;

(lii) the $V_H$ comprises an alanine at position 107 of SEQ ID NO: 42 and the $V_L$ comprises a threonine at position 76 of SEQ ID NO: 46;

(liii) the $V_H$ comprises a serine at position 107 of SEQ ID NO: 42 and the $V_L$ comprises a threonine at position 76 of SEQ ID NO: 46;

(liv) the $V_H$ comprises a histidine at position 107 of SEQ ID NO: 42 and the $V_L$ comprises a threonine at position 76 of SEQ ID NO: 46;

(lv) the $V_H$ comprises a leucine at position 107 of SEQ ID NO: 42 and the $V_L$ comprises a threonine at position 76 of SEQ ID NO: 46;

(lvi) the $V_H$ comprises an aspartic acid at position 107 of SEQ ID NO: 42 and the $V_L$ comprises a threonine at position 76 of SEQ ID NO: 46;

(lvii) the $V_H$ comprises a tyrosine at position 107 of SEQ ID NO: 42 and the $V_L$ comprises a threonine at position 76 of SEQ ID NO: 46;

(lviii) the $V_H$ comprises a proline at position 107 of SEQ ID NO: 42 and the $V_L$ comprises a threonine at position 76 of SEQ ID NO: 46;

(lix) the $V_H$ comprises a glutamine at position 107 of SEQ ID NO: 42 and the $V_L$ comprises a threonine at position 76 of SEQ ID NO: 46;

(lx) the $V_H$ comprises a lysine at position 107 of SEQ ID NO: 42 and the $V_L$ comprises a threonine at position 76 of SEQ ID NO: 46;

(lxi) the $V_H$ comprises a threonine at position 41 of SEQ ID NO: 42 and the $V_L$ comprises an alanine at position 23 of SEQ ID NO: 46;

(lxii) the $V_H$ comprises a threonine at position 41 of SEQ ID NO: 42 and the $V_L$ comprises an aspartic acid at position 28 of SEQ ID NO: 46;

(lxiii) the $V_H$ comprises a threonine at position 41 of SEQ ID NO: 42 and the $V_L$ comprises a tyrosine at position 33 of SEQ ID NO: 46;

(lxiv) the $V_H$ comprises a threonine at position 41 of SEQ ID NO: 42 and the $V_L$ comprises an aspartic acid at position 34 of SEQ ID NO: 46;

(lxv) the $V_H$ comprises a threonine at position 41 of SEQ ID NO: 42 and the $V_L$ comprises an asparagine at position 53 of SEQ ID NO: 46;

(lxvi) the $V_H$ comprises a threonine at position 41 of SEQ ID NO: 42 and the $V_L$ comprises a serine at position 54 of SEQ ID NO: 46;

(lxvii) the $V_H$ comprises a threonine at position 41 of SEQ ID NO: 42 and the $V_L$ comprises a alanine at position 82 of SEQ ID NO: 46;

(lxviii) the $V_H$ comprises a threonine at position 41 of SEQ ID NO: 42 and the $V_L$ comprises a serine at position 95 of SEQ ID NO: 46;

(lxix) the $V_H$ comprises a threonine at position 41 of SEQ ID NO: 42 and the $V_L$ comprises a serine at position 96 of SEQ ID NO: 46;

(lxx) the $V_H$ comprises a threonine at position 41 of SEQ ID NO: 42 and the $V_L$ comprises a threonine at position 76 of SEQ ID NO: 46;

(lxxi) the $V_H$ comprises a serine at position 47 of SEQ ID NO: 42 and the $V_L$ comprises an threonine at position 23 of SEQ ID NO: 46;

(lxxii) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 76 of SEQ ID NO: 46;

(lxxiii) the $V_H$ comprises a proline at position 41, a leucine at position 51 and a glutamic acid at position 102 each relative to SEQ ID NO: 42 and the $V_L$ comprises a serine at position 24 and a threonine at position 76 each relative to SEQ ID NO: 46;

(lxxiv) the $V_H$ comprises a proline at position 41, a leucine at position 51 and a glutamic acid at position 102 each relative to SEQ ID NO: 42 and the $V_L$ comprises a threonine at position 23, a serine at position 24 and a threonine at position 76 each relative to SEQ ID NO: 46;

(lxxv) the $V_H$ comprises a proline at position 41, a leucine at position 51 and a glutamic acid at position 102 each relative to SEQ ID NO: 42 and the $V_L$ comprises a threonine at position 23 and a threonine at position 76 each relative to SEQ ID NO: 46;

(lxxvi) the $V_H$ comprises a proline at position 41, a leucine at position 51 and a glutamic acid at position 102 each relative to SEQ ID NO: 42 and the $V_L$ comprises a threonine at position 76 of SEQ ID NO: 46;

(lxxvii) the $V_H$ comprises a proline at position 41, a leucine at position 51, a glutamic acid at position 102 and an alanine at position 105 each relative to SEQ ID NO: 42 and the $V_L$ comprises a threonine at position 23, a serine at position 24 and a threonine at position 76 each relative to SEQ ID NO: 46;

(lxxviii) the $V_H$ comprises a proline at position 41, a leucine at position 51, a glutamic acid at position 102 and an alanine at position 105 each relative to SEQ ID NO: 42 and the $V_L$ comprises a threonine at position 76 of SEQ ID NO: 46;

(lxxix) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24 and a threonine at position 76 each relative to SEQ ID NO: 46;

(lxxx) the $V_H$ comprises a proline at position 41, an alanine at position 72, an aspartic acid at position 73 an arginine at position 74 and a threonine at position 76 each relative to SEQ ID NO: 42 and the $V_L$ comprises a threonine at position 23, a serine at position 24, a threonine at position 76 and a glutamic acid at position 51 each relative to SEQ ID NO: 46;

(lxxxi) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glutamic acid at position 51 each relative to SEQ ID NO: 46; or (lxxxii) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glycine at position 51 each relative to SEQ ID NO: 46.

In one example, a TL1a-binding protein of the disclosure comprises a human or non-human primate heavy chain immunoglobulin constant region selected from a group consisting of IgG1, IgG2, IgG3, IgG4, IgD, IgM, IgE and IgA. An exemplary heavy chain immunoglobulin constant region is an IgG constant region, e.g., an IgG1 constant region, such as a human IgG1 constant region. For example, a human IgG1 constant region comprises a Fc region comprising a sequence set forth in SEQ ID NO: 134. In one example, the human or non-human primate heavy chain immunoglobulin constant region lacks a C-terminal lysine residue.

In another example, a TL1a-binding protein of the disclosure comprises a human or non-human primate light chain immunoglobulin constant region selected from a group consisting of kappa or lambda. In one example, the TL1a-binding protein comprises a human light chain constant region comprising a sequence set forth in SEQ ID NO: 135 (kappa) or SEQ ID NO: 136 (lambda).

The disclosure also provides an isolated or recombinant nucleic acid encoding the TL1a-binding protein of the disclosure or a sequence having at least about 80% identity thereto or a sequence that hybridizes thereto under moderate or high stringency conditions. In this regard, the disclosure is not limited to the specific exemplified nucleic acids described herein, but also encompasses any nucleic acid that encodes a TL1a-binding protein of the disclosure as a result of degeneracy of the genetic code. For example, the nucleic acid may be codon optimized for expression in a particular cell type.

In one example, the nucleic acid comprises a sequence set forth in any one of SEQ ID NOs: 96 to 118 or a sequence having at least about 80% identity thereto or a sequence that hybridizes thereto under moderate or high stringency conditions.

In one example, the nucleic acid comprises a sequence set forth in SEQ ID NO: 102 or a sequence having at least about 80% identity thereto or a sequence that hybridizes thereto under moderate or high stringency conditions.

In one example, the nucleic acid comprises a sequence set forth in SEQ ID NO: 103 or a sequence having at least about 80% identity thereto or a sequence that hybridizes thereto under moderate or high stringency conditions.

In one example, the nucleic acid comprises a sequence set forth in SEQ ID NO: 102 and a sequence set forth in SEQ ID NO: 103 or a sequence having at least about 80% identity thereto or a sequence that hybridizes thereto under moderate or high stringency conditions.

In one example, the nucleic acid comprises a sequence set forth in SEQ ID NO: 104 or a sequence having at least about 80% identity thereto or a sequence that hybridizes thereto under moderate or high stringency conditions.

In one example, the nucleic acid comprises a sequence set forth in SEQ ID NO: 105 or a sequence having at least about 80% identity thereto or a sequence that hybridizes thereto under moderate or high stringency conditions.

In one example, the nucleic acid comprises a sequence set forth in SEQ ID NO: 104 and a sequence set forth in SEQ ID NO: 105 or a sequence having at least about 80% identity thereto or a sequence that hybridizes thereto under moderate or high stringency conditions.

In one example, the nucleic acid comprises a sequence set forth in SEQ ID NO: 106 or a sequence having at least about 80% identity thereto or a sequence that hybridizes thereto under moderate or high stringency conditions.

In one example, the nucleic acid comprises a sequence set forth in SEQ ID NO: 107 or a sequence having at least about 80% identity thereto or a sequence that hybridizes thereto under moderate or high stringency conditions.

In one example, the nucleic acid comprises a sequence set forth in SEQ ID NO: 106 and a sequence set forth in SEQ ID NO: 107 or a sequence having at least about 80% identity thereto or a sequence that hybridizes thereto under moderate or high stringency conditions.

In one example, the nucleic acid comprises a sequence at least 95% identical to a sequence set forth in any one of SEQ ID NOs: 106, 107 or 222 to 233 or a nucleic acid that hybridizes thereto under moderate to high stringency conditions.

In one example, the nucleic acid comprises one or more of the following:

(i) a nucleic acid comprising a sequence at least about 95% identical to the sequence set forth in SEQ ID NO: 106 or a nucleic acid that hybridizes thereto under moderate to high stringency conditions and a nucleic acid comprising a sequence at least about 95% identical to the sequence set forth in SEQ ID NO: 107 or a nucleic acid that hybridizes thereto under moderate to high stringency conditions;

(ii) a nucleic acid comprising a sequence at least about 95% identical to the sequence set forth in SEQ ID NO: 222 or a nucleic acid that hybridizes thereto under moderate to high stringency conditions and a nucleic acid comprising a sequence at least about 95% identical to the sequence set forth in SEQ ID NO: 228 or a nucleic acid that hybridizes thereto under moderate to high stringency conditions;

(iii) a nucleic acid comprising a sequence at least about 95% identical to the sequence set forth in SEQ ID NO: 223 or a nucleic acid that hybridizes thereto under moderate to high stringency conditions and a nucleic acid comprising a sequence at least about 95% identical to the sequence set forth in SEQ ID NO: 228 or a nucleic acid that hybridizes thereto under moderate to high stringency conditions;

(iv) a nucleic acid comprising a sequence at least about 95% identical to the sequence set forth in SEQ ID NO: 224 or a nucleic acid that hybridizes thereto under moderate to high stringency conditions and a nucleic acid comprising a sequence at least about 95% identical to the sequence set forth in SEQ ID NO: 229 or a nucleic acid that hybridizes thereto under moderate to high stringency conditions;

(v) a nucleic acid comprising a sequence at least about 95% identical to the sequence set forth in SEQ ID NO: 224 or a nucleic acid that hybridizes thereto under moderate to high stringency conditions and a nucleic acid comprising a sequence at least about 95% identical to the sequence set forth in SEQ ID NO: 230 or a nucleic acid that hybridizes thereto under moderate to high stringency conditions;

(vi) a nucleic acid comprising a sequence at least about 95% identical to the sequence set forth in SEQ ID NO: 224 or a nucleic acid that hybridizes thereto under moderate to high stringency conditions and a nucleic acid comprising a sequence at least about 95% identical to the sequence set forth in SEQ ID NO: 231 or a nucleic acid that hybridizes thereto under moderate to high stringency conditions;

(vii) a nucleic acid comprising a sequence at least about 95% identical to the sequence set forth in SEQ ID NO: 224 or a nucleic acid that hybridizes thereto under moderate to high stringency conditions and a nucleic acid comprising a sequence at least about 95% identical to the sequence set forth in SEQ ID NO: 228 or a nucleic acid that hybridizes thereto under moderate to high stringency conditions;

(viii) a nucleic acid comprising a sequence at least about 95% identical to the sequence set forth in SEQ ID NO: 225 or a nucleic acid that hybridizes thereto under moderate to high stringency conditions and a nucleic acid comprising a sequence at least about 95% identical to the sequence set forth in SEQ ID NO: 230 or a nucleic acid that hybridizes thereto under moderate to high stringency conditions;

(ix) a nucleic acid comprising a sequence at least about 95% identical to the sequence set forth in SEQ ID NO: 226 or a nucleic acid that hybridizes thereto under moderate to high stringency conditions and a nucleic acid comprising a sequence at least about 95% identical to the sequence set forth in SEQ ID NO: 230 or a nucleic acid that hybridizes thereto under moderate to high stringency conditions;

(x) a nucleic acid comprising a sequence at least about 95% identical to the sequence set forth in SEQ ID NO: 226 or a nucleic acid that hybridizes thereto under moderate to high stringency conditions and a nucleic acid comprising a sequence at least about 95% identical to the sequence set forth in SEQ ID NO: 232 or a nucleic acid that hybridizes thereto under moderate to high stringency conditions;

(xi) a nucleic acid comprising a sequence at least about 95% identical to the sequence set forth in SEQ ID NO: 227 or a nucleic acid that hybridizes thereto under moderate to high stringency conditions and a nucleic acid comprising a sequence at least about 95% identical to the sequence set forth in SEQ ID NO: 232 or a nucleic acid that hybridizes thereto under moderate to high stringency conditions; or (xii) a nucleic acid comprising a sequence at least about 95% identical to the sequence set forth in SEQ ID NO: 227 or a nucleic acid that hybridizes thereto under moderate to high stringency conditions and a nucleic acid comprising a sequence at least about 95% identical to the sequence set forth in SEQ ID NO: 233 or a nucleic acid that hybridizes thereto under moderate to high stringency conditions.

Sequences of exemplary nucleic acids and combinations thereof are set out in Table 1 and are to be taken to provide literal support for each individual sequence and combination thereof.

In one example, such a nucleic acid is included in an expression construct in which the nucleic acid is operably linked to a promoter. Such an expression construct can be in a vector, e.g., a plasmid.

In examples of the disclosure directed to single polypeptide TL1a-binding proteins, the expression construct may comprise a promoter linked to a nucleic acid encoding that polypeptide chain.

In examples directed to multiple polypeptides that form a TL1a-binding protein, an expression construct of the disclosure comprises a nucleic acid encoding one of the polypeptides (e.g., comprising a $V_H$) operably linked to a promoter and a nucleic acid encoding another of the polypeptides (e.g., comprising a $V_L$) operably linked to a promoter.

In another example, the expression construct is a bicistronic expression construct, e.g., comprising the following operably linked components in 5' to 3' order:

(i) a promoter (ii) a nucleic acid encoding a first polypeptide;

(iii) an internal ribosome entry site; and (iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The disclosure also contemplates separate expression constructs one of which encodes a first polypeptide (e.g., comprising a $V_H$) and another of which encodes a second polypeptide (e.g., comprising a $V_L$). For example, the disclosure also provides a composition comprising:

(i) a first expression construct comprising a nucleic acid encoding a polypeptide (e.g., comprising a $V_H$ operably linked to a promoter); and (ii) a second expression construct comprising a nucleic acid encoding a polypeptide (e.g., comprising a $V_L$ operably linked to a promoter), wherein the first and second polypeptides associate to form a TL1a-binding protein of the disclosure.

The disclosure also provides an isolated cell expressing a TL1a-binding protein of the disclosure or a recombinant cell genetically-modified to express a TL1a-binding protein of the disclosure.

In one example, the cell comprises the expression construct of the disclosure or:

(i) a first expression construct comprising a nucleic acid encoding a polypeptide (e.g., comprising a $V_H$) operably linked to a promoter; and (ii) a second expression construct comprising a nucleic acid encoding a polypeptide (e.g., comprising a $V_L$) operably linked to a promoter, wherein the first and second polypeptides associate to form a TL1a-binding protein of the disclosure.

Examples of cells of the disclosure include bacterial cells, yeast cells, insect cells or mammalian cells. Exemplary cells are mammalian.

The disclosure additionally provides methods for producing a TL1a-binding protein of the disclosure. For example, such a method involves maintaining the expression construct(s) of the disclosure under conditions sufficient for the TL1a-binding protein to be produced.

In one example, a method for producing a TL1a-binding protein of the disclosure comprises culturing the cell of the disclosure under conditions sufficient for the protein to be produced and, optionally, secreted.

In one example, the method for producing a TL1a-binding protein of the disclosure additionally comprises isolating the protein.

The disclosure also provides a composition comprising the TL1a-binding protein, nucleic acid, expression construct or cell of the disclosure and a suitable carrier. In one example, the composition comprises the TL1a-binding protein of the disclosure and a suitable carrier. In one example, the carrier is pharmaceutically acceptable, e.g., the composition is a pharmaceutical composition.

The disclosure also provides a method for treating or preventing symptoms of a condition (e.g., a TL1a-mediated condition) in a cell, tissue, organ or subject, the method comprising administering the TL1a-binding protein, nucleic acid, expression construct, cell or composition of the disclosure to the cell, tissue, organ or subject. In one example, the disclosure provides a method for treating or preventing a condition (e.g., a TL1a-mediated condition) in a subject, the method comprising administering the TL1a-binding protein, nucleic acid, expression construct, cell or composition of the disclosure to the subject. In this regard, a method of preventing a condition can prevent a relapse of a condition having a relapsing-remitting form, such as multiple sclerosis, e.g., the protein is administered during remission to thereby prevent a relapse.

The disclosure also provides a method for inducing or enhancing angiogenesis in a subject, the method comprising administering the TL1a-binding protein, nucleic acid, expression construct, cell or composition of the disclosure to the subject.

The disclosure also provides for use of the TL1a-binding protein, nucleic acid, expression construct, cell or composition of the disclosure in medicine.

The disclosure also provides for use of the TL1a-binding protein, nucleic acid, expression construct, or cell in the manufacture of a medicament or prevention for treating or preventing symptoms of a condition (e.g., a TL1a-mediated condition) or for treating or preventing a condition (e.g., a TL1a-mediated condition) or for inducing or enhancing angiogenesis in a subject.

The disclosure also provides the TL1a-binding protein, nucleic acid, expression construct, or cell for use in treating or preventing symptoms of a condition (e.g., a TL1a-mediated condition) or for treating or preventing a condition (e.g., a TL1a-mediated condition) or for inducing or enhancing angiogenesis in a subject.

In one example, a method of treatment or prophylaxis of the disclosure additionally comprises diagnosing the condition, e.g., by performing a method described herein.

In one example, a method of treatment or prophylaxis of the disclosure additionally comprises detecting the level of TL1a in a subject and administering a further dose of the TL1a-binding protein, nucleic acid, expression construct, cell or composition of the disclosure if the level of TL1a is not significantly reduced or is not reduced to a level not associated with a condition.

The disclosure also provides a method for inhibiting interaction of TL1a and DR3 (and in one example, not inhibiting interaction of TL1a and DcR3) in a cell, tissue, organ or subject, the method comprising administering the TL1a-binding protein, nucleic acid, expression construct, cell or composition of the disclosure to the cell, tissue, organ or subject. In one example, the subject suffers from a condition (e.g., a TL1a-mediated condition).

The disclosure also provides a method for detecting TL1a in a sample, the method comprising contacting a sample with the TL1a-binding protein of the disclosure such that an antigen-protein complex forms and detecting the complex, wherein detecting the complex is indicative of TL1a in the sample.

The disclosure also provides a method for detecting TL1a in a subject, the method comprising detecting the TL1a-binding protein of the disclosure in the subject, wherein the protein is conjugated to a detectable label. In one example, the method comprises administering the protein to the subject.

The disclosure also provides a method for diagnosing a TL1a-mediated condition in a subject, the method comprising performing the method of the disclosure to detect TL1a in a sample from the subject, wherein detection of TL1a in the sample is indicative of the TL1a-mediated condition.

In one example, the method comprises determining the level of TL1a in the sample, wherein an increased or decreased level of TL1a in the sample compared to a control sample is indicative of the TL1a-mediated condition.

In one example, the results of a method to detect TL1a or diagnose/prognose a condition are provided, e.g., in paper or machine-readable form.

The disclosure also provides a method comprising obtaining the results of a method to detect TL1a or diagnose/prognose a condition of the disclosure and administering a therapeutic or prophylactic composition or recommending such administration. In one example, the composition is a composition of the disclosure.

Exemplary conditions to be treated, prevented, diagnosed or prognosed are $T_H17$-mediated conditions, inflammatory conditions, autoimmune conditions or conditions associated with or caused by insufficient angiogenesis. Suitable conditions are described herein.

In one example, a condition to be treated, prevented, diagnosed or prognosed is an autoimmune disease. For example, the condition is uveitis, ulcerative colitis, Crohn's disease, irritable bowel syndrome, rheumatoid arthritis, polyarthritis, multiple sclerosis, asthma or chronic obstructive pulmonary disease.

In one example, the condition is an inflammatory bowel condition, such as, colitis, e.g., ulcerative colitis or Crohn's disease.

The disclosure also provides a method of selecting a TL1a-binding protein which binds specifically to TL1a and inhibits interaction of TL1a and DR3 and which does not inhibit interaction of TL1a and DcR3 from a plurality of TL1a-binding proteins, the method comprising:

contacting the plurality of TL1a-binding proteins to a TL1a mutein in which the arginine at amino acid position 32 of SEQ ID NO:202 has been substituted with an alanine and/or the arginine at amino acid position 85 has been substituted with alanine under conditions sufficient to allow binding of TL1a-binding proteins to the mutein to form a TL1a-binding protein-TL1a mutein complex and a depleted plurality of TL1a-binding proteins which do not bind the TL1a mutein, and collecting TL1a-binding proteins which do not bind to the TL1a mutein from the depleted plurality of TL1a-binding proteins, wherein the collected TL1a-binding proteins bind specifically to TL1a and inhibit interaction of TL1a and DR3 and do not inhibit interaction of TL1a and DcR3.

The disclosure also provides a method of isolating a TL1a-binding protein which binds specifically to TL1a and inhibits interaction of TL1a and DR3 and which does not inhibit interaction of TL1a and DcR3 from a plurality of TL1a-binding proteins, the method comprising isolating from the plurality of TL1a-binding proteins one or more TL1a-binding proteins that do not bind to a TL1a mutein in which the arginine at amino acid position 32 of SEQ ID NO:202 has been substituted with an alanine and/or the arginine at amino acid position 85 has been substituted with alanine.

The plurality of TL1a-binding proteins may be present in a library of antibodies or antigen binding domains, such as, a phage display, ribosome display or yeast display library. The plurality of TL1a-binding proteins may be present in an antiserum. The plurality of TL1a-binding proteins may be present in hybridoma culture supernatants.

The disclosure also provides an isolated polypeptide comprising a sequence set forth in SEQ ID NO: 202 in which the arginine at amino acid position 32 as been substituted with an alanine and/or the arginine at amino acid position 85 has been substituted with alanine.

BRIEF DESCRIPTION OF THE FIGURES

FIGS. 1A to 1H are diagrammatic representations showing sequences of variable regions of antibodies. In alignments shown in FIGS. 1D to 1H any identical amino acids are indicated by a period, i.e., ".". FIG. 1A shows sequences of $V_H$ regions of human anti-TL1a antibodies. FIG. 1B shows sequences of $V_L$ regions of human anti-TL1a antibodies. FIG. 1C shows sequences of $V_H$ regions of anti-TL1a antibody C320 and some derivatives thereof. FIG. 1D shows alignment of $V_H$ sequences of selected human antibodies into which the $V_H$ CDRs 1, 2 and 3 of C320 were grafted.

FIG. 1E shows a consensus sequence of $V_H$ regions of derivatives of C320. FIG. 1F shows sequences of $V_L$ regions of anti-TL1a antibody C320 and derivatives thereof. FIG. 1G shows an alignment of human $V_L$ sequences of antibodies into which the $V_L$ CDRs 1, 2 and 3 of C320 were grafted. FIG. 1H shows a consensus sequence of $V_L$ regions of derivatives of C320. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined.

FIG. 6 is a graphical representation showing the ability of antibodies C320, C321, C323 and 1B4 to bind to cell surface TL1a. Binding was assessed using flow cytometry, in which results are presented as mean fluorescence intensity (MFI). All antibodies, except the isotype control, bound TL1a FIG. 7A is a graphical representation showing production of cell surface TL1a by mitogen (Concanavalin A)-stimulated peripheral blood mononuclear cells (PBMCs). The shaded graph represents an isotype control antibody and the line graph represents cell surface TL1a as detected by a chimeric rat/human anti-human TL1a.

FIG. 9A is a diagrammatic representation showing an alignment of the light chain sequence of C320 (SEQ ID NO: 46) against the germline sequence of highest homology, IGLV1-40*01 (SEQ ID NO: 201). Any identical amino acids are indicated by a period, i.e., ".". Differences in amino acid sequences in the CDR regions are identified.

FIG. 9B is a diagrammatic representation showing an alignment of $V_H$ regions of antibodies identified herein.

FIG. 9C is a diagrammatic representation showing an alignment of $V_L$ regions of antibodies identified herein.

FIG. 11B is a graphical representation showing the weight change (%) in rats in the days following DSS-induced colitis. Rats were treated with antibody C320-168 (10 mg/kg or isotype control (10 mg/kg) twice weekly from day 4 after disease induction or sulfasalazine (SoC (5-ASA); standard of care compound) daily from day 4 after disease induction (with results for each treatment group indicated). C320-168 ameliorated weight loss relative to the isotype control antibody to a similar extent as sulfasalazine FIG. 12 is a graphical representation showing the results of an ELISA assay to identify the binding of antibodies to different TL1a isoforms. Both C320-168 and C320-179 bound the longer (72-251) and shorter (84-251) isoforms of soluble, cleaved TL1a.

DETAILED DESCRIPTION OF THE INVENTION

Figure 2:
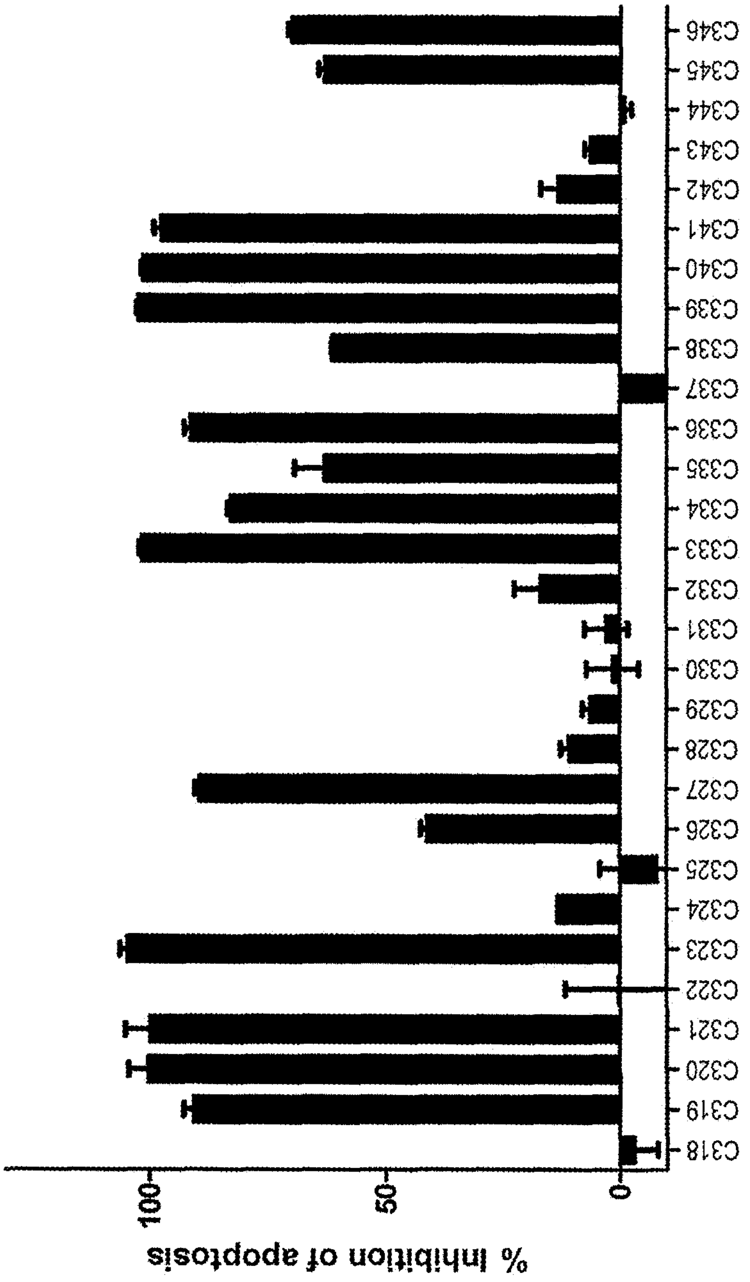
FIG. 2 is a graphical representation showing results of a potency assay demonstrating the ability of a range of anti-TL1a antibodies to inhibit TL1a-induced apoptosis of TF-1 cells. Five μg/ml of anti-TL1a antibodies were screened for their ability to inhibit TL1a-induced apoptosis in TF-1 cells.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The disclosure is not to be limited in scope by the specific examples described herein, which are intended for the purpose of exemplification only. Functionally-equivalent products, compositions and methods are clearly within the scope of the disclosure, as described herein.

The disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al., pp 35-81; Sproat et al., pp 83-115; and Wu et al., pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (lnteractiva, Germany); Sakakibara *Biochem. Biophys. Res. Commun.* 73: 336-342, 1976; Merrifield *J. Am. Chem. Soc.* 85: 2149-2154, 1963; Barany and Merrifield (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky *Int. J. Peptide Protein Res.* 25: 449-474, 1985; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Key to Sequence Listing

SEQ ID NO: 1: amino acid sequence of human TL1a extracellular domain with N-terminal HIS and FLAG tags
SEQ ID NO 2: amino acid sequence of C336 $V_H$
SEQ ID NO: 3: amino acid sequence of C336 HCDR1
SEQ ID NO: 4: amino acid sequence of C336 HCDR2
SEQ ID NO: 5: amino acid sequence of C336 HCDR3
SEQ ID NO: 6: amino acid sequence of C336 $V_L$
SEQ ID NO: 7: amino acid sequence of C336 LCDR1
SEQ ID NO: 8: amino acid sequence of C336 LCDR2
SEQ ID NO: 9: amino acid sequence of C336 LCDR3
SEQ ID NO: 10: amino acid sequence of C334 $V_H$
SEQ ID NO: 11: amino acid sequence of C334 HCDR1
SEQ ID NO: 12: amino acid sequence of C334 HCDR2
SEQ ID NO: 13: amino acid sequence of C334 HCDR3
SEQ ID NO: 14: amino acid sequence of C334 $V_L$
SEQ ID NO: 15: amino acid sequence of C334 LCDR1
SEQ ID NO: 16: amino acid sequence of C334 LCDR2
SEQ ID NO: 17: amino acid sequence of C334 LCDR3
SEQ ID NO: 18: amino acid sequence of C333 $V_H$
SEQ ID NO: 19: amino acid sequence of C333 HCDR1
SEQ ID NO: 20: amino acid sequence of C333 HCDR2
SEQ ID NO: 21: amino acid sequence of C333 HCDR3
SEQ ID NO: 22: amino acid sequence of C333 $V_L$
SEQ ID NO: 23: amino acid sequence of C333 LCDR1
SEQ ID NO: 24: amino acid sequence of C333 LCDR2
SEQ ID NO: 25: amino acid sequence of C333 LCDR3
SEQ ID NO: 26: amino acid sequence of C323 $V_H$
SEQ ID NO: 27: amino acid sequence of C323 HCDR1
SEQ ID NO: 28: amino acid sequence of C323 HCDR2
SEQ ID NO: 29: amino acid sequence of C323 HCDR3
SEQ ID NO: 30: amino acid sequence of C323 $V_L$
SEQ ID NO: 31: amino acid sequence of C323 LCDR1
SEQ ID NO: 32: amino acid sequence of C323 LCDR2
SEQ ID NO: 33: amino acid sequence of C323 LCDR3
SEQ ID NO: 34: amino acid sequence of C321 $V_H$
SEQ ID NO: 35: amino acid sequence of C321 HCDR1
SEQ ID NO: 36: amino acid sequence of C321 HCDR2
SEQ ID NO: 37: amino acid sequence of C321 HCDR3
SEQ ID NO: 38: amino acid sequence of C321 $V_L$
SEQ ID NO: 39: amino acid sequence of C321 LCDR1
SEQ ID NO: 40: amino acid sequence of C321 LCDR2
SEQ ID NO: 41: amino acid sequence of C321 LCDR3
SEQ ID NO: 42: amino acid sequence of C320 $V_H$
SEQ ID NO: 43: amino acid sequence of C320 HCDR1
SEQ ID NO: 44: amino acid sequence of C320 HCDR2
SEQ ID NO: 45: amino acid sequence of C320 HCDR3
SEQ ID NO: 46: amino acid sequence of C320 $V_L$
SEQ ID NO: 47: amino acid sequence of C320 LCDR1
SEQ ID NO: 48: amino acid sequence of C320 LCDR2
SEQ ID NO: 49: amino acid sequence of C320 LCDR3
SEQ ID NO: 50: amino acid sequence of C319 $V_H$
SEQ ID NO: 51: amino acid sequence of C319 HCDR1
SEQ ID NO: 52: amino acid sequence of C319 HCDR2
SEQ ID NO: 53: amino acid sequence of C319 HCDR3
SEQ ID NO: 54: amino acid sequence of C319 $V_L$
SEQ ID NO: 55: amino acid sequence of C319 LCDR1
SEQ ID NO: 56: amino acid sequence of C319 LCDR2
SEQ ID NO: 57: amino acid sequence of C319 LCDR3
SEQ ID NO: 58: amino acid sequence of C320-3 $V_H$
SEQ ID NO: 59: amino acid sequence of C320-3 HCDR1
SEQ ID NO: 60: amino acid sequence of C320-3 HCDR2
SEQ ID NO: 61: amino acid sequence of C320-3 HCDR3
SEQ ID NO: 62: amino acid sequence of C320-5 $V_L$
SEQ ID NO: 63: amino acid sequence of C320-5 LCDR1
SEQ ID NO: 64: amino acid sequence of C320-5 LCDR2
SEQ ID NO: 65: amino acid sequence of C320-5 LCDR3
SEQ ID NO: 66: amino acid sequence of C320-90 $V_H$
SEQ ID NO: 67: amino acid sequence of C320-90 HCDR1
SEQ ID NO: 68: amino acid sequence of C320-90 HCDR2
SEQ ID NO: 69: amino acid sequence of C320-90 HCDR3
SEQ ID NO: 70: amino acid sequence of C320-103 $V_H$
SEQ ID NO: 71: amino acid sequence of C320-103 HCDR1
SEQ ID NO: 72: amino acid sequence of C320-103 HCDR2
SEQ ID NO: 73: amino acid sequence of C320-103 HCDR3
SEQ ID NO: 74: amino acid sequence of C320-114 $V_H$
SEQ ID NO: 75: amino acid sequence of C320-114 HCDR1
SEQ ID NO: 76: amino acid sequence of C320-114 HCDR2
SEQ ID NO: 77: amino acid sequence of C320-114 HCDR3

SEQ ID NO: 78: amino acid sequence of C320-115 $V_H$
SEQ ID NO: 79: amino acid sequence of C320-115 HCDR1
SEQ ID NO: 80: amino acid sequence of C320-115 HCDR2
SEQ ID NO: 81: amino acid sequence of C320-115 HCDR3
SEQ ID NO: 82: amino acid sequence of C320-120 $V_L$
SEQ ID NO: 83: amino acid sequence of C320-120 LCDR1
SEQ ID NO: 84: amino acid sequence of C320-120 LCDR2
SEQ ID NO: 85: amino acid sequence of C320-120 LCDR3
SEQ ID NO: 86: amino acid sequence of C320-129 $V_H$
SEQ ID NO: 87: amino acid sequence of C320-129 HCDR1
SEQ ID NO: 88: amino acid sequence of C320-129 HCDR2
SEQ ID NO: 89: amino acid sequence of C320-129 HCDR3
SEQ ID NO: 90: amino acid sequence of C320-130 $V_H$
SEQ ID NO: 91: amino acid sequence of C320-130 HCDR1
SEQ ID NO: 92: amino acid sequence of C320-130 HCDR2
SEQ ID NO: 93: amino acid sequence of C320-130 HCDR3
SEQ ID NO: 94: amino acid sequence of $V_H$ consensus sequence of C320 and derivatives
SEQ ID NO: 95: amino acid sequence of $V_L$ consensus sequence of C320 and derivatives
SEQ ID NO: 96: nucleotide sequence encoding $V_H$ of C336
SEQ ID NO: 97: nucleotide sequence encoding $V_L$ of C336
SEQ ID NO: 98: nucleotide sequence encoding $V_H$ of C334
SEQ ID NO: 99: nucleotide sequence encoding $V_L$ of C334
SEQ ID NO: 100: nucleotide sequence encoding $V_H$ of C333
SEQ ID NO: 101: nucleotide sequence encoding $V_L$ of C333
SEQ ID NO: 102: nucleotide sequence encoding $V_H$ of C323
SEQ ID NO: 103: nucleotide sequence encoding $V_L$ of C323
SEQ ID NO: 104: nucleotide sequence encoding $V_H$ of C321
SEQ ID NO: 105: nucleotide sequence encoding $V_L$ of C321
SEQ ID NO: 106: nucleotide sequence encoding $V_H$ of C320
SEQ ID NO: 107: nucleotide sequence encoding $V_L$ of C320
SEQ ID NO: 108: nucleotide sequence encoding $V_H$ of C319
SEQ ID NO: 109: nucleotide sequence encoding $V_L$ of C319
SEQ ID NO: 110: nucleotide sequence encoding $V_H$ of C320-3
SEQ ID NO: 111: nucleotide sequence encoding $V_L$ of C320-5
SEQ ID NO: 112: nucleotide sequence encoding $V_H$ of C320-90
SEQ ID NO: 113: nucleotide sequence encoding $V_H$ of C320-103
SEQ ID NO: 114: nucleotide sequence encoding $V_H$ of C320-114
SEQ ID NO: 115: nucleotide sequence encoding $V_H$ of C320-115
SEQ ID NO: 116: nucleotide sequence encoding $V_L$ of C320-120
SEQ ID NO: 117: nucleotide sequence encoding $V_H$ of C320-129
SEQ ID NO: 118: nucleotide sequence encoding $V_H$ of C320-130
SEQ ID NO: 119: amino acid sequence of $V_H$ of humanized antibody 1B4
SEQ ID NO: 120: amino acid sequence of $V_L$ of humanized antibody 1B4
SEQ ID NO: 121: nucleotide sequence encoding $V_H$ of humanized antibody 1B4
SEQ ID NO: 122: nucleotide sequence encoding $V_L$ of humanized antibody 1B4
SEQ ID NO: 123: amino acid sequence of human TL1a (derived from GenBank Gene accession no 9966 as of 8 May 2011)
SEQ ID NO: 124: amino acid sequence of mouse TL1a Extracellular Domain
SEQ ID NO: 125: amino acid sequence of cynomolgus/Rhesus TL1a Extracellular Domain
SEQ ID NO: 126: amino acid sequence of rat TL1a Extracellular Domain
SEQ ID NO: 127: amino acid sequence of rabbit TL1a Extracellular Domain
SEQ ID NO: 128: amino acid sequence of guinea Pig TL1a Extracellular Domain
SEQ ID NO: 129: amino acid sequence of human Death Receptor 3 (derived from Genbank Gene Accession No. 8718 as of 8 May 2011)
SEQ ID NO: 130: amino acid sequence of human Decoy Receptor 3 (derived from Genbank Gene Accession No. 8771 as of 8 May 2011)
SEQ ID NO: 131: sequence of region of TL1a
SEQ ID NO: 132: sequence of region of TL1a
SEQ ID NO: 133: sequence of region of TL1a
SEQ ID NO: 134: amino acid sequence of human IgG1 Fc region
SEQ ID NO: 135: amino acid sequence of human kappa constant region
SEQ ID NO: 136: amino acid sequence of human lambda constant region.
SEQ ID NO: 137: amino acid sequence of $V_H$ consensus sequence of C320 and derivatives
SEQ ID NO: 138: amino acid sequence of $V_L$ consensus sequence of C320 and derivatives
SEQ ID NO 139: amino acid sequence of LCDR1 consensus sequence of C320 and derivatives
SEQ ID NO 140: amino acid sequence of LCDR2 consensus sequence of C320 and derivatives
SEQ ID NO 141: amino acid sequence of LCDR3 consensus sequence of C320 and derivatives
SEQ ID NO 142: amino acid sequence of HCDR2 consensus sequence of C320 and derivatives
SEQ ID NO 143: amino acid sequence of HCDR3 consensus sequence of C320 and derivatives
SEQ ID NO: 144: amino acid sequence of HFR1 consensus sequence of C320 and derivatives
SEQ ID NO: 145: amino acid sequence of HFR2 consensus sequence of C320 and derivatives
SEQ ID NO: 146: amino acid sequence of HFR3 consensus sequence of C320 and derivatives
SEQ ID NO: 147: amino acid sequence of HFR4 consensus sequence of C320 and derivatives
SEQ ID NO: 148: amino acid sequence of LFR1 consensus sequence of C320 and derivatives
SEQ ID NO: 149: amino acid sequence of LFR2 consensus sequence of C320 and derivatives
SEQ ID NO: 150: amino acid sequence of LFR3 consensus sequence of C320 and derivatives
SEQ ID NO: 151: amino acid sequence of LFR4 consensus sequence of C320 and derivatives
SEQ ID NO: 152: amino acid sequence of $V_H$ consensus sequence of C320 and derivatives
SEQ ID NO: 153: amino acid sequence of $V_L$ consensus sequence of C320 and derivatives
SEQ ID NO: 154: amino acid sequence of $V_H$ comprising CDRs from C320 grafted onto FRs of antibody 1TZG.
SEQ ID NO: 155: amino acid sequence of $V_H$ comprising CDRs from C320 grafted onto FRs of antibody 1RHH.
SEQ ID NO: 156: amino acid sequence of $V_H$ comprising CDRs from C320 grafted onto FRs of antibody 2DD8.
SEQ ID NO: 157: amino acid sequence of $V_H$ comprising CDRs from C320 grafted onto FRs of antibody 2J B5.
SEQ ID NO: 158: amino acid sequence of $V_H$ comprising CDRs from C320 grafted onto FRs of antibody 3FKU.
SEQ ID NO: 159: amino acid sequence of $V_H$ comprising CDRs from C320 grafted onto FRs of antibody 3GBM.

SEQ ID NO: 160: amino acid sequence of $V_H$ comprising CDRs from C320 grafted onto FRs of antibody 3LMJ.
SEQ ID NO: 161: amino acid sequence of $V_H$ comprising CDRs from C320 grafted onto FRs of antibody 3P30.
SEQ ID NO: 162: amino acid sequence of $V_H$ consensus sequence of C320 and derivatives
SEQ ID NO: 163: amino acid sequence of $V_L$ comprising CDRs from C320 grafted onto FRs of antibody 1RHH.
SEQ ID NO: 164: amino acid sequence of $V_L$ comprising CDRs from C320 grafted onto FRs of antibody 1TZGL.
SEQ ID NO: 165: amino acid sequence of $V_L$ comprising CDRs from C320 grafted onto FRs of antibody 2DD8.
SEQ ID NO: 166: amino acid sequence of $V_L$ comprising CDRs from C320 grafted onto FRs of antibody 2J B5.
SEQ ID NO: 167: amino acid sequence of $V_L$ comprising CDRs from C320 grafted onto FRs of antibody 3FKU.
SEQ ID NO: 168: amino acid sequence of $V_L$ comprising CDRs from C320 grafted onto FRs of antibody 3GBM.
SEQ ID NO: 169: amino acid sequence of $V_L$ comprising CDRs from C320 grafted onto FRs of antibody 3LMJ.
SEQ ID NO: 170: amino acid sequence of $V_L$ comprising CDRs from C320 grafted onto FRs of antibody 3P30.
SEQ ID NO: 171: amino acid sequence of $V_L$ comprising CDRs from C320 grafted onto FRs of antibody 31YW.
SEQ ID NO: 172: amino acid sequence of $V_L$ consensus sequence of C320 and derivatives
SEQ ID NO: 173: amino acid sequence of $V_H$ consensus sequence of C320 and derivatives
SEQ ID NO: 174: amino acid sequence of $V_L$ consensus sequence of C320 and derivatives
SEQ ID NO: 175: amino acid sequence of $V_H$ of antibody C320-162
SEQ ID NO: 176: amino acid sequence of $V_H$ of antibody C320-163
SEQ ID NO: 177: amino acid sequence of $V_H$ of antibody C320-164
SEQ ID NO: 178: amino acid sequence of $V_H$ of antibody C320-165
SEQ ID NO: 179: amino acid sequence of $V_H$ of antibody C320-166
SEQ ID NO: 180: amino acid sequence of $V_H$ of antibody C320-167
SEQ ID NO: 181: amino acid sequence of $V_H$ of antibody C320-168
SEQ ID NO: 182: amino acid sequence of $V_H$ of antibody C320-169
SEQ ID NO: 183: amino acid sequence of $V_H$ of antibody C320-170
SEQ ID NO: 184: amino acid sequence of $V_H$ of antibody C320-171
SEQ ID NO: 185: amino acid sequence of $V_H$ of antibody C320-172
SEQ ID NO: 186: amino acid sequence of $V_H$ of antibody C320-179
SEQ ID NO: 187: amino acid sequence of $V_H$ of antibody C320-183
SEQ ID NO: 188: amino acid sequence of $V_L$ of antibody C320-162
SEQ ID NO: 189: amino acid sequence of $V_L$ of antibody C320-163
SEQ ID NO: 190: amino acid sequence of $V_L$ of antibody C320-164
SEQ ID NO: 191: amino acid sequence of $V_L$ of antibody C320-165
SEQ ID NO: 192: amino acid sequence of $V_L$ of antibody C320-166
SEQ ID NO: 193: amino acid sequence of $V_L$ of antibody C320-167
SEQ ID NO: 194: amino acid sequence of $V_L$ of antibody C320-168
SEQ ID NO: 195: amino acid sequence of $V_L$ of antibody C320-169
SEQ ID NO: 196: amino acid sequence of $V_L$ of antibody C320-170
SEQ ID NO: 197: amino acid sequence of $V_L$ of antibody C320-171
SEQ ID NO: 198: amino acid sequence of $V_L$ of antibody C320-172
SEQ ID NO: 199: amino acid sequence of $V_L$ of antibody C320-179
SEQ ID NO: 200: amino acid sequence of $V_L$ of antibody C320-183
SEQ ID NO: 201: amino acid sequence of $V_L$ of germline sequence IGLV1-40*1
SEQ ID NO: 202: amino acid sequence of soluble human TL1a
SEQ ID NO: 203: amino acid sequence of N-linked glycosylation site in $V_H$ of C320
SEQ ID NO: 204: amino acid sequence from $V_H$ of 1TZG corresponding to N-linked glycosylation site in $V_H$ Of C320
SEQ ID NO: 205: amino acid sequence of peptide from $V_H$ of C320-168
SEQ ID NO: 206: amino acid sequence of peptide from $V_L$ Of C320-168
SEQ ID NO: 207: amino acid sequence of influenza peptide
SEQ ID NO: 208: amino acid sequence of mutant peptide from $V_L$ of C320-168
SEQ ID NO: 209: amino acid sequence of mutant peptide from $V_L$ of C320-168
SEQ ID NO: 210: amino acid sequence of mutant peptide from $V_L$ Of C320-168
SEQ ID NO: 211: amino acid sequence of mutant peptide from $V_L$ of C320-168
SEQ ID NO: 212: amino acid sequence of mutant peptide from $V_L$ Of C320-168
SEQ ID NO: 213: amino acid sequence of mutant peptide from $V_L$ of C320-168
SEQ ID NO: 214: amino acid sequence of mutant peptide from $V_L$ of C320-168
SEQ ID NO: 215: amino acid sequence of mutant peptide from $V_L$ of C320-168
SEQ ID NO: 216: amino acid sequence of mutant peptide from $V_L$ of C320-168
SEQ ID NO: 217: amino acid sequence of mutant peptide from $V_L$ of C320-168
SEQ ID NO: 218: amino acid sequence of mutant peptide from $V_L$ of C320-168
SEQ ID NO: 219: amino acid sequence of mutant peptide from $V_L$ of C320-168
SEQ ID NO: 220: amino acid sequence of mutant peptide from $V_L$ of C320-168
SEQ ID NO: 221: amino acid sequence of mutant peptide from $V_L$ of C320-168
SEQ ID NO: 222: nucleotide sequence encoding $V_H$ of antibody C320-162
SEQ ID NO: 223: nucleotide sequence encoding $V_H$ of antibody C320-163
SEQ ID NO: 224: nucleotide sequence encoding $V_H$ of antibodies C320-164, C320-165, C320-166 and C320-167
SEQ ID NO: 225: nucleotide sequence encoding $V_H$ of antibodies C320-168 and C320-169
SEQ ID NO: 226: nucleotide sequence encoding $V_H$ of antibodies C320-170 and C320-172

SEQ ID NO: 227: nucleotide sequence encoding $V_H$ of antibodies C320-179 and C320-183

SEQ ID NO: 228: nucleotide sequence encoding $V_L$ of antibodies C320-162, C320-163, C320-167 and C320-169

SEQ ID NO: 229: nucleotide sequence encoding $V_L$ of antibody C320-164

SEQ ID NO: 230: nucleotide sequence encoding $V_L$ of antibodies C320-165, C320-168 and C320-170

SEQ ID NO: 231: nucleotide sequence encoding $V_L$ of antibody C320-166

SEQ ID NO: 232: nucleotide sequence encoding $V_L$ of antibodies C320-172 and C320-179

SEQ ID NO: 233: nucleotide sequence encoding $V_L$ of antibody C320-183

SEQ ID NO: 234: amino acid sequence of C320-13 and C320-22

SEQ ID NO: 235: amino acid sequence of consensus of HCDR3 of C320 and derivatives For the purposes of nomenclature and not limitation the amino acid sequence of human TL1a is set forth in SEQ ID NO: 123. Additional sequences of human TL1a are set out in Genbank Gene Accession No. 9966. Accordingly, in one example, the amino acid sequence of human TL1a comprises a sequence set forth in SEQ ID NO: 123. Other isoforms of TL1a have been described: 72-251 (Position 72 to 251 of SEQ ID No: 123), 84-251 (Position 84 to 251 of SEQ ID No: 123); 101-251 or VEGI-174 (Position 101 to 251 of SEQ ID No: 123) and 86-251 or VEGI-192 (Position 86 to 251 in SEQ ID No: 123). The sequences of the extracellular domain of TL1a from various species are set forth in SEQ ID NO: 1 (amino acids 16 to 184; human), SEQ ID NO: 124 (mouse), SEQ ID NO: 125 (cynomolgus/rhesus monkey), SEQ ID NO: 126 (rat), SEQ ID NO: 127 (rabbit) and SEQ ID NO: 128 (guinea pig). TL1a generally forms a homotrimer in a subject and signals through DR3. Exemplary TL1a-binding proteins of the disclosure bind to or bind specifically to human TL1a (abbreviated herein as human TL1a), including recombinant forms thereof.

For the purposes of nomenclature and not limitation, a sequence of a human DR3 is set forth in SEQ ID NO: 129. Additional sequences of human DR3 are set out in Genbank Gene Accession No. 8718. In one example, DR3 encompassed by the disclosure is human DR3 comprising a sequence set forth in SEQ ID NO: 129.

For the purposes of nomenclature and not limitation, a sequence of a human DcR3 is set forth in SEQ ID NO: 130. Additional sequences of human DcR3 are set out in Genbank Gene Accession No. 8771. In one example, DcR3 encompassed by the disclosure is human DcR3 comprising a sequence set forth in SEQ ID NO: 130.

The term "isolated protein" or "isolated polypeptide" is intended to mean a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antigen binding domain, this term does not encompass an antibody naturally-occurring within a subject's body that is the product of natural recombination that occurs during B cell maturation. However, if such an antibody is isolated, it is to be considered an isolated protein comprising an antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "TL1a-binding protein" shall be taken to include a single polypeptide chain (i.e., a series of contiguous amino acids linked by peptide bonds), or a series of polypeptide chains covalently or non-covalently linked to one another (i.e., a polypeptide complex) capable of binding to TL1a in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the disclosure, the term "antibody" includes a protein capable of specifically binding to one or a few closely related antigens (e.g., TL1a) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a K light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain ($V_H$ or $V_L$) typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (www.bioinfo.org.uk/mdex.html). According to the numbering system of Kabat, $V_H$ FRs and CDRs are positioned as follows: residues 1 to 30 (FRI), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FRI), 24 to 34 (CDR1), 35 to 49 (FR2), 50 to 56 (CDR2), 57 to 88 (FR3), 89 to 97 (CDR3) and 98 to 107 (FR4). The disclosure is not limited to FRs and CDRs as defined by the Kabat numbering system, but includes all numbering systems, including the canonical numbering system or of Chothia and Lesk *J. Mol. Biol.* 196: 901-917, 1987; Chothia et al., *Nature* 342: 877-883, 1989; and/or AI-Lazikani et al., *J. Mol. Biol.* 273: 927-948, 1997; the numbering system of Honnegher and Plukthun *J. Mol. Biol.* 309: 657-670, 2001; or the IMGT system discussed in Giudicelli et al., *Nucleic Acids Res.* 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., *FASEB J.,* 9: 133-139, 1995 established that the five C-terminal amino acids of heavy chain CDR2 and/or the four N-terminal amino acids of light chain CDR1 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an antibody, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_{H3}$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a TL1a-binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein that specifically binds to an antigen binds that antigen with greater affinity, avidity, more readily, and/or with greater duration than it binds to other antigens. For example, a protein binds to TL1a (e.g., human TL1a) with materially greater affinity than it does to other TNF superfamily ligands or to antigens commonly recognized by polyreactive natural antibodies (i.e., by naturally occurring antibodies known to bind a variety of antigens naturally found in humans). It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". In one example, "specific binding" of a TL1a-binding protein of the disclosure to an antigen, means that the protein binds to the antigen with an equilibrium constant ($K_D$) of 100 nM or less, such as 50 nM or less, for example 20 nM or less, such as, 15 nM or less or 10 nM or less or 5 nM or less.

As used herein, the term "does not detectably bind" shall be understood to mean that a TL1a-binding protein, e.g., an antibody, binds to a candidate antigen at a level less than 20%, or 10% or 6% or 5% above background. The background can be the level of binding signal detected in the absence of the TL1a-binding protein and/or in the presence of a negative control protein (e.g., an isotype control antibody) and/or the level of binding detected in the presence of a negative control antigen. The level of binding is detected, for example, using ELISA in which the antigen is immobilized and contacted with a TL1a-binding protein.

As used herein, the term "epitope" (syn. "antigenic determinant") shall be understood to mean a region of TL1a to which a protein comprising an antigen binding domain of an antibody binds. This term is not necessarily limited to the specific residues or structure to which the protein makes contact. For example, this term includes the region spanning amino acids contacted by the protein and/or at least 5 to 10 or 2 to 5 or 1 to 3 amino acids outside of this region. In some examples, the epitope is a linear series amino acids. An epitope may also comprise a series of discontinuous amino acids that are positioned close to one another when TL1a is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics. An epitope or peptide or polypeptide comprising same can be administered to an animal to generate antibodies against the epitope.

As used herein, the term "inhibits interaction of TL1a and DR3" shall be understood to mean that in an assay to measure binding of TL1a and DR3, a protein is capable of inhibiting 50% of binding (i.e., has an $EC_{50}$) of less than about 13 nM, for example, less than about 10 nM, such as less than about 7 nM, e.g., less than about 5 nM, for example, less than about 3 nM.

As used herein, the term "does not inhibit interaction of TL1a and DcR3" will be understood to mean that a TL1a-binding protein described herein does not inhibit interaction of TL1a and DcR3 (i.e., such that interaction is no longer detectable, e.g., using an ELISA assay described herein). For example, at a concentration of 100 μg/ml, the protein does not completely inhibit interaction of TL1a and DcR3. In some examples, the protein reduces the interaction of TL1a and DcR3 by less than about 20% or 15% or 10%, e.g., when tested at a concentration of 10 μg/ml or 100 μg/ml.

As used herein, the term "does not detectably reduce" shall be understood to mean that a protein as described herein reduces binding of TL1a (or a biotinylated form thereof) to DcR3 by no more than 20% or 8% or 6% or 5% or 4% or 3% or 2% above the level of interaction in the absence of the protein or above the level of background interaction, when tested at a concentration of 10 μg/ml or 100 μg/ml. The background can be the level of binding signal detected in the absence of the protein and/or in the presence of a negative control protein (e.g., an isotype control antibody).

As used herein, the term "neutralize" shall be taken to mean that a TL1a-binding protein is capable of reducing or preventing TL1a-mediated activity in a cell. Methods for determining neutralization are known in the art and/or described herein. For example, TF-1 cells are contacted with TL1a, such as human TL1a (e.g., expressed by a mammalian cell) and cycloheximide in the presence or absence of the TL1a-binding protein. A TL1a-binding protein that reduces the level of apoptosis of the cells compared to the level in the absence of the protein is considered to "neutralize" TL1a activity.

As used herein, the term "condition" refers to a disruption of or interference with normal function, and is not to be limited to any specific condition, and will include diseases or disorders.

As used herein, a "TL1a-associated condition" refers to any condition that is caused by or associated with TL1a or a cell expressing TL1a. The skilled artisan will be readily able to determine such conditions based on the disclosure herein and/or by performing an assay to diagnose a TL1a-associated condition as described herein. In this regard, in some examples the condition is an inflammatory condition, an autoimmune condition and a condition that can be treated by enhancing angiogenesis. A description of exemplary conditions is included herein.

As used herein, the terms "preventing", "prevent" or "prevention" include administering a protein of the disclosure to thereby stop or hinder the development of at least one symptom of a condition. This term also encompasses treatment of a subject in remission to prevent or hinder relapse. For example, a subject suffering from relapsing-remitting multiple sclerosis is treated during remission to thereby prevent a relapse.

As used herein, the terms "treating", "treat" or "treatment" include administering a protein described herein to thereby reduce or eliminate at least one symptom of a specified disease or condition.

As used herein, the term "subject" shall be taken to mean any animal, such as, a mammal. In one example, the mammal is a human or non-human primate. In one example, the mammal is a human.

Reference herein to a "sample" should be understood as a reference to any sample derived from a subject such as, but not limited to, a body fluid (e.g., blood or blood fraction such as serum or plasma, tears, urine, synovial fluid or cerebrospinal fluid), cellular material (e.g. tissue aspirate), tissue biopsy specimens or surgical specimens. In some examples, the "sample" is any one or more of serum, plasma, PBMCs, or a buffy coat fraction.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence or the outcome of treatment.

The term "expression construct" is to be taken in its broadest context and includes a nucleic acid comprising one or more promoter sequences operably linked with one or more nucleic acids as described herein.

The term "expression vector" refers to a nucleic acid comprising an expression construct that is additionally capable of maintaining and or replicating nucleic acid in an expressible format. For example, an expression vector may comprise a plasmid, bacteriophage, phagemid, cosmid, virus sub-genomic or genomic fragment. Selection of appropriate vectors is within the knowledge of those having skill in the art.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked.

An exemplary promoter can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter. A promoter can be operably linked to numerous nucleic acids, e.g., through an internal ribosome entry site.

Antibodies

Immunization-Based Methods

To generate antibodies, TL1a or an epitope bearing fragment or portion thereof or a modified form thereof (e.g., a fusion protein comprising a human epitope within a mouse TL1a protein) or nucleic acid encoding same, optionally formulated with any suitable or desired adjuvant and/or pharmaceutically acceptable carrier, is administered to a subject (for example, a non-human animal subject, such as, a mouse, a rat, a chicken etc.) in the form of an injectable composition. Exemplary non-human animals are mammals, such as murine animals (e.g., rats or mice). Injection may be intranasal, intramuscular, sub-cutaneous, intravenous, intradermal, intraperitoneal, or by other known route. Optionally, the TL1a or epitope bearing fragment or portion thereof or a nucleic acid encoding same is administered numerous times. Means for preparing and characterizing antibodies are known in the art (See, e.g., Antibodies: A Laboratory Manual, Cold Spring Harbor Laboratory, 1988).

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the disclosure. Generally, production of monoclonal antibodies involves, immunizing a subject (e.g., a rodent, e.g., mouse or rat) with TL1a or an epitope bearing fragment or portion thereof or a nucleic acid encoding same under conditions sufficient to stimulate antibody producing cells. In some examples, a mouse genetically-engineered to express human immunoglobulin proteins and not express murine immunoglobulin proteins, is immunized to produce an antibody (e.g., as described in PCT/US2007/008231 and/or Lonberg et al., *Nature* 368: 856-859, 1994). Following immunization, antibody producing somatic cells (e.g., B lymphocytes) are fused with immortal cells, e.g., immortal myeloma cells. Various methods for producing such fused cells (hybridomas) are known in the art and described, for example, in Kohler and Milstein, *Nature* 256: 495-497, 1975. The hybridoma cells can then be cultured under conditions sufficient for antibody production.

The disclosure contemplates other methods for producing antibodies, e.g., ABL-MYC technology (as described, for example in Largaespada et al., *Curr. Top. Microbiol. Immunol,* 166: 91-96, 1990). Suitable antibodies are then selected based on methods described herein.

Library-Based Methods

The disclosure also encompasses screening of libraries of antibodies or proteins comprising antigen binding domains thereof (e.g., comprising variable regions thereof) to identify a TL1a-binding protein of the disclosure.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or U.S. Pat. No. 6,248,516.

The TL1a-binding proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, e.g., as described in U.S. Pat. Nos. 6,300,064; 5,885,793; 6,204,023; 6,291,158; or U.S. Pat. No. 6,248,516. Other phage display methods are known in the art and are contemplated by the disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the disclosure is screened using affinity purification, e.g., as described in Scopes (In: Protein purification: principles and practice, Third Edition, Springer Verlag, 1994). Methods of affinity purification typically involve contacting proteins comprising antigen binding domains displayed by the library with a target antigen (e.g., TL1a) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., *J. Immunol. Methods* 354: 85-90, 2010; or Jostock et al., *J. Immunol. Methods,* 289: 65-80, 2004. Alternatively, or additionally, standard cloning methods are used, e.g., as described in Ausubel et al., (In: Current Protocols in Molecular Biology. Wiley Interscience, ISBN 047 150338, 1987), and/or (Sambrook et al., (In: Molecular Cloning: Molecular Cloning: A Laboratory Manual, Cold Spring Harbor Laboratories, New York, Third Edition 2001).

Deimmunized, Chimeric, CDR Grafted, Humanized, Synhumanized, Primatized, Human and Composite TL1a-Binding Proteins The TL1a-binding proteins of the disclosure may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite protein comprising, for example, one or more CDR grafted variable regions and one or more, e.g., human variable regions, chimeric variable regions, synhumanized variable regions or primatized variable regions. Such proteins are exemplified herein by the antibodies designated C320-16 to C320-33.

The TL1a-binding proteins of the disclosure may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to as a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized protein" also encompasses a super-humanized protein, e.g., as described in U.S. Pat. No. 7,732,578. This term also encompasses a composite protein comprising, for example, one or more humanized variable regions and one or more, e.g., human variable regions, chimeric variable regions, synhumanized variable regions or primatized variable regions.

In one example, a humanized TL1a-binding protein comprises the regions between 27d and 34, 50 and 55, and 89 and 96 in a light chain sequence disclosed herein; and 31 and 35b, 50 and 58, and 95 and 101 in a heavy chain sequence disclosed herein (numbering according to the Kabat numbering system). In this regard, Padlan et al., *FASEB J.,* 9: 133-139, 1995 presents evidence that these regions are those most likely to bind or contact antigen.

The TL1a-binding proteins of the disclosure may be human proteins. The term "human protein" as used herein refers to proteins having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the disclosure, a human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Exemplary human TL1a-binding proteins are antibodies comprising the following pairs of variable regions:

(i) a $V_H$ comprising a sequence set forth in SEQ ID NO: 2 and a $V_L$ comprising a sequence set forth in SEQ ID NO: 6;

(ii) a $V_H$ comprising a sequence set forth in SEQ ID NO: 10 and a $V_L$ comprising a sequence set forth in SEQ ID NO: 14;

(iii) a $V_H$ comprising a sequence set forth in SEQ ID NO: 18 and a $V_L$ comprising a sequence set forth in SEQ ID NO: 22;

(iv) a $V_H$ comprising a sequence set forth in SEQ ID NO: 26 and a $V_L$ comprising a sequence set forth in SEQ ID NO: 30;

(v) a $V_H$ comprising a sequence set forth in SEQ ID NO: 34 and a $V_L$ comprising a sequence set forth in SEQ ID NO:38;

(vi) a $V_H$ comprising a sequence set forth in SEQ ID NO: 42 and a $V_L$ comprising a sequence set forth in SEQ ID NO: 46;

(vii) a $V_H$ comprising a sequence set forth in SEQ ID NO: 50 and a $V_L$ comprising a sequence set forth in SEQ ID NO: 54;

(viii) a $V_H$ comprising a sequence set forth in SEQ ID NO: 58 and a $V_L$ comprising a sequence set forth in SEQ ID NO: 46;

(ix) a $V_H$ comprising a sequence set forth in SEQ ID NO: 42 and a $V_L$ comprising a sequence set forth in SEQ ID NO: 62;

(x) a $V_H$ comprising a sequence set forth in SEQ ID NO: 66 and a $V_L$ comprising a sequence set forth in SEQ ID NO: 62;

(xi) a $V_H$ comprising a sequence set forth in SEQ ID NO: 70 and a $V_L$ comprising a sequence set forth in SEQ ID NO: 62;

(xii) a $V_H$ comprising a sequence set forth in SEQ ID NO: 74 and a $V_L$ comprising a sequence set forth in SEQ ID NO: 62;

(xiii) a $V_H$ comprising a sequence set forth in SEQ ID NO: 78 and a $V_L$ comprising a sequence set forth in SEQ ID NO: 62;

(xiv) a $V_H$ comprising a sequence set forth in SEQ ID NO: 58 and a $V_L$ comprising a sequence set forth in SEQ ID NO: 82;

(xv) a $V_H$ comprising a sequence set forth in SEQ ID NO: 86 and a $V_L$ comprising a sequence set forth in SEQ ID NO: 46;

(xvi) a $V_H$ comprising a sequence set forth in SEQ ID NO: 90 and a $V_L$ comprising a sequence set forth in SEQ ID NO: 46;

(xvii) a $V_H$ comprising a sequence set forth in SEQ ID NO: 58 and a $V_L$ comprising a sequence set forth in SEQ ID NO: 62;

(xviii) a $V_H$ comprising a sequence set forth in SEQ ID NO: 154 and a $V_L$ comprising a sequence set forth in SEQ ID NO: 164;

(xix) a $V_H$ comprising a sequence set forth in SEQ ID NO: 155 and a $V_L$ comprising a sequence set forth in SEQ ID NO: 163;

(xx) a $V_H$ comprising a sequence set forth in SEQ ID NO: 156 and a $V_L$ comprising a sequence set forth in SEQ ID NO: 165;

(xxi) a $V_H$ comprising a sequence set forth in SEQ ID NO: 157 and a $V_L$ comprising a sequence set forth in SEQ ID NO: 166;

(xxii) a $V_H$ comprising a sequence set forth in SEQ ID NO: 158 and a $V_L$ comprising a sequence set forth in SEQ ID NO: 167;

(xxiii) a $V_H$ comprising a sequence set forth in SEQ ID NO: 159 and a $V_L$ comprising a sequence set forth in SEQ ID NO: 168;

(xxiv) a $V_H$ comprising a sequence set forth in SEQ ID NO: 160 and a $V_L$ comprising a sequence set forth in SEQ ID NO: 169;

(xxv) a $V_H$ comprising a sequence set forth in SEQ ID NO: 161 and a $V_L$ comprising a sequence set forth in SEQ ID NO: 170;

(xxvi) a $V_H$ comprising a sequence set forth in SEQ ID NO: 234 and a $V_L$ comprising a sequence set forth in SEQ ID NO: 169;

(xxvii) a $V_H$ comprising a sequence set forth in SEQ ID NO: 154 and a $V_L$ comprising a sequence set forth in SEQ ID NO: 46;

(xxviii) a $V_H$ comprising a sequence set forth in SEQ ID NO: 155 and a $V_L$ comprising a sequence set forth in SEQ ID NO: 46;

(xxix) a $V_H$ comprising a sequence set forth in SEQ ID NO: 156 and a $V_L$ comprising a sequence set forth in SEQ ID NO: 46;

(xxx) a $V_H$ comprising a sequence set forth in SEQ ID NO: 157 and a $V_L$ comprising a sequence set forth in SEQ ID NO: 46;

(xxxi) a $V_H$ comprising a sequence set forth in SEQ ID NO: 158 and a $V_L$ comprising a sequence set forth in SEQ ID NO: 46;

(xxxii) a $V_H$ comprising a sequence set forth in SEQ ID NO: 159 and a $V_L$ comprising a sequence set forth in SEQ ID NO: 46;

(xxxiii) a $V_H$ comprising a sequence set forth in SEQ ID NO: 160 and a $V_L$ comprising a sequence set forth in SEQ ID NO: 46;

(xxxiv) a $V_H$ comprising a sequence set forth in SEQ ID NO: 161 and a $V_L$ comprising a sequence set forth in SEQ ID NO: 46;

(xxxv) a $V_H$ comprising a sequence set forth in SEQ ID NO: 234 and a $V_L$ comprising a sequence set forth in SEQ ID NO: 46;

(xxxvi) a $V_H$ comprising a sequence set forth in SEQ ID NO: 42 and a $V_L$ comprising a sequence set forth in SEQ ID NO: 164;

(xxxvii) a $V_H$ comprising a sequence set forth in SEQ ID NO: 42 and a $V_L$ comprising a sequence set forth in SEQ ID NO: 165;

(xxxviii) a $V_H$ comprising a sequence set forth in SEQ ID NO: 42 and a $V_L$ comprising a sequence set forth in SEQ ID NO: 166;

(xxxix) a $V_H$ comprising a sequence set forth in SEQ ID NO: 42 and a $V_L$ comprising a sequence set forth in SEQ ID NO: 167;

(xl) a $V_H$ comprising a sequence set forth in SEQ ID NO: 42 and a $V_L$ comprising a sequence set forth in SEQ ID NO: 168;

(xli) a $V_H$ comprising a sequence set forth in SEQ ID NO: 42 and a $V_L$ comprising a sequence set forth in SEQ ID NO: 169;

(xlii) a $V_H$ comprising a sequence set forth in SEQ ID NO: 42 and a $V_L$ comprising a sequence set forth in SEQ ID NO: 170;

(xliii) a $V_H$ comprising a sequence set forth in SEQ ID NO: 42 and a $V_L$ comprising a sequence set forth in SEQ ID NO: 171;

(xliv) a $V_H$ comprising a sequence set forth in SEQ ID NO: 42 and a $V_L$ comprising a sequence set forth in SEQ ID NO: 172;

(xlv) a $V_H$ comprising a sequence set forth in SEQ ID NO: 175 and a $V_L$ comprising a sequence set forth in SEQ ID NO: 188;

(xlvi) a $V_H$ comprising a sequence set forth in SEQ ID NO: 176 and a $V_L$ comprising a sequence set forth in SEQ ID NO: 189;

(xlvii) a $V_H$ comprising a sequence set forth in SEQ ID NO: 177 and a $V_L$ comprising a sequence set forth in SEQ ID NO: 190;

(xlviii) a $V_H$ comprising a sequence set forth in SEQ ID NO: 178 and a $V_L$ comprising a sequence set forth in SEQ ID NO: 191;

(xlix) a $V_H$ comprising a sequence set forth in SEQ ID NO: 179 and a $V_L$ comprising a sequence set forth in SEQ ID NO: 192;

(l) a $V_H$ comprising a sequence set forth in SEQ ID NO: 180 and a $V_L$ comprising a sequence set forth in SEQ ID NO: 193;

(li) a $V_H$ comprising a sequence set forth in SEQ ID NO: 181 and a $V_L$ comprising a sequence set forth in SEQ ID NO: 194;

(lii) a $V_H$ comprising a sequence set forth in SEQ ID NO: 182 and a $V_L$ comprising a sequence set forth in SEQ ID NO: 195;

(liii) a $V_H$ comprising a sequence set forth in SEQ ID NO: 183 and a $V_L$ comprising a sequence set forth in SEQ ID NO: 196;

(liv) a $V_H$ comprising a sequence set forth in SEQ ID NO: 184 and a $V_L$ comprising a sequence set forth in SEQ ID NO: 197;

(lv) a $V_H$ comprising a sequence set forth in SEQ ID NO: 185 and a $V_L$ comprising a sequence set forth in SEQ ID NO: 198;

(lvi) a $V_H$ comprising a sequence set forth in SEQ ID NO: 186 and a $V_L$ comprising a sequence set forth in SEQ ID NO: 199; or (lvii) a $V_H$ comprising a sequence set forth in SEQ ID NO: 187 and a $V_L$ comprising a sequence set forth in SEQ ID NO: 200.

Additional exemplary human TL1a-binding proteins are antibodies comprising a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:

(i) the $V_H$ comprises an alanine at position 16 of SEQ ID NO: 42;

(ii) the $V_H$ comprises an alanine at position 100 of SEQ ID NO: 42 and the $V_L$ comprises a threonine at position 76 of SEQ ID NO: 46;

(iii) the $V_H$ comprises a serine at position 100 of SEQ ID NO: 42 and the $V_L$ comprises a threonine at position 76 of SEQ ID NO: 46;

(iv) the $V_H$ comprises a histidine at position 100 of SEQ ID NO: 42 and the $V_L$ comprises a threonine at position 76 of SEQ ID NO: 46;

(v) the $V_H$ comprises a leucine at position 100 of SEQ ID NO: 42 and the $V_L$ comprises a threonine at position 76 of SEQ ID NO: 46;

(vi) the $V_H$ comprises an aspartic acid at position 100 of SEQ ID NO: 42 and the $V_L$ comprises a threonine at position 76 of SEQ ID NO: 46;
(vii) the $V_H$ comprises a tyrosine at position 100 of SEQ ID NO: 42 and the $V_L$ comprises a threonine at position 76 of SEQ ID NO: 46;
(viii) the $V_H$ comprises a proline at position 100 of SEQ ID NO: 42 and the $V_L$ comprises a threonine at position 76 of SEQ ID NO: 46;
(ix) the $V_H$ comprises a glutamine at position 100 of SEQ ID NO: 42 and the $V_L$ comprises a threonine at position 76 of SEQ ID NO: 46;
(x) the $V_H$ comprises a lysine at position 100 of SEQ ID NO: 42 and the $V_L$ comprises a threonine at position 76 of SEQ ID NO: 46;
(xi) the $V_H$ comprises an alanine at position 101 of SEQ ID NO: 42 and the $V_L$ comprises a threonine at position 76 of SEQ ID NO: 46;
(xii) the $V_H$ comprises a serine at position 101 of SEQ ID NO: 42 and the $V_L$ comprises a threonine at position 76 of SEQ ID NO: 46;
(xiii) the $V_H$ comprises a histidine at position 101 of SEQ ID NO: 42 and the $V_L$ comprises a threonine at position 76 of SEQ ID NO: 46;
(xiv) the $V_H$ comprises a leucine at position 101 of SEQ ID NO: 42 and the $V_L$ comprises a threonine at position 76 of SEQ ID NO: 46;
(xv) the $V_H$ comprises an aspartic acid at position 101 of SEQ ID NO: 42 and the $V_L$ comprises a threonine at position 76 of SEQ ID NO: 46;
(xvi) the $V_H$ comprises a tyrosine at position 101 of SEQ ID NO: 42 and the $V_L$ comprises a threonine at position 76 of SEQ ID NO: 46;
(xvii) the $V_H$ comprises a glutamine at position 101 of SEQ ID NO: 42 and the $V_L$ comprises a threonine at position 76 of SEQ ID NO: 46;
(xviii) the $V_H$ comprises a lysine at position 101 of SEQ ID NO: 42 and the $V_L$ comprises a threonine at position 76 of SEQ ID NO: 46;
(xix) the $V_H$ comprises an alanine at position 102 of SEQ ID NO: 42 and the $V_L$ comprises a threonine at position 76 of SEQ ID NO: 46;
(xx) the $V_H$ comprises a serine at position 102 of SEQ ID NO: 42 and the $V_L$ comprises a threonine at position 76 of SEQ ID NO: 46;
(xxi) the $V_H$ comprises a histidine at position 102 of SEQ ID NO: 42 and the $V_L$ comprises a threonine at position 76 of SEQ ID NO: 46;
(xxii) the $V_H$ comprises a leucine at position 102 of SEQ ID NO: 42 and the $V_L$ comprises a threonine at position 76 of SEQ ID NO: 46;
(xxiii) the $V_H$ comprises a tyrosine at position 102 of SEQ ID NO: 42 and the $V_L$ comprises a threonine at position 76 of SEQ ID NO: 46;
(xxiv) the $V_H$ comprises a proline at position 102 of SEQ ID NO: 42 and the $V_L$ comprises a threonine at position 76 of SEQ ID NO: 46;
(xxv) the $V_H$ comprises a glutamine at position 102 of SEQ ID NO: 42 and the $V_L$ comprises a threonine at position 76 of SEQ ID NO: 46;
(xxvi) the $V_H$ comprises a lysine at position 102 of SEQ ID NO: 42 and the $V_L$ comprises a threonine at position 76 of SEQ ID NO: 46;
(xxvii) the $V_H$ comprises an alanine at position 103 of SEQ ID NO: 42 and the $V_L$ comprises a threonine at position 76 of SEQ ID NO: 46;
(xxviii) the $V_H$ comprises a serine at position 103 of SEQ ID NO: 42 and the $V_L$ comprises a threonine at position 76 of SEQ ID NO: 46;
(xxix) the $V_H$ comprises a histidine at position 103 of SEQ ID NO: 42 and the $V_L$ comprises a threonine at position 76 of SEQ ID NO: 46;
(xxx) the $V_H$ comprises a leucine at position 103 of SEQ ID NO: 42 and the $V_L$ comprises a threonine at position 76 of SEQ ID NO: 46;
(xxxi) the $V_H$ comprises an aspartic acid at position 103 of SEQ ID NO: 42 and the $V_L$ comprises a threonine at position 76 of SEQ ID NO: 46;
(xxxii) the $V_H$ comprises a tyrosine at position 103 of SEQ ID NO: 42 and the $V_L$ comprises a threonine at position 76 of SEQ ID NO: 46;
(xxxiii) the $V_H$ comprises a proline at position 103 of SEQ ID NO: 42 and the $V_L$ comprises a threonine at position 76 of SEQ ID NO: 46;
(xxxiv) the $V_H$ comprises a glutamine at position 103 of SEQ ID NO: 42 and the $V_L$ comprises a threonine at position 76 of SEQ ID NO: 46;
(xxxv) the $V_H$ comprises a lysine at position 103 of SEQ ID NO: 42 and the $V_L$ comprises a threonine at position 76 of SEQ ID NO: 46;
(xxxvi) the $V_H$ comprises a serine at position 104 of SEQ ID NO: 42 and the $V_L$ comprises a threonine at position 76 of SEQ ID NO: 46;
(xxxvii) the $V_H$ comprises a histidine at position 104 of SEQ ID NO: 42 and the $V_L$ comprises a threonine at position 76 of SEQ ID NO: 46;
(xxxviii) the $V_H$ comprises a leucine at position 104 of SEQ ID NO: 42 and the $V_L$ comprises a threonine at position 76 of SEQ ID NO: 46;
(xxxix) the $V_H$ comprises an aspartic acid at position 104 of SEQ ID NO: 42 and the $V_L$ comprises a threonine at position 76 of SEQ ID NO: 46;
(xl) the $V_H$ comprises a tyrosine at position 104 of SEQ ID NO: 42 and the $V_L$ comprises a threonine at position 76 of SEQ ID NO: 46;
(xli) the $V_H$ comprises a proline at position 104 of SEQ ID NO: 42 and the $V_L$ comprises a threonine at position 76 of SEQ ID NO: 46;
(xlii) the $V_H$ comprises a glutamine at position 104 of SEQ ID NO: 42 and the $V_L$ comprises a threonine at position 76 of SEQ ID NO: 46;
(xliii) the $V_H$ comprises a lysine at position 104 of SEQ ID NO: 42 and the $V_L$ comprises a threonine at position 76 of SEQ ID NO: 46;
(xliv) the $V_H$ comprises an alanine at position 105 of SEQ ID NO: 42 and the $V_L$ comprises a threonine at position 76 of SEQ ID NO: 46;
(xlv) the $V_H$ comprises a histidine at position 105 of SEQ ID NO: 42 and the $V_L$ comprises a threonine at position 76 of SEQ ID NO: 46;
(xlvi) the $V_H$ comprises a leucine at position 105 of SEQ ID NO: 42 and the $V_L$ comprises a threonine at position 76 of SEQ ID NO: 46;
(xlvii) the $V_H$ comprises an aspartic acid at position 105 of SEQ ID NO: 42 and the $V_L$ comprises a threonine at position 76 of SEQ ID NO: 46;
(xlviii) the $V_H$ comprises a tyrosine at position 105 of SEQ ID NO: 42 and the $V_L$ comprises a threonine at position 76 of SEQ ID NO: 46;
(xlix) the $V_H$ comprises a proline at position 105 of SEQ ID NO: 42 and the $V_L$ comprises a threonine at position 76 of SEQ ID NO: 46;

(l) the $V_H$ comprises a glutamine at position 105 of SEQ ID NO: 42 and the $V_L$ comprises a threonine at position 76 of SEQ ID NO: 46;
(li) the $V_H$ comprises a lysine at position 105 of SEQ ID NO: 42 and the $V_L$ comprises a threonine at position 76 of SEQ ID NO: 46;
(lii) the $V_H$ comprises an alanine at position 107 of SEQ ID NO: 42 and the $V_L$ comprises a threonine at position 76 of SEQ ID NO: 46;
(liii) the $V_H$ comprises a serine at position 107 of SEQ ID NO: 42 and the $V_L$ comprises a threonine at position 76 of SEQ ID NO: 46;
(liv) the $V_H$ comprises a histidine at position 107 of SEQ ID NO: 42 and the $V_L$ comprises a threonine at position 76 of SEQ ID NO: 46;
(lv) the $V_H$ comprises a leucine at position 107 of SEQ ID NO: 42 and the $V_L$ comprises a threonine at position 76 of SEQ ID NO: 46;
(lvi) the $V_H$ comprises an aspartic acid at position 107 of SEQ ID NO: 42 and the $V_L$ comprises a threonine at position 76 of SEQ ID NO: 46;
(lvii) the $V_H$ comprises a tyrosine at position 107 of SEQ ID NO: 42 and the $V_L$ comprises a threonine at position 76 of SEQ ID NO: 46;
(lviii) the $V_H$ comprises a proline at position 107 of SEQ ID NO: 42 and the $V_L$ comprises a threonine at position 76 of SEQ ID NO: 46;
(lix) the $V_H$ comprises a glutamine at position 107 of SEQ ID NO: 42 and the $V_L$ comprises a threonine at position 76 of SEQ ID NO: 46;
(lx) the $V_H$ comprises a lysine at position 107 of SEQ ID NO: 42 and the $V_L$ comprises a threonine at position 76 of SEQ ID NO: 46;
(lxi) the $V_H$ comprises a threonine at position 41 of SEQ ID NO: 42 and the $V_L$ comprises an alanine at position 23 of SEQ ID NO: 46;
(lxii) the $V_H$ comprises a threonine at position 41 of SEQ ID NO: 42 and the $V_L$ comprises an aspartic acid at position 28 of SEQ ID NO: 46;
(lxiii) the $V_H$ comprises a threonine at position 41 of SEQ ID NO: 42 and the $V_L$ comprises a tyrosine at position 33 of SEQ ID NO: 46;
(lxiv) the $V_H$ comprises a threonine at position 41 of SEQ ID NO: 42 and the $V_L$ comprises an aspartic acid at position 34 of SEQ ID NO: 46;
(lxv) the $V_H$ comprises a threonine at position 41 of SEQ ID NO: 42 and the $V_L$ comprises an asparagine at position 53 of SEQ ID NO: 46;
(lxvi) the $V_H$ comprises a threonine at position 41 of SEQ ID NO: 42 and the $V_L$ comprises a serine at position 54 of SEQ ID NO: 46;
(lxvii) the $V_H$ comprises a threonine at position 41 of SEQ ID NO: 42 and the $V_L$ comprises an alanine at position 82 of SEQ ID NO: 46;
(lxviii) the $V_H$ comprises a threonine at position 41 of SEQ ID NO: 42 and the $V_L$ comprises a serine at position 95 of SEQ ID NO: 46;
(lxix) the $V_H$ comprises a threonine at position 41 of SEQ ID NO: 42 and the $V_L$ comprises a serine at position 96 of SEQ ID NO: 46;
(lxx) the $V_H$ comprises a threonine at position 41 of SEQ ID NO: 42 and the $V_L$ comprises a threonine at position 76 of SEQ ID NO: 46;
(lxxi) the $V_H$ comprises a serine at position 47 of SEQ ID NO: 42 and the $V_L$ comprises a threonine at position 23 of SEQ ID NO: 46;
(lxxii) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 76 of SEQ ID NO: 46;
(lxxiii) the $V_H$ comprises a proline at position 41, a leucine at position 51 and a glutamic acid at position 102 each relative to SEQ ID NO: 42 and the $V_L$ comprises a serine at position 24 and a threonine at position 76 each relative to SEQ ID NO: 46;
(lxxiv) the $V_H$ comprises a proline at position 41, a leucine at position 51 and a glutamic acid at position 102 each relative to SEQ ID NO: 42 and the $V_L$ comprises a threonine at position 23, a serine at position 24 and a threonine at position 76 each relative to SEQ ID NO: 46;
(lxxv) the $V_H$ comprises a proline at position 41, a leucine at position 51 and a glutamic acid at position 102 each relative to SEQ ID NO: 42 and the $V_L$ comprises a threonine at position 23 and a threonine at position 76 each relative to SEQ ID NO: 46;
(lxxvi) the $V_H$ comprises a proline at position 41, a leucine at position 51 and a glutamic acid at position 102 each relative to SEQ ID NO: 42 and the $V_L$ comprises a threonine at position 76 of SEQ ID NO: 46;
(lxxvii) the $V_H$ comprises a proline at position 41, a leucine at position 51, a glutamic acid at position 102 and an alanine at position 105 each relative to SEQ ID NO: 42 and the $V_L$ comprises a threonine at position 23, a serine at position 24 and a threonine at position 76 each relative to SEQ ID NO: 46;
(lxxviii) the $V_H$ comprises a proline at position 41, a leucine at position 51, a glutamic acid at position 102 and an alanine at position 105 each relative to SEQ ID NO: 42 and the $V_L$ comprises a threonine at position 76 of SEQ ID NO: 46;
(lxxix) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 23, a serine at position 24 and a threonine at position 76 each relative to SEQ ID NO: 46;
(lxxx) the $V_H$ comprises a proline at position 41, an alanine at position 72, an aspartic acid at position 73, an arginine at position 74 and a threonine at position 76 each relative to SEQ ID NO: 42 and the $V_L$ comprises a threonine at position 23, a serine at position 24, a threonine at position 76 and a glutamic acid at position 51 each relative to SEQ ID NO: 46;
(lxxxi) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glutamic acid at position 51 each relative to SEQ ID NO: 46; and
(i) the $V_H$ comprises a proline at position 41, a leucine at position 51, an alanine at position 72, an aspartic acid at position 73, an arginine at position 74, a threonine at position 76, a glutamic acid at position 102 and an alanine at position 105 each relative to SEQ ID NO: 42 and the $V_L$ comprises a threonine at position 23, a serine at position 24, a threonine at position 76 and a glycine at position 51 each relative to SEQ ID NO: 46.

Optionally, the $V_H$ is linked to a heavy chain constant region, e.g., an IgG1 heavy chain constant region. In one example, the heavy chain constant region lacks the c-terminal lysine residue.

Optionally, the $V_L$ is linked to a light chain constant region.

The TL1a-binding proteins of the disclosure may be synhumanized proteins. The term "synhumanized protein" refers to a protein prepared by a method described in WO2007/019620. A synhumanized TL1a-binding protein includes a variable region of an antibody, wherein the variable region comprises FRs from a New World primate antibody variable region and CDRs from a non-New World primate antibody variable region. For example, a synhumanized TL1a-binding protein includes a variable region of an antibody, wherein the variable region comprises FRs from a New World primate antibody variable region and CDRs from a mouse or rat antibody. In one example, the synhumanized TL1a-binding protein is a TL1a-binding antibody in which one or both of the variable regions are synhumanized. This term also encompasses a composite protein comprising, for example, one or more synhumanized variable regions and one or more, e.g., human variable regions or humanized variable regions or chimeric variable regions.

The TL1a-binding proteins of the disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, e.g., human variable regions or humanized variable regions or chimeric variable regions.

In one example a TL1a-binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397). This term also encompasses a composite protein comprising, for example, one or more chimeric variable regions and one or more, e.g., human variable regions or humanized variable regions or chimeric variable regions.

The disclosure also contemplates a deimmunized TL1a-binding protein, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein. For example, a TL1a-binding protein of the disclosure is analyzed to identify one or more B or T cell epitopes and one or more amino acid residues within the epitope is mutated to thereby reduce the immunogenicity of the TL1a-binding protein. The present inventors have used such techniques to identify epitopes that are predicted to bind to MHC Class II molecules and identify TL1a binding proteins less likely to induce an immune response in a subject.

It will be apparent to the skilled artisan from the foregoing disclosure that a "composite" protein comprises one form of $V_H$ (e.g., human) and another form of $V_L$ (e.g., humanized). The disclosure explicitly encompasses all combinations of forms of $V_H$ and $V_L$.

Other TL1a-Binding Proteins Comprising an Antigen Binding Domain

The disclosure also contemplates other TL1a-binding proteins comprising a variable region or antigen binding domain of an antibody, such as:

(i) a single-domain antibody, which is a single polypeptide chain comprising all or a portion of the $V_H$ or a $V_L$ of an antibody (see, e.g., U.S. Pat. No. 6,248,516);

(ii) diabodies, triabodies and tetrabodies, e.g., as described in U.S. Pat. No. 5,844,094 and/or US2008152586;

(iii) scFvs, e.g., as described in U.S. Pat. No. 5,260,203;

(iv) minibodies, e.g., as described in U.S. Pat. No. 5,837,821;

(v) "key and hole" bispecific proteins as described in U.S. Pat. No. 5,731,168;

(vi) heteroconjugate proteins, e.g., as described in U.S. Pat. No. 4,676,980;

(vii) heteroconjugate proteins produced using a chemical cross-linker, e.g., as described in U.S. Pat. No. 4,676,980;

(viii) Fab'-SH fragments, e.g., as described in Shalaby et al., *J. Exp. Med.,* 175: 217-225, 1992; or (ix) $Fab_3$ (e.g., as described in EP19930302894).

Constant Domain Fusions

The disclosure encompasses a TL1a-binding protein comprising an antigen binding domain of an antibody and a constant region or Fc or a domain thereof, e.g., $C_H2$ and/or $C_H3$ domain. Suitable constant regions and/or domains will be apparent to the skilled artisan and/or the sequences of such polypeptides are readily available from publicly available databases. Kabat et al also provide description of some suitable constant regions/domains.

Constant regions and/or domains thereof are useful for providing biological activities such as, dimerization, extended serum half life (e.g., by binding to FcRn), antibody-dependent cell cytotoxicity (ADCC), complement dependent cytotoxicity (CDC), antibody-dependent cell phagocytosis (ADCP).

The disclosure also contemplates TL1a-binding proteins comprising mutant constant regions or domains, e.g., as described in U.S. Pat. Nos. 7,217,797; 7,217,798; or US20090041770 (having increased half-life) or US2005037000 (increased ADCC).

The C-terminal lysine of the heavy chain constant region of an antibody of the disclosure or TL1a-binding protein of the disclosure comprising a constant region or Fc may be removed, for example, during production or purification of the antibody, or by recombinantly engineering the nucleic acid encoding a heavy chain of the antibody or protein. Accordingly, whole antibodies or proteins may comprise antibody or protein populations with all C-terminal lysine residues removed, antibody or protein populations with no C-terminal lysine residues removed, or antibody or protein populations having a mixture of antibodies with and without the C-terminal lysine residue. In some examples, the antibody or protein populations may additionally comprise antibodies or proteins in which the C-terminal lysine residue is removed in one of the heavy chain constant regions. Similarly, a composition of antibodies or proteins may comprise the same or a similar mix of antibody or protein populations with or without the C-terminal lysine residue.

Enhancing Effector Function

In one example, a TL1a-binding protein of the disclosure may induce effector function or enhanced effector function.

In the context of the disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity; antibody-dependent-cell-mediated cytotoxicity (ADCC); antibody-dependent-cell-phagocytosis (ADCP); and B-cell activation.

In one example, a TL1a-binding protein of the disclosure binds to TL1a on the surface of a cell in such a manner that it is capable of inducing an effector function, such as, ADCC or CDC.

For example, the TL1a-binding protein remains bound to the TL1a on the surface of the cell for a time sufficient to induce an effector function, such as ADCC and/or CDC.

In one example, a TL1a-binding protein of the disclosure is capable of inducing enhanced effector function, e.g., by virtue of a modified Fc region or by virtue of comprising a region capable of binding to an immune effector cell. For example, the level of effector function is increased compared to the level induced by a human IgG1 or IgG3 Fc region. Enhancing effector function induced by a TL1a-binding protein of the disclosure may result in enhanced therapeutic or prophylactic effects, e.g., by not only blocking the action of TL1a but also by killing or depleting cells causing a condition, e.g., by killing auto-reactive T cells.

In one example, the Fc region of a TL1a-binding protein of the disclosure is modified to increase the level of effector function it is capable of inducing compared to the Fc region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

In one example, the Fc region comprises one or more amino acid modifications that increase its ability to induce enhanced effector function. In one example, the Fc region binds with greater affinity to one or more FcγRs, such as FcγRIII. In one example, the Fc region comprise at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprises the following amino acid substitutions S239D/I332E, numbered according to the EU index of Kabat. This Fc region has about 14 fold increase in affinity for FcγRIIIa compared to a wild-type Fc region and about 3.3 increased ability to induce ADCC compared to a wild-type Fc region. In one example, the Fc region comprises the following amino acid substitutions S239D/A330L/I332E, numbered according to the EU index of Kabat. This Fc region has about 138 fold increase in affinity for FcγRIIIa compared to a wild-type Fc region and about 323 fold increased ability to induce ADCC compared to a wild-type Fc region.

Additional amino acid substitutions that increase ability of a Fc region to induce effector function are known in the art and/or described, for example, in U.S. Pat. No. 6,737,056 or 7,317,091.

In one example, the glycosylation of the Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the Fc region. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some examples, Fc regions according to the disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the antibody or antigen binding fragment thereof in a cell line incapable of expressing α-1,6-fucosyltransferase (FUT8) (e.g., as described in Yumane-Ohnuki et al., *Biotechnol. Bioengineer.* 87: 614-622, 2004), expressing the antibody or antigen binding fragment thereof in cells expressing a small interfering RNA against FUT8 (e.g., as described in Mori et al., *Biotechnol. Bioengineer.*, 88: 901-908, 2004), expressing the antibody or antigen binding fragment thereof in cells incapable of expressing guanosine diphosphate (GDP)-mannose 4,6-dehydratase (GMD) (e.g., as described in Kanda et al., *J. Biotechnol.*, 130: 300-310, 2007). The disclosure also contemplates the use of proteins having a reduced level of fucosylation, e.g., produced using a cell line modified to express β-(1,4)-N-acetylglucosaminyltransferase III (GnT-III) (e.g., as described in Umana et al., *Nat. Biotechnol.* 17: 176-180, 1999).

Other methods include the use of cell lines which inherently produce antibodies capable of inducing enhanced Fc-mediated effector function (e.g. duck embryonic derived stem cells for the production of viral vaccines, WO2008/129058; Recombinant protein production in avian EBX® cells, WO 2008/142124).

TL1a-binding proteins of the disclosure also include those with bisected oligosaccharides, e.g., in which a biantennary oligosaccharide attached to the Fc region is bisected by GlcNAc. Such proteins may have reduced fucosylation and/or improved ADCC function. Examples of such proteins are described, e.g., in U.S. Pat. No. 6,602,684 and US20050123546.

TL1a-binding proteins with at least one galactose residue in the oligosaccharide attached to the Fc region are also contemplated. Such proteins may have improved CDC function. Such proteins are described, e.g., in WO1997/30087 and WO1999/22764.

TL1a-binding proteins can also comprise a Fc region capable of inducing enhanced levels of CDC. For example, hybrids of IgG1 and IgG3 produce antibodies having enhanced CDC activity (Natsume et al., *Cancer Res.* 68: 3863-3872, 2008).

TL1a-binding proteins can also or alternatively be fused to or conjugated to proteins (e.g., antibody variable regions) that bind to immune effector cells, e.g., by virtue of binding to CD3 or CD16.

Methods for determining effector function are known in the art. In one example, the level of ADCC activity is assessed using a $^{51}Cr$ release assay, an europium release assay or a $^{35}S$ release assay. In each of these assays, cells expressing TL1a are cultured with one or more of the recited compounds for a time and under conditions sufficient for the compound to be taken up by the cell. In the case of a $^{35}S$ release assay, the cells can be cultured with $^{35}S$-labeled methionine and/or cysteine for a time sufficient for the labeled amino acids to be incorporated into newly synthesized proteins. Cells are then cultured in the presence or absence of the protein and in the presence of immune effector cells, e.g., PBMCs and/or NK cells. The amount of $^{51}Cr$, europium and/or $^{35}S$ in cell culture medium is then detected, and an increase in the presence of the protein compared to in the absence of protein indicates that the binding molecule/agent has effector function. Exemplary publications disclosing assays for assessing the level of ADCC induced by a protein include Hellstrom et al. *Proc. Nati Acad. Sci. USA* 83: 7059-7063, 1986 and Bruggemann et al., *J. Exp. Med.* 166: 1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

Alternatively, or additionally, effector function of a TL1a-binding protein is assessed by determining its affinity for one or more FcγRs, e.g., as described in U.S. Pat. No. 7,317,091.

C1q binding assays may also be carried out to confirm that the TL1a-binding protein is able to bind C1q and may induce CDC. To assess complement activation, a CDC assay may be performed (see, for example, Gazzano-Santoro et al., *J. Immunol. Methods* 202: 163, 1996).

In another example, the TL1a-binding protein comprises one or more amino acid substitutions that increase the half-life of the protein. For example, the TL1a-binding protein comprises a constant region comprising one or more amino acid substitutions that increase the affinity of the constant region for the neonatal Fc region (FcRn). For example, the constant region has increased affinity for FcRn at lower pH, e.g., about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half life of a TL1a-binding protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Stabilized TL1a-Binding Proteins

Neutralizing TL1a-binding proteins of the disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half-antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half-antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. USA,* 63: 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Mutant TL1a-Binding Proteins

The disclosure also provides a TL1-binding protein or a nucleic acid encoding same having at least 80% identity to a sequence disclosed herein. In one example, a TL1a-binding protein or nucleic acid of the disclosure comprises sequence at least about 85% or 90% or 95% or 97% or 98% or 99% identical to a sequence disclosed herein, wherein the protein specifically binds to TL1a and inhibits interaction of TL1a and DR3 and does not inhibit interaction of TL1a and DcR3.

Alternatively, or additionally, the TL1a-binding protein comprises a CDR (e.g., three CDRs) at least about 80% or 85% or 90% or 95% or 97% or 98% or 99% identical to CDR(s) of a $V_H$ or $V_L$ as described herein according to any example, wherein the protein is capable of specifically binding to TL1a and inhibiting interaction of TL1a and DR3, wherein the protein does not inhibit interaction of TL1a and DcR3. In this regard, the inventors have produced numerous antibodies having diverse sequences within their CDRs. Methods for determining binding of a protein TL1a and determining the interaction of TL1a and DR3 or TL1a and DcR3 are described herein.

For example, the inventors have identified a group of TL1a-binding proteins sharing 60% identity in their HCDR1 according to the Kabat numbering system and another subgroup of proteins sharing 80% identity in their HCDR1 according to the Kabat numbering system.

The inventors have also identified a subclass of TL1a-binding proteins sharing 40% identity or 47% identity in their HCDR2 according to the Kabat numbering system.

As discussed herein, it is also known in the art that the five C-terminal residues of heavy chain CDR2 can be mutated to conservative or non-conservative amino acid substitutions (31% of residues) (Padlan et al., *FASEB J.* 9: 133-139, 1995). Thus, a protein can comprise a CDR2 having at least about 69% identity to a heavy chain CDR2 sequence disclosed herein.

The inventors have also identified a class of proteins comprising variants of the variable regions of antibody C320 described herein. These variants permit identification of sites within the variable regions that can be substituted without loss of function.

For example, the inventors have identified several residues in a $V_H$ comprising a sequence set forth in SEQ ID NO: 42 that can be substituted without loss of function. Accordingly, the disclosure encompasses proteins comprising a $V_H$ with at least about 86% identity to a sequence set forth in SEQ ID NO: 42. In this regard, the inventors have produced a modified form of SEQ ID NO: 42 having about 17 amino acid substitutions (i.e., about 86% identity thereto) that retains a function recited herein. In this regard, the inventors have also produced a modified forms of SEQ ID NO: 42 having about 90 or 94% identity thereto that retains a function recited herein. In one example, the sequence has at least about 95% or 96% or 97% or 98% identity to a sequence set forth in SEQ ID NO: 42. In this regard, the inventors have produced proteins having about 97% or 98% or 99% identity to a sequence set forth in SEQ ID NO: 42. In one example, the sequence has at least about 99% identity to a sequence set forth in SEQ ID NO: 42. In one example, the sequence has at least about 99.2% identity to a sequence set forth in SEQ ID NO: 42.

In one example, the TL1a-binding protein comprises between 1 and 17 amino acid substitutions compared to SEQ ID NO: 42. For example, the TL1a-binding protein comprises 1 or 2 or 3 or 4 or 5 or 6 or 7 or 8 or 9 or 10 or 11 or 12 or 13 or 14 or 15 or 16 or 17 amino acid substitutions compared to SEQ ID NO: 42.

In one example, the TL1a-binding protein comprises between 1 and 17 amino acid substitutions in the FRs compared to SEQ ID NO: 42. For example, the TL1a-binding protein comprises 1 or 2 or 3 or 4 or 5 or 6 or 7 or 8 or 9 or 10 or 11 or 12 or 13 or 14 or 15 or 16 or 17 amino acid substitutions in the FRs compared to SEQ ID NO: 42. In one example, the substitution is not at position 73 of SEQ ID NO: 42.

In one example, the TL1a-binding protein comprises between 1 and 3 amino acid substitutions in CDR3 compared to SEQ ID NO: 42. For example, the TL1a-binding protein comprises 1 or 2 or 3 amino acid substitutions in the CDR3 compared to SEQ ID NO: 42. In one example, the substitution is not at one or more of positions 99 or 101 or 104 or 108 of SEQ ID NO: 42.

In one example, TL1a-binding protein comprises one or more substitutions to prevent or reduce glycosylation of the protein, wherein the substitution(s) are between amino acids 72 to 76 of SEQ ID NO: 42. For example, the protein comprises an alanine in place of the arginine at position 71 and/or an aspartic acid in place of the asparagine at position 72 and/or an arginine in place of the threonine at position 73 and/or a threonine in place of the isoleucine at position 75 of SEQ ID NO: 42.

In one example, the $V_H$ of the protein is not glycosylated and/or does not comprise a consensus site for N-linked glycosylation.

In one example, a TL1a-binding protein of the disclosure comprises a mutant of a sequence set forth in SEQ ID NO: 42, wherein the mutant sequence at least comprises a serine at position 16 of SEQ ID NO: 42.

In one example, a TL1a-binding protein of the disclosure comprises a mutant of a sequence set forth in SEQ ID NO: 42, wherein the mutant sequence at least comprises a proline at position 41.

In one example, a TL1a-binding protein of the disclosure comprises a mutant of a sequence set forth in SEQ ID NO: 42, wherein the mutant sequence at least comprises a arginine at position 74.

In one example, a TL1a-binding protein of the disclosure comprises a mutant of a sequence set forth in SEQ ID NO: 42, wherein the mutant sequence at least comprises a glutamic acid or glycine at position 49 of SEQ ID NO: 42.

In one example, a TL1a-binding protein of the disclosure comprises a mutant of a sequence set forth in SEQ ID NO: 42, wherein the mutant sequence at least comprises a proline at position 41 and a leucine at position 51 and a glutamic acid at position 102 and an alanine at position 105 each relative to SEQ ID NO: 42.

In one example, a TL1a-binding protein of the disclosure comprises a mutant of a sequence set forth in SEQ ID NO: 42, wherein the mutant sequence at least comprises a proline at position 41 and a leucine at position 51 and an alanine at position 72 and an aspartic acid at position 73 and an arginine at position 74 and a glutamic acid at position 102 and an alanine at position 105 each relative to SEQ ID NO: 42.

In one example, a TL1a-binding protein of the disclosure comprises a mutant of a sequence set forth in SEQ ID NO: 42, wherein the mutant sequence at least comprises a proline at position 41 and a leucine at position 51 and an alanine at position 72 and an aspartic acid at position 73 and an arginine at position 74 and a threonine at position 76 and a glutamic acid at position 102 and an alanine at position 105 each relative to SEQ ID NO: 42.

The inventors have identified a site within HCDR2 that can be substituted. Coupled with the observations of Padlan et al., supra, the disclosure thus provides a protein comprising a $V_H$ comprising a CDR2 having a sequence at least about 65% identical to a sequence set forth in SEQ ID NO: 44. In one example, the percentage identity is at least about 70% or 75% or 80% or 90%. In one example, the percentage identity is at least about 94%.

The inventors have identified numerous sites within HCDR3 that can be substituted. The disclosure thus provides a protein comprising a $V_H$ comprising a CDR3 having a sequence at least about 60% identical to a sequence set forth in SEQ ID NO: 45. In one example, the percentage identity is at least about 70% identical to a sequence set forth in SEQ ID NO: 45, e.g., as exemplified herein. In one example, the percentage identity is at least about 75% or 80% or 90%. In one example, the percentage identity is at least about 90%.

In one example, a mutant form of SEQ ID NO: 45 comprises a glutamic acid at position 1 of SEQ ID NO: 45 and/or a proline at position 3 of SEQ ID NO: 45 and/or an alanine at position 6 of SEQ ID NO: 45. Optionally, the mutant form additionally comprises a phenylalanine at position 8 of SEQ ID NO: 45 and/or a tyrosine at position 10 of SEQ ID NO: 45.

Additional residues that can be mutated are set out in FIGS. 1C-1E and in SEQ ID NOs: 94, 137, 152, 162 and 173.

In one example, the inventors have identified several residues in a $V_L$ comprising a sequence set forth in SEQ ID NO: 46 that can be substituted without loss of function. Accordingly, the disclosure encompasses proteins comprising a $V_L$ with at least about 95% identity to a sequence set forth in SEQ ID NO: 46. For example, the inventors have mutated 32 residues in the $V_L$ without loss of function, meaning that the disclosure provides a protein having at least about 71% identity to a sequence set forth in SEQ ID NO: 46. In one example, the percentage identity is at least about 75% or 80% or 90% or 95% or 97%. In one example, the percentage identity is at least about 98%. In one example, the percentage identity is at least about 99%. In one example, the percentage identity is at least about 99.1%.

In one example, the TL1a-binding protein comprises between 1 and 17 amino acid substitutions compared to SEQ ID NO: 42. For example, the TL1a-binding protein comprises 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 amino acid substitutions compared to SEQ ID NO: 46.

In one example, the TL1a-binding protein comprises between 1 and 32 amino acid substitutions in the FRs compared to SEQ ID NO: 46. For example, the TL1a-binding protein comprises 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 amino acid substitutions in the FRs compared to SEQ ID NO: 46.

In one example, the TL1a-binding protein comprises between 1 and 3 amino acid substitutions in a CDR compared to SEQ ID NO: 46. For example, the TL1a-binding protein comprises 1 or 2 or 3 amino acid substitutions in a CDR compared to SEQ ID NO: 46. In one example, the substitution is not at one or more of positions 34, 54, 94 of SEQ ID NO: 46.

In one example, a TL1a-binding protein of the disclosure comprises a mutant of a sequence set forth in SEQ ID NO: 46, wherein the mutant sequence at least comprises a serine at position 24 of SEQ ID NO: 46.

In one example, a TL1a-binding protein of the disclosure comprises a mutant of a sequence set forth in SEQ ID NO: 46, wherein the mutant sequence at least comprises a threonine at position 76 of SEQ ID NO: 46.

In one example, a TL1a-binding protein of the disclosure comprises a mutant of a sequence set forth in SEQ ID NO: 46, wherein the mutant sequence at least comprises a glutamine at position 81 of SEQ ID NO: 46.

In one example, a TL1a-binding protein of the disclosure comprises a mutant of a sequence set forth in SEQ ID NO: 46, wherein the mutant sequence at least comprises a threonine at position 23 and a serine at position 24 and a threonine at position 76 each relative to SEQ ID NO: 46.

In one example, a TL1a-binding protein of the disclosure comprises a mutant of a sequence set forth in SEQ ID NO: 46, wherein the mutant sequence at least comprises a threonine at position 23 and a serine at position 24 and a threonine at position 76 and a glutamic acid at position 51 each relative to SEQ ID NO: 46.

The inventors have identified a plurality of sites within LCDR1 that can be substituted. The disclosure thus provides a protein comprising a $V_L$ comprising a CDR1 having a sequence at least about 60% identical to a sequence set forth in SEQ ID NO: 47. In one example, the percentage identity is at least about 70% or 75% or 80% or 90%. For example, the inventors have mutated two sites within LCDR1 comprising a sequence set forth in SEQ ID NO: 47, thus producing a protein having at least about 86 identity to the recited sequence. In one example, the percentage identity is at least about 90%.

In one example, a TL1a binding protein of the disclosure comprises a $V_H$ comprising a sequence set forth in SEQ ID NO: 42 and a $V_L$ comprising a sequence set forth in SEQ ID NO: 46, wherein the $V_H$ and/or $V_L$ comprise one or more of the following substitutions or groups of substitutions:

(i) the $V_H$ comprises at least a serine at position 16 of SEQ ID NO: 42;

(ii) the $V_L$ comprises at least a threonine at position 76 of SEQ ID NO: 46;

(iii) the $V_L$ comprises at least a glutamine at position 81 of SEQ ID NO: 46;

(iv) the $V_H$ comprises at least a proline at position 41 and a leucine at position 51 and a glutamic acid at position 102 and an alanine at position 105 each relative to SEQ ID NO: 42 and the $V_L$ comprises at least a threonine at position 23 and a serine at position 24 and a threonine at position 76 each relative to SEQ ID NO: 46; or (v) the VH comprises at least a proline at position 41 and a leucine at position 51 and an alanine at position 72 and an aspartic acid at position 73 and an arginine at position 74 and a glutamic acid at position 102 and an alanine at position 105 each relative to SEQ ID NO: 42 and a VL comprises at least a threonine at position 23 and a serine at position 24 and a threonine at position 76 and a glutamic acid at position 51 each relative to SEQ ID NO: 46.

In another example, a nucleic acid of the disclosure comprises a sequence at least about 80% or 85% or 90% or 95% or 97% or 98% or 99% identical to a sequence set forth herein and encoding a TL1a-binding protein which is capable of specifically binding to TL1a and inhibiting interaction of TL1a and DR3, wherein the protein does not inhibit interaction of TL1a and DcR3. The disclosure also encompasses nucleic acids encoding a TL1a-binding protein of the disclosure, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

As discussed above, the disclosure also contemplates a nucleic acid that hybridizes under stringent hybridization conditions to a nucleic acid encoding a TL1a-binding protein described herein, e.g., nucleic acid encoding a $V_H$ or $V_L$ of antibody C319, C320, C321, C323, C333, C334, C336, C320-3, C320-5, C320-90, C320-103, C320-114, C320-115, C320-120, C320-129, C320-130, C320-135, C320-162, C320-163, C320-164, C320-165, C320-166, C320-167, C320-168, C320-169, C320-170, C320-171, C320-172, C320-179 or, C320-183. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The disclosure also contemplates mutant forms of a TL1a-binding protein of the disclosure comprising one or more conservative amino acid substitutions compared to a sequence set forth herein. In some examples, the TL1a-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), 6-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.*, 157: 105-132, 1982 and hydrophylic indices are described in, e.g., U.S. Pat. No. 4,554,101.

The disclosure also contemplates non-conservative amino acid changes. For example, of particular interest are substitutions of charged amino acids with another charged amino acid and with neutral or positively charged amino acids. In some examples, the TL1a-binding protein comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of a TL1a-binding protein of the disclosure. In another example, the mutation(s) occur within a CDR of a TL1a-binding protein of the disclosure.

Exemplary methods for producing mutant forms of a TL1a-binding protein include:

- mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology,* 7: 18, 2007; and WO1999/058661);
- introducing a nucleic acid encoding the polypeptide into a mutator cell, e.g., XL-1Red, XL-mutS and XL-mutS-Kanr bacterial cells (Stratagene);
- DNA shuffling, e.g., as disclosed in Stemmer, *Nature* 370: 389-91, 1994; and
- site directed mutagenesis, e.g., as described in Dieffenbach (ed) and Dveksler (ed) (In: PCR Primer: A Laboratory Manual, Cold Spring Harbor Laboratories, N Y, 1995).

Exemplary methods for determining biological activity of the mutant TL1a-binding proteins of the disclosure will be apparent to the skilled artisan and/or described herein, e.g., antigen binding. For example, methods for determining antigen binding, competitive inhibition of binding, affinity, association, dissociation and therapeutic efficacy are described herein.

Exemplary TL1a-Binding Proteins

Exemplary variable region containing TL1a-binding proteins produced by the inventors and their encoding nucleic acids are described in Tables 1 and 2.

TABLE 1

Sequences of exemplary TL1a-binding proteins and encoding nucleic acids

| | Antibody Name | $V_H$ amino acid SEQ ID NO | $V_H$ chain nucleotide SEQ ID NO | $V_L$ amino acid SEQ ID NO | $V_L$ chain nucleotide SEQ ID NO |
|---|---|---|---|---|---|
| 1 | C336 | 2 | 96 | 6 | 97 |
| 2 | C334 | 10 | 98 | 14 | 99 |
| 3 | C333 | 18 | 100 | 22 | 101 |
| 4 | C323 | 26 | 102 | 30 | 103 |
| 5 | C321 | 34 | 104 | 38 | 105 |
| 6 | C320 | 42 | 106 | 46 | 107 |
| 7 | C319 | 50 | 108 | 54 | 109 |
| 8 | C320-3 | 58 | 110 | 46 | 107 |
| 9 | C320-5 | 42 | 106 | 62 | 111 |
| 10 | C320-90 | 66 | 112 | 62 | 111 |
| 11 | C320-103 | 70 | 113 | 62 | 111 |
| 12 | C320-114 | 74 | 114 | 62 | 111 |
| 13 | C320-115 | 78 | 115 | 62 | 111 |
| 14 | C320-120 | 58 | 110 | 82 | 116 |
| 15 | C320-129 | 86 | 117 | 46 | 107 |
| 16 | C320-130 | 90 | 118 | 46 | 107 |
| 17 | C320-135 | 58 | 110 | 62 | 111 |
| 18 | C320-7 | 154 | | 164 | |
| 19 | C320-8 | 155 | | 163 | |
| 20 | C320-9 | 156 | | 165 | |
| 21 | C320-10 | 157 | | 166 | |
| 22 | C320-11 | 158 | | 167 | |
| 23 | C320-12 | 159 | | 168 | |
| 24 | C320-13 | 234 | | 169 | |
| 25 | C320-14 | 160 | | 170 | |
| 26 | C320-15 | 161 | | 171 | |
| 27 | C320-16 | 154 | | 46 | |
| 28 | C320-17 | 155 | | 46 | |
| 29 | C320-18 | 156 | | 46 | |
| 30 | C320-19 | 157 | | 46 | |
| 31 | C320-20 | 158 | | 46 | |
| 32 | C320-21 | 159 | | 46 | |
| 33 | C320-22 | 234 | | 46 | |
| 34 | C320-23 | 160 | | 46 | |
| 35 | C320-24 | 161 | | 46 | |
| 36 | C320-25 | 42 | | 164 | |
| 37 | C320-26 | 42 | | 163 | |
| 38 | C320-27 | 42 | | 165 | |
| 39 | C320-28 | 42 | | 166 | |
| 40 | C320-29 | 42 | | 167 | |
| 41 | C320-30 | 42 | | 168 | |
| 42 | C320-31 | 42 | | 169 | |
| 43 | C320-32 | 42 | | 170 | |
| 44 | C320-33 | 42 | | 171 | |
| 45 | C320-162 | 175 | 222 | 188 | 228 |
| 46 | C320-163 | 176 | 223 | 189 | 228 |
| 47 | C320-164 | 177 | 224 | 190 | 229 |
| 48 | C320-165 | 178 | 224 | 191 | 230 |
| 49 | C320-166 | 179 | 224 | 192 | 231 |
| 50 | C320-167 | 180 | 224 | 193 | 228 |
| 51 | C320-168 | 181 | 225 | 194 | 230 |
| 52 | C320-169 | 182 | 225 | 195 | 228 |
| 53 | C320-170 | 183 | 226 | 196 | 230 |
| 54 | C320-171 | 184 | | 197 | |
| 55 | C320-172 | 185 | 226 | 198 | 232 |
| 56 | C320-179 | 186 | 227 | 199 | 232 |
| 57 | C320-183 | 187 | 227 | 200 | 233 |

TABLE 2

Amino acid substitutions in $V_H$ (relative to SEQ ID NO: 42) and $V_L$ (relative to SEQ ID NO: 46) of exemplary TL1a-binding proteins.

| | Antibody name | $V_H$ substitution[1] | $V_L$ substitution[1] |
|---|---|---|---|
| 1 | C320-2 | A16S | none |
| 2 | C320-53 | E99S | A76T |
| 3 | C320-54 | E99H | A76T |
| 4 | C320-55 | E99L | A76T |
| 5 | C320-56 | E99D | A76T |
| 6 | C320-57 | E99Y | A76T |
| 7 | C320-58 | E99P | A76T |
| 8 | C320-59 | E99Q | A76T |
| 9 | C320-60 | E99K | A76T |
| 10 | C320-61 | V100A | A76T |
| 11 | C320-62 | V100S | A76T |
| 12 | C320-63 | V100H | A76T |
| 13 | C320-64 | V100L | A76T |
| 14 | C320-65 | V100D | A76T |
| 15 | C320-66 | V100Y | A76T |
| 16 | C320-67 | V100P | A76T |
| 17 | C320-68 | V100Q | A76T |
| 18 | C320-69 | V100K | A76T |
| 19 | C320-70 | P101A | A76T |
| 20 | C320-71 | P101S | A76T |
| 21 | C320-72 | P101H | A76T |
| 22 | C320-73 | P101L | A76T |
| 23 | C320-74 | P101D | A76T |
| 24 | C320-75 | P101Y | A76T |
| 25 | C320-76 | P101Q | A76T |
| 26 | C320-77 | P101K | A76T |
| 27 | C320-78 | D102A | A76T |
| 28 | C320-79 | D102S | A76T |
| 29 | C320-80 | D102H | A76T |
| 30 | C320-81 | D102L | A76T |
| 31 | C320-82 | D102Y | A76T |
| 32 | C320-83 | D102P | A76T |
| 33 | C320-84 | D102Q | A76T |
| 34 | C320-85 | D102K | A76T |
| 35 | C320-86 | T103A | A76T |
| 36 | C320-87 | T103S | A76T |
| 37 | C320-88 | T103H | A76T |
| 38 | C320-89 | T103L | A76T |
| 39 | C320-90 | T103D | A76T |
| 40 | C320-91 | T103Y | A76T |
| 41 | C320-92 | T103P | A76T |
| 42 | C320-93 | T103Q | A76T |
| 43 | C320-94 | T103K | A76T |
| 44 | C320-95 | A104S | A76T |
| 45 | C320-96 | A104H | A76T |
| 46 | C320-97 | A104L | A76T |
| 47 | C320-98 | A104D | A76T |
| 48 | C320-99 | A104Y | A76T |
| 49 | C320-100 | A104P | A76T |
| 50 | C320-101 | A104Q | A76T |
| 51 | C320-102 | A104K | A76T |
| 52 | C320-103 | S105A | A76T |
| 53 | C320-104 | S105H | A76T |
| 54 | C320-105 | S105L | A76T |
| 55 | C320-106 | S105D | A76T |
| 56 | C320-107 | S105Y | A76T |
| 57 | C320-108 | S105P | A76T |
| 58 | C320-109 | S105Q | A76T |
| 59 | C320-110 | S105K | A76T |
| 60 | C320-111 | E107A | A76T |
| 61 | C320-112 | E107S | A76T |
| 62 | C320-113 | E107H | A76T |
| 63 | C320-114 | E107L | A76T |
| 64 | C320-115 | E107D | A76T |
| 65 | C320-116 | E107Y | A76T |
| 66 | C320-117 | E107P | A76T |
| 67 | C320-118 | E107Q | A76T |
| 68 | C320-119 | E107K | A76T |
| 69 | C320-120 | T41P | A23T |
| 70 | C320-121 | T41P | D28N |
| 71 | C320-122 | T41P | L33Y |
| 72 | C320-123 | T41P | G34D |
| 73 | C320-124 | T41P | Y53N |
| 74 | C320-125 | T41P | Y54S |

TABLE 2-continued

Amino acid substitutions in $V_H$ (relative to SEQ ID NO: 42) and $V_L$ (relative to SEQ ID NO: 46) of exemplary TL1a-binding proteins.

| | Antibody name | $V_H$ substitution[1] | $V_L$ substitution[1] |
|---|---|---|---|
| 75 | C320-126 | T41P | P82A |
| 76 | C320-127 | T41P | G95S |
| 77 | C320-128 | T41P | T96S |
| 78 | C320-129 | D102E | None |
| 79 | C320-130 | M51L | None |
| 80 | C320-131 | None | D49E |
| 81 | C320-135 | T41P | A76T |
| 82 | C320-162 | T41P + M51L + S75A + D102E | A76T |
| 83 | C320-163 | T41P + R72A + N73D + T74R + I76T | A76T |
| 84 | C320-164 | T41P + M51L + D102E | G24S + A76T |
| 85 | C320-165 | T41P + M51L + D102E | A23T + G24S + A76T |
| 86 | C320-166 | T41P + M51L + D102E | A23T + A76T |
| 87 | C320-167 | T41P + M51L + D102E | A76T |
| 98 | C320-168 | T41P + M51L + D102E + S105A | A23T + G24S + A76T |
| 89 | C320-169 | T41P + M51L + D102E + S105A | A76T |
| 90 | C320-170 | T41P + R72A + N73D + T74R + I76T | A23T + G24S + A76T |
| 91 | C320-171 | T41P + R72A + N73D + T74R + I76T | A23T + G24S + A76T + Y51P |
| 92 | C320-172 | T41P + R72A + N73D + T74R + I76T | A23T + G24S + A76T + Y51E |
| 93 | C320-179 | T41P + M51L + R72A + N73D + T74R + I76T + D102E + S105A | A23T + G24S + A76T + Y51E |
| 94 | C320-183 | T41P + M51L + R72A + N73D + T74R + I76T + D102E + S105A | A23T + G24S + A76T + Y51G |

[1]substitutions are listed as: residue in SEQ ID NO: 42 or 46; position in SEQ ID NO: 42 or 46; substituted amino acid. i.e., A16S in $V_H$, means that at position 16 of SEQ ID NO: 42 there is an alanine that has been substituted with a serine in the TL1a-binding protein.

Recombinant Expression

As discussed herein, a nucleic acid encoding a TL1a-binding protein of the disclosure (and/or polypeptides included in such a TL1a-binding protein) is introduced into an expression construct, such that it is operably linked to a promoter to thereby facilitate its expression. Methods for producing expression constructs, e.g., cloning into expression constructs/vectors are known in the art and/or described in Ausubel et al., (In: Current Protocols in Molecular Biology. Wiley Interscience, ISBN 047 150338, 1987), and (Sambrook et al., (In: Molecular Cloning: Molecular Cloning: A Laboratory Manual, Cold Spring Harbor Laboratories, New York, Third Edition 2001) and U.S. Pat. No. 7,270,969.

In one example, the TL1a-binding protein of the disclosure is expressed in a bacterial cell. Typical promoters suitable for expression in bacterial cells such as for example a bacterial cell selected from the group comprising *E. coli*, *Staphylococcus* sp, *Corynebacterium* sp., *Salmonella* sp., *Bacillus* sp., and *Pseudomonas* sp., include, but are not limited to a promoter such as lacz, lpp, a temperature-sensitive ($(_L$ or $(_R$ promoters, T7, T3, SP6 or semi-artificial promoters such as the IPTG-inducible tac promoter or lacUV5 promoter.

In another example, the TL1a-binding protein is expressed in a yeast cell. Typical promoters suitable for expression in yeast cells such as, *Pichia pastoris*, *Saccharomyces cerevisiae* and *S. pombe*, include, but are not limited to promoters from the following genes ADH1, GAL1, GAL4, CUP1, PHO5, nmt, RPR1, or TEF1.

In a further example, the TL1a-binding protein is expressed in an insect cell. Typical promoters suitable for expression in insect cells, or in insects, include, but are not limited to, the OPEI2 promoter, the insect actin promoter isolated from *Bombyx muri*, the *Drosophila* sp. dsh promoter (Marsh et al., *Hum. Mol. Genet.* 9: 13-25, 2000).

A TL1a-binding protein of the disclosure can also be expressed in plant cells. Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

In one example, a TL1a-binding protein of the disclosure is expressed in a mammalian cell or in a mammal. Typical promoters suitable for expression in a mammalian cell include, for example a promoter selected from the group consisting of, retroviral LTR elements, the SV40 early promoter, the SV40 late promoter, the CMV IE (cytomegalovirus immediate early) promoter, the $EF_1$ promoter (from human elongation factor 1), the EM7 promoter, the UbC promoter (from human ubiquitin C). Examples of useful mammalian host cell lines include monkey kidney CVI line transformed by SV40 (COS-7); human embryonic kidney line (HEK-293 cells); baby hamster kidney cells (BHK); Chinese hamster ovary cells (CHO); African green monkey kidney cells (VERO-76); or myeloma cells (e.g., NS/0 cells).

Other elements of expression constructs/vectors are known in the art and include, for example, enhancers, transcriptional terminators, polyadenylation sequences, nucleic acids encoding selectable or detectable markers and origins of replication.

In one example, an expression construct is a bicistronic expression construct. By "bicistronic" is meant a single nucleic acid molecule that is capable of encoding two distinct polypeptides from different regions of the nucleic acid, for example, a single nucleic acid capable of encoding a $V_H$ containing polypeptide and a $V_L$ containing polypeptide as distinct polypeptides. Generally, the regions encoding each distinct polypeptide are separated by an internal ribosome entry site (IRES) and the region 5' of the IRES does not comprise a transcription termination sequence. Exemplary IRESs are described, for example, in US20090247455.

Following production of a suitable expression construct, it is introduced into a suitable cell using any method known in the art. Exemplary methods include microinjection, transfection mediated by DEAE-dextran, transfection mediated by liposomes such as using commercially available reagents, PEG-mediated DNA uptake, electroporation and microparticle bombardment such as by using DNA-coated tungsten or gold particles (Agracetus Inc., WI, USA) amongst others.

The cells used to produce the TL1a-binding protein of this disclosure are then cultured under conditions known in the art to produce a TL1a-binding protein of the disclosure.

Cell free expression systems are also contemplated by the disclosure, e.g., the TNT T7 and TNT T3 systems (Promega), the pEXP1-DEST and pEXP2-DEST vectors (Invitrogen).

Protein Purification

Following production/expression, a TL1a-binding protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g. 95%, 98% or 99%) of the protein in the preparation is a TL1a-binding protein of the disclosure.

Standard methods of peptide purification are employed to obtain an isolated TL1a-binding protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a TL1a-binding protein comprising a Fc region of an antibody, protein A or protein G or modified forms thereof can be used for affinity purification. Protein A is useful for isolating purified proteins comprising a human γI, γ2, or γ4 heavy chain Fc region. Protein G is recommended for all mouse Fc isotypes and for human γ3.

In one example, a TL1a-binding protein of the disclosure is conjugated to a compound. For example, the compound is selected from the group consisting of a radioisotope, a detectable label, a therapeutic compound, a colloid, a toxin, a nucleic acid, a peptide, a protein, a compound that increases the half life of the TL1a-binding protein in a subject and mixtures thereof.

The other compound can be directly or indirectly bound to the TL1a-binding protein (e.g., can comprise a linker in the case of indirect binding). Examples of compounds include, a radioisotope (e.g., iodine-131, yttrium-90 or indium-ill), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half life of the TL1a-binding protein in a subject (e.g., polyethylene glycol or other water soluble polymer having this activity) and mixtures thereof. Exemplary compounds that can be conjugated to a TL1a-binding protein of the disclosure and methods for such conjugation are known in the art and described, for example, in WO2010/059821.

The TL1a-binding protein may be conjugated to nanoparticles (for example as reviewed in Kogan et al., *Nanomedicine* (*Lond*). 2: 287-306, 2007). The nanoparticles may be metallic nanoparticles.

The TL1a-binding protein may be comprised in antibody-targeted bacterial minicells (for example as described in PCT/IB2005/000204).

Some exemplary compounds that can be conjugated to a TL1a-binding protein of the disclosure are listed in Table 3.

TABLE 3

Compounds useful in conjugation.

| Group | Detail |
|---|---|
| Radioisotopes (either directly or indirectly) | $^{123}I$, $^{125}I$, $^{130}I$, $^{133}I$, $^{135}I$, $^{47}Sc$, $^{72}As$, $^{72}Sc$, $^{90}Y$, $^{88}Y$, $^{97}Ru$, $^{100}Pd$, $^{101m}Rh$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Gu$, $^{68}Gu$, $^{67}Cu$, $^{75}Br$, $^{76}Br$, $^{77}Br$, $^{99m}Tc$, $^{11}C$, $^{13}N$, $^{15}O$, $^{18}I$, $^{188}Rc$, $^{203}Pb$, $^{64}Cu$, $^{105}Rh$, $^{198}Au$, $^{199}Ag$ or $^{177}Lu$ |
| Half life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators or proteins, such as cytokines, e.g., an interferon<br>toxins<br>an immunoglobulin or antibody or antibody variable region<br>half life extenders such as albumin or antibody variable regions or peptides that bind to albumin |
| Chemotherapeutics | Taxol<br>5-FU<br>Doxorubicin<br>Idarubicin |

TL1a-binding proteins comprising antibody binding domains of the disclosure are readily screened for biological activity, e.g., as described below.

Binding Assays

One form of assay is an antigen binding assay, e.g., as described in Scopes (In: Protein purification: principles and practice, Third Edition, Springer Verlag, 1994). Such a method generally involves labeling the TL1a-binding protein and contacting it with immobilized antigen. Following washing to remove non-specific bound protein, the amount of label and, as a consequence, bound protein is detected. Of course, the TL1a-binding protein can be immobilized and the antigen labeled. Panning-type assays, e.g., as described or exemplified herein can also be used. Alternatively, or additionally, surface plasmon resonance assays can be used.

In one example, a binding assay is performed with peptide comprising an epitope of TL1a. In this way, TL1a-binding proteins that bind to a specific region of TL1a are selected.

Inhibition of Interaction of TL1a and DR3

Methods for identifying TL1a-binding proteins that inhibit interaction of TL1a and DR3 will be apparent to the skilled artisan based on the description herein.

For example, DR3 (e.g., 2 μg/ml of DR3) is immobilized on a surface and contacted with TL1a (e.g., 1 μg/ml TL1a) and with a TL1a-binding protein to be tested (in the case of controls, an isotype matched control antibody is added). A reduced level of TL1a bound to the DR3 in the presence of the TL1a-binding protein compared to in the absence of the TL1a-binding protein indicates that the TL1a-binding protein inhibits binding of TL1a to DR3. The assay can also be performed with immobilized TL1a to which DR3 is contacted. The assay can also be performed with labeled TL1a and/or DR3 to assist with detection.

In some examples, various concentrations of the TL1a-binding protein are tested and the concentration at which 50% of the maximum inhibition of binding of TL1a to DR3 by the TL1a-binding protein is determined (this concentration is known as $EC_{50}$). In one example, the $EC_{50}$ of a TL1a-binding protein of the disclosure is less than about 5 nM or 4 nM or 3.5 nM or 3 nM or 2.5 nM or 2.3 nM or 1 nM or 0.5 nM. In one example, the $EC_{50}$ is less than 3 nM. In one example, the $EC_{50}$ is less than 2.5 nM. In one example, the $EC_{50}$ is less than 1 nM. In one example, the $EC_{50}$ is less than 0.5 nM.

In some examples, the maximal inhibition of interaction of TL1a and DR3 is assessed by determining the level of interaction of TL1a and DR3 in the presence and absence of a TL1a-binding protein. The level of inhibition of interaction of TL1a and DR3 in the presence of the protein is then expressed as a percentage of the level of interaction in the absence of the protein. In one example, the TL1a-binding protein inhibits at least about 80% of interaction between TL1a and DR3. For example, the percentage inhibition is at least about 84% or 85% or 90% or 93% or 94% or 95%. In one example, the percentage inhibition is at least about 93%. In one example, the percentage inhibition is at least about 94%. In one example, the percentage inhibition is assessed using a polypeptide comprising DR3 fused to an antibody Fc region. In one example, the TL1a-binding protein is used at a concentration of about 10 μg/ml.

Selective Inhibition of Interaction of TL1a and DR3

Methods for identifying TL1a-binding proteins that inhibit interaction of TL1a and DR3 but not TL1a and DcR3 will be apparent to the skilled artisan and/or described herein.

For example, DcR3 (e.g., 2 μg/ml DcR3) is immobilized on a surface and contacted with TL1a (e.g., 1 μg/ml TL1a) and a TL1a-binding protein to be tested (in the case of negative controls, an isotype-matched control antibody is used). The level of TL1a bound to DcR3 is then determined. A reduced level of TL1a bound to the DcR3 in the presence of the TL1a-binding protein compared to in the absence of the TL1a-binding protein indicates that the TL1a-binding protein inhibits binding of TL1a to DcR3. A similar level of bound TL1a in the presence or absence of the TL1a-binding protein indicates that the TL1a-binding protein does not inhibit interaction of TL1a and DcR3. The assay can also be performed with immobilized TL1a to which DcR3 is contacted.

In some examples, various concentrations of the TL1a-binding protein are tested to determine the level of inhibition of TL1a interaction with DcR3 at different concentrations.

In some examples, the maximal inhibition of interaction of TL1a and DcR3 is assessed by determining the level of interaction of TL1a and DcR3 in the presence and absence of a TL1a-binding protein. The level of inhibition of interaction of TL1a and DcR3 in the presence of the protein is then expressed as a percentage of the level of interaction in the absence of the protein. In one example, the TL1a-binding protein at a concentration of 10 μg/ml inhibits 25% or less of the interaction between TL1a and DcR3. For example, the percentage inhibition is 20% or less or 18% or less or 15% or less or 12% or less or 10% or less or 8% or less or 5% or less. In one example, the percentage inhibition is about 18% or less. In one example, the percentage inhibition is about 7% or less. In one example, the percentage inhibition is about 5% or less. In one example, the percentage inhibition is assessed using a polypeptide comprising DcR3 fused to an antibody Fc region. In one example, the TL1a-binding protein is used at a concentration of about 10 μg/ml.

Neutralization Assays

Methods for identifying TL1a-binding proteins that neutralize TL1a activity through DR3 will also be apparent to the skilled artisan, e.g., based on the description herein.

For example, DR3-expressing cells (e.g., TF-1 cells) (e.g., about $7\times10^4$ cells to $8\times10^4$ cells (e.g., $7.5\times10^4$ cells) are contacted with TL1a and a protein synthesis inhibitor (e.g. cycloheximide) in the presence or absence of a TL1a-binding protein to be tested. The level of apoptosis of the cells is then assessed, e.g., by detecting activation of caspases or propidium iodide uptake or other known assays. A TL1a-binding protein that reduces the level of apoptosis compared to the level of apoptosis in the absence of the TL1a-binding protein is considered to inhibit TL1a activity or neutralize TL1a activity through DR3.

In some examples, various concentrations of the TL1a-binding protein are tested to determine the level of neutralization at different concentrations. In some examples, the concentration at which 50% of the maximum inhibition of apoptosis by the TL1a-binding protein is determined (this concentration is known as $EC_{50}$). In one example, the $EC_{50}$ of a TL1a-binding protein of the disclosure is 3 nM or less, for example, about 2.5 nM or less, such as about 2.4 nM or less, for example, about 2 nM or less, such as about 1.5 nM or less, such as about 1 nM or less. In one example, the $EC_{50}$ of a TL1a-binding protein of the disclosure about 0.99 nM or less. In one example, the $EC_{50}$ of a TL1a-binding protein of the disclosure is about 0.6 nM or less. In one example, the $EC_{50}$ of a TL1a-binding protein of the disclosure is about 0.4 nM or less.

The ability of a TL1a-binding protein of the disclosure to neutralize TL1a-activity can also be assessed by determining their ability to reduce cytokine secretion by immune cells. For example, PBMCs are contacted with Concanavalin A in the presence or absence of a TL1a-binding protein. The level of secretion of a TL1a-induced cytokine (e.g., interferon γ or IL-13) is then assessed, e.g., using an ELISA. Reduction of cytokine secretion in the presence of the TL1a-binding protein compared to in the absence of the protein indicates that the TL1a-binding protein neutralizes TL1a activity.

In some examples, various concentrations of the TL1a-binding protein are tested to determine the level of reduction in cytokine secretion at different concentrations. In some examples, the concentration at which 50% of the maximum inhibition of cytokine secretion by the TL1a-binding protein is determined (this concentration is known as $EC_{50}$). For example, the $EC_{50}$ for inhibiting secretion of interferon-γ is 4 nM or less, such as 3 nM or less or 2.5 nm or less or 2 nM or less. In another example, the $EC_{50}$ for inhibition of secretion of IL-13 is 15 nM or less, such as 10 nM or less, for example, 5 nM or less, such as 1 nM or less. For example, the $EC_{50}$ for inhibition of secretion of IL-13 is 0.5 nM or less.

Other assays for determining neutralization of TL1a activity include determining the level of proliferation, migration and tube formation of endothelial cells in the presence and absence of the TL1a-binding protein. For example, endothelial cells are cultured in an extracellular matrix, e.g., Matrigel™, and the level of migration and/or tube formation is determined, e.g., using microscopy. An increase in migration and/or tube formation in the presence of the TL1a-binding protein compared to in the absence of the TL1a-binding protein indicates that the TL1a-binding protein neutralizes TL1a activity through DR3.

In vivo Matrigel™ plug assays can also be performed, e.g., essentially as described in Bagley et al., *Cancer Res* 63: 5866, 2003.

Additional assays include assessing the ability of a TL1a-binding protein to reduce or prevent interferon γ secretion from peripheral blood T cells and/or NK cells stimulated with IL-12 and/or IL-18 or in FcγR activated monocytes.

In Vivo Assays

TL1a-binding proteins of the disclosure can also be assessed for therapeutic efficacy in an animal model of a condition, e.g., a TL1a-mediated condition. For example, the TL1a-binding protein is administered to a model of inflammatory bowel disease or colitis (e.g., dextran sodium sulphate (DSS)-induced colitis or CD45Rb adoptive transfer model of colitis (e.g., Kanai et al., *Inflamm. Bowel Dis.* 12: 89-99, 2006). In another example, a TL1a-binding protein is administered to a model of multiple sclerosis, e.g., EAE models in which a mouse or rat is immunized with a myelin sheath protein or peptide derived therefrom (e.g., MOG, MBP or PLP) and an immune response is generated against the protein thereby inducing a model of multiple sclerosis. Exemplary EAE models are reviewed in, for example Tsunoda and Fujinami, *J. Neuropathol. Exp. Neurol.* 55: 673-686, 1996. The TL1a-binding protein can also or alternatively be tested in a model of arthritis e.g., a SKG strain of mouse (Sakaguchi et al., *Nature* 426: 454-460, 1995), rat type II collagen arthritis model, mouse type II collagen arthritis model or antigen induced arthritis models (Bendele *J. Musculoskel. Neuron. Interact.* 1: 377-385, 2001) and/or a model of inflammatory airway disease (for example, OVA challenge or cockroach antigen challenge), or in a model of inflammatory uveitis for example interphotoreceptor retinoid binding protein immunization-induced uveoretinitis (Caspi, *Curr Protoc Immunol* Chapter 15: unit 15.6, 2003).

The ability of a TL1a-binding protein of the disclosure to neutralize TL1a activity can also or alternatively be assessed in a model of graft-versus-host-response, e.g., in which splenocytes from one animal are injected into an allogeneic animal (e.g., a MHC or HLA unmatched animal).

Epitope Mapping Assays

In another example, the epitope bound by a protein described herein is mapped. Epitope mapping methods will be apparent to the skilled artisan. For example, a series of overlapping peptides spanning the TL1a sequence or a region thereof comprising an epitope of interest, e.g., peptides comprising 10 to 15 amino acids are produced. The TL1a-binding protein is then contacted to each peptide or a combination thereof and the peptide(s) to which it binds determined. This permits determination of peptide(s) comprising the epitope to which the TL1a-binding protein binds. If multiple non-contiguous peptides are bound by the protein, the protein may bind a conformational epitope.

Alternatively, or in addition, amino acid residues within TL1a are mutated, e.g., by alanine scanning mutagenesis, and mutations that reduce or prevent protein binding are determined. Any mutation that reduces or prevents binding of the TL1a-binding protein is likely to be within the epitope bound by the protein. A form of this method is exemplified herein.

A further method involves binding TL1a or a region thereof to an immobilized TL1a-binding protein of the disclosure and digesting the resulting complex with proteases. Peptide that remains bound to the immobilized protein are then isolated and analyzed, e.g., using mass spectrometry, to determine their sequence.

Affinity Assays Optionally, the dissociation constant (Kd) or association constant (Ka) or equilibrium constant ($K_D$) of a TL1a-binding protein for TL1a or a peptide comprising an epitope thereof is determined. These constants for a TL1a-binding protein are in one example measured by a radiolabeled or fluorescently-labeled TL1a binding assay. This assay equilibrates the protein with a minimal concentration of labeled TL1a in the presence of a titration series of unlabeled TL1a. Following washing to remove unbound TL1a, the amount of label is determined.

Affinity measurements can be determined by standard methodology for antibody reactions, for example, immunoassays, surface plasmon resonance (SPR) (Rich and Myszka *Curr. Opin. Biotechnol* 11: 54, 2000; Englebienne *Analyst.* 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized TL1a or a region thereof. Exemplary SPR methods are described in U.S. Pat. No. 7,229,619.

In one example, a TL1a-binding protein as described herein according to any example has a $K_D$ for TL1a of 100 nM or less, such as 50 nM or less, for example, 20 nM or less, for example, 10 nM or less or 6 nM or less. For example, a TL1a-binding protein has a $K_D$ of 5.5 nM or less. For example, a TL1a-binding protein has a $K_D$ of 5 nM or less. For example, a TL1a-binding protein has a $K_D$ of 4 nM or less.

Half Life Assays

Some TL1a-binding proteins encompassed by the disclosure have an improved half-life, e.g., are modified to extend their half-life compared to TL1a-binding proteins that are unmodified. Methods for determining a TL1a-binding protein with an improved half-life will be apparent to the skilled person. For example, the ability of a TL1a-binding protein to bind to a neonatal Fc receptor (FcRn) is assessed. In this regard, increased binding affinity for FcRn increased the serum half-life of the TL1a-binding protein (see for example, Kim et al., *Eur. J. Immunol.* 24: 2429, 1994).

The half-life of a TL1a-binding protein of the disclosure can also be measured by pharmacokinetic studies, e.g., according to the method described by Kim et al, *Eur. J. of Immunol.* 24: 542, 1994. According to this method radiolabeled TL1a-binding protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the TL1a-binding protein, the clearance rate in beta-phase is calculated and compared with that of the wild type or unmodified TL1a-binding protein.

Stability Assays

Stability of a TL1a-binding protein of the disclosure can be assessed by any of a variety of assays. For example, the TL1a-binding protein is exposed to a condition, e.g., heat or acid or stored for a period of time (e.g., 1 month) at room temperature. Aggregation of the TL1a-binding protein can then be assessed by determining turbidity (with an increase in turbidity following exposure to the condition indicating instability), size exclusion chromatography, non-reducing gel electrophoresis or a binding or neutralization study described herein.

The TL1a-binding protein of the disclosure or nucleic acid encoding same or cell expressing same (syn. active ingredient) is useful for parenteral, topical, oral, or local administration, aerosol administration, or transdermal administration, for prophylactic or for therapeutic treatment.

Formulation of a TL1a-binding protein or nucleic acid encoding same or cell expressing same to be administered will vary according to the route of administration and formulation (e.g., solution, emulsion, capsule) selected. An appropriate pharmaceutical composition comprising TL1a-binding protein or nucleic acid encoding same or cell expressing same to be administered can be prepared in a physiologically acceptable carrier. A mixture of TL1a-binding proteins can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The TL1a-binding protein of this disclosure can be lyophilized for storage and reconstituted in a suitable carrier prior to use according to art-known lyophilization and reconstitution techniques.

The optimum concentration of the active ingredient(s) in the chosen medium can be determined empirically, according to procedures well known to the skilled artisan, and will depend on the ultimate pharmaceutical formulation desired.

The dosage ranges for the administration of the TL1a-binding protein of the disclosure are those large enough to produce the desired effect. For example, the composition comprises a therapeutically or prophylactically effective amount of the TL1a-binding protein or nucleic acid encoding same or cell expressing same.

As used herein, the term "effective amount" shall be taken to mean a sufficient quantity of the TL1a-binding protein, nucleic acid or cells to induce/increase or inhibit/reduce/prevent signaling of TL1a in a subject. The skilled artisan will be aware that such an amount will vary depending on, for example, the TL1a-binding protein, nucleic acid or cells and/or the particular subject and/or the type or severity of a condition being treated. Accordingly, this term is not to be construed to limit the disclosure to a specific quantity, e.g., weight or number of TL1a-binding proteins, nucleic acids or cells.

As used herein, the term "therapeutically effective amount" shall be taken to mean a sufficient quantity of TL1a-binding protein, nucleic acid or cells to reduce or inhibit one or more symptoms of a condition.

As used herein, the term "prophylactically effective amount" shall be taken to mean a sufficient quantity of TL1a-binding protein, nucleic acid or cells to prevent or inhibit or delay the onset of one or more detectable symptoms of a condition.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In one example, the TL1a-binding protein is administered at a dosage of between about 1 mg/kg to about 15 mg/kg. In one example, the TL1a-binding protein is administered at a dosage of between about 2 mg/kg to about 10 mg/kg. In one example, the TL1a-binding protein is administered subcutaneously or intravenously.

In some examples, the TL1a-binding protein or other active ingredient is administered at an initial (or loading) dose which is higher than subsequent (maintenance doses). For example, the binding molecule is administered at an initial dose of between about 1 mg/kg to about 30 mg/kg.

The binding molecule is then administered at a maintenance dose of between about 0.0001 mg/kg to about 1 mg/kg. The maintenance doses may be administered every 7 to 35 days, such as, every 14 or 21 or 28 days.

In some examples, a dose escalation regime is used, in which a TL1a-binding protein or other active ingredient is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

One or more TL1a-binding proteins of the disclosure can be administered to an individual by an appropriate route, either alone or in combination with (before, simultaneous with, or after) another drug or agent. For example, the TL1a-binding protein of the disclosure can also be used in combination with proteins, e.g., a TNF antagonist, an anti-IL-12/23 antibody, an anti-inflammatory, a corticosteroid, methotrexate or a painkiller. The TL1a-binding protein of the disclosure can be used as separately administered compositions given in conjunction with antibiotics and/or antimicrobial agents.

It will be appreciated by those skilled in the art that the TL1a-binding proteins of the disclosure may be introduced into a subject by administering an expression construct of the disclosure or a cell expressing a TL1a-binding protein of the disclosure. A variety of methods can be used for introducing a nucleic acid encoding the antibody into a target cell in vivo. For example, the naked nucleic acid may be injected at the target site, may be encapsulated into liposomes, or may be introduced by way of a viral vector.

The following assays can be performed with a TL1a-binding protein of the disclosure, e.g., a TL1a-binding protein conjugated to a detectable label as discussed herein. Detection of TL1a with an assay described herein is useful for diagnosing or prognosing a condition.

An immunoassay is an exemplary assay format for diagnosing a condition in a subject or detecting TL1a in a sample. The disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form such an assay involves immobilizing a TL1a-binding protein of the disclosure onto a solid matrix, such as, for example a polystyrene or polycarbonate microwell or dipstick, a membrane, or a glass support (e.g. a glass slide). A test sample is then brought into direct contact with the TL1a-binding protein and TL1a in the sample is bound or captured. Following washing to remove any unbound protein in the sample, a protein that binds to TL1a at a distinct epitope is brought into direct contact with the captured TL1a. This detector protein is generally labeled with a detectable reporter molecule, such as for example, an enzyme (e.g. horseradish peroxidase (HRP), alkaline phosphatase (AP) or 3-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as for example hydrogen peroxide, TMB, or toluidine, or 5-bromo-4-chloro-3-indol-beta-D-galaotopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled artisan, other detection methods based on an immunosorbent assay are useful in the performance of the disclosure. For example, an immunosorbent method based on the description supra using a radiolabel for detection, or a gold label (e.g. colloidal gold) for detection, or a liposome, for example, encapsulating NAD+ for detection or an acridinium linked immunosorbent assay.

In some examples of the disclosure, the level of TL1a is determined using a surface plasmon resonance detector (e.g., BIAcore™, GE Healthcare, Piscataway, N.J.), a flow through device, for example, as described in U.S. Pat. No. 7,205,159; a micro- or nano-immunoassay device (e.g., as described in US20030124619); a lateral flow devices (e.g., as described in US20040228761 or US20040265926); a fluorescence polarization immunoassay (FPIA e.g., as described in U.S. Pat. No. 4,593,089 or 4,751,190); or an immunoturbidimetric assay (e.g., as described in U.S. Pat. No. 5,571,728 or 6,248,597).

Samples and Control Samples

As will be apparent to the skilled artisan, some of the examples described herein require some degree of quantification to determine the level of TL1a. Such quantification may be determined by the inclusion of a suitable control sample in an assay of the disclosure.

In one example, a suitable control sample is a sample that is derived from a healthy subject or a normal subject.

In the present context, the term "healthy subject" shall be taken to mean an individual who is known not to suffer from a condition associated with TL1a, e.g., an inflammatory condition.

The term "normal subject" shall be taken to mean an individual having a normal level of TL1a in a sample compared to a population of individuals.

The disclosure also contemplates the control sample as being a data set obtained from a normal and/or healthy subject or a population of normal and/or healthy subjects.

In one example, a method of the disclosure additionally comprises determining the level of TL1a in a control sample, e.g., using a method described herein.

In one example, a sample from the subject and a control sample are assayed at approximately or substantially the same time.

In one example, the sample from the subject and the control sample are assayed using the same method of the disclosure as described herein in any one or more examples to allow for comparison of results.

Exemplary conditions that can be treated/prevented/diagnosed/prognosed by performing a method of the disclosure include autoimmune diseases, inflammatory conditions, and conditions characterized by insufficient angiogenesis.

In one example, the condition is an autoimmune disease.

Exemplary conditions include inflammatory bowel disease (IBD), irritable bowel syndrome (IBS), Crohn's disease, ulcerative colitis, diverticular disease, systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, demyelinating diseases of the central and peripheral nervous systems such as multiple sclerosis, idiopathic polyneuropathy, autoimmune or immune-mediated eye disease such as autoimmune uveitis and uveitis associated with various vasculitides, autoimmune or immune-mediated skin diseases including bullous skin diseases, erythema multiforme and contact dermatitis, psoriasis, allergic diseases of the lung such as asthma, airway hypersensitivity, eosinophilic pneumonia, chronic obstructive pulmonary disease (COPD), idiopathic pulmonary fibrosis and hypersensitivity pneumonitis, atherosclerosis or graft versus host disease.

In one example, the condition is arthritis, e.g., rheumatoid arthritis, polyarthritis, osteoarthritis or a spondyloarthropathy. In this regard, Bull et al., *J. Exp. Med.* 205: 2457, 2008 have shown that antibodies that antagonize TL1a are useful for the treatment of rheumatoid arthritis. The selective nature of the TL1a-binding proteins of the disclosure make them useful for treating rheumatoid arthritis.

In one example, the condition is multiple sclerosis. In this regard, US20090317388 shows that mice deficient in TL1a do not develop experimental autoimmune encephalomyelitis (EAE), which is an accepted model of multiple sclerosis.

In one example, the inflammatory condition is an inflammatory mucosal condition, e.g., an inflammatory disease of the bowel (e.g., inflammatory bowel disease, Crohn's disease or ulcerative colitis), or an inflammatory disease of the lung (e.g., airway hyperreactivity or asthma).

In one example, the condition is inflammatory bowel disease and/or colitis. In this regard, Takedatsu et al., *Gastroenterology* 135: 552, 2008 have shown that antibodies that antagonize TL1a are useful for the treatment of colitis.

In one example, the condition is asthma or airway hypersensitivity or chronic obstructive pulmonary disease (COPD).

In another example, the condition is an inflammatory skin disease (e.g., an autoimmune or immune-mediated skin disease), e.g., a bullous skin diseases, erythema multiforme, contact dermatitis. Alternatively, the skin disease is psoriasis.

Exemplary conditions characterized by insufficient angiogenesis include cardiovascular disease, autoimmune conditions (e.g., rheumatoid arthritis, psoriatic arthritis, systemic lupus erythematosus (SLE) and systemic sclerosis), antineutrophil cytoplasmic antibodies (ANCA)-associated vasculitis, ischemia (including ischemia resulting from a transplant) or necrosis.

The disclosure additionally comprises a kit comprising one or more of the following:

(i) a TL1a-binding protein of the disclosure or expression construct(s) encoding same;

(ii) a cell of the disclosure; or (iii) a pharmaceutical composition of the disclosure.

In the case of a kit for detecting TL1a, the kit can additionally comprise a detection means, e.g., linked to a TL1a-binding protein of the disclosure.

In the case of a kit for therapeutic/prophylactic use, the kit can additionally comprise a pharmaceutically acceptable carrier.

Optionally a kit of the disclosure is packaged with instructions for use in a method described herein according to any example.

The disclosure includes the following non-limiting Examples.

Example 1: Materials and Methods

In the following examples, reference to a position of a residue is a reference to the position in the relevant sequence as set forth herein, unless otherwise indicated.

1.1 HEK293/pTT5 Expression System

For all transfections involving the HEK293E/pTT5 expression system (Durocher et al., *Nucl. Acids Res.*, 30: E9, 2002), HEK293E cells were cultured in complete cell growth media (1 L of F17 medium (Invitrogen), 9 ml of Pluronic F68 (Invitrogen), 2 mM Glutamine containing 20% (w/v) Tryptone NI (Organotechnie) with Geneticin™ (50 mg/ml, Invitrogen) at 50 μl/100 ml culture). At the day before transfection, the cells were harvested by centrifugation and re-suspended in fresh media without Geneticin™. The next day, DNA was mixed with a commercial transfection reagent and the DNA transfection mix added to the culture drop-wise. The culture was incubated overnight at 37° C., 5% $CO_2$ and 120 rpm without Geneticin™. The next day 12.5 ml of Tryptone and 250 μl of Geneticin™ were added per 500 ml culture. The culture was incubated at 37° C., 5% $CO_2$ and 120 rpm for seven days, then the supernatants were harvested and purified.

1.2 TL1a Protein

Human TL1a was purchased (Peprotech and Genscript: both *E. coli*-expressed) or produced in the mammalian HEK293E/pTT5 expression system, using a DNA expression construct coding for the extracellular domain (ECD) of human TL1a with an N-terminally located HIS and FLAG tag (SEQ ID NO: 1). Culture supernatant containing the secreted TL1a protein was harvested by centrifugation at 2000 g for 10 mins to remove the cells. The TL1a protein was purified from the supernatant using a HisTrap™ HP column (GE Healthcare). The eluted protein was buffer-exchanged into PBS using a HiLoad 16/60 Superdex 200 prep grade column (GE Healthcare) and ~70 kDa fraction was separated by gel filtration on a HiLoad 26/60 Superdex 200 prep grade column (GE Healthcare).

For phage display experiments, recombinant human TL1a (Peprotech, Genscript HEK293E-derived) was biotinylated using an EZ-link Sulfo-NHS-LC-biotin kit (Pierce) at a 3:1 ratio of biotin:TL1a. Free biotin was removed from the protein preparation by dialysis against PBS using a Slide-A-Lyzer dialysis cassette with a 3.5 kDa molecular weight cut-off.

TL1a was also produced with a tag that allowed for single site biotinylation. This TL1a protein was expressed in HEK-293 cells and purified as described previously. It was then biotinylated using a enzyme that selectively incorporates a biotin on the TL1a protein.

1.3 Phage Display

Antibodies that bind specifically to TL1a were isolated from a naive phagemid library comprising more than $10\times10^{10}$ individual human FAb fragments.

Anti-TL1a antibodies were isolated from the phage display library over the course of several panning 'campaigns' (i.e. discrete phage display experiments with different reagents or panning conditions). The general protocol followed the method outlined by Marks and Bradbury (*Methods Mol. Biol.* 248: 161-176, 2004)

Each phage display campaign involved three rounds of panning. For each round, $\sim1\times10^{13}$ phage particles were blocked by mixing 1:1 with blocking buffer (5% skim milk in phosphate buffered saline (PBS) pH 7.4) and incubating for 1 hr at room temperature. The blocked phage library was then pre-depleted for streptavidin binders by incubation for 45 mins with 100 μL of streptavidin-coupled Dynabeads (Invitrogen), which were blocked as described for the library. The beads (and streptavidin binders attached to them) were discarded after the incubation step.

Recombinant human TL1a antigen was prepared for panning by capture onto the surface of streptavidin-coupled Dynabeads (Invitrogen). To achieve this, 10 to 100 pmol of biotinlyated TL1a was incubated with 100 μL of beads for 45 mins at room temperature. The resulting TL1a-bead complexes were washed with PBS to remove free TL1a and then used in the subsequent panning reaction.

Library panning was conducted by mixing the blocked and pre-depleted library with the TL1a-bead complexes in a 1.5 mL microcentrifuge tube and rotating for 2 hrs at room temperature. Non-specifically bound phage were removed using a series of washes. Each wash involved pulling the bead complexes from the solution onto the tube wall using a magnetic rack, aspirating the supernatant and then re-suspending the beads in fresh wash buffer. This was repeated a number of times with either PBS wash buffer (PBS with 0.5% skim milk) or PBS-T wash buffer (PBS with 0.05% TWEEN-20 (Sigma) and 0.5% skim milk). Phage that remained bound after the washing process were eluted from the TL1a-bead complexes by incubation with 0.5 mL of 100 mM triethylamine (TEA) (Merck) for 20 mins at room temperature. The eluted 'output' phage were neutralized by adding 0.25 mL of 1 M Tris-HCl pH 7.4 (Sigma).

At the end of the first and second rounds of panning, the output phage were added to a 10 mL culture of exponentially growing TG1 *E. coli* (yeast-tryptone (YT) growth media) and allowed to infect the cells by incubating for 30 mins at 37° C. without shaking, then with shaking at 250 rpm for 30 mins. The phagemids encoding the phage display output were then rescued as phage particles following a standard protocol (Marks and Bradbury, supra).

At the end of the third panning round TG1 cells were infected with output phage, but the cells were plated on solid YT growth media (supplemented with 2% glucose and 100 µg/mL carbenicillin) at a sufficient dilution to produce discrete *E. coli* colonies. These colonies were used to inoculate 1 mL liquid cultures to allow expression of FAb fragments for use in screening experiments.

1.4 SPR-Based Screening of FAbs for TL1a Binding

Each individual *E. coli* colony was used to express a FAb that could be screened for TL1a binding activity. Colonies were inoculated into 1 mL YT starter cultures (supplemented with 100 µg/mL carbenicillin and 2% glucose) in 96-well deepwell plates (Costar) and incubated overnight at 30° C. with shaking at 650 rpm. These starter cultures were diluted 1:50 into a 1 mL expression culture (YT supplemented with 100 µg/mL carbenicillin only) and grown to an optical density of 0.8 to 1.0 at 600 nm. FAb expression was induced by adding isopropyl-beta-D-thiogalactopyranoside to a final concentration of 1 mM. Cultures were incubated at 20° C. for 16 hrs.

FAb samples were prepared by harvesting cells by centrifugation (2500 g, 10 mins) and performing a periplasmic extraction. The cell pellet was resuspended in 75 µL of extraction buffer (30 mM Tris-HCl, pH 8.0, 1 mM EDTA, 20% Sucrose) and shaken at 1000 rpm for 10 mins at 4° C. Extract preparation was completed by adding 225 µL of $H_2O$, shaking at 1000 rpm for 1 hr and clearing the extract by centrifugation at 2500 g for 10 mins. The supernatants were recovered, filtered through Acroprep 100 kDa molecular-weight cutoff plates (Pall Corporation) and stored at 4° C. until required for further experiments.

The FAb samples were screened for TL1a-binding activity using a surface plasmon resonance (SPR) assay. High-throughput SPR screening was conducted using a BIAcore 4000 Biosensor (GE Healthcare) in a single concentration analyte pass assay. Approximately 10,000 RU of antiV5 antibody (Invitrogen cat # R960CUS) was immobilized on a CM5 Series S Sensor chip, using standard amine coupling chemistry at pH 5.5 on spots 1, 2, 4 & 5 of each of the four flow cells leaving spot 3 unmodified. The running buffer used was HBS-EP+ (GE Healthcare) and all interactions measured at 25° C. and data collection rate set to 10 Hz. Crude periplasmic preparations of V5-tagged FAbs, were diluted two-fold in running buffer before capturing at a flow rate of 10 ul/min for 100 sec (typically around 200 RU of FAb was captured) on spot 1 or 5 of each flow cell. Following a short stabilization period, human TL1a trimer was passed over all spots of all four flow cells simultaneously at a flow rate of 30 µl/min for 100 sec. Dissociation of the interaction was measured for 100 sec prior to regeneration back to the antiV5 antibody using a 30 sec pulse of 100 mM phosphoric acid. Generated sensorgrams were referenced against an adjacent antiV5 antibody spot for each flow cell, and fitted using a 1:1 Langmuir equation to determine $k_a$, $k_d$ and $K_D$.

The data from the SPR screening process was used to select potential TL1a-binders. FAb $k_d$ values were ranked and up to 200 of the strongest binders were submitted for DNA sequence analysis. FAb with unique sequences were selected for conversion to full-length human $IgG_1$ antibodies.

1.5 Variable Region Sequencing

DNA sequencing was conducted by the Applied Genetic Diagnostics group at the Melbourne University Department of Pathology (Melbourne, Australia). Phagemid DNA (~500 ng) was mixed with 5 pmols of the appropriate primer for sequencing either the Fab $V_H$ or $V_L$ chain. Sequencing reactions were conducted using a BigDye® Terminator v3.1 Cycle Sequencing Kit (Applied Biosystems) according to manufacturer's instructions. Samples were analyzed by capillary separation on 3130xl Genetic Analyzers (Applied Biosystems). Sequence chromatogram data was analyzed using the Chromas Lite software package (Technelysium, Brisbane, QLD, Australia). Sequence text files were translated to amino acid sequences and analyzed using the SeqAgent software package (Xoma, Berkely, Calif., USA).

1.6 Construction of Vectors Expressing Antibodies $V_H$ amino acid chains were expressed with a human constant region (human IgG1 heavy chain $C_H1$, hinge, $C_H2$ and $C_H3$ domains (e.g., SwissProt No. P01857)). This was achieved by back-translation of amino acid sequences into DNA sequences which were synthesized de novo by assembly of synthetic oligonucleotides. Following gene synthesis the whole sequence was subcloned into the multiple cloning site of the pTT5 heavy chain vector (Durocher et al., *Nucl. Acids Res.* 30: E9, 2002). $V_L$ amino acid chains were expressed with a human kappa light chain constant region (SwissProt No. P01834.1) or a human lambda light chain constant region (SwissProt No. P0CG05.1) by subcloning the sequence into the multiple cloning site of the pTT5 light chain vector.

Alternatively, FAb $V_H$ and $V_L$ sequences were amplified directly from phagemid DNA by PCR and subcloned into IgG expression vectors. PCR reactions were carried out using a Platinum PCR Supermix kit (Invitrogen) as per manufacturer's instructions. Approximately 50 ng of template phagemid DNA encoding a FAb was mixed with 10 pmols of the appropriate forward and reverse PCR primers and the PCR Supermix reagent to a final volume of 50 µL. Each reaction used a sequence-specific forward primer combined with a generic $V_H$ or $V_L$ specific reverse primer. To facilitate cloning into IgG expression vectors, primers for $V_H$ amplification were designed to add 5' BsiWI and 3' NheI restriction enzyme sites, primers for $V_L$-kappa amplification added 5' BssHII and 3' BsiWI sites and primers for $V_L$-lambda amplification added 5' BssHII and 3' AvrII sites.

PCRs were carried out in thin-walled PCR (96-well GENEAMP® PCR system 9700, Applied Biosystems, Scoresby, Victoria, Australia). Cycling conditions comprised an initial five minute denaturation step at 94-C, followed by 30 amplification cycles (denaturation at 94° C. for 30 seconds, followed by primer annealing at 55° C. for 30 seconds, then extension at 68° C. for 30 to 90 seconds), and a final extension step at 68° C. for seven minutes. The amplified $V_H$ genes were purified using a Minelute PCR purification kit (Qiagen), digested with BsiWI and NheI enzymes (New England Biolabs) and re-purified using a Minelute Reaction Clean-up kit (Qiagen). Amplified $V_L$-kappa genes were prepared similarly, but digestion was carried out using BssHII and BsiWI. Amplified $V_L$-lambda genes were also prepared in the same way, but digested with BssHII and AvrII. The resulting $V_H$ and $V_L$ gene fragments were cloned into the multicloning site of the appropriate pTT5 heavy or light chain vector (either kappa or lambda light chain), as described above.

1.7 Expression and Purification of Antibodies

Heavy and light chain DNA were co-transfected into the HEK293/pTT5 expression system and cultured for seven days. The supernatants derived from these transfections were adjusted to pH 7.4 before being loaded onto a HiTrap Protein A column (5 ml, GE Healthcare). The column was washed with 50 ml of PBS (pH 7.4). Elution was performed using 0.1M citric acid pH 2.5. The eluted antibody was desalted using Zeba Desalting columns (Pierce) into PBS (pH 7.4). The antibody was analyzed using SDS-PAGE. The concentration of the antibody was determined using a BCA assay kit (Pierce). For conversion between antibody concentrations in μg/ml and molar concentrations an assumed molecular weight of 150 kDa was used for all antibodies.

1.8 TF-1 Cell Line Potency Assay

To determine which anti-TL1a antibodies functionally neutralize the biological activity of TL1a, antibodies were tested for their ability to neutralize TL1a-induced apoptosis in a TF-1 cell line. The TF-1 human erythroleukemic cell line (ATCC: CRL-2003) was maintained in culture under standard conditions. TF-1 cells ($7.5\times10^4$/well) were incubated in black-sided 96-well plates (Greiner) with recombinant human TL1a 100 ng/ml and cycloheximide 10 μg/ml to induce apoptosis. Test antibodies at a concentration of 10 μg/mL (66.7 nM) or less were added to the plates and incubated for 4 to 5 hours. Induction of apoptosis was then assessed using the Homogeneous Caspases Kit (Roche) according to manufacturer's instructions. In experiments to test the ability of antibodies to neutralize function of TL1a from cynomolgus and rhesus macaque, mouse, rat, guinea pig, pig or rabbit, the appropriate species TL1a was substituted for human TL1a in this protocol.

Data were normalized by expression as a percentage of maximum apoptosis (apoptosis levels achieved by recombinant human TL1a plus cycloheximide in the absence of anti-TL1a antibody).

1.9 Receptor Selectivity of Lead Antibodies

TL1a binds both to its cognate signaling receptor, DR3, and to a decoy receptor, DcR3, which also serves as a decoy receptor for TNF family members Fas-L and LIGHT.

Antibodies were assessed for their ability to inhibit binding of TL1a to its receptors in a competition ELISA. DR3/Fc Chimera (R&D Systems) or DcR3/Fc Chimera (R&D Systems) was coated onto a 96-well plate (Maxisorp, Nunc) at a concentration of 21 μg/ml. Serially diluted test antibodies were pre-incubated with single-site biotinylated recombinant human TL1a 1 μg/ml for 30 minutes then added to the DR3/Fc or DcR3/Fc coated wells. Bound TL1a was detected using streptavidin-horseradish peroxidase 1:2000 (BD Pharmingen). Data were normalized by expression as a percentage of maximum binding of TL1a to receptor in the absence of anti-TL1a antibody.

An antibody described to inhibit TL1a activity (1B4; which has a $V_H$ comprising a sequence set forth in SEQ ID NO: 119 and a $V_L$ comprising a sequence set forth in SEQ ID NO: 120, which is described in WO 2009/064854 and US patent application publication US 200900280116) was included in assays for comparison 1.10 Epitope Mapping Epitope mapping was performed using alanine scanning experiments. Modeling analysis was carried out to determine probable exposed residues on TL1a. TL1a constructs were then designed in which each of these theoretically exposed residues was substituted with an alanine. These constructs were then expressed and supernatant from the expression cultures tested for protein expression and binding to anti-TL1a antibody C320 using SPR. A Ni-NTA sensor chip (Biacore) was used to capture the HIS tagged TL1a mutein from the supernatant of transfected HEK-293E cells. The mutein was captured on flow cell 2 (or 4) and then C320 was passed over flow cell 1+2 (or 3+4). The mutein expression (RU) was determined as the change in RU at the end of injection of the mutein. The C320 binding (RU) was determined as the change in RU determined at the end of the C320 injection.

TL1a constructs that expressed but had apparently lost binding to C320 were re-transfected and purified for testing by ELISA. ELISA plates were coated with polyclonal rabbit anti-human TL1a (Peprotech) (1 μg/ml), DR3/Fc chimera (R&D systems) (2 μg/ml) or DcR3/Fc chimera (R&D systems) (1 μg/ml). TL1a muteins or unsubstituted TL1a were added to the plates at a concentration of 1 μg/ml. Bound TL1a was then detected with biotinylated polyclonal rabbit anti-human TL1a (Peprotech) (250 ng/ml) and streptavidin-horseradish peroxidase (BD Pharmingen) 1:2000. Constructs that could be detected by polyclonal anti-TL1a were deemed to have expressed and folded appropriately. Appropriately expressed and folded constructs that did not bind to one or either of the receptors were considered to be important for TL1a binding to that receptor. Binding of test antibodies to TL1a muteins was tested by direct ELISA. ELISA plates were coated with different TL1a muteins (1 μg/ml). Serially diluted test antibodies were then added, and bound antibodies were detected with anti-human IgG-horseradish peroxidase (Invitrogen) 1:2000. Binding of test antibodies to different TL1a isoforms was detected using the same method.

1.11 Creation of Membrane Bound TL1a (mbTL1a)-Expressing Cell Line

HEK 293 cells were electroporated with a vector containing a sequence encoding full length TL1a (SEQ ID NO: 123) and maintained in selective media (media supplemented with blasticidin 6 μg/ml). After multiple passages, the cells were tested for cell surface expression of TL1a by flow cytometry. $2.5\times10^5$ cells per well were plated into 96-well round bottom plates (Corning) and incubated with biotinylated polyclonal rabbit anti-human TL1a (Peprotech) on ice for 30 minutes. Samples were washed then incubated with streptavidin-FITC for a further 30 minutes on ice. Samples were then washed, resuspended and data acquired on a flow cytometer.

1.12 Flow Cytometry Detection

After stable cell surface expression of TL1a had been confirmed (as described in Example 1.10), antibodies C320, C321 and C323 were screened using both transfected and untransfected cells ($2.5\times10^5$ cells per well in 96-well round bottom plates (Corning)) at decreasing concentrations starting from 10 μg/ml. Polyclonal goat anti-human IgG-FITC (Sigma) at a dilution of 1:200 was used as detection antibody. Anti-TL1a antibody 1B4 was included for comparison.

1.13 Inhibition of Cytokine Production

To further characterize antibodies described herein, their function on primary human cells was tested. To confirm endogenous TL1a production, PBMCs were isolated from buffy coats over a lymphoprep (Nycomed) gradient and cultured in 96-well tissue culture plates (Corning) with Concanavalin A at decreasing concentrations starting from 2

μg/ml. Plates were incubated overnight then supernatants were harvested and assayed for TL1a using the human TL1a ELISA kit (Peprotech).

Additionally, adherent cells were harvested and assessed for TL1a expression by flow cytometry using biotinylated anti-human TL1a (Peprotech) 1:100 and streptavidin-FITC (Zymed) 1:200.

1.14 Isoelectric Focusing Gel Experiments

Isoelectric focusing gels were performed using the NOVEX® Xcell Surelock™ system (Life Technologies) according to manufacturer's instructions.

1.15 Protein A HPLC

Supernatants from HEK-293E cells transfected to transiently express antibodies were analysed by Protein A HPLC using a POROS® A/20 2.1×30 mm Id column (Applied Biosystems) connected to an Agilent 1100 chromatography system. The column was equilibrated with phosphate buffered saline (PBS) pH7.4, 0.2 ml of HEK-293E supernatant containing protein was loaded and the protein eluted with PBS adjusted to pH 2.2. The chromatograms at the wavelengths of 215 nm or 280 nm were integrated using the manufacturer's software and the area under the curve (AUC) reported.

1.16 Antibody Expression and Antigen Binding as Determined by SPR

Using a CM5 sensor chip (Biacore™) Protein A was coupled to the chip surface using amine coupling. Protein A was coupled on flow cell 1 and 2 (or alternatively 3 and 4) using a Biacore 3000. Cell supernatant for HEK-293 cells containing antibody were passed over the surface of flow cell 2, while buffer (HBS-EP) was passed over flow cell 1. At the end of injection of the supernatant the change in response units was measured. This value is reported as Protein A capture (SPR). The % expression is the Protein A capture (SPR) of the tested antibody as a percentage of the Protein A capture (SPR) of C320 in the same experiment. To determine if the antibody binds TL1a, the TL1a was then passed over the flow cell 1 and 2. The sensorgrams were double referenced (Flow cell 2 is subtracted from flow cell 1 and a buffer blank).

Example 2: Results of Phage Display

Phage display campaigns were conducted against recombinant human TL1a. Six discreet campaigns were conducted using recombinant bacterial-expressed recombinant TL1a. A low number of FAbs were isolated that bound to TL1a, with no neutralizing antibodies isolated.

Subsequent campaigns were conducted with mammalian-expressed TL1a. The percentage of FAbs isolated that bound TL1a was substantially higher using mammalian derived TL1a than bacterially derived TL1a. The number of FAbs that were shown to be positive for TL1a binding across the total phage display campaigns was in excess of 200. From these, 55 FAbs with unique sequences were identified, of which 29 were selected for conversion to full length $IgG_1$ antibody.

Example 3: Neutralization of TL1a Activity

The ability of full length IgG1 antibodies comprising FAbs isolated using phage display to inhibit or reduce TL1a-induced apoptosis was assessed as described above (Example 1.8). Under these conditions, 15/29 of the antibodies tested showed better than 50% inhibition of TL1a-induced apoptosis (FIG. 2). These antibodies included: C319, C320, C321, C323, C333, C334, C335, C336.

These data demonstrate that while antibodies can be isolated that bind to TL1a, only a limited subset of these antibodies have the specificity required to functionally inhibit TL1a activity.

Figure 3:
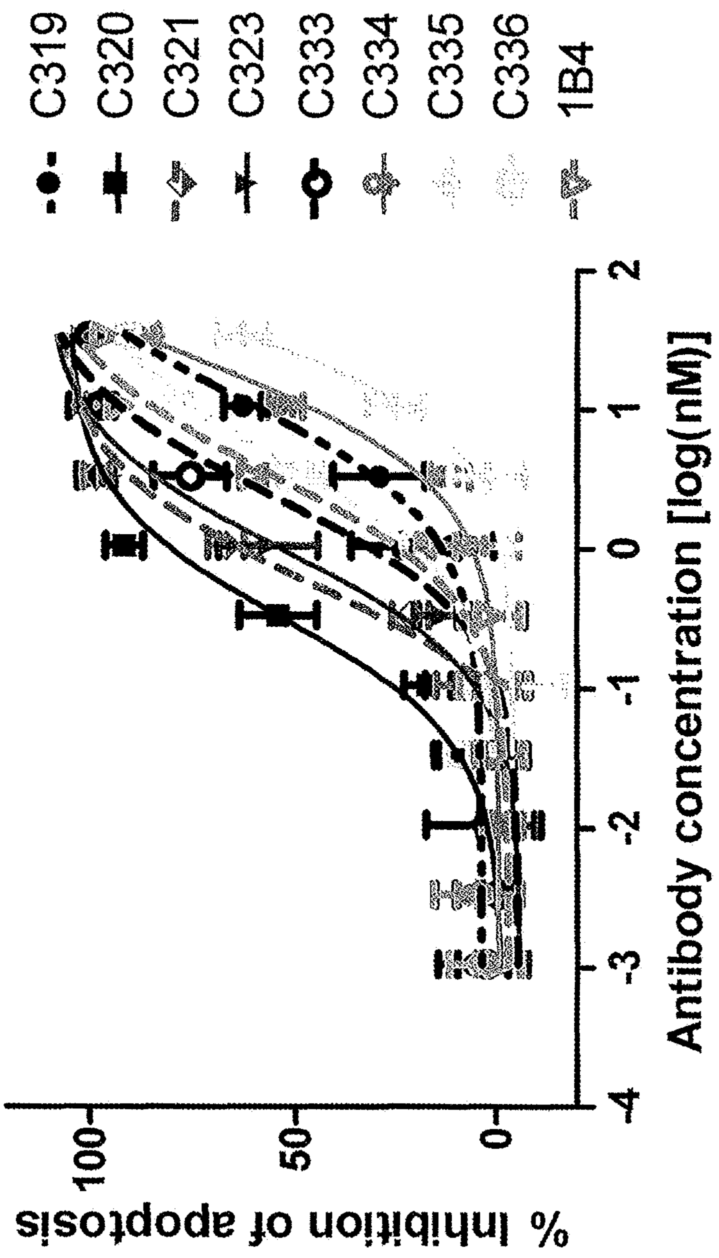
FIG. 3 is a graphical representation of results of an assay to identify highly potent anti-TL1a antibodies. Results depicted show the level of inhibition of TL1a-induced apoptosis of TF-1 cells achieved at various concentrations of test antibodies (maximum concentration tested 5 μg/mL). These levels permit determination of the $EC_{50}$ of anti-TL1a antibodies for the inhibition of TL1a-induced apoptosis of TF-1 cells, which allows for functional comparisons based on relative potency.

Within the group of antibodies that demonstrated inhibition of recombinant human TL1a, the relative inhibition profile of each antibody was assessed using the $EC_{50}$ value (Table 4 and FIG. 3). Only antibodies C320, C321 and C323 had an inhibitory $EC_{50}$ value of 1 nM or below.

TABLE 4

Antibody $EC_{50}$ values for inhibition of TL1a-induced apoptosis

| Antibody Designation | Variable Heavy Chain (SEQ ID NO) | Variable Light Chain (SEQ ID NO) | $EC_{50}$ (nM) |
|---|---|---|---|
| C336 | 2 | 6 | 4.05 |
| C334 | 10 | 14 | 22.14 |
| C333 | 18 | 22 | 2.34 |
| C323 | 26 | 30 | 0.99 |
| C321 | 34 | 38 | 0.56 |
| C320 | 42 | 46 | 0.31 |
| C319 | 50 | 54 | 11.17 |
| 1B4 | 74 | 75 | 3.37 |

Example 4: Receptor Selectivity

Figure 4A:
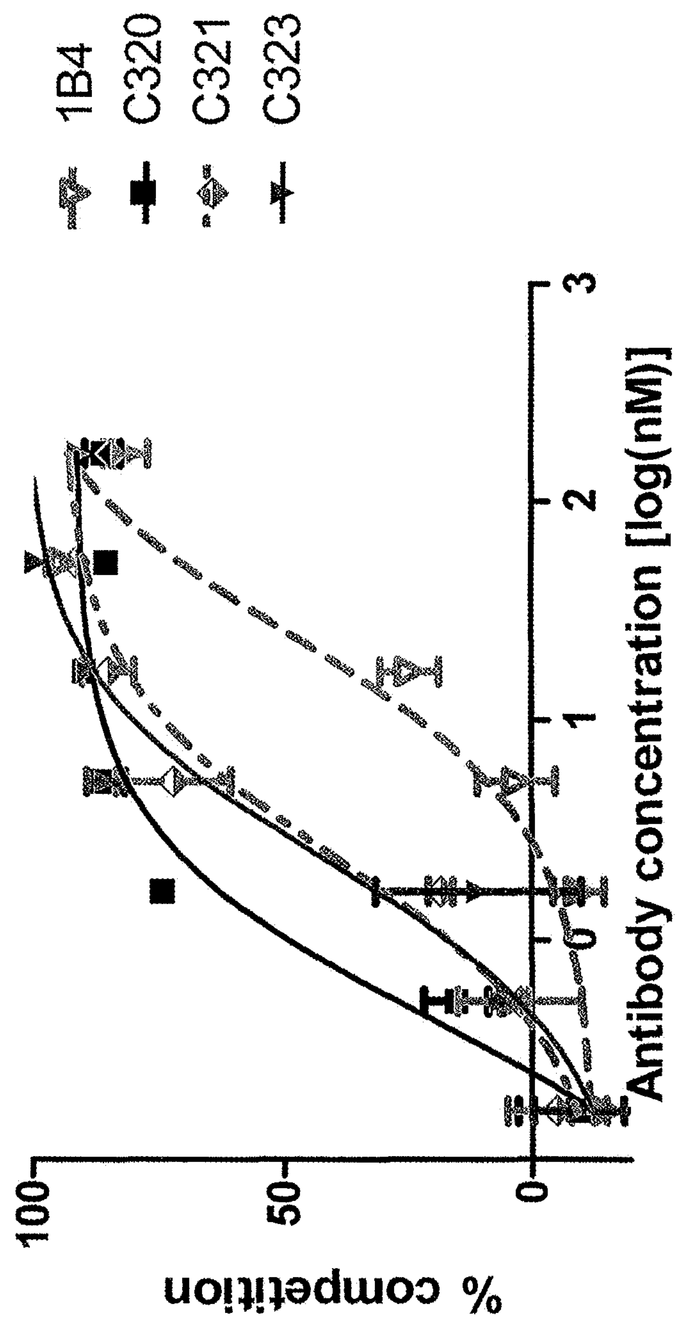
FIG. 4A is a graphical representation showing the level of inhibition of interaction of TL1a with DR3 achieved at various concentrations of test antibodies (maximum concentration tested 25 μg/mL). Antibodies C320, C321 and C323 inhibited the interaction between TL1a and DR3 at numerous concentrations.
Figure 4B:
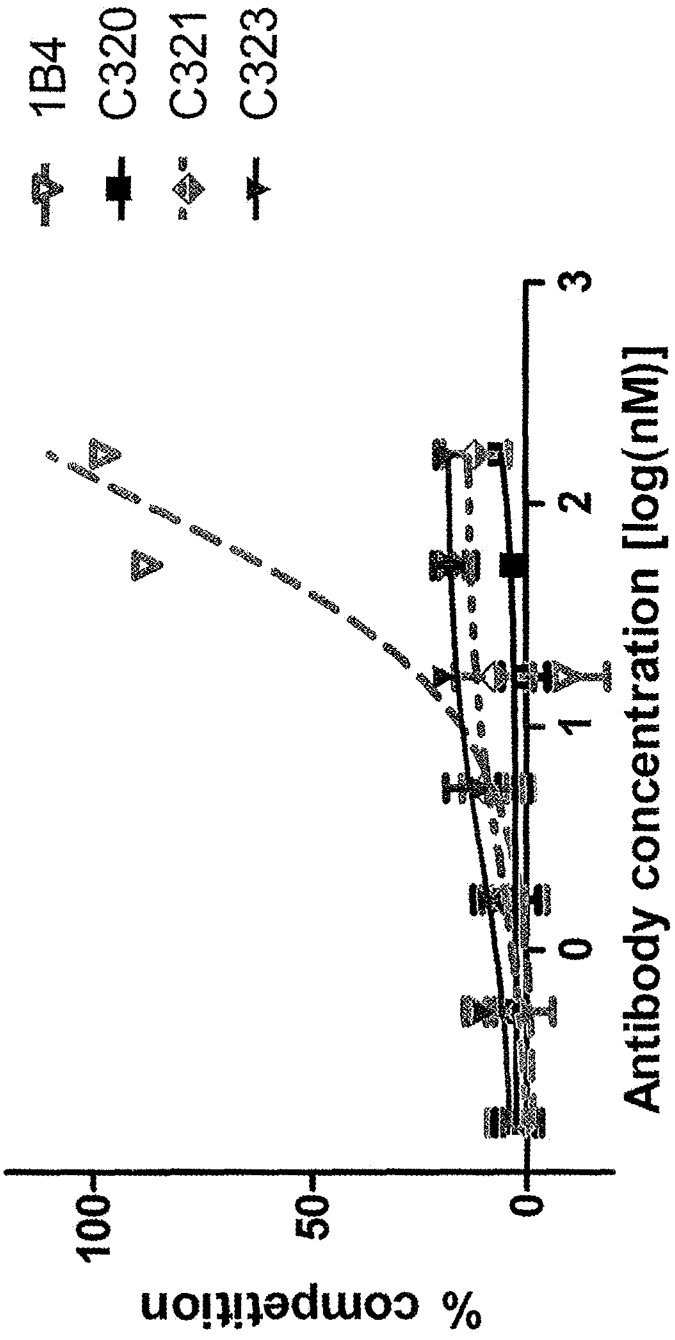
FIG. 4B is a graphical representation showing the level of inhibition of interaction of TL1a with DcR3 achieved at various concentrations of test antibodies (maximum concentration tested 25 μg/mL). Antibodies C320, C321 and C323 did not detectably inhibit the interaction between TL1a and DcR3 at antibody concentrations of 10 μg/mL or less.

Antibodies C320, C321 and C323 inhibit interaction of TL1a with DR3 (FIG. 4A) but do not inhibit interaction of TL1a with DcR3 (FIG. 4B). Using the same assay, antibodies C319, C333, C334 and C336 were shown to demonstrate the same selective neutralization.

Figure 4C:
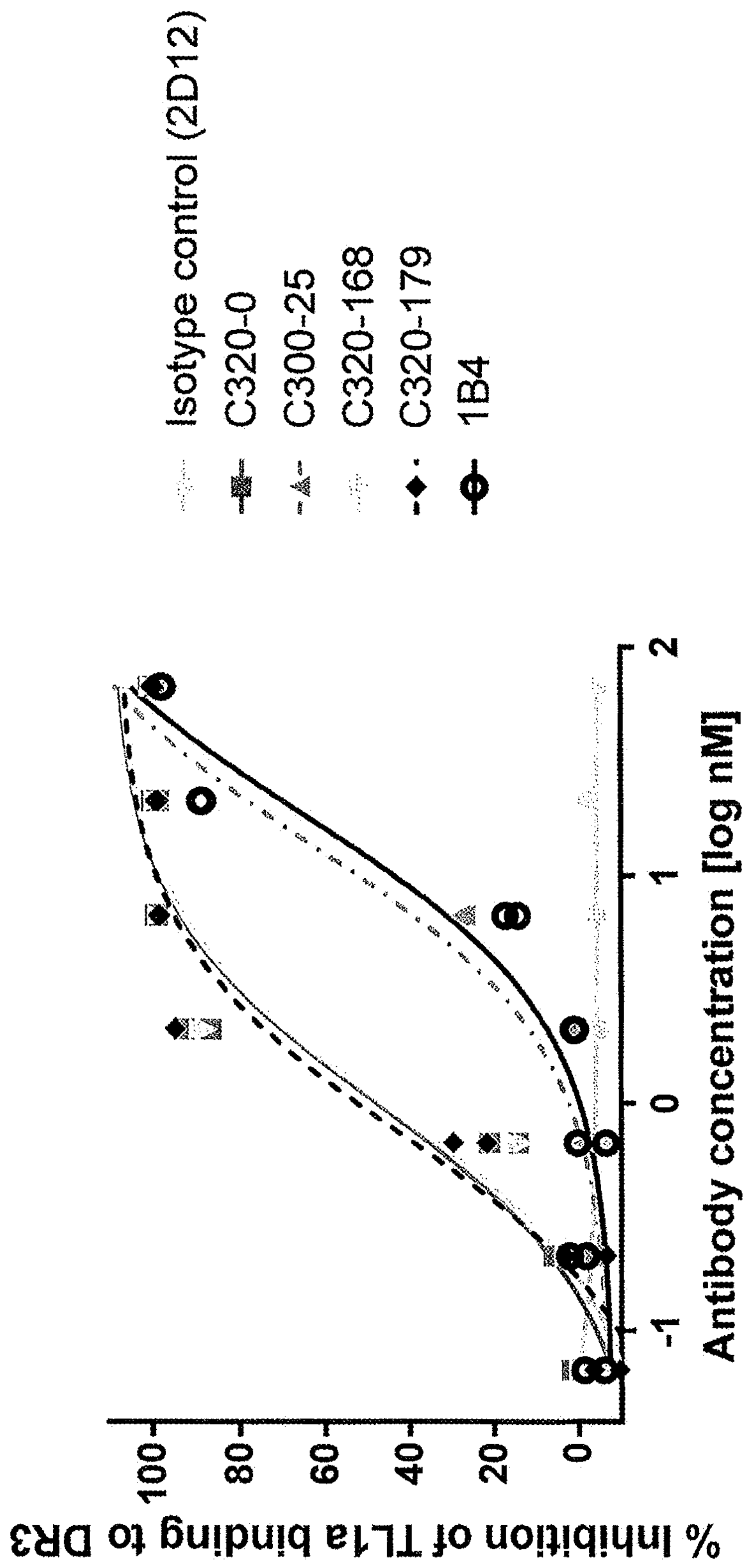
FIG. 4C is a graphical representation showing the level of inhibition of interaction of TL1a with DR3 achieved at various concentrations of test antibodies (maximum concentration tested 10 μg/mL). Antibodies C320-0, C320-168 and C320-179 inhibited the interaction between TL1a and DR3 at numerous concentrations. Antibodies 1B4 and C300-25 are included for the purposes of comparison
Figure 4D:
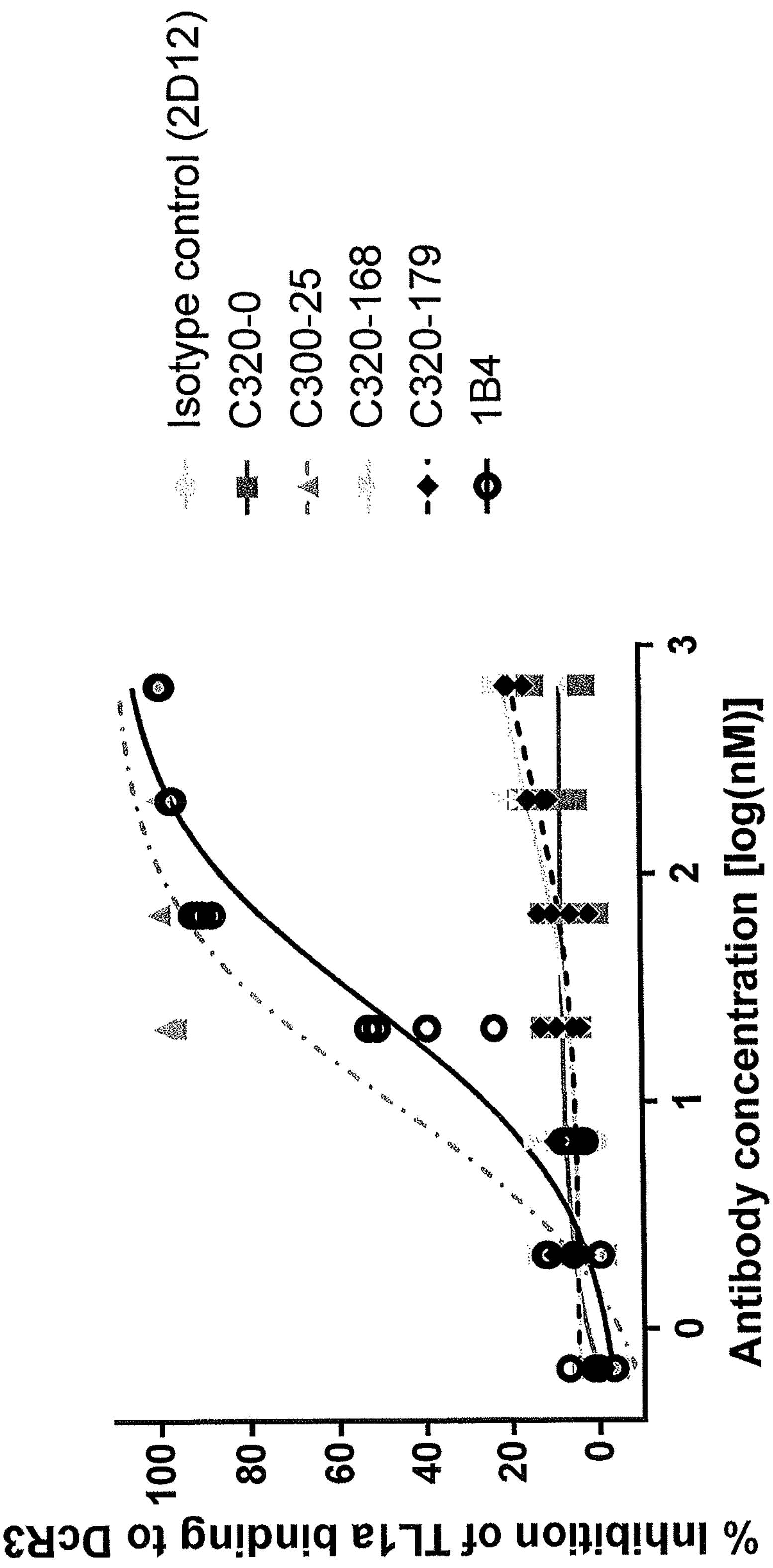
FIG. 4D is a graphical representation showing the level of inhibition of interaction of TL1a and DcR3 achieved at various concentrations of test antibodies (maximum concentration tested 100 μg/mL). Antibodies C320-0, C320-168 and C320-179 did not detectably inhibit the interaction between TL1a and DcR3. Antibodies 1B4 and C300-25 inhibited the interaction between TL1a and DcR3 at various concentrations and are included for the purposes of comparison FIG. 5A includes two a graphical representations showing the binding of various concentrations of test antibodies to soluble human TL1a (SEQ ID NO: 202; top panel) and soluble human TL1a in which arginine at residue 32 has been substituted with alanine (R32A mutein, bottom panel). Antibodies C320-0, C320-168 and C320-179 all bound TL1a at various concentrations but not R32A mutein TL1a. Anti-TL1a antibodies 1B4 and 16H2 (as described in US20090280116) bound both TL1a and R32A mutein TL1a at various concentrations. The isotype control antibody did not bind any form of TL1a FIG. 5B is a graphical representation showing the binding of various concentrations of test antibodies to soluble human TL1a in which arginine at residue 85 has been substituted with alanine (R85A mutein, top panel) and soluble human TL1a in which arginines at residue 32 and residue 85 have been substituted with alanine (R32A+R85A mutein, bottom panel). Antibodies C320-0, C320-168 and C320-179 did not bind either R85A or R32A+R85A mutein TL1a. Anti-TL1a antibodies 1B4 and 16H2 (as described in US20090280116) bound both R85A or R32A+R85A mutein TL1a at various concentrations. The isotype control antibody did not bind any form of TL1a FIG. 5C is a graphical representation showing the binding of soluble human TL1a, R32A mutein TL1a and R85A mutein TL1a at a concentration of 1 μg/ml to receptors DR3 and DcR3. TL1a bound both receptors equally well. R32A and R85A mutein TL1a bound DcR3 to a similar extent as did TL1a but bound DR3 at a level approximately 50% or more lower than TL1a binding to DcR3

Using a similar assay the binding of antibodies C320 and derivatives thereof described below, particularly C320-168 and C320-179, were shown to inhibit interaction of TL1a with DR3 (FIG. 4C) with an $EC_{50}$ 1 nM or less. These antibodies also did not inhibit interaction of TL1a with DcR3 (FIG. 4D) when tested at concentrations ranging from 0.1 μg/mL to 100 μg/mL. These results contrast with those of antibodies C300-25 and 1B4. In this regard, antibody C300-25 is a rat monoclonal antibody produced by the inventors.

TABLE 5

Antibody $EC_{50}$ values for inhibition of TL1a interaction with receptors DR3 and DcR3

| Antibody | $EC_{50}$ (nM) DR3 | $EC_{50}$ (nM) DcR3 |
|---|---|---|
| C320 | 0.97 | DNI |
| C320-179 | 0.72 | DNI |
| C320-168 | 0.97 | DNI |
| C300-25 | 13.5 | 9.84 |
| 1B4 | 17.8 | 26.5 |

DNI—did not inhibit

DR3 and DcR3 have been shown to compete for binding to TL1a. Therefore it was unexpected that antibodies have been isolated with specificity, targeting an epitope on TL1a that is neutralizing for DR3, but not DcR3. These results indicate that antibodies described herein are capable of preventing TL1a activity through its cognate receptor DR3 without disturbing either the natural antagonistic function of DcR3 or a homeostatic balance of DcR3 binding. Without being bound by any theory or mode of action, such selective inhibition may be biologically relevant because DcR3 regulates the amount of free Fas-L and LIGHT available for binding to their cognate signaling receptors (Fas and H-VEM, respectively). Consequently, inhibiting the interaction between TL1a and DcR3 could increase the amount of Fas-L and LIGHT bound by DcR3 thus decreasing the amount available for signaling through their cognate receptors. As Fas-mediated killing plays a role in cancer surveillance, potential downstream consequences of increasing the amount of DcR3 to bind to Fas-L could include increased susceptibility to cancer. Again, without being bound by theory or mode of action, isolating antibodies that specifically inhibit interaction of TL1a and DR3, but not DcR3, could be advantageous in treating disease but without compromising safety.

Example 5: Epitope Mapping

Amino acid substitutions were introduced into the sequence of soluble TL1a (SEQ ID NO: 202) to generate a series of TL1a muteins.

Using the SPR-based mutein analysis assay described in Example 1.10, TL1a muteins in supernatants from transfected HEK-293E cells were tested for expression levels and binding to C320. The results are presented in Table 6.

TABLE 6

Expression and binding of soluble human TL1a and muteins thereof to antibody C320

| Amino acid substitution | Mutein Expression (RU) | C320 Binding (RU) | Amino acid substitution | Mutein Expression (RU) | C320 Binding (RU) |
|---|---|---|---|---|---|
| Wild Type | 3244.9 | 125.6 | A55S | 2933.1 | 33.2 |
| L1A | 3264.3 | 115 | A55L | 2746.5 | −7.6 |
| K2A | 3094.4 | 152 | A55R | 2307.7 | −12.3 |
| Q4A | 3366.2 | 120 | A55G | 1991.2 | −5.8 |
| E5A | 3086.5 | 360.4 | A55D | 2386.5 | −21.1 |
| F6A | 2948.3 | 240.2 | T57A | 3335.6 | 42.7 |
| P8A | 3455.9 | 124.3 | K58A | 3241.5 | 4.3 |
| S9A | 3594.2 | 94.5 | N59A | 3382.9 | 73.8 |
| H10A | 3372.5 | 122.7 | R60A | 3405.8 | 116.5 |
| Q11A | 3572.9 | 71.4 | N62A | 3264.9 | 117.4 |
| Q12A | 3098.5 | 193.8 | T64A | 3083.6 | 289.8 |
| V13A | 3213.9 | 167.8 | N65A | 3226.8 | 156.6 |
| Y14A | 2883.5 | 401 | K66A | 3183.3 | 27.1 |
| P16A | 2938 | 225 | F67A | 3216.1 | 304.7 |
| L17A | 2904.1 | 194.5 | L69A | 3389.8 | 212.6 |
| R18A | 3102.5 | 132.2 | E72A | 3171.5 | 136.2 |
| D20A | 3247.6 | 154.6 | S73A | 3129.3 | 146 |
| G21S | 2915.3 | 184.8 | R85A | 3047.1 | −33.5 |
| G21L | 3424.4 | 72.8 | M87A | 3161.2 | 46.1 |
| G21R | 3197 | 116.2 | S89A | 3600.3 | 10.8 |
| G21A | 3483 | 85 | E90A | 3129.7 | 1089.1 |
| G21D | 3032 | 158.6 | E93A | 3181.6 | 343.9 |
| D22A | 3185.6 | 169.8 | I94A | 3125.1 | 352.3 |
| R32A | 3103.7 | −36.5 | R95A | 3634.8 | 28.8 |
| T34A | 3278.7 | 389.2 | Q96A | 3256.5 | 149.4 |
| P35A | 3385 | −28.6 | R99A | 3351.3 | 105.2 |
| T36A | 2771.9 | 486.1 | P100A | 2898.5 | 199.5 |
| Q37A | 2789.3 | 319.2 | K102A | 3420.8 | 155.7 |
| H38A | 3133 | 147.4 | D104A | 2982.9 | 533.2 |
| F39A | 2509.8 | 445.5 | S105A | 3425.8 | 127.1 |
| K40A | 3213.5 | 55.5 | D115A | 3648.5 | 110.1 |
| N41A | 2967.5 | 248.5 | S116A | 2962.4 | 282.1 |
| Q42A | 3073 | 175.7 | Y117A | 3323.8 | 189.8 |
| F43A | 3245.8 | 109.3 | P118A | 3254.9 | 161.7 |
| P44A | 3180.1 | 200.4 | E119A | 3263.7 | 278.5 |
| A45S | 3407.3 | 61.5 | P120A | 3143 | 164.8 |
| A45L | 3087.7 | 35.6 | Q122A | 3189 | 148.5 |
| A45R | 3167 | 107.2 | S135A | 3109.4 | 95.4 |
| A45G | 3385.9 | 77.1 | F138A | 3496.7 | 21 |
| A45D | 3395.1 | 38.9 | S148A | 2883.9 | 228.7 |
| H47A | 3466.4 | 159.1 | Q150A | 3151.1 | 193.5 |

TABLE 6-continued

Expression and binding of soluble human TL1a and muteins thereof to antibody C320

| Amino acid substitution | Mutein Expression (RU) | C320 Binding (RU) | Amino acid substitution | Mutein Expression (RU) | C320 Binding (RU) |
|---|---|---|---|---|---|
| H50A | 3249.3 | 132.4 | E151A | 3796.5 | 90.8 |
| E51A | 3136.5 | 33.8 | K154A | 3610.3 | 86.7 |
| L52A | 3105.5 | 52.7 | S160A | 1272.2 | 901.6 |
| G53S | 3238.5 | 19 | D161A | 3391.4 | 223.4 |
| G53L | 1299.7 | −3.9 | I162A | 3139.2 | 72.4 |
| G53R | 3796.7 | 7.2 | S163A | 3054 | 481 |
| G53A | 3652.4 | −4.8 | Y167A | 2942.2 | 70.7 |
| G53D | 2130.3 | −6.1 | T168A | 3335.1 | 2.6 |
| | | | K169A | 3005 | 69.7 |
| | | | E170A | 3418.7 | 16 |

Muteins that expressed well (Mutein expression greater than 2000 RU) but failed to bind antibody C320 (TL1a binding less than 17 RU) were selected for further analysis.

Muteins with substitutions at amino acids G53 and A55 expressed poorly and had reduced binding to polyclonal anti-TL1a, suggesting that these are important residues for TL1a structural integrity. The other muteins all expressed adequately, bound polyclonal anti-TL1a and ran equivalently to wild-type TL1a on both reducing and non-reducing SDS-PAGE gels. These characteristics all suggest that the muteins were appropriately expressed and folded into TL1a proteins.

Figure 5A:
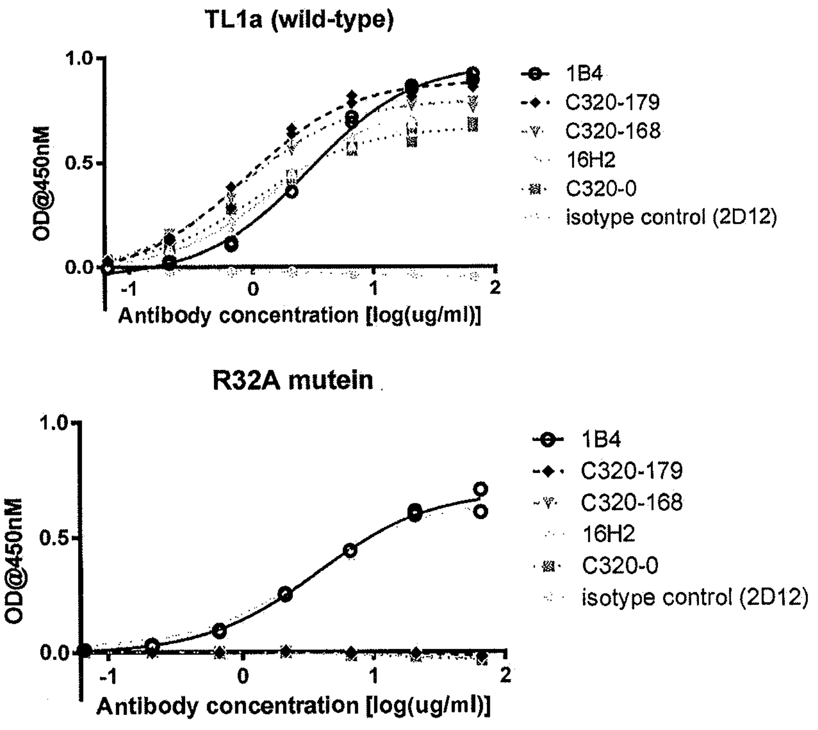
FIG. 5D is a diagrammatic representation depicting the X-ray crystal structure of trimeric human TL1a (PDB: 3K51) (gray) with the residues R32 and R85 highlighted in black on each monomer.
Figure 5B:
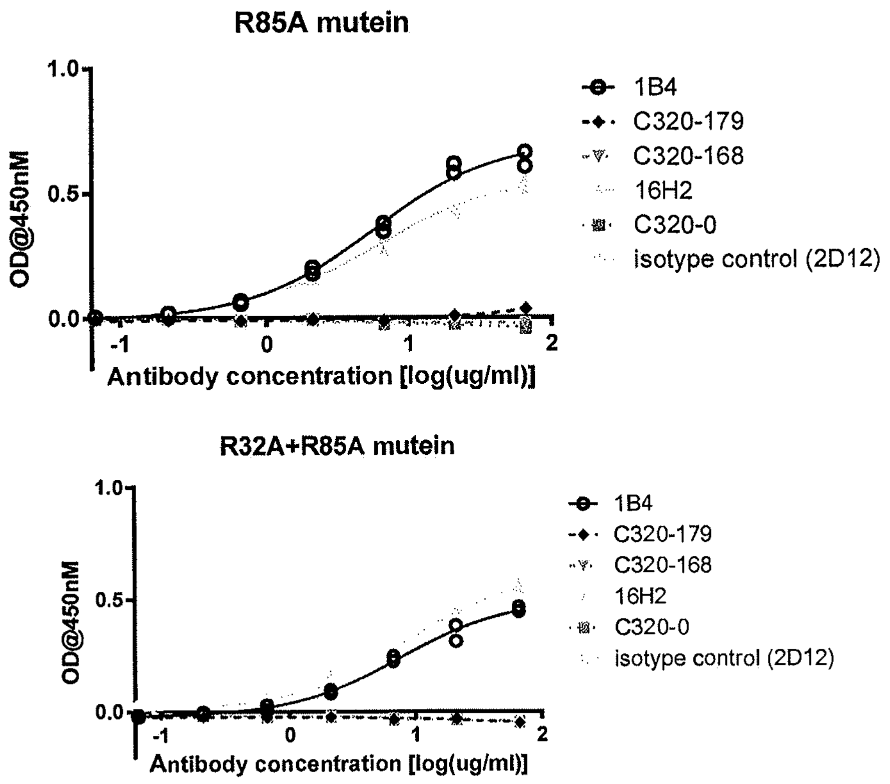

The muteins exhibited differential binding patterns to the different monoclonal anti-TL1a antibodies described herein. Antibodies C320, C320-168 and C320-179 did not detectably bind to the R32A and R85A muteins or to a mutein containing both of these substitutions (FIGS. 5A and B). C320 also showed negligible binding to the P35A, T168A and E170A muteins while C320-168 and C320-179 had reduced binding to these muteins but not to the same extent as C320. In contrast, TL1a-binding antibodies 1B4 and 16H2 showed binding to the muteins R32A, R85A, P35A, T168A at greater than 50% of the wild-type TL1a, indicating that amino acids at these positions are not crucial to the binding of 1B4 and 16H2 to TL1a.

Figure 5C:
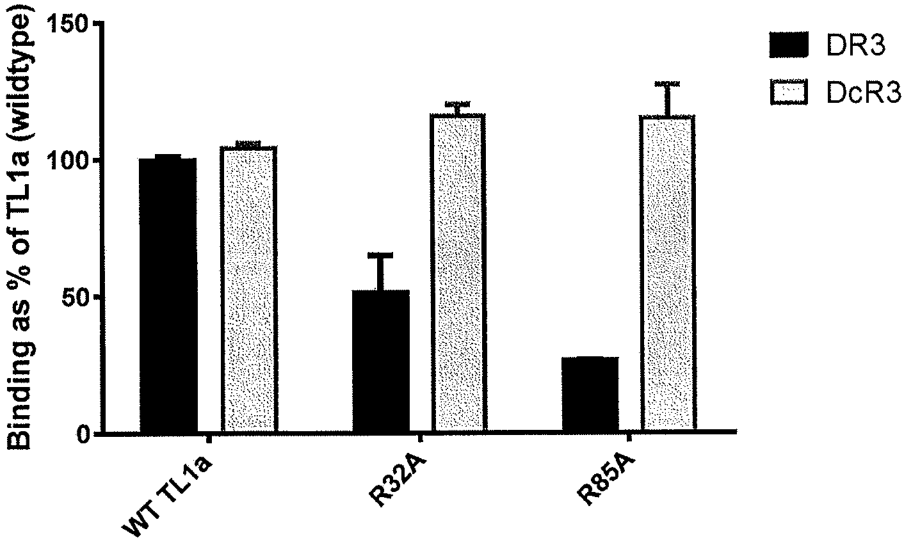

Given that the antibodies C320, C320-168 and C320-179 inhibit the binding of TL1a to DR3 but not DcR3, the antibodies are likely bind to amino acids involved in the binding of DR3 to TL1a and disrupt this interaction. DR3, but not DcR3, had significantly decreased binding to the R32A and R85A muteins, suggesting that these residues are involved with TL1a binding to DR3 (FIG. 5C).

Figure 5D:
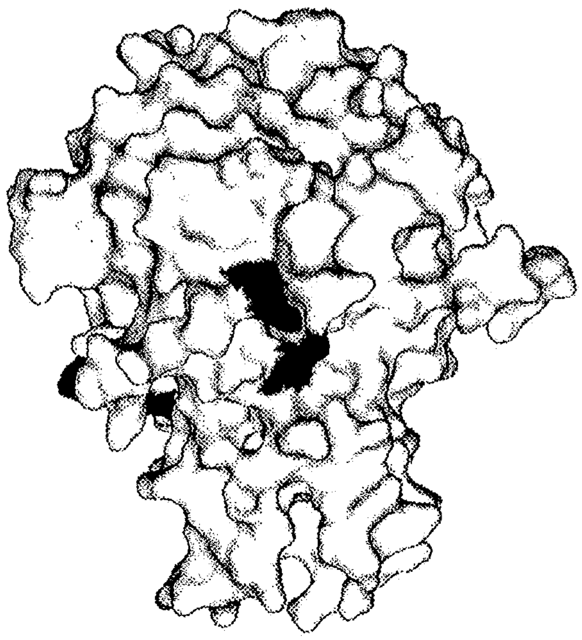

The binding site of the antibodies C320, C320-168 and C320-179 on TL1a is illustrated in FIG. 5D. As can be seen from the diagram, the residues R32 and R85, while being distant in primary amino acid sequence are located adjacent to each other in the protein's tertiary structure. Hence, these can be considered key residues within the epitope on TL1a to which the antibodies C320, C320-168 and C320-179 bind.

Example 6: Characterization of Antibodies Binding to Cell-Surface TL1a

TL1a, like most TNF-ligand superfamily members, is present as a cell surface form that is cleaved to generate soluble TL1a and as for other members the membrane form of TL1 (mbTL1a) has been shown to have biological function. Therefore to neutralize the activity of TL1a it would be advantageous to have antibodies that bind strongly to both membrane and soluble TL1a. Antibodies that displayed functional inhibition of TL1a were screened by flow cytometry on a human cell line transfected stably with a membrane anchored TL1a (produced as described in Example 1.11).

Figure 6:
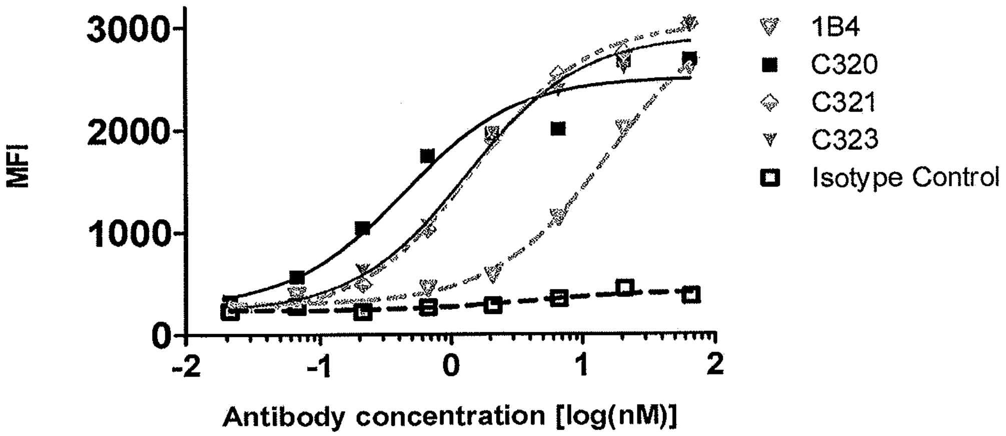

Antibodies C320, C321, C323 and 1B4 all bound to the TL1a transfected cell line (FIG. 6) with $EC_{50}$s of 0.5 to 2 nM, but not normal untransfected cells.

Figure 7A:
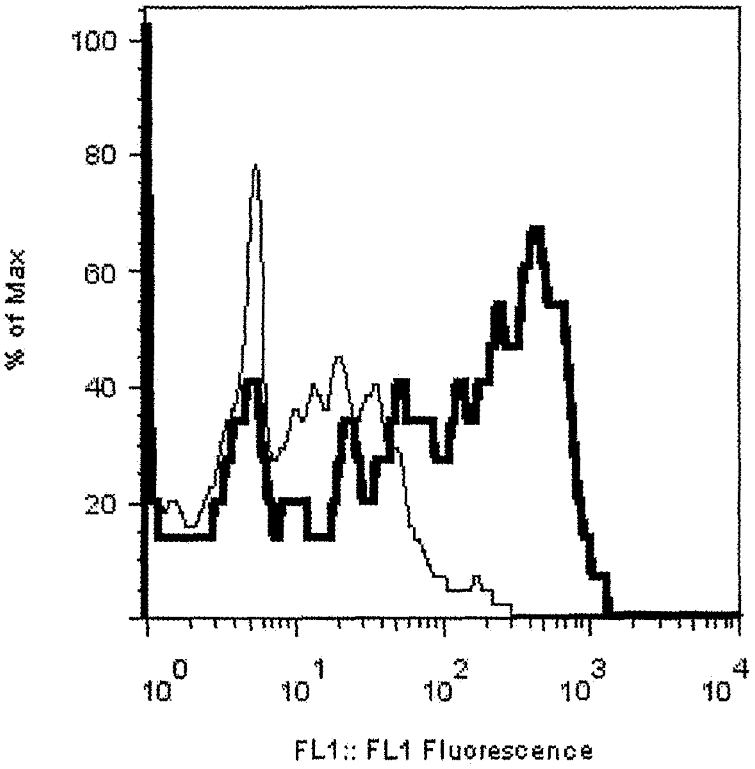
FIG. 7B is a graphical representation showing increased production of secreted TL1a in PBMCs as mitogen (Concanavalin A)-stimulation is increased.
Figure 7B:
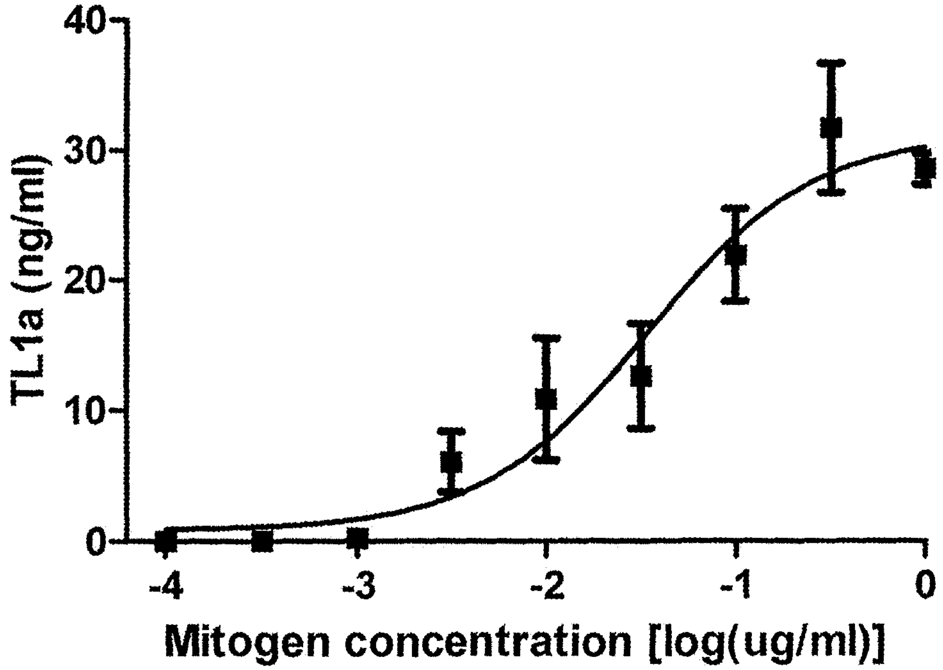

To further characterize antibodies described herein, their function on primary human cells was tested. PBMCs were isolated as described in Example 1.12. Using the assay conditions described in Example 1.13 these cells were shown to produce both mbTL1a (FIG. 7A) and soluble TL1a (FIG. 7B).

Figure 8A:
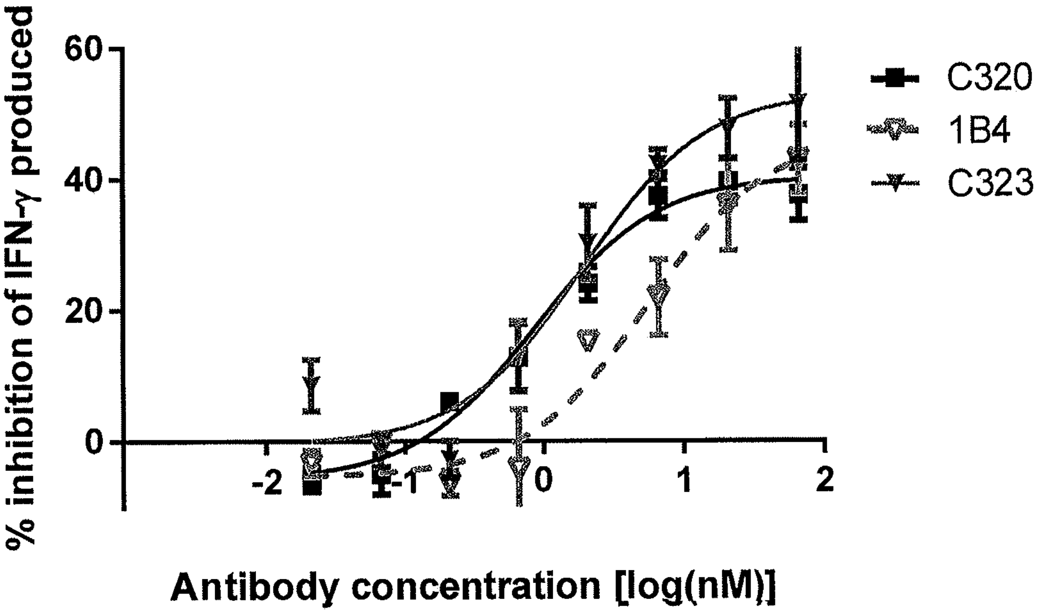
FIG. 8A is a graphical representation showing the ability of anti-TL1a antibodies (maximum concentration tested 50 μg/mL) to inhibit interferon gamma (IFN-γ) production induced by endogenous human TL1a. Endogenous TL1a enhanced cytokine production by stimulated PBMCs. Antibodies C320 and C323 inhibited the production of IFN-γ. Antibody 1B4 is included for the purposes of comparison
Figure 8B:
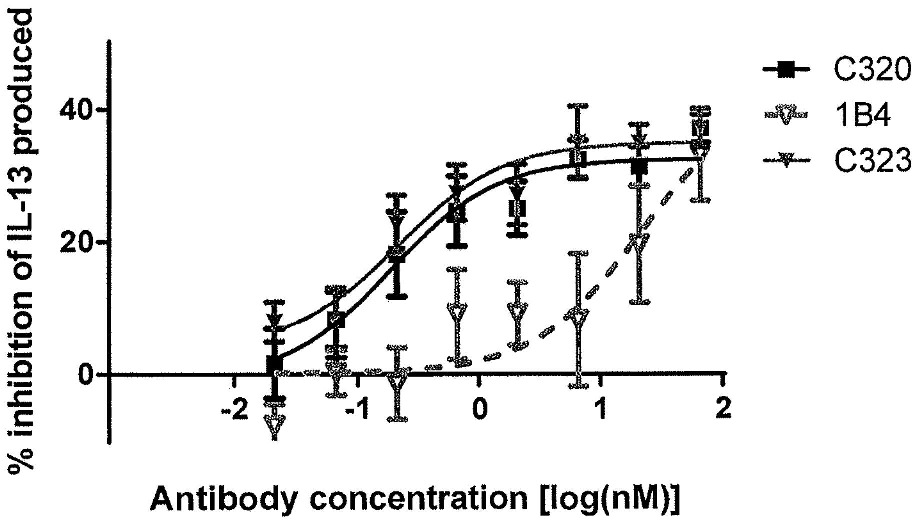
FIG. 8B is a graphical representation showing the ability of anti-TL1a antibodies (maximum concentration tested 50 μg/mL) to inhibit IL-13 production induced by endogenous human TL1a. Endogenous TL1a enhanced cytokine production by stimulated PBMCs. Antibodies C320 and C323 inhibited the production of IL-13 Antibody 1B4 is included for the purposes of comparison.

PBMCs were stimulated as described in Example 1.13 and assayed for cytokine production in the presence of anti-TL1a antibodies. Since no exogenous TL1a was added to the cell culture, the effects of anti-TL1a antibodies were due to neutralization of endogenous TL1a. Antibodies, C320 and C323 demonstrated good inhibition of endogenous TL1a-induced cytokine production by PBMCs (FIG. 8). This inhibition was apparent on cytokines typically produced by Th1 cells (IFN-γ FIG. 8A) and Th2 cells (IL-13; FIG. 8B). These data demonstrate that these antibodies are likely to be capable of inhibiting TL1a produced from primary human cells, and that these antibodies could be used as diagnostic reagents to detect TL1a on cells or in sera.

Example 7: Generating Improved Variants of C320

The C320 antibody was further optimized through alterations to the antibody's sequence with the aim of yielding a positive effect on the antibody's biophysical properties whilst having minimal impact on the potency of C320.

For example, alterations that enhance the expression level of the antibody with concomitantly increased production levels are desirable. Removal of a N-linked glycosylation site in the $V_H$ through amino acid substitution to reduce product heterogeneity may further enhance C320.

Substitution of amino acid residues with the potential to impact the stability of the antibody through oxidation or isomerization during purification or storage with amino acids that do not undergo such transitions (Wang et al., *Journal of Pharmaceutical Sciences* 96:1-26, 2006) may further improve C320. Substitution of rare or non-germ-line C320 sequences which may potentially contribute to immunogenicity with those of lower predicted immunogenicity could further improve C320. Such changes are described in more detail as follows.

Enhancing the Expression of C320

A database of human antibody germline amino acid sequences was interrogated by Basic Local Alignment Search Tool searches (BLAST: Altschul et al., *J Mol Biol* 215: 403-410, 1990) using the C320 $V_H$ and $V_L$ amino acid sequences. This identified twenty of the most homologous human antibody germline sequences to those of the C320 $V_H$ and C320 $V_L$, respectively. Aligning the human germline sequences with those of C320 enabled the identification of residues present in C320 but not common in the majority of the germlines. The most common amino acid from the germline sequences was substituted into the C320 amino acid sequence. Table 7 lists the amino acid substitutions and the resultant impact on the expression level of each antibody from a transient transfection in HEK-293E cells.

TABLE 7

Effect of amino acid substitutions on expression and potency

| Antibody Designation | Amino Acid Substitution (chain) | % Expression Level relative to C320 | Potency TF-1 EC-50 (pM) |
|---|---|---|---|
| C320 | N/A | 100 | 233 |
| C320-2 | A16S (Heavy) | 156 | 159 |
| C320-3 | T41P (Heavy) | 338 | 428 |
| C320-4 | N73D (Heavy) | DNE | N/A |
| C320-5 | A76T (Light) | 231 | 89 |
| C320-6 | L81Q (Light) | 98 | 67 |
| C320-135 | T41P (Heavy) & A76T (Light) | 288 | 462 |

Amino acid substitutions are relative to SEQ ID NO: 42 for heavy chain and SEQ ID NO: 46 for light chain.

Two substitutions, present in C320-3 and C320-5 raised the expression level of the antibody greater than two-fold and whilst minimally impacting the potency of the antibody in a TF-1 potency assay. A further antibody incorporating both substitutions, C320-135, had largely equivalent potency and maintained the improved expression level.

C320-4 contained a N73D (N72D according to the numbering system of Kabat) substitution which aimed to improve expression while also attempted to remove an N-linked glycosylation motif. However, the N73D substitution abolished antibody expression, suggesting N73 is desirable for expression of the antibody.

To further improve C320 expression the CDRs of C320 were grafted onto other frameworks of antibodies possessing a known crystal structure. This unusual approach was adopted as antibodies of known crystal structure usually possess a matched $V_H$:$V_L$ pair. To select antibodies with suitable $V_H$- and $V_L$ frameworks BLAST searches of a database of crystal structures were performed to identify antibodies of similar amino acid sequence to C320. BLAST searches using the C320 $V_H$ were used to identify the 100 most homologous antibody sequences with known crystal structures. Similarly, the 100 most homologous antibody sequences to the C320 $V_L$ with known crystal structures were identified. Crystal structures appearing in both heavy- and light chain lists were deemed suitable acceptor frameworks for CDR grafting. These were 1TZG, 1RHH, 2DD8, 2JB5, 3FKU, 3GBM, 31YW, 3LMJ, and 3P30. The CDRs of C320 were then used to replace the CDR sequences present in each of the above antibody sequences. An alignment of each of the sequence containing the C320 CDR regions is given in FIG. 1D (heavy chain) and FIG. 1G (light chain). The antibody heavy and light chains were then paired as follows and assessed for protein expression and TL1a binding and the results listed in Table 8.

TABLE 8

Results of CDR grafting on expression and TL1a binding

| Antibody Designation | Heavy Chain | Light Chain | Protein A capture (RU) | AUC Protein A HPLC (215 nm) | TL1a binding (RU) |
|---|---|---|---|---|---|
| C320 | C320 | C320 | 779 | 2764 | 282 |
| mock | N/A | N/A | 25 | 376 | N/D |
| C320-7 | 1TZG | 1TZG | 187 | 912 | N/D |
| C320-8 | 1RHH | 1RHH | 437 | 1718 | 29 |
| C320-9 | 2DD8 | 2DD8 | 2235 | 8687 | 305 |
| C320-10 | 2JB5 | 2JB5 | 2098 | 11406 | 368 |
| C320-11 | 3FKU | 3FKU | 129 | 637 | N/D |

TABLE 8-continued

| Results of CDR grafting on expression and TL1a binding | | | | | |
|---|---|---|---|---|---|
| Antibody Designation | Heavy Chain | Light Chain | Protein A capture (RU) | AUC Protein A HPLC (215 nm) | TL1a binding (RU) |
| C320-12 | 3GBM | 3GBM | 100 | 697 | N/D |
| C320-13 | 3IYW | 3IYW | 1566 | 4488 | 524 |
| C320-14 | 3LMJ | 3LMJ | 570 | 1125 | 171 |
| C320-15 | 3P30 | 3P30 | 1063 | 2192 | 318 |
| C320-16 | 1TZG | C320 | 2527 | 11604 | 653 |
| C320-17 | 1RHH | C320 | 2241 | 11980 | 683 |
| C320-18 | 2DD8 | C320 | 1528 | 5786 | 408 |
| C320-19 | 2JB5 | C320 | 1805 | 8018 | 465 |
| C320-20 | 3FKU | C320 | 986 | 1909 | 310 |
| C320-21 | 3GBM | C320 | 39 | 428 | N/D |
| C320-22 | 3IYW | C320 | 2107 | 8622 | 665 |
| C320-23 | 3LMJ | C320 | 1119 | 2044 | 324 |
| C320-24 | 3P30 | C320 | 1023 | 2353 | 311 |
| C320-25 | C320 | 1TZG | 376 | 1062 | 42 |
| C320-26 | C320 | 1RHH | 438 | 1012 | 81 |
| C320-27 | C320 | 2DD8 | 2272 | 9795 | 578 |
| C320-28 | C320 | 2JB5 | 2176 | 11771 | 623 |
| C320-29 | C320 | 3FKU | 1549 | 3195 | 355 |
| C320-30 | C320 | 3GBM | 1288 | 3356 | 455 |
| C320-31 | C320 | 3IYW | 1061 | 2806 | 381 |
| C320-32 | C320 | 3LMJ | 892 | 1888 | 331 |
| C320-33 | C320 | 3P30 | 1527 | 4473 | 521 |

Note:
The sequences of heavy and light chains of these antibodies are listed in FIG. 1D and 1G.
RU is response units - a measure of binding to the surface using SPR and AEC is area under the curve.

When the CDRs of C320 were grafted onto different antibody frameworks a large number of the resultant antibodies expressed at a level above that of the C320 antibody. The antibody C320-16, in which the heavy chain C320 CDRs were grafted on the antibody 1TZG framework and was paired with the C320 light chain, expressed 3-fold better than C320. This experiment also demonstrated that it is possible to change the isotype of the antibody and retain protein expression and binding to TL1a using this approach, as some of the light chain antibody frameworks into which the C320 light chain CDRs were grafted were of the kappa isotype as opposed to the lambda isotype present in C320.

To further improve the expression of the antibody, amino acid substitutions were introduced into the CDR3 region of the variable heavy chain of C320 and the antibodies transfected into HEK-293E cells and screened for expression levels using Protein A HPLC and Protein A capture using surface plasmon resonance (SPR). The results are described in Table 9.

TABLE 9

| Effect of HCDR3 substitutions on expression | | | | |
|---|---|---|---|---|
| Antibody Designation | Heavy Chain Substitution (relative to SEQ ID NO: 42) | Light Chain Substitution (relative to SEQ ID NO: 46) | Protein A capture (RU) | AUC (Protein A HPLC) (280 nm) |
| C320-0 | N/A | N/A | 6413 | 487 |
| mock | N/A | N/A | 198 | N/D |
| C320-53 | E99S | A76T | 6831 | 581 |
| C320-54 | E99H | A76T | 6594 | 444 |
| C320-55 | E99L | A76T | 6797 | 540 |
| C320-56 | E99D | A76T | 5823 | 343 |
| C320-57 | E99Y | A76T | 7789 | 670 |
| C320-58 | E99P | A76T | 5679 | 335 |
| C320-59 | E99Q | A76T | 8534 | 1149 |
| C320-60 | E99K | A76T | 8293 | 839 |

TABLE 9-continued

| Effect of HCDR3 substitutions on expression | | | | |
|---|---|---|---|---|
| Antibody Designation | Heavy Chain Substitution (relative to SEQ ID NO: 42) | Light Chain Substitution (relative to SEQ ID NO: 46) | Protein A capture (RU) | AUC (Protein A HPLC) (280 nm) |
| C320-61 | V100A | A76T | 8381 | 863 |
| C320-62 | V100S | A76T | 8423 | 803 |
| C320-63 | V100H | A76T | 8828 | 751 |
| C320-64 | V100L | A76T | 8288 | 910 |
| C320-65 | V100D | A76T | 8816 | 1003 |
| C320-66 | V100Y | A76T | 7750 | 570 |
| C320-67 | V100P | A76T | 7831 | 660 |
| C320-68 | V100Q | A76T | 8170 | 715 |
| C320-69 | V100K | A76T | 8741 | 706 |
| C320-70 | P101A | A76T | 5022 | 234 |
| C320-71 | P101S | A76T | 5083 | 268 |
| C320-72 | P101H | A76T | 5403 | 230 |
| C320-73 | P101L | A76T | 5518 | 283 |
| C320-74 | P101D | A76T | 5756 | 297 |
| C320-75 | P101Y | A76T | 5084 | 212 |
| C320-76 | P101Q | A76T | 5036 | 263 |
| C320-77 | P101K | A76T | 5702 | 309 |
| C320-78 | D102A | A76T | 8249 | 684 |
| C320-79 | D102S | A76T | 8964 | 1102 |
| C320-80 | D102H | A76T | 8957 | 830 |
| C320-81 | D102L | A76T | 7969 | 515 |
| C320-82 | D102Y | A76T | 8135 | 558 |
| C320-83 | D102P | A76T | 7765 | 462 |
| C320-84 | D102Q | A76T | 7826 | 635 |
| C320-85 | D102K | A76T | 8487 | 890 |
| C320-86 | T103A | A76T | 10209 | 1882 |
| C320-87 | T103S | A76T | 8236 | 567 |
| C320-88 | T103H | A76T | 4934 | 227 |
| C320-89 | T103L | A76T | 7580 | 822 |
| C320-90 | T103D | A76T | 8694 | 1106 |
| C320-91 | T103Y | A76T | 3838 | 130 |
| C320-92 | T103P | A76T | 4792 | 219 |
| C320-93 | T103Q | A76T | 4104 | 164 |
| C320-94 | T103K | A76T | 3592 | 149 |
| C320-95 | A104S | A76T | 4811 | 240 |
| C320-96 | A104H | A76T | 4882 | 251 |
| C320-97 | A104L | A76T | 4557 | 189 |
| C320-98 | A104D | A76T | 5371 | 279 |
| C320-99 | A104Y | A76T | 6305 | 410 |
| C320-100 | A104P | A76T | 5678 | 339 |
| C320-101 | A104Q | A76T | 6634 | 508 |
| C320-102 | A104K | A76T | 5826 | 438 |
| C320-103 | S105A | A76T | 8159 | 825 |
| C320-104 | S105H | A76T | 6664 | 426 |
| C320-105 | S105L | A76T | 6193 | 357 |
| C320-106 | S105D | A76T | 7752 | 992 |
| C320-107 | S105Y | A76T | 8209 | 1072 |
| C320-108 | S105P | A76T | 6132 | 483 |
| C320-109 | S105Q | A76T | 6767 | 465 |
| C320-110 | S105L | A76T | 6999 | 452 |
| C320-111 | E105K | A76T | 6919 | 500 |
| C320-112 | E107S | A76T | 7713 | 631 |
| C320-113 | E107H | A76T | 6723 | 459 |
| C320-114 | E107L | A76T | 7739 | 839 |
| C320-115 | E107D | A76T | 8505 | 1034 |
| C320-116 | E107Y | A76T | 6465 | 375 |
| C320-117 | E107P | A76T | 6699 | 400 |
| C320-118 | E107Q | A76T | 8109 | 704 |
| C320-119 | E107K | A76T | 8776 | 952 |

Note:
Substitutions in this table refer to those made into the C320 antibody

Several antibodies were generated that had significant expression levels above that of C320 as determined by capture on a Protein A surface. Several of the high expressing antibodies were re-transfected, purified by Protein A chromatography and their potency measured in a TF-1 assay. The results are listed in Table 10.

TABLE 10

| Effect of HCDR3 substitutions on TL1a inhibition | | | |
|---|---|---|---|
| Antibody Designation | Heavy Chain Substitution (relative to SEQ ID NO: 42) | Light Chain Substitution (relative to SEQ ID NO: 46) | Potency TF-1 EC-50 (pM) |
| C320-0 | N/A | N/A | 233 |
| C320-61 | V100A | A76T | 272 |
| C320-63 | V100H | A76T | 1067 |
| C320-65 | V100D | A76T | 546 |
| C320-68 | V100Q | A76T | 535 |
| C320-86 | T103A | A76T | 303 |
| C320-87 | T103S | A76T | 356 |
| C320-90 | T103D | A76T | 370 |
| C320-103 | S105A | A76T | 455 |
| C320-104 | S105H | A76T | 349 |
| C320-106 | S105D | A76T | 1587 |
| C320-112 | E107S | A76T | 242 |
| C320-114 | E107L | A76T | 514 |
| C320-115 | E107D | A76T | 321 |
| C320-117 | E107P | A76T | 251 |
| C320-119 | E107K | A76T | 4142 |

Note:
Substitutions in this table refer to those made into the C320 antibody

The potency of the resulting antibodies ranged from reduced compared to C320, such as C320-119, to levels equivalent to that of C320.

The light chain sequence of C320 was aligned against the germline sequence of highest homology, IGLV1-40*01. Differences in amino acid sequences in the CDR regions were identified, as shown in FIG. 9A. At a position in which the sequences differed a back substitution of the amino acid from the germline sequence into C320 was performed. The antibodies were expressed in HEK-293 cells, purified and the protein yield relative to C320 determined. A potency assay using TF-1 cells was used to characterize the inhibition profile of the antibodies. The results are displayed in Table 11.

TABLE 11

| Effect of germlining C320 on TF1a inhibition | | | | |
|---|---|---|---|---|
| Antibody Designation | Heavy Chain Substitution (relative to SEQ ID NO: 42) | Light Chain Substitution (relative to SEQ ID NO: 46) | % Expression Level relative to C320 | Potency TF-1 EC-50 (pM) |
| C320 | N/A | N/A | 100 | 233 |
| C320-120 | T41P | A23T | 279 | 343 |
| C320-121 | T41P | D28N | 239 | 1433 |
| C320-122 | T41P | L33Y | 247 | 5480 |
| C320-123 | T41P | G34D | 207 | DNI |
| C320-124 | T41P | Y53N | 128 | 1613 |
| C320-125 | T41P | Y54S | 259 | 13393 |
| C320-126 | T41P | P82A | 187 | 539 |
| C320-127 | T41P | G95S | 140 | 541 |
| C320-128 | T41P | T96S | 134 | 328 |

Note:
Substitutions in this table refer to those made into the C320 antibody

The antibody C320-120 demonstrated a good level of expression and the highest potency of all the antibodies tested in this experiment. Some of the substitutions, such as those in C320-123 and C320-125 resulted in antibodies that expressed but no longer inhibited or weakly inhibited TL1a induced apoptosis on TF-1 cells. This suggested that the amino acids at the positions G34 (G32 according to the numbering system of Kabat) and Y54 (Y52 according to the numbering system of Kabat) of the variable light chain may be important in enabling the antibody to inhibit the activity of TL1a.

Removal of Putative Oxidation and Isomerization Sites from C320

Amino acid analysis of the variable heavy and light chain sequences identified several amino acids that may undergo oxidation or isomerization. Particular emphasis was placed on amino acids present in the CDRs of the antibody. Changes to these amino acids may, over time, alter the binding profile of the antibody. In the variable heavy chain M51 (M51 according to the numbering system of Kabat) was identified as a potential oxidation site along with the potential aspartate isomerization site D102 (D98 according to the numbering system of Kabat). In the light chain, D94 (D92 according to the numbering system of Kabat) was identified as a potential isomerization site. To reduce the potential impact of these predicted issues variants of C320 were produced containing conservative or semi-conservative amino acid substitutions in these positions. These substitutions and their impact on the potency of the resulting C320 variants are listed in Table 12.

TABLE 12

| Effect of amino acid substitutions on expression and TL1a inhibition | | | |
|---|---|---|---|
| Antibody Designation | Amino Acid Substitution from C320 (chain) | % Expression Level relative to C-320 | Potency TF-1 EC-50 (pM) |
| C320 | N/A | 100 | 233 |
| C320-129 | D102E (Heavy) | 201 | 433 |
| C320-130 | M51L (Heavy) | 185 | 528 |
| C320-131 | D94E (Light) | 103 | 10680 |

Note:
Substitutions in this table refer to those made into the C320 antibody, with heavy chain substitutions relative to SEQ ID NO: 42 and light chain substitutions relative to SEQ ID NO: 46

The potential oxidation and isomerization site present in the heavy chain were successfully substituted with conservative amino acids which resulted in improved expression and retention of potency. The substitution of D94E in the light chain CDR region resulted in an antibody that expressed at similar levels to C320, but had significantly reduced potency, indicating that D94 of the light chain may be important in mediating the functional activity of C320.

Removal of the N-Glycosylation Site from the C320 Heavy Chain

As an earlier attempt to remove the $V_H$ glycosylation site NTS by substitution to DTS (N73D; N72D according to the numbering system of Kabat) was not successful, further attempts to disrupt the N-linked glycosylation motif, NX(S/T) (where X≠P) using a more comprehensive range of substitutions were made. Firstly, further residues were tested in place of the asparagine at position 73. Secondly the substitution T74P (T73P according to the numbering system of Kabat) was tested, since proline in this position is known to prevent N-linked glycosylation. A range of amino acids were also tested in place of S75 (S74 according to the numbering system of Kabat). The constructs tested in attempts to remove this glycosylation site and their impact on antibody expression levels are listed in Table 13.

TABLE 13

| Effect of amino acid substitutions on expression levels | | | |
|---|---|---|---|
| Antibody Designation | Heavy Chain Substitution relative to SEQ ID NO: 42 | Light Chain Substitution relative to SEQ ID NO: 46 | AUC (Protein A HPLC) |
| C320-0 | N/A | N/A | 162 |
| C320-120 | T41P | A23T | 710 |
| mock | N/A | N/A | N/D |
| C320-138 | N73S | A23T | 87 |
| C320-139 | N73K | A23T | 58 |
| C320-140 | N73H | A23T | N/D |
| C320-141 | N73T | A23T | 66 |
| C320-142 | N73Q | A23T | 70 |
| C320-143 | N73G | A23T | N/D |
| C320-144 | N73P | A23T | N/D |
| C320-145 | N73L | A23T | 54 |
| C320-146 | N73Y | A23T | N/D |
| C320-147 | T74P | A23T | 110 |
| C320-148 | S75L | A23T | 115 |
| C320-149 | S75I | A23T | 96 |
| C320-150 | S75A | A23T | 194 |
| C320-151 | S75Y | A23T | 88 |
| C320-152 | S75K | A23T | 115 |
| C320-153 | S75E | A23T | 110 |
| C320-154 | S75F | A23T | 78 |
| C320-155 | S75H | A23T | 118 |

Note:
Substitutions in this table refer to those made into the C320 antibody

The majority of the C320 variants tested exhibited lower levels of expression compared to C320, suggesting that substituting individual amino acids present in the NTS motif, in C320, reduces the expression of the antibody.

A result of earlier attempts to enhance the expression of C320 by grafting the C320 CDRs onto different antibody frameworks was the antibody designated C320-16, which used the frameworks of 1TZG. This antibody expressed well and bound TL1a (Table 7). The frameworks of 1TZG and C320-16 were devoid of the N-linked glycosylation sequence motif, as the RNTSI (SEQ ID NO: 203) at positions 72 through 76 of SEQ ID NO: 42 (71 through 75 according to the numbering system of Kabat) of C320 $V_H$ sequence is replaced by ADRST (SEQ ID NO: 204) in the corresponding $V_H$ sequence of 1TZG.

Variant C320-135 comprising expression enhancing substitutions $V_H$ T41P and $V_L$ A73T was subjected to further heavy chain engineering. C320 $V_H$ sequence RNTSI (SEQ ID NO: 203) at positions 71 through 75 was replaced by ADRST (SEQ ID NO: 204) from the corresponding $V_H$ sequence of 1TZG to produce antibody C320-163. This antibody, now devoid of an N-linked glycosylation site, expressed when transfected into HEK-293E cells and, when purified, was capable of functional inhibition of TL1a mediated apoptosis of TF-1 cells (Table 14).

Improved Variants of C320

The amino acid substitutions identified in previous experiments as conferring advantageous properties over C320 were subsequently combined and the resultant antibodies expressed, purified and assayed for potency. The sequences of these are listed in FIG. 9B (variable heavy) and FIG. 9C (variable light). Comparative potency and expression data of each antibody is listed in Table 14.

TABLE 14

| Effect of amino acid substitutions on expression and TL1a inhibition | | |
|---|---|---|
| Antibody Designation | % expression compared to C320 | Potency TF-1 EC-50 (pM) |
| C320 | 100 | 233 |
| C320-162 | 74 | 1053 |
| C320-163 | 170 | 1160 |
| C320-164 | 299 | 338 |
| C320-165 | 380 | 240 |
| C320-166 | 339 | 793 |
| C320-167 | 344 | 239 |
| C320-168 | 219 | 46 |
| C320-169 | N/A | 477 |
| C320-170 | 232 | 287 |
| C320-171 | 102 | DNI |
| C320-172 | 140 | 269 |
| C320-179 | 161 | 96 |
| C320-183 | 129 | 439 |

* Note:
DNI = did not inhibit

Figure 9D:
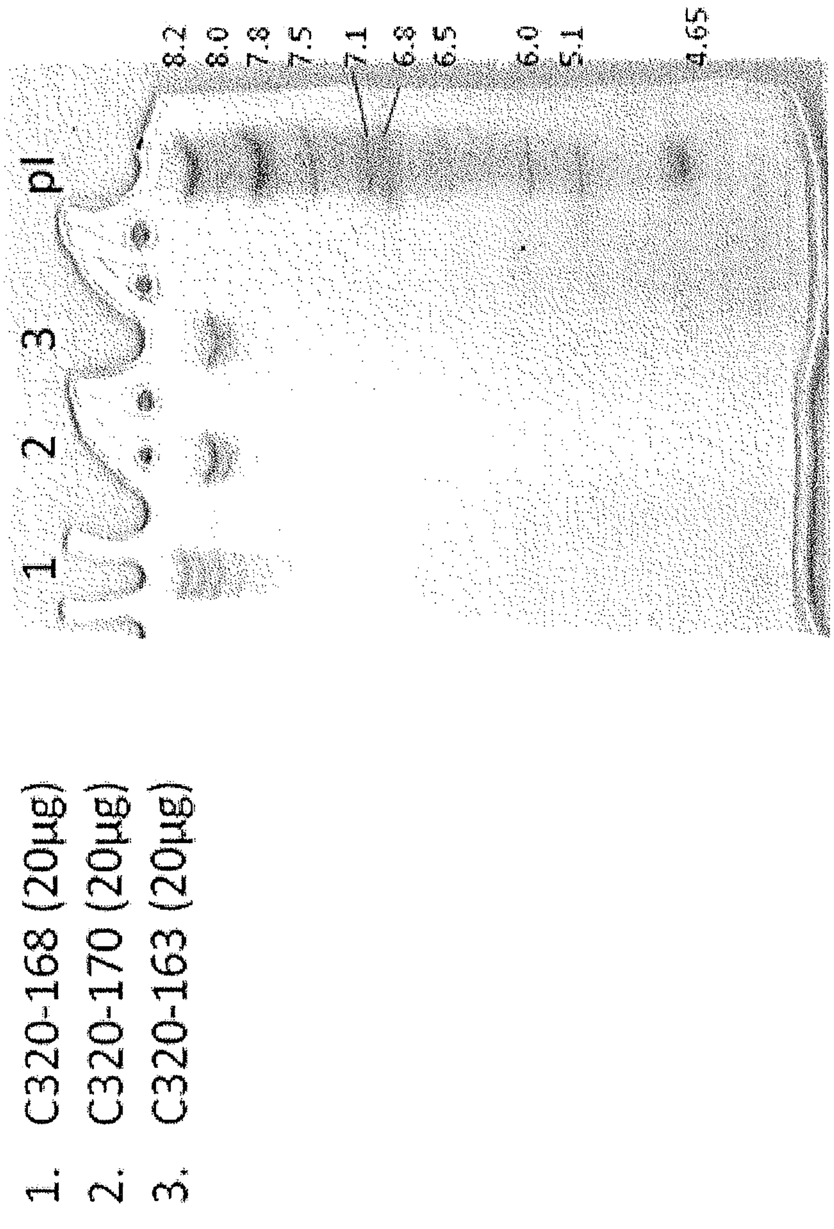
FIG. 9D is a copy of a photographic representation showing results of isoelectric focusing gel comparing C320-168, C320-163 and C320-170. C320-168 has 5-6 distinct charged isoforms compared to 1-2 isoforms visualized for C320-163 and C320-170.

Comparing antibodies C320-168 (containing a N-linked glycan motif) with C320-163 and C320-170 (lacking a N-linked glycan motif) on an isoelectric focusing (IEF) gel demonstrated removal of charge heterogeneity from the antibody profile on removing the N-linked glycosylation site (FIG. 9D). C320-168 has 5 to 6 distinct charged isoforms compared to 1-2 isoforms visualized for C320-163 and C320-170. This reduction in charge heterogeneity is an advantageous property providing improved batch to batch consistency in large scale manufacturing processes (Wang et al., *Journal of Pharmaceutical Sciences* 96:1-26, 2006).

Figure 9E:
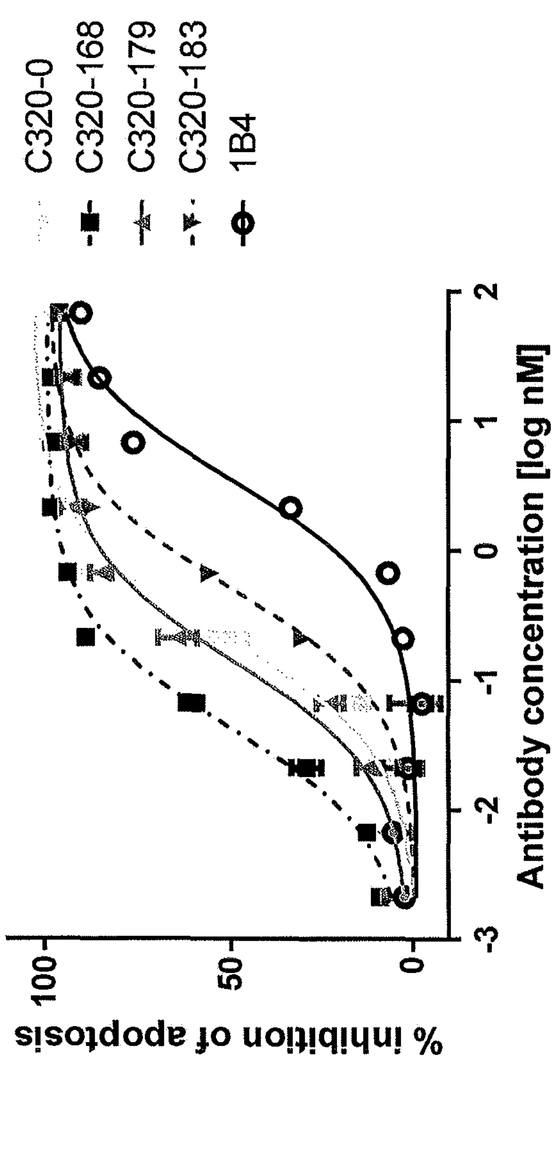
FIG. 9E is a graphical representation showing the ability of antibodies C320-168, C320-179 and C320-183 to neutralize TL1a-induced apoptosis of TF-1 cells at various concentrations (maximum concentration tested 10 μg/mL). Antibodies C320-0 and 1B4 are included for comparison. All antibodies inhibit TL1a-induced apoptosis of TF-1 cells at multiple concentrations.

Of the antibodies tested, two were more potent than the parental C320 antibody—C320-168 and C320-179 (FIG. 9E). Both of these C320 variants include the light chain variable region substitution G24S (G25S according to the numbering system of Kabat) that was found to improve potency in TF-1 assays in combination with the other advantageous amino acids substitutions described previously.

Removal of Predicted MHC Class II Binding Peptides from Antibodies

The amino acid sequence of C320-168 variable heavy and light chain regions were analysed in silico using the software package Epibase™ (LONZA). This software predicts the propensity of peptide sequences present in C320-168 to bind to MHC Class II alleles. Such binding of peptides to MHC Class II alleles is an important step in a host immune response against the administered antibody.

A peptide sequence in the heavy chain of C320-168, GLEWMGWLNPNSGNT (SEQ ID NO: 205), was predicted to strongly bind to DRB1*0401. A peptide sequence in the light chain of C320-168, LLIYGYYNRPSGVPD (SEQ ID NO: 206), was predicted to strongly bind to DRB1*1101, DRB1*1104 and DRB1*1501.

The above listed peptide sequences and modified versions of these peptide sequences were synthesized and incubated with the corresponding MHC Class II protein and an ELISA performed to determine if the peptide formed a complex with the MHC Class II protein. The influenza peptide, PKYVKQNTLKLAT (SEQ ID NO: 207), was used as positive control in these assays to indicated the formation of a peptide:MHC Class II complex. The binding of each peptide to the MHC Class II allele is listed in Table 14.

TABLE 14

| Binding of peptides to MHC Class II | | |
|---|---|---|
| Peptide | MHC Class II Allele | Binding (% of positive control) |
| GLEWMGWLNPNSGNT (SEQ ID NO: 205) | DRB1*0401 | 6 |
| LLIYGYYNRPSGVPD (SEQ ID NO: 206) | DRB1*1501 | 123 |
| LLIEGYYNRPSGVPD (SEQ ID NO: 208) | DRB1*1501 | 41 |
| LLIGGYYNRPSGVPD (SEQ ID NO: 209) | DRB1*1501 | 42 |
| LLIPGYYNRPSGVPD (SEQ ID NO: 210) | DRB1*1501 | 0 |
| LLIKGYYNRPSGVPD (SEQ ID NO: 211) | DRB1*1501 | 74 |
| LLIYGYYNRPSGVPD (SEQ ID NO: 212) | DRB1*1101 | 1 |
| LLIEGYYNRPSGVPD (SEQ ID NO: 213) | DRB1*1101 | 0 |
| LLIGGYYNRPSGVPD (SEQ ID NO: 214) | DRB1*1101 | 0 |
| LLIPGYYNRPSGVPD (SEQ ID NO: 215) | DRB1*1101 | 0 |
| LLIKGYYNRPSGVPD (SEQ ID NO: 216) | DRB1*1101 | 0 |
| LLIYGYYNRPSGVPD (SEQ ID NO: 217) | DRB1*1104 | 1 |
| LLIEGYYNRPSGVPD (SEQ ID NO: 218) | DRB1*1104 | 0 |
| LLIGGYYNRPSGVPD (SEQ ID NO: 219) | DRB1*1104 | 1 |
| LLIPGYYNRPSGVPD (SEQ ID NO: 220) | DRB1*1104 | 0 |
| LLIKGYYNRPSGVPD (SEQ ID NO: 221) | DRB1*1104 | 0 |

Peptides that may be immunologically significant or warrant further investigation as good binders are considered to be those peptides with scores>15% of the positive control. Therefore the peptide GLEWMGWLNPNSGNT (SEQ ID NO: 205) has a low likelihood of being immunogenic and no attempt was made to modify this motif in C320 related antibodies.

The peptide LLIYGYYNRPSGVPD (SEQ ID NO: 206) was shown to form a complex with MHC Class II protein DRB1*1501 (123% binding) but not DRB1*1101 or DRB1*1104. An attempt to reduce the formation of the peptide:MHC Class II complex was made by modifying the tyrosine residue at the fourth position of the peptide (corresponding to position 51 (position 49 according to the numbering system of Kabat) in the C320-168 variable light chain sequence) to one of either glutamic acid, glycine, proline, or lysine. The introduction of a glutamic acid or a glycine residue at this position reduced the complex formation by over 50% (Table 14). Introducing proline at this position prevented complex formation. Antibodies C320-172 and C320-179 incorporated substitution Y51E (Y49E according to the numbering system of Kabat), in their $V_L$ region, whilst C320-183 incorporated the change Y51G (Y49G according to the numbering system of Kabat) in the $V_L$ region. All three antibodies expressed and functionally inhibited TL1a, as illustrated in Table 13. Expression of antibody C320-171 incorporating substitution Y51E (Y49P according to the numbering system of Kabat) was detected, however, this antibody failed to functionally inhibit TL1a, indicating that not all amino acids are tolerated at position 49 in the light chain (Table 13).

Example 8: Generation of High Potency DR3-Selective Antibodies

New antibodies capable of neutralizing TL1a activity with high potency and capable of selective inhibition of TL1a-DR3-mediated activity are generated by focusing on the C320 antibody epitope on TL1a. For example, mutant variable regions and/or individual substitutions showing improved expression and/or TL1a-neutralization (e.g., as described in Example 7) are combined and re-tested to determine if the improvement is additive.

In other approaches antibodies that bind to the epitope bound by C320 are selected by any of a variety of techniques.

8.1 Selection from an Antibody Library Using the C320 Antibody

A phage display protocol is used where a first panning round is conducted using an antigen density (i.e. biotinlyated TL1a) of about 100 pmol and a TEA-based elution step as described previously. The second and third rounds use a reduced antigen density (e.g., about 50 pmol). Phage are eluted by adding the C320 IgG at a 10-fold molar excess and incubating the reactions at room temperature for 2, 5, 10 or 20 mins. The IgG is expected to specifically displace and elute phage expressing FAbs that bound to the C320 epitope. Non-specific binders and phage bound to other regions on the TL1a surface are less likely to elute under these conditions.

The washing regimen comprises six washes with M-PBS for round 1 and 2. For round 3 the washes are three washes with PBST and then three washes with PBS.

Eluted phage are used to infect TG1 *E. coli* for phagemid rescue or generation of colonies for screening as described for other phage display experiments.

8.2 Selection/Production of Antibodies Using Mutant TL1a

Using mutated versions of TL1a as panning reagents for phage display, antibodies that recognize an epitope similar to that of C320 may be obtained. A phage display library may be depleted of antibodies that recognize TL1a with an amino acid substitution of R32A and/or R85A. The library may then be panned against TL1a. The resultant isolated antibodies will likely bind to the residues R32 and/or R85.

Example 9: Affinity Maturation of C320

Antibody C320 is already a potent inhibitor of TL1a activity. However, potency may be enhanced using affinity maturation approaches. Enhanced potency frequently confers dosing and efficacy advantages.

Numerous methods for affinity maturation of antibodies are known in the art. Many of these are based on the general strategy of generating panels or libraries of variant proteins by mutagenesis followed by selection and/or screening for improved affinity. Mutagenesis is often performed at the DNA level, for example by error prone PCR (Thie et al., *Methods Mol. Biol.* 525: 309-322, xv, 2009), by gene shuffling (Kolkman and Stemmer, *Nat. Biotechnol.* 19: 423-428, 2001), by use of mutagenic chemicals or irradiation, by use of 'mutator' strains with error prone replication machinery (Greener et al., In Vitro Mutagenesis Protocols. (Humana press, NJ), 1996) or by somatic hypermutation approaches that harness natural affinity maturation machinery (Peled et al., *Annu. Rev. Immunol.* 26: 481-511, 2008). Mutagenesis is also performed at the RNA level, for example by use of Qβ replicase (Kopsidas et al., *Immunol. Lett.* 107: 163-168, 2006). Library-based methods allowing screening for improved variant proteins are based on various display technologies such as phage, yeast, ribosome, bacterial or mammalian cells, and are known in the art (Benhar, *Expert Opin. Biol. Ther.* 7: 763-779, 2007). Affinity maturation is also achieved by more directed/predictive methods for example by site-directed mutagenesis or gene synthesis guided by findings from 3D protein modeling (see for example U.S. Pat. No. 6,180,370 or 5,225,539).

Affinity maturation using ribosome display (Kopsidas et al., *BMC Biotechnol.* 7: 18, 2007) is performed using RNA encoding the $V_L$ and $V_H$ domains of a C320-related antibody in scFv format. A library of variants of this RNA is generated using Qβ replicase (typically 1 to 3 changes per molecule) and this library is displayed and selected on ribosomes for binding to TL1a. Phenotype-genotype linkage is achieved because the RNA constructs used remain attached to the ribosome translating the functional scFv protein. C320-related scFv-RNA-ribosome complexes are panned against TL1a and isolated. The RNA is converted into DNA and incorporated into a bacterial expression system.

Individual bacteria encoding a single scFv are then isolated and induced to express the scFv. Using a competition ELISA, scFvs with a higher affinity for TL1a than a C320-related ScFv are identified. These scFvs are converted into full length antibodies which are screened in the TF-1 apoptosis assay as described in Example 1.8 to determine improvement in inhibition of TL1a biological activity over C320.

Example 11: Efficacy of Anti-TL1a Antibodies in Animal Models of Colitis

Rodent cross-reactive anti-TL1a antibodies described herein were tested in rodent models of acute colitis induced by intrarectal administration of di- or tri-nitrobenzenesulfonic acid (D/TNBS) or oxazolone, and chronic colitis induced by administration of DSS in drinking water (as described in Wirtz et al., *Nat. Protoc.* 2: 541-546, 2007). DNBS and oxazolone induce localized ulceration and inflammation. DSS administration induces robust generalized inflammation of the intestinal tract characterized by erosive lesions and inflammatory infiltrate. Symptoms of all these models usually include diarrhea, occult blood, weight loss and occasionally rectal prolapse.

In a prophylactic model, antibody treatment was commenced at the start of administration of the colitis-inducing compound. In a therapeutic model, antibody treatment was commenced several days after commencement of induction. The effect of the treatment on weight, stool consistency and occult blood, as well as microscopic effects on epithelial integrity and degree of inflammatory infiltrate was determined. Daily clinical scoring was performed based on stool consistency and presence of occult blood giving a disease activity index (DAI) score.

Figure 10A:
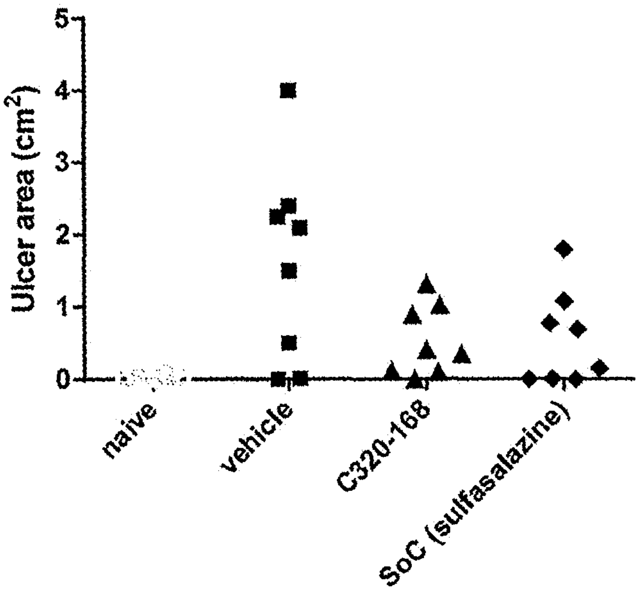
FIG. 10A is a graphical representation showing the total area of colon ulcerated ($cm^2$) in rats in the days following DNBS-induced colitis. Rats were treated with antibody C320-168 (10 mg/kg), vehicle (negative control) days 0 and 4 or sulfasalazine (standard of care compound) daily from day 0 (with results for each treatment group indicated). C320-168 reduced average ulcer area compared to vehicle treated animals to a comparable extent as sulfasalazine.
Figure 10B:
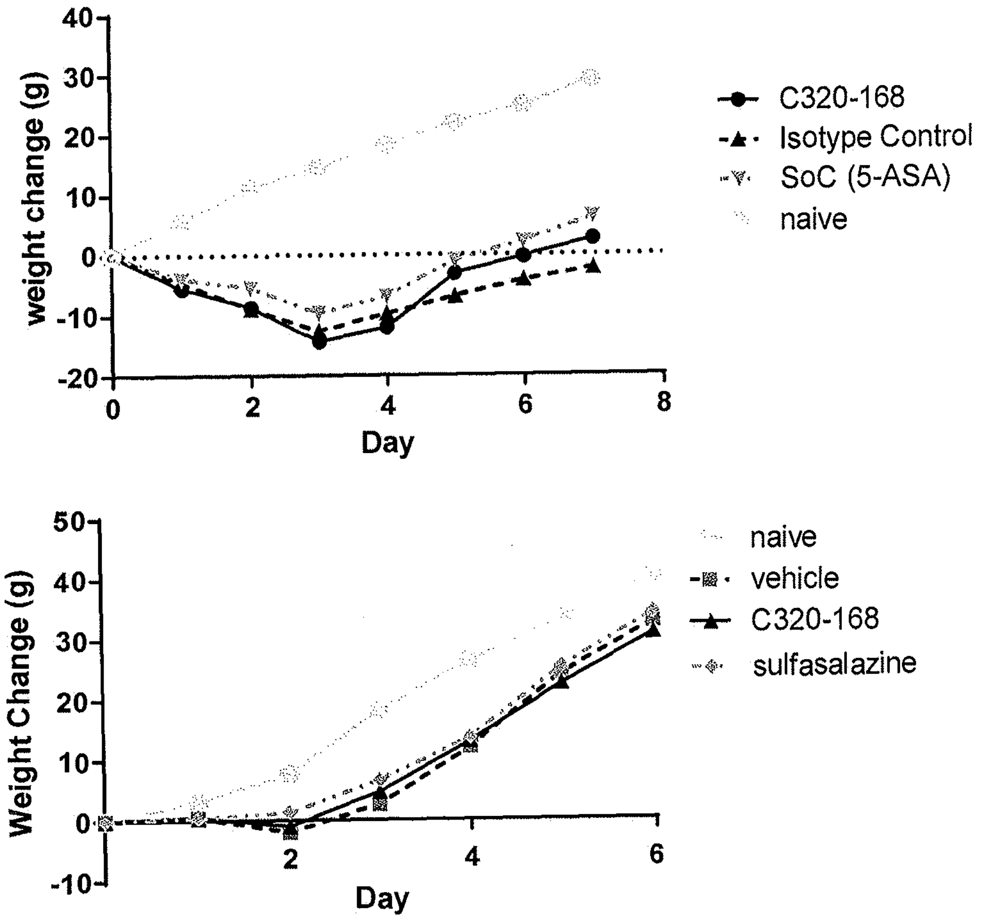
FIG. 10B is a graphical representation showing the weight change (g) in rats in the days following oxazalone-induced colitis. Rats were treated with antibody C320-168 (10 mg/kg) or isotype control (10 mg/kg) on days 0 and 4 or sulfasalazine (SoC (5-ASA); standard of care compound) daily from day 0 (with results for each treatment group indicated.) C320-168 ameliorated weight loss relative to the isotype control antibody to a comparable extent as sulfasalazine.
Figure 10C:
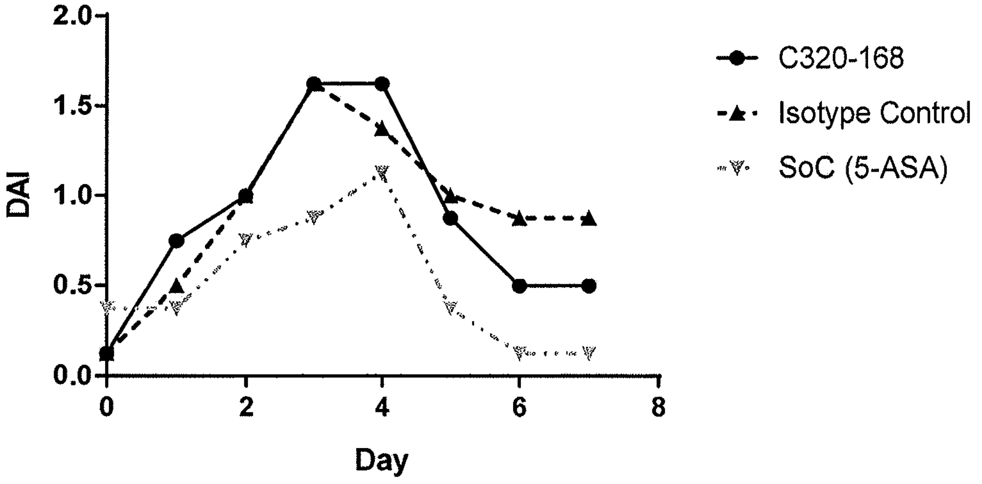
FIG. 10C is a graphical representation showing stool consistency (DAI—Disease Activity Index) in rats in the days following oxazalone-induced colitis. Rats were treated with antibody C320-168 (10 mg/kg) or isotype control (10 mg/kg) on days 0 and 4 or sulfasalazine (SoC (5-ASA); standard of care compound) daily from day 0 (with results for each treatment group indicated). C320-168 improved the clinical signs of disease (stool consistency) relative to the isotype control antibody.
Figure 11A:
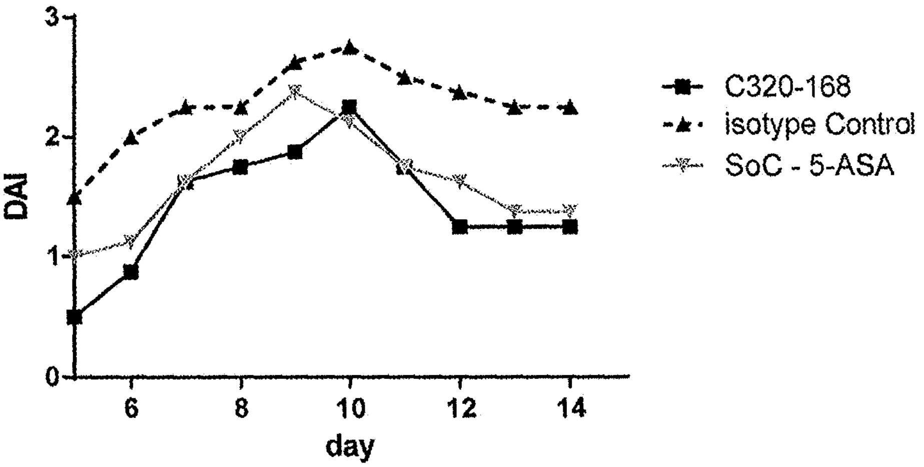
FIG. 11A is a graphical representation showing stool consistency (DAI—Disease Activity Index) in rats in the days following dextran sulphate sodium (DSS)-induced colitis. Rats were treated with antibody C320-168 (10 mg/kg), or isotype control (10 mg/kg) twice weekly from day 4 after disease induction or sulfasalazine (SoC (5-ASA); standard of care compound) daily from day 4 after disease induction (with results for each treatment group indicated). C320-168 improved the clinical signs of disease (stool consistency) relative to the isotype control antibody to a similar extent as sulfasalazine.
Figure 11B:
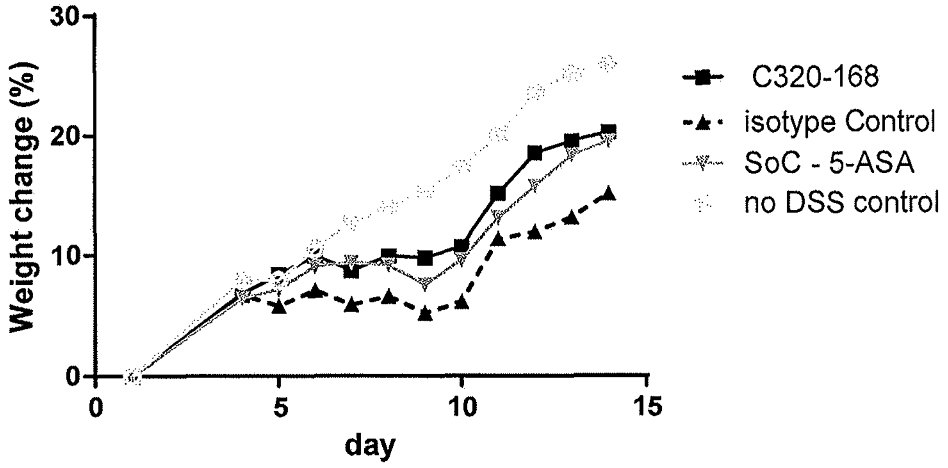
Figure 12:
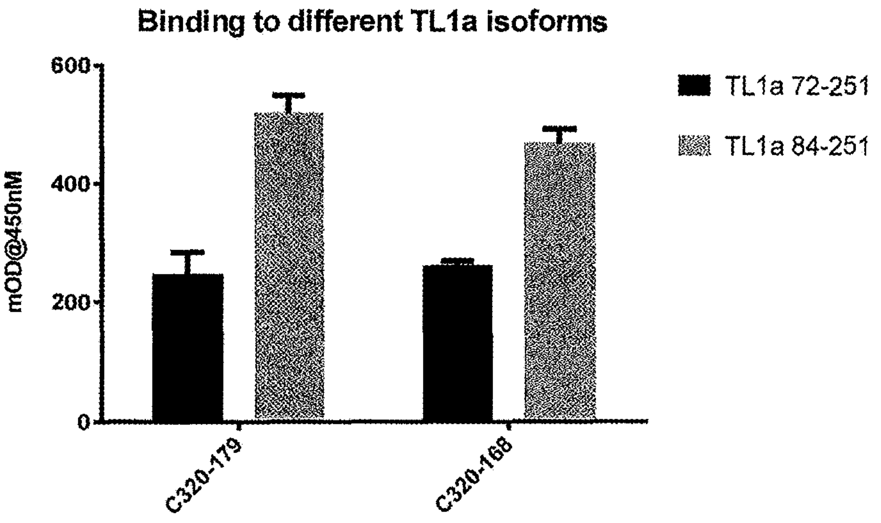

Antibody C320-168 showed comparable efficacy to a standard of care compound when dosed prophylactically in DNBS- or oxazolone-induced colitis (FIGS. 10A-10C), and when dosed therapeutically in DSS-induced colitis (FIGS. 11A and 11B).

Example 12: Efficacy of Anti-TL1a Antibodies in Animal Models of Disease

Antibodies are additionally tested in a rodent model of multiple sclerosis (Racke, *Curr. Protoc. Neurosci.* Chapter 9, Unit 9 7, 2001). In this model either acute or chronic central demyelination is induced by administration of spinal cord homogenate or purified myelin peptides in adjuvant. This administration causes autoimmune destruction of the myelin sheath around the spinal cord neurons leading to lower limb weakness which may develop to paralysis, and is characterized by significant inflammatory infiltrate into the spinal cord. The acute form is monophasic and animals recover spontaneously. The chronic form resembles relapsing-remitting multiple sclerosis and consists of two or more episodes of hind limb weakness/paralysis.

We claim:

1. An antibody or antigen binding domain thereof which specifically binds to TNF-like ligand (TL1a), wherein the antibody or antigen binding domain comprises the HCDR1, HCDR2, HCDR3, LCDR1, LCDR2, and LCDR3 sequences of:

amino acids 31-35 of SEQ ID NO: 186, amino acids 50 to 66 of SEQ ID NO: 186, amino acids 99 to 108 of SEQ ID NO: 186; amino acids 23-36 of SEQ ID NO: 199, amino acids 52 to 58 of SEQ ID NO: 199, and amino acids 91 to 100 of SEQ ID NO: 199, respectively.

2. A composition comprising the antibody or antigen binding domain of claim 1 and a suitable carrier.

3. The antibody or antigen binding domain of claim 1, wherein the antibody or antigen binding domain comprises an IgG1 heavy chain constant domain.

4. The antibody or antigen binding domain of claim 1, wherein the antibody or antigen binding domain comprises a lambda light chain constant domain.

5. The antibody or antigen binding domain of claim 1, wherein the antibody or antigen binding domain comprises a human IgG1 heavy chain constant domain and a human lambda light chain constant domain.

6. A nucleic acid encoding the variable heavy chain and/or the variable light chain of the antibody or antigen binding domain of claim 1.

7. An isolated cell expressing an antibody or antigen binding domain which specifically binds to TNF-like ligand (TL1a), wherein the antibody or antigen binding domain comprises the HCDR1, HCDR2, HCDR3, LCDR1, LCDR2, and LCDR3 sequences of: amino acids 31-35 of SEQ ID NO: 186, amino acids 50 to 66 of SEQ ID NO: 186, amino acids 99 to 108 of SEQ ID NO: 186; amino acids 23-36 of SEQ ID NO: 199, amino acids 52 to 58 of SEQ ID NO: 199, and amino acids 91 to 100 of SEQ ID NO: 199, respectively.

8. A method of producing an antibody or antigen binding domain comprising culturing the isolated cell of claim 7 under conditions sufficient for the antibody or antigen binding domain to be produced.

9. An antibody or antigen binding domain thereof which specifically binds to TL1a, wherein the antibody or antigen binding domain comprises a variable heavy chain and a variable light chain wherein the variable heavy chain and the variable light chain sequences comprise amino acid sequences of:

SEQ ID NOs: 186 and 199, respectively.

10. A composition comprising the antibody or antigen binding domain of claim 9 and a suitable carrier.

11. The antibody or antigen binding domain of claim 9, wherein the antibody or antigen binding domain comprises an IgG1 heavy chain constant domain.

12. The antibody or antigen binding domain of claim 9 wherein the antibody or antigen binding domain comprises a lambda light chain constant domain.

13. The antibody or antigen binding domain of claim 9, wherein the antibody or antigen binding domain comprises a human IgG1 heavy chain constant domain and a human lambda light chain constant domain.

* * * * *

SEQUENCE LISTING

```
<160> NUMBER OF SEQ ID NOS: 235

<210> SEQ ID NO 1
<211> LENGTH: 207
<212> TYPE: PRT
<213> ORGANISM: Homo sapiens

<400> SEQUENCE: 1

Asp Asp Asp Asp Lys Gly Ser His His His His His His His His Gly
1               5                   10                  15

Ser Gly Ser Leu Val Pro Arg Gly Ser Gly Ser Leu Lys Gly Gln Glu
            20                  25                  30

Phe Ala Pro Ser His Gln Gln Val Tyr Ala Pro Leu Arg Ala Asp Gly
        35                  40                  45

Asp Lys Pro Arg Ala His Leu Thr Val Val Arg Gln Thr Pro Thr Gln
    50                  55                  60

His Phe Lys Asn Gln Phe Pro Ala Leu His Trp Glu His Glu Leu Gly
65                  70                  75                  80
```

```
Leu Ala Phe Thr Lys Asn Arg Met Asn Tyr Thr Asn Lys Phe Leu Leu
                85                  90                  95

Ile Pro Glu Ser Gly Asp Tyr Phe Ile Tyr Ser Gln Val Thr Phe Arg
            100                 105                 110

Gly Met Thr Ser Glu Cys Ser Glu Ile Arg Gln Ala Gly Arg Pro Asn
        115                 120                 125

Lys Pro Asp Ser Ile Thr Val Val Ile Thr Lys Val Thr Asp Ser Tyr
    130                 135                 140

Pro Glu Pro Thr Gln Leu Leu Met Gly Thr Lys Ser Val Cys Glu Val
145                 150                 155                 160

Gly Ser Asn Trp Phe Gln Pro Ile Tyr Leu Gly Ala Met Phe Ser Leu
                165                 170                 175

Gln Glu Gly Asp Lys Leu Met Val Asn Val Ser Asp Ile Ser Leu Val
            180                 185                 190

Asp Tyr Thr Lys Glu Asp Lys Thr Phe Phe Gly Ala Phe Leu Leu
        195                 200                 205


<210> SEQ ID NO 2
<211> LENGTH: 117
<212> TYPE: PRT
<213> ORGANISM: Artificial
<220> FEATURE:
<223> OTHER INFORMATION: amino acid sequence of C336 VH

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Gly Gln Thr His Leu Asp Val Trp Gly Gln Gly Thr Thr
            100                 105                 110

Val Thr Val Ser Ser
        115


<210> SEQ ID NO 3
<211> LENGTH: 5
<212> TYPE: PRT
<213> ORGANISM: Artificial
<220> FEATURE:
<223> OTHER INFORMATION: amino acid sequence of C336 HCDR1

<400> SEQUENCE: 3

Gly Tyr Tyr Met His
1               5


<210> SEQ ID NO 4
<211> LENGTH: 17
<212> TYPE: PRT
<213> ORGANISM: Artificial
<220> FEATURE:
<223> OTHER INFORMATION: amino acid sequence of C336 HCDR2
```

<400> SEQUENCE: 4

Trp Ile Asn Pro Asn Ser Gly Gly Thr Asn Tyr Ala Gln Lys Phe Gln
1 5 10 15

Gly

<210> SEQ ID NO 5
<211> LENGTH: 8
<212> TYPE: PRT
<213> ORGANISM: Artificial
<220> FEATURE:
<223> OTHER INFORMATION: amino acid sequence of C336 HCDR3

<400> SEQUENCE: 5

Gly Gly Gln Thr His Leu Asp Val
1 5

<210> SEQ ID NO 6
<211> LENGTH: 108
<212> TYPE: PRT
<213> ORGANISM: Artificial
<220> FEATURE:
<223> OTHER INFORMATION: amino acid sequence of C336 VL

<400> SEQUENCE: 6

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asp Tyr
20 25 30

Leu Asn Trp Tyr Gln Gln Arg Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Tyr Phe Thr Phe Thr Ile Ser Ser Leu Gln Pro
65 70 75 80

Glu Asp Phe Ala Thr Tyr Tyr Cys Gln Gln Tyr Asp Asn Leu Pro Ile
85 90 95

Thr Phe Gly Gln Gly Thr Arg Leu Glu Ile Lys Arg
100 105

<210> SEQ ID NO 7
<211> LENGTH: 11
<212> TYPE: PRT
<213> ORGANISM: Artificial
<220> FEATURE:
<223> OTHER INFORMATION: amino acid sequence of C336 LCDR1

<400> SEQUENCE: 7

Gln Ala Ser Gln Asp Ile Thr Asp Tyr Leu Asn
1 5 10

<210> SEQ ID NO 8
<211> LENGTH: 7
<212> TYPE: PRT
<213> ORGANISM: Artificial
<220> FEATURE:
<223> OTHER INFORMATION: amino acid sequence of C336 LCDR2

<400> SEQUENCE: 8

Asp Ala Ser Asn Leu Glu Thr
1 5

<210> SEQ ID NO 9
<211> LENGTH: 9
<212> TYPE: PRT
<213> ORGANISM: Artificial
<220> FEATURE:
<223> OTHER INFORMATION: amino acid sequence of C336 LCDR3

<400> SEQUENCE: 9

```
Gln Gln Tyr Asp Asn Leu Pro Ile Thr
1               5
```

<210> SEQ ID NO 10
<211> LENGTH: 122
<212> TYPE: PRT
<213> ORGANISM: Artificial
<220> FEATURE:
<223> OTHER INFORMATION: amino acid sequence of C334 VH

<400> SEQUENCE: 10

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn His Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Thr Asn Ser Tyr Ser Ser Ser Trp Tyr Asp Ala Phe Asp Ile Trp
            100                 105                 110

Gly Gln Gly Thr Met Val Thr Val Ser Ser
        115                 120
```

<210> SEQ ID NO 11
<211> LENGTH: 5
<212> TYPE: PRT
<213> ORGANISM: Artificial
<220> FEATURE:
<223> OTHER INFORMATION: amino acid sequence of C334 HCDR1

<400> SEQUENCE: 11

```
Ser Tyr Thr Ile Ser
1               5
```

<210> SEQ ID NO 12
<211> LENGTH: 17
<212> TYPE: PRT
<213> ORGANISM: Artificial
<220> FEATURE:
<223> OTHER INFORMATION: amino acid sequence of C334 HCDR2

<400> SEQUENCE: 12

```
Gly Ile Ile Pro Ile Phe Gly Thr Ala Asn His Ala Gln Ser Phe Gln
1               5                   10                  15

Gly
```

<210> SEQ ID NO 13
<211> LENGTH: 13
<212> TYPE: PRT
<213> ORGANISM: Artificial

```
<220> FEATURE:
<223> OTHER INFORMATION: amino acid sequence of C334 HCDR3

<400> SEQUENCE: 13

Asn Ser Tyr Ser Ser Ser Trp Tyr Asp Ala Phe Asp Ile
1               5                   10


<210> SEQ ID NO 14
<211> LENGTH: 108
<212> TYPE: PRT
<213> ORGANISM: Artificial
<220> FEATURE:
<223> OTHER INFORMATION: amino acid sequence of C334 VL

<400> SEQUENCE: 14

Asp Val Val Met Thr Gln Ser Pro Ala Phe Leu Ser Val Ser Pro Gly
1               5                   10                  15

Glu Arg Ala Thr Leu Ser Cys Arg Ala Ser Gln Ser Ile Ser Asn Asn
            20                  25                  30

Leu Ala Trp Tyr Gln Gln Met Pro Gly Gln Ala Pro Arg Leu Leu Leu
        35                  40                  45

Tyr Asp Ala Ser Thr Arg Ala Thr Asp Ile Pro Ala Arg Phe Ser Gly
    50                  55                  60

Ser Gly Ser Gly Ser Glu Phe Thr Leu Thr Ile Ser Gly Leu Gln Ser
65                  70                  75                  80

Ala Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys Arg
            100                 105


<210> SEQ ID NO 15
<211> LENGTH: 11
<212> TYPE: PRT
<213> ORGANISM: Artificial
<220> FEATURE:
<223> OTHER INFORMATION: amino acid sequence of C334 LCDR1

<400> SEQUENCE: 15

Arg Ala Ser Gln Ser Ile Ser Asn Asn Leu Ala
1               5                   10


<210> SEQ ID NO 16
<211> LENGTH: 7
<212> TYPE: PRT
<213> ORGANISM: Artificial
<220> FEATURE:
<223> OTHER INFORMATION: amino acid sequence of C334 LCDR2

<400> SEQUENCE: 16

Asp Ala Ser Thr Arg Ala Thr
1               5


<210> SEQ ID NO 17
<211> LENGTH: 9
<212> TYPE: PRT
<213> ORGANISM: Artificial
<220> FEATURE:
<223> OTHER INFORMATION: amino acid sequence of C334 LCDR3

<400> SEQUENCE: 17

Gln Gln Tyr Asn Asn Trp Pro Leu Thr
1               5
```

<210> SEQ ID NO 18
<211> LENGTH: 122
<212> TYPE: PRT
<213> ORGANISM: Artificial
<220> FEATURE:
<223> OTHER INFORMATION: amino acid sequence of C333 VH

<400> SEQUENCE: 18

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ser Thr Asn Ser Tyr Ser Ser Ser Trp Tyr Asp Ala Phe Asp Ile Trp
            100                 105                 110

Gly Gln Gly Thr Met Val Thr Val Ser Ser
        115                 120
```

<210> SEQ ID NO 19
<211> LENGTH: 5
<212> TYPE: PRT
<213> ORGANISM: Artificial
<220> FEATURE:
<223> OTHER INFORMATION: amino acid sequence of C333 HCDR1

<400> SEQUENCE: 19

```
Ser Tyr Thr Ile Ser
1               5
```

<210> SEQ ID NO 20
<211> LENGTH: 17
<212> TYPE: PRT
<213> ORGANISM: Artificial
<220> FEATURE:
<223> OTHER INFORMATION: amino acid sequence of C333 HCDR2

<400> SEQUENCE: 20

```
Gly Ile Ile Pro Ile Phe Gly Thr Thr Asn Tyr Ala Gln Arg Phe Gln
1               5                   10                  15

Gly
```

<210> SEQ ID NO 21
<211> LENGTH: 13
<212> TYPE: PRT
<213> ORGANISM: Artificial
<220> FEATURE:
<223> OTHER INFORMATION: amino acid sequence of C333 HCDR3

<400> SEQUENCE: 21

```
Asn Ser Tyr Ser Ser Ser Trp Tyr Asp Ala Phe Asp Ile
1               5                   10
```

<210> SEQ ID NO 22
<211> LENGTH: 108
<212> TYPE: PRT
<213> ORGANISM: Artificial

<220> FEATURE:
<223> OTHER INFORMATION: amino acid sequence of C333 VL

<400> SEQUENCE: 22

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Thr Asn Asn
            20                  25                  30

Leu Ala Trp Tyr Gln Gln Leu Pro Gly Gln Ala Pro Arg Leu Leu Ile
        35                  40                  45

Tyr Asp Ala Ser Thr Arg Ala Thr Asp Ile Pro Ala Arg Phe Ser Gly
    50                  55                  60

Thr Gly Ser Gly Ser Glu Phe Thr Leu Thr Ile Ser Gly Leu Gln Ser
65                  70                  75                  80

Ala Asp Phe Ala Val Tyr Tyr Cys Gln Gln Tyr Asn Asn Trp Pro Leu
                85                  90                  95

Thr Phe Gly Gly Gly Thr Lys Val Asp Ile Lys Arg
            100                 105
```

<210> SEQ ID NO 23
<211> LENGTH: 11
<212> TYPE: PRT
<213> ORGANISM: Artificial
<220> FEATURE:
<223> OTHER INFORMATION: amino acid sequence of C333 LCDR1

<400> SEQUENCE: 23

```
Arg Ala Ser Gln Ser Ile Thr Asn Asn Leu Ala
1               5                   10
```

<210> SEQ ID NO 24
<211> LENGTH: 7
<212> TYPE: PRT
<213> ORGANISM: Artificial
<220> FEATURE:
<223> OTHER INFORMATION: amino acid sequence of C333 LCDR2

<400> SEQUENCE: 24

```
Asp Ala Ser Thr Arg Ala Thr
1               5
```

<210> SEQ ID NO 25
<211> LENGTH: 9
<212> TYPE: PRT
<213> ORGANISM: Artificial
<220> FEATURE:
<223> OTHER INFORMATION: amino acid sequence of C333 LCDR3

<400> SEQUENCE: 25

```
Gln Gln Tyr Asn Asn Trp Pro Leu Thr
1               5
```

<210> SEQ ID NO 26
<211> LENGTH: 122
<212> TYPE: PRT
<213> ORGANISM: Artificial
<220> FEATURE:
<223> OTHER INFORMATION: amino acid sequence of C323 VH

<400> SEQUENCE: 26

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ser Thr Asn Ser Tyr Ser Ser Ser Trp Tyr Asp Ala Phe Asp Ile Trp
            100                 105                 110

Gly Gln Gly Thr Met Val Thr Val Ser Ser
        115                 120


<210> SEQ ID NO 27
<211> LENGTH: 5
<212> TYPE: PRT
<213> ORGANISM: Artificial
<220> FEATURE:
<223> OTHER INFORMATION: amino acid sequence of C323 HCDR1

<400> SEQUENCE: 27

Ser Tyr Thr Ile Ser
1               5


<210> SEQ ID NO 28
<211> LENGTH: 17
<212> TYPE: PRT
<213> ORGANISM: Artificial
<220> FEATURE:
<223> OTHER INFORMATION: amino acid sequence of C323 HCDR2

<400> SEQUENCE: 28

Gly Ile Ile Pro Ile Phe Gly Thr Thr Asn Tyr Ala Gln Arg Phe Gln
1               5                   10                  15

Gly


<210> SEQ ID NO 29
<211> LENGTH: 13
<212> TYPE: PRT
<213> ORGANISM: Artificial
<220> FEATURE:
<223> OTHER INFORMATION: amino acid sequence of C323 HCDR3

<400> SEQUENCE: 29

Asn Ser Tyr Ser Ser Ser Trp Tyr Asp Ala Phe Asp Ile
1               5                   10


<210> SEQ ID NO 30
<211> LENGTH: 108
<212> TYPE: PRT
<213> ORGANISM: Artificial
<220> FEATURE:
<223> OTHER INFORMATION: amino acid sequence of C323 VL

<400> SEQUENCE: 30

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45
```

Tyr Asp Ala Ser Ser Leu Gln Ser Gly Val Pro Ser Arg Tyr Ser Gly
50 55 60

Ser Gly Ser Gly Thr Asp Phe Thr Leu Thr Ile Ser Gly Leu Gln Pro
65 70 75 80

Glu Asp Phe Ala Thr Tyr Tyr Cys Gln Gln Phe Ser Tyr Tyr Pro Leu
85 90 95

Thr Phe Gly Gly Gly Thr Lys Leu Glu Ile Lys Arg
100 105

<210> SEQ ID NO 31
<211> LENGTH: 11
<212> TYPE: PRT
<213> ORGANISM: Artificial
<220> FEATURE:
<223> OTHER INFORMATION: amino acid sequence of C323 LCDR1

<400> SEQUENCE: 31

Arg Ala Ser Gln Gly Ile Gly Ser Ala Leu Ala
1 5 10

<210> SEQ ID NO 32
<211> LENGTH: 7
<212> TYPE: PRT
<213> ORGANISM: Artificial
<220> FEATURE:
<223> OTHER INFORMATION: amino acid sequence of C323 LCDR2

<400> SEQUENCE: 32

Asp Ala Ser Ser Leu Gln Ser
1 5

<210> SEQ ID NO 33
<211> LENGTH: 9
<212> TYPE: PRT
<213> ORGANISM: Artificial
<220> FEATURE:
<223> OTHER INFORMATION: amino acid sequence of C323 LCDR3

<400> SEQUENCE: 33

Gln Gln Phe Ser Tyr Tyr Pro Leu Thr
1 5

<210> SEQ ID NO 34
<211> LENGTH: 122
<212> TYPE: PRT
<213> ORGANISM: Artificial
<220> FEATURE:
<223> OTHER INFORMATION: amino acid sequence of C321 VH

<400> SEQUENCE: 34

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

```
Ala Arg Asp Ser His Ile Tyr Asp Ile Leu Thr Gly Tyr Asp Tyr Trp
            100                 105                 110

Gly Gln Gly Thr Leu Val Thr Val Ser Ser
        115                 120


<210> SEQ ID NO 35
<211> LENGTH: 5
<212> TYPE: PRT
<213> ORGANISM: Artificial
<220> FEATURE:
<223> OTHER INFORMATION: amino acid sequence of C321 HCDR1

<400> SEQUENCE: 35

Ser Tyr Gly Ile Ser
1               5


<210> SEQ ID NO 36
<211> LENGTH: 17
<212> TYPE: PRT
<213> ORGANISM: Artificial
<220> FEATURE:
<223> OTHER INFORMATION: amino acid sequence of C321 HCDR2

<400> SEQUENCE: 36

Trp Ile Ser Ala Tyr Asn Gly Asn Thr Asn Tyr Ala Gln Lys Leu Gln
1               5                   10                  15

Gly


<210> SEQ ID NO 37
<211> LENGTH: 13
<212> TYPE: PRT
<213> ORGANISM: Artificial
<220> FEATURE:
<223> OTHER INFORMATION: amino acid sequence of C321 HCDR3

<400> SEQUENCE: 37

Asp Ser His Ile Tyr Asp Ile Leu Thr Gly Tyr Asp Tyr
1               5                   10


<210> SEQ ID NO 38
<211> LENGTH: 113
<212> TYPE: PRT
<213> ORGANISM: Artificial
<220> FEATURE:
<223> OTHER INFORMATION: amino acid sequence of C321 VL

<400> SEQUENCE: 38

Asp Val Val Met Thr Gln Thr Pro Leu Ser Ser Pro Val Thr Leu Gly
1               5                   10                  15

Gln Pro Ala Ser Ile Ser Cys His Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Thr Gln Phe Pro Gln Thr Phe Gly Gln Gly Thr Lys Val Glu Ile Lys
            100                 105                 110
```

Arg

<210> SEQ ID NO 39
<211> LENGTH: 16
<212> TYPE: PRT
<213> ORGANISM: Artificial
<220> FEATURE:
<223> OTHER INFORMATION: amino acid sequence of C321 LCDR1

<400> SEQUENCE: 39

His Ser Ser Gln Ser Leu Val His Ser Asp Gly Asn Thr Tyr Leu Ser
1 5 10 15

<210> SEQ ID NO 40
<211> LENGTH: 7
<212> TYPE: PRT
<213> ORGANISM: Artificial
<220> FEATURE:
<223> OTHER INFORMATION: amino acid sequence of C321 LCDR2

<400> SEQUENCE: 40

Lys Ile Ser Asn Arg Phe Ser
1 5

<210> SEQ ID NO 41
<211> LENGTH: 9
<212> TYPE: PRT
<213> ORGANISM: Artificial
<220> FEATURE:
<223> OTHER INFORMATION: amino acid sequence of C321 LCDR3

<400> SEQUENCE: 41

Met Gln Asp Thr Gln Phe Pro Gln Thr
1 5

<210> SEQ ID NO 42
<211> LENGTH: 119
<212> TYPE: PRT
<213> ORGANISM: Artificial
<220> FEATURE:
<223> OTHER INFORMATION: amino acid sequence of C320 VH

<400> SEQUENCE: 42

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Thr Gly Gln Gly Leu Glu Trp Met
35 40 45

Gly Trp Met Asn Pro Asn Ser Gly Asn Thr Gly Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Asp Thr Ala Ser Phe Glu Tyr Trp Gly Gln Gly
100 105 110

Thr Leu Val Thr Val Ser Ser
115

<210> SEQ ID NO 43
<211> LENGTH: 5
<212> TYPE: PRT

<213> ORGANISM: Artificial
<220> FEATURE:
<223> OTHER INFORMATION: amino acid sequence of C320 HCDR1

<400> SEQUENCE: 43

Ser Tyr Asp Ile Asn
1 5

<210> SEQ ID NO 44
<211> LENGTH: 17
<212> TYPE: PRT
<213> ORGANISM: Artificial
<220> FEATURE:
<223> OTHER INFORMATION: amino acid sequence of C320 HCDR2

<400> SEQUENCE: 44

Trp Met Asn Pro Asn Ser Gly Asn Thr Gly Tyr Ala Gln Lys Phe Gln
1 5 10 15

Gly

<210> SEQ ID NO 45
<211> LENGTH: 10
<212> TYPE: PRT
<213> ORGANISM: Artificial
<220> FEATURE:
<223> OTHER INFORMATION: amino acid sequence of C320 HCDR3

<400> SEQUENCE: 45

Glu Val Pro Asp Thr Ala Ser Phe Glu Tyr
1 5 10

<210> SEQ ID NO 46
<211> LENGTH: 111
<212> TYPE: PRT
<213> ORGANISM: Artificial
<220> FEATURE:
<223> OTHER INFORMATION: amino acid sequence of C320 VL

<400> SEQUENCE: 46

Gln Ser Val Leu Thr Gln Pro Pro Ser Val Ser Gly Ala Pro Gly Gln
1 5 10 15

Arg Val Thr Ile Ser Cys Ala Gly Ser Ser Ser Asp Ile Gly Ala Gly
20 25 30

Leu Gly Val His Trp Tyr Gln Gln Leu Pro Gly Thr Ala Pro Lys Leu
35 40 45

Leu Ile Tyr Gly Tyr Tyr Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Leu Pro Glu Asp Glu Gly Asp Tyr Tyr Cys Gln Ser Tyr Asp Gly Thr
85 90 95

Leu Ser Ala Leu Phe Gly Gly Gly Thr Lys Leu Thr Val Leu Gly
100 105 110

<210> SEQ ID NO 47
<211> LENGTH: 14
<212> TYPE: PRT
<213> ORGANISM: Artificial
<220> FEATURE:
<223> OTHER INFORMATION: amino acid sequence of C320 LCDR1

<400> SEQUENCE: 47

Ala Gly Ser Ser Ser Asp Ile Gly Ala Gly Leu Gly Val His

```
1               5                   10


<210> SEQ ID NO 48
<211> LENGTH: 7
<212> TYPE: PRT
<213> ORGANISM: Artificial
<220> FEATURE:
<223> OTHER INFORMATION: amino acid sequence of C320 LCDR2

<400> SEQUENCE: 48

Gly Tyr Tyr Asn Arg Pro Ser
1               5


<210> SEQ ID NO 49
<211> LENGTH: 10
<212> TYPE: PRT
<213> ORGANISM: Artificial
<220> FEATURE:
<223> OTHER INFORMATION: amino acid sequence of C320 LCDR3

<400> SEQUENCE: 49

Gln Ser Tyr Asp Gly Thr Leu Ser Ala Leu
1               5                   10


<210> SEQ ID NO 50
<211> LENGTH: 123
<212> TYPE: PRT
<213> ORGANISM: Artificial
<220> FEATURE:
<223> OTHER INFORMATION: amino acid sequence of C319 VH

<400> SEQUENCE: 50

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Arg
            20                  25                  30

Asn Trp Trp Ser Trp Val Arg Gln Ser Pro Gly Lys Gly Leu Glu Trp
        35                  40                  45

Ile Gly Glu Ile Tyr His Ser Asp Ile Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Lys Asp Gly Glu Ala Gly Gly Thr Tyr Ile Asp Ala Phe Asp Val
            100                 105                 110

Trp Gly Gln Gly Thr Met Val Thr Val Ser Ser
        115                 120


<210> SEQ ID NO 51
<211> LENGTH: 6
<212> TYPE: PRT
<213> ORGANISM: Artificial
<220> FEATURE:
<223> OTHER INFORMATION: amino acid sequence of C319 HCDR1

<400> SEQUENCE: 51

Ser Arg Asn Trp Trp Ser
1               5


<210> SEQ ID NO 52
<211> LENGTH: 16
<212> TYPE: PRT
```

```
<213> ORGANISM: Artificial
<220> FEATURE:
<223> OTHER INFORMATION: amino acid sequence of C319 HCDR2

<400> SEQUENCE: 52

Glu Ile Tyr His Ser Asp Ile Thr Asn Tyr Asn Pro Ser Leu Lys Ser
1               5                   10                  15


<210> SEQ ID NO 53
<211> LENGTH: 14
<212> TYPE: PRT
<213> ORGANISM: Artificial
<220> FEATURE:
<223> OTHER INFORMATION: amino acid sequence of C319 HCDR3

<400> SEQUENCE: 53

Asp Gly Glu Ala Gly Gly Thr Tyr Ile Asp Ala Phe Asp Val
1               5                   10


<210> SEQ ID NO 54
<211> LENGTH: 111
<212> TYPE: PRT
<213> ORGANISM: Artificial
<220> FEATURE:
<223> OTHER INFORMATION: amino acid sequence of C319 VL

<400> SEQUENCE: 54

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ile Tyr
            20                  25                  30

Asn Tyr Val Ser Trp Tyr Gln Gln His Pro Gly Lys Ala Pro Lys Leu
        35                  40                  45

Ile Ile Tyr Asp Val Ser Glu Arg Pro Ser Gly Val Pro Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Tyr Ser Tyr Ala Gly Thr
                85                  90                  95

Tyr Thr Ser Leu Phe Gly Gly Gly Thr Lys Val Thr Val Leu Gly
            100                 105                 110


<210> SEQ ID NO 55
<211> LENGTH: 14
<212> TYPE: PRT
<213> ORGANISM: Artificial
<220> FEATURE:
<223> OTHER INFORMATION: amino acid sequence of C319 LCDR1

<400> SEQUENCE: 55

Thr Gly Thr Ser Ser Asp Val Gly Ile Tyr Asn Tyr Val Ser
1               5                   10


<210> SEQ ID NO 56
<211> LENGTH: 7
<212> TYPE: PRT
<213> ORGANISM: Artificial
<220> FEATURE:
<223> OTHER INFORMATION: amino acid sequence of C319 LCDR2

<400> SEQUENCE: 56

Asp Val Ser Glu Arg Pro Ser
1               5
```

<210> SEQ ID NO 57
<211> LENGTH: 10
<212> TYPE: PRT
<213> ORGANISM: Artificial
<220> FEATURE:
<223> OTHER INFORMATION: amino acid sequence of C319 LCDR3

<400> SEQUENCE: 57

Tyr Ser Tyr Ala Gly Thr Tyr Thr Ser Leu
1 5 10

<210> SEQ ID NO 58
<211> LENGTH: 119
<212> TYPE: PRT
<213> ORGANISM: artificial
<220> FEATURE:
<223> OTHER INFORMATION: amino acid sequence of C320-3 VH

<400> SEQUENCE: 58

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Pro Gly Gln Gly Leu Glu Trp Met
35 40 45

Gly Trp Met Asn Pro Asn Ser Gly Asn Thr Gly Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Asp Thr Ala Ser Phe Glu Tyr Trp Gly Gln Gly
100 105 110

Thr Leu Val Thr Val Ser Ser
115

<210> SEQ ID NO 59
<211> LENGTH: 5
<212> TYPE: PRT
<213> ORGANISM: artificial
<220> FEATURE:
<223> OTHER INFORMATION: amino acid sequence of C320-3 HCDR1

<400> SEQUENCE: 59

Ser Tyr Asp Ile Asn
1 5

<210> SEQ ID NO 60
<211> LENGTH: 17
<212> TYPE: PRT
<213> ORGANISM: artificial
<220> FEATURE:
<223> OTHER INFORMATION: amino acid sequence of C320-3 HCDR2

<400> SEQUENCE: 60

Trp Met Asn Pro Asn Ser Gly Asn Thr Gly Tyr Ala Gln Lys Phe Gln
1 5 10 15

Gly

<210> SEQ ID NO 61
<211> LENGTH: 10
<212> TYPE: PRT

<213> ORGANISM: artificial
<220> FEATURE:
<223> OTHER INFORMATION: amino acid sequence of C320-3 HCDR3

<400> SEQUENCE: 61

Glu Val Pro Asp Thr Ala Ser Phe Glu Tyr
1 5 10

<210> SEQ ID NO 62
<211> LENGTH: 111
<212> TYPE: PRT
<213> ORGANISM: artificial
<220> FEATURE:
<223> OTHER INFORMATION: amino acid sequence of C320-5 VL

<400> SEQUENCE: 62

Gln Ser Val Leu Thr Gln Pro Pro Ser Val Ser Gly Ala Pro Gly Gln
1 5 10 15

Arg Val Thr Ile Ser Cys Ala Gly Ser Ser Ser Asp Ile Gly Ala Gly
20 25 30

Leu Gly Val His Trp Tyr Gln Gln Leu Pro Gly Thr Ala Pro Lys Leu
35 40 45

Leu Ile Tyr Gly Tyr Tyr Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Leu Pro Glu Asp Glu Gly Asp Tyr Tyr Cys Gln Ser Tyr Asp Gly Thr
85 90 95

Leu Ser Ala Leu Phe Gly Gly Gly Thr Lys Leu Thr Val Leu Gly
100 105 110

<210> SEQ ID NO 63
<211> LENGTH: 14
<212> TYPE: PRT
<213> ORGANISM: artificial
<220> FEATURE:
<223> OTHER INFORMATION: amino acid sequence of C320-5 LCDR1

<400> SEQUENCE: 63

Ala Gly Ser Ser Ser Asp Ile Gly Ala Gly Leu Gly Val His
1 5 10

<210> SEQ ID NO 64
<211> LENGTH: 7
<212> TYPE: PRT
<213> ORGANISM: artificial
<220> FEATURE:
<223> OTHER INFORMATION: amino acid sequence of C320-5 LCDR2

<400> SEQUENCE: 64

Gly Tyr Tyr Asn Arg Pro Ser
1 5

<210> SEQ ID NO 65
<211> LENGTH: 10
<212> TYPE: PRT
<213> ORGANISM: artificial
<220> FEATURE:
<223> OTHER INFORMATION: amino acid sequence of C320-5 LCDR3

<400> SEQUENCE: 65

Gln Ser Tyr Asp Gly Thr Leu Ser Ala Leu
1 5 10

<210> SEQ ID NO 66
<211> LENGTH: 119
<212> TYPE: PRT
<213> ORGANISM: artificial
<220> FEATURE:
<223> OTHER INFORMATION: amino acid sequence of C320-90 VH

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Asp Ala Ser Phe Glu Tyr Trp Gly Gln Gly
            100                 105                 110

Thr Leu Val Thr Val Ser Ser
        115
```

<210> SEQ ID NO 67
<211> LENGTH: 5
<212> TYPE: PRT
<213> ORGANISM: artificial
<220> FEATURE:
<223> OTHER INFORMATION: amino acid sequence of C320-90 HCDR1

<400> SEQUENCE: 67

```
Ser Tyr Asp Ile Asn
1               5
```

<210> SEQ ID NO 68
<211> LENGTH: 17
<212> TYPE: PRT
<213> ORGANISM: artificial
<220> FEATURE:
<223> OTHER INFORMATION: amino acid sequence of C320-90 HCDR2

<400> SEQUENCE: 68

```
Trp Met Asn Pro Asn Ser Gly Asn Thr Gly Tyr Ala Gln Lys Phe Gln
1               5                   10                  15

Gly
```

<210> SEQ ID NO 69
<211> LENGTH: 10
<212> TYPE: PRT
<213> ORGANISM: artificial
<220> FEATURE:
<223> OTHER INFORMATION: amino acid sequence of C320-90 HCDR3

<400> SEQUENCE: 69

```
Glu Val Pro Asp Asp Ala Ser Phe Glu Tyr
1               5                   10
```

<210> SEQ ID NO 70
<211> LENGTH: 119
<212> TYPE: PRT

<213> ORGANISM: artificial
<220> FEATURE:
<223> OTHER INFORMATION: amino acid sequence of C320-103 VH

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ala Phe Glu Tyr Trp Gly Gln Gly
            100                 105                 110

Thr Leu Val Thr Val Ser Ser
        115
```

<210> SEQ ID NO 71
<211> LENGTH: 5
<212> TYPE: PRT
<213> ORGANISM: artificial
<220> FEATURE:
<223> OTHER INFORMATION: amino acid sequence of C320-103 HCDR1

<400> SEQUENCE: 71

```
Ser Tyr Asp Ile Asn
1               5
```

<210> SEQ ID NO 72
<211> LENGTH: 17
<212> TYPE: PRT
<213> ORGANISM: artificial
<220> FEATURE:
<223> OTHER INFORMATION: amino acid sequence of C320-103 HCDR2

<400> SEQUENCE: 72

```
Trp Met Asn Pro Asn Ser Gly Asn Thr Gly Tyr Ala Gln Lys Phe Gln
1               5                   10                  15

Gly
```

<210> SEQ ID NO 73
<211> LENGTH: 10
<212> TYPE: PRT
<213> ORGANISM: artificial
<220> FEATURE:
<223> OTHER INFORMATION: amino acid sequence of C320-103 HCDR3

<400> SEQUENCE: 73

```
Glu Val Pro Asp Thr Ala Ala Phe Glu Tyr
1               5                   10
```

<210> SEQ ID NO 74
<211> LENGTH: 119
<212> TYPE: PRT
<213> ORGANISM: artificial
<220> FEATURE:
<223> OTHER INFORMATION: amino acid sequence of C320-114 VH

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Leu Tyr Trp Gly Gln Gly
            100                 105                 110

Thr Leu Val Thr Val Ser Ser
        115

<210> SEQ ID NO 75
<211> LENGTH: 5
<212> TYPE: PRT
<213> ORGANISM: artificial
<220> FEATURE:
<223> OTHER INFORMATION: amino acid sequence of C320-114 HCDR1

<400> SEQUENCE: 75

Ser Tyr Asp Ile Asn
1               5

<210> SEQ ID NO 76
<211> LENGTH: 17
<212> TYPE: PRT
<213> ORGANISM: artificial
<220> FEATURE:
<223> OTHER INFORMATION: amino acid sequence of C320-114 HCDR2

<400> SEQUENCE: 76

Trp Met Asn Pro Asn Ser Gly Asn Thr Gly Tyr Ala Gln Lys Phe Gln
1               5                   10                  15

Gly

<210> SEQ ID NO 77
<211> LENGTH: 10
<212> TYPE: PRT
<213> ORGANISM: artificial
<220> FEATURE:
<223> OTHER INFORMATION: amino acid sequence of C320-114 HCDR3

<400> SEQUENCE: 77

Glu Val Pro Asp Thr Ala Ser Phe Leu Tyr
1               5                   10

<210> SEQ ID NO 78
<211> LENGTH: 119
<212> TYPE: PRT
<213> ORGANISM: artificial
<220> FEATURE:
<223> OTHER INFORMATION: amino acid sequence of C320-115 VH

<400> SEQUENCE: 78

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Asp Tyr Trp Gly Gln Gly
            100                 105                 110

Thr Leu Val Thr Val Ser Ser
        115


<210> SEQ ID NO 79
<211> LENGTH: 5
<212> TYPE: PRT
<213> ORGANISM: artificial
<220> FEATURE:
<223> OTHER INFORMATION: amino acid sequence of C320-115 HCDR1

<400> SEQUENCE: 79

Ser Tyr Asp Ile Asn
1               5


<210> SEQ ID NO 80
<211> LENGTH: 17
<212> TYPE: PRT
<213> ORGANISM: artificial
<220> FEATURE:
<223> OTHER INFORMATION: amino acid sequence of C320-115 HCDR2

<400> SEQUENCE: 80

Trp Met Asn Pro Asn Ser Gly Asn Thr Gly Tyr Ala Gln Lys Phe Gln
1               5                   10                  15

Gly


<210> SEQ ID NO 81
<211> LENGTH: 10
<212> TYPE: PRT
<213> ORGANISM: artificial
<220> FEATURE:
<223> OTHER INFORMATION: amino acid sequence of C320-115 HCDR3

<400> SEQUENCE: 81

Glu Val Pro Asp Thr Ala Ser Phe Asp Tyr
1               5                   10


<210> SEQ ID NO 82
<211> LENGTH: 111
<212> TYPE: PRT
<213> ORGANISM: artificial
<220> FEATURE:
<223> OTHER INFORMATION: amino acid sequence of C320-120 VL

<400> SEQUENCE: 82

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
            20                  25                  30
```

-continued

```
Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 83
<211> LENGTH: 14
<212> TYPE: PRT
<213> ORGANISM: artificial
<220> FEATURE:
<223> OTHER INFORMATION: amino acid sequence of C320-120 LCDR1

<400> SEQUENCE: 83

Thr Gly Ser Ser Ser Asp Ile Gly Ala Gly Leu Gly Val His
1               5                   10


<210> SEQ ID NO 84
<211> LENGTH: 7
<212> TYPE: PRT
<213> ORGANISM: artificial
<220> FEATURE:
<223> OTHER INFORMATION: amino acid sequence of C320-120 LCDR2

<400> SEQUENCE: 84

Gly Tyr Tyr Asn Arg Pro Ser
1               5


<210> SEQ ID NO 85
<211> LENGTH: 10
<212> TYPE: PRT
<213> ORGANISM: artificial
<220> FEATURE:
<223> OTHER INFORMATION: amino acid sequence of C320-120 LCDR3

<400> SEQUENCE: 85

Gln Ser Tyr Asp Gly Thr Leu Ser Ala Leu
1               5                   10


<210> SEQ ID NO 86
<211> LENGTH: 119
<212> TYPE: PRT
<213> ORGANISM: artificial
<220> FEATURE:
<223> OTHER INFORMATION: amino acid sequence of C320-129 VH

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 87
<211> LENGTH: 5
<212> TYPE: PRT
<213> ORGANISM: artificial
<220> FEATURE:
<223> OTHER INFORMATION: amino acid sequence of C320-129 HCDR1

<400> SEQUENCE: 87

Ser Tyr Asp Ile Asn
1               5


<210> SEQ ID NO 88
<211> LENGTH: 17
<212> TYPE: PRT
<213> ORGANISM: artificial
<220> FEATURE:
<223> OTHER INFORMATION: amino acid sequence of C320-129 HCDR2

<400> SEQUENCE: 88

Trp Met Asn Pro Asn Ser Gly Asn Thr Gly Tyr Ala Gln Lys Phe Gln
1               5                   10                  15

Gly


<210> SEQ ID NO 89
<211> LENGTH: 10
<212> TYPE: PRT
<213> ORGANISM: artificial
<220> FEATURE:
<223> OTHER INFORMATION: amino acid sequence of C320-129 HCDR3

<400> SEQUENCE: 89

Glu Val Pro Glu Thr Ala Ser Phe Glu Tyr
1               5                   10


<210> SEQ ID NO 90
<211> LENGTH: 119
<212> TYPE: PRT
<213> ORGANISM: artificial
<220> FEATURE:
<223> OTHER INFORMATION: amino acid sequence of C320-130 VH

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
```

```
            100                 105                 110

Thr Leu Val Thr Val Ser Ser
        115


<210> SEQ ID NO 91
<211> LENGTH: 5
<212> TYPE: PRT
<213> ORGANISM: artificial
<220> FEATURE:
<223> OTHER INFORMATION: amino acid sequence of C320-130 HCDR1

<400> SEQUENCE: 91

Ser Tyr Asp Ile Asn
1               5


<210> SEQ ID NO 92
<211> LENGTH: 17
<212> TYPE: PRT
<213> ORGANISM: Artificial
<220> FEATURE:
<223> OTHER INFORMATION: amino acid sequence of C320-130 HCDR2

<400> SEQUENCE: 92

Trp Leu Asn Pro Asn Ser Gly Asn Thr Gly Tyr Ala Gln Lys Phe Gln
1               5                   10                  15

Gly


<210> SEQ ID NO 93
<211> LENGTH: 10
<212> TYPE: PRT
<213> ORGANISM: artificial
<220> FEATURE:
<223> OTHER INFORMATION: amino acid sequence of C320-130 HCDR3

<400> SEQUENCE: 93

Glu Val Pro Asp Thr Ala Ser Phe Glu Tyr
1               5                   10


<210> SEQ ID NO 94
<211> LENGTH: 119
<212> TYPE: PRT
<213> ORGANISM: artificial
<220> FEATURE:
<223> OTHER INFORMATION: amino acid sequence of VH consensus sequence
      of C320 and derivatives
<220> FEATURE:
<221> NAME/KEY: VARIANT
<222> LOCATION: (41)..(41)
<223> OTHER INFORMATION: X=T or P
<220> FEATURE:
<221> NAME/KEY: VARIANT
<222> LOCATION: (51)..(51)
<223> OTHER INFORMATION: X=M or L
<220> FEATURE:
<221> NAME/KEY: VARIANT
<222> LOCATION: (102)..(102)
<223> OTHER INFORMATION: X=E or D
<220> FEATURE:
<221> NAME/KEY: VARIANT
<222> LOCATION: (103)..(103)
<223> OTHER INFORMATION: X=T or D
<220> FEATURE:
<221> NAME/KEY: VARIANT
<222> LOCATION: (105)..(105)
<223> OTHER INFORMATION: X=S or A
<220> FEATURE:
<221> NAME/KEY: VARIANT
<222> LOCATION: (107)..(107)
<223> OTHER INFORMATION: X=L or D or E
```

<400> SEQUENCE: 94

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Xaa Gly Gln Gly Leu Glu Trp Met
35 40 45

Gly Trp Xaa Asn Pro Asn Ser Gly Asn Thr Gly Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Xaa Xaa Ala Xaa Phe Xaa Tyr Trp Gly Gln Gly
100 105 110

Thr Leu Val Thr Val Ser Ser
115

<210> SEQ ID NO 95
<211> LENGTH: 111
<212> TYPE: PRT
<213> ORGANISM: artificial
<220> FEATURE:
<223> OTHER INFORMATION: amino acid sequence of VL consensus sequence of C320 and derivatives
<220> FEATURE:
<221> NAME/KEY: VARIANT
<222> LOCATION: (23)..(23)
<223> OTHER INFORMATION: X=A or T
<220> FEATURE:
<221> NAME/KEY: VARIANT
<222> LOCATION: (76)..(76)
<223> OTHER INFORMATION: X=A or T

<400> SEQUENCE: 95

Gln Ser Val Leu Thr Gln Pro Pro Ser Val Ser Gly Ala Pro Gly Gln
1 5 10 15

Arg Val Thr Ile Ser Cys Xaa Gly Ser Ser Ser Asp Ile Gly Ala Gly
20 25 30

Leu Gly Val His Trp Tyr Gln Gln Leu Pro Gly Thr Ala Pro Lys Leu
35 40 45

Leu Ile Tyr Gly Tyr Tyr Asn Arg Pro Ser Gly Val Pro Asp Arg Phe
50 55 60

Ser Gly Ser Lys Ser Gly Thr Ser Ala Ser Leu Xaa Ile Thr Gly Leu
65 70 75 80

Leu Pro Glu Asp Glu Gly Asp Tyr Tyr Cys Gln Ser Tyr Asp Gly Thr
85 90 95

Leu Ser Ala Leu Phe Gly Gly Gly Thr Lys Leu Thr Val Leu Gly
100 105 110

<210> SEQ ID NO 96
<211> LENGTH: 351
<212> TYPE: DNA
<213> ORGANISM: Artificial
<220> FEATURE:
<223> OTHER INFORMATION: nucleotide sequence encoding VH of C336

<400> SEQUENCE: 96
gaggtccagc tggtacagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagtgggggc 300
cagacccacc tggacgtctg ggccaagggg accacggtca ccgtctcctc a 351

<210> SEQ ID NO 97
<211> LENGTH: 324
<212> TYPE: DNA
<213> ORGANISM: Artificial
<220> FEATURE:
<223> OTHER INFORMATION: nucleotide sequence encoding VL of C336

<400> SEQUENCE: 97
gacatccaga tgacccagtc tccatcctcc ctgtctgcat ctgtgggaga cagagtcacc 60
atcacttgcc aggcgagtca ggacattacc gactatttaa attggtatca gcagagacca 120
gggaaagccc ctaagctcct gatctacgat gcatccaatt tggaaacagg ggttccatca 180
aggttcagtg gaagtggatc tgggacatat tttactttca ccatcagcag cctgcagcct 240
gaagattttg cgacatatta ctgtcaacag tatgataatc tcccgatcac cttcggccag 300
gggacacgac tggagattaa acgt 324

<210> SEQ ID NO 98
<211> LENGTH: 366
<212> TYPE: DNA
<213> ORGANISM: Artificial
<220> FEATURE:
<223> OTHER INFORMATION: nucleotide sequence encoding VH of C334

<400> SEQUENCE: 98
caaatgcagc tggtgcagtc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaggg atcatcccta tctttggtac agcaaaccac 180
gcacagagct tccagggcag agtcacgatt accgcggacg aatccacgag cacagcctac 240
atggagctga gcagcctgag atctgaggac acggccgtat attattgttc aaccaactcg 300
tatagcagca gctggtatga tgcttttgat atctggggcc aagggacaat ggtcaccgtc 360
tcttca 366

<210> SEQ ID NO 99
<211> LENGTH: 324
<212> TYPE: DNA
<213> ORGANISM: Artificial
<220> FEATURE:
<223> OTHER INFORMATION: nucleotide sequence encoding VL of C334

<400> SEQUENCE: 99
gatgttgtga tgacacagtc tccagctttc ctctctgtgt ctcctgggga aagagccacc 60
ctctcctgca gggccagtca gagtattagc aacaacttag cctggtatca gcaaatgcct 120
ggccaggctc ccaggctcct tctttatgat gcatccacca gggccactga tatcccagcc 180
aggttcagtg gcagtgggtc tgggtcagag ttcactctca ccatcagcgg cctgcagtct 240
gcagattttg cagtttatta ctgtcaacaa tacaataact ggcctctcac tttcggcgga 300
gggaccaagc tggagatcaa acgt 324

<210> SEQ ID NO 100

<211> LENGTH: 366
<212> TYPE: DNA
<213> ORGANISM: Artificial
<220> FEATURE:
<223> OTHER INFORMATION: nucleotide sequence encoding VH of C333

<400> SEQUENCE: 100
caggtccagc ttgtgcagtc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaggg atcatcccta tctttggtac aacaaactac 180
gcacagaggt tccagggcag agtcacgatt accgcggacg aatccacgag cacagcctac 240
atggagctga gcagcctgag atctgaggac acggccatat attactgttc aaccaactcc 300
tatagcagca gctggtatga tgcttttgat atctggggcc aagggacaat ggtcaccgtc 360
tcttca 366

<210> SEQ ID NO 101
<211> LENGTH: 324
<212> TYPE: DNA
<213> ORGANISM: Artificial
<220> FEATURE:
<223> OTHER INFORMATION: nucleotide sequence encoding VL of C333

<400> SEQUENCE: 101
gaaattgtgt tgacgcagtc tccagccacc ctgtctgtgt ctcctgggga aagagccacc 60
ctctcctgca gggccagtca gagtattacc aacaacttag cctggtatca acaactgcct 120
ggccaggctc ccaggctcct tatttacgat gcatccacca gggccactga tatcccagcc 180
aggttcagtg gcactgggtc tgggtcagag ttcactctca ccatcagcgg cctgcagtct 240
gcggattttg cagtttatta ctgtcaacaa tacaataact ggcctctcac tttcggcgga 300
gggaccaaag tggatatcaa acgt 324

<210> SEQ ID NO 102
<211> LENGTH: 366
<212> TYPE: DNA
<213> ORGANISM: Artificial
<220> FEATURE:
<223> OTHER INFORMATION: nucleotide sequence encoding VH of C323

<400> SEQUENCE: 102
caaatgcagc tggtgcagtc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaggg atcatcccta tctttggtac aacaaactac 180
gcacagaggt tccagggcag agtcacgatt accgcggacg aatccacgag cacagcctac 240
atggagctga gcagcctgag atctgaggac acggccatat attactgttc aaccaactcc 300
tatagcagca gctggtatga tgcttttgat atctggggcc aagggacaat ggtcaccgtc 360
tcttca 366

<210> SEQ ID NO 103
<211> LENGTH: 324
<212> TYPE: DNA
<213> ORGANISM: Artificial
<220> FEATURE:
<223> OTHER INFORMATION: nucleotide sequence encoding VL of C323

<400> SEQUENCE: 103
gccatccagt tgacccagtc tccatcctcc ctgtctgcat ctgtaggaga cagagtcacc 60
atcacttgcc gcgcaagtca gggcattggc agtgctttag cctggtatca gcagaaacca 120
gggaaagctc ctaagctcct gatctatgat gcctccagtt tgcaaagtgg ggtcccatca 180
aggtacagcg gcagtggatc tgggacagat ttcactctca ccatcagcgg cctgcagcct 240
gaagattttg caacttatta ctgtcaacag tttagttatt acccgctcac tttcggcgga 300
gggaccaagc tggagatcaa acgt 324

<210> SEQ ID NO 104
<211> LENGTH: 366
<212> TYPE: DNA
<213> ORGANISM: Artificial
<220> FEATURE:
<223> OTHER INFORMATION: nucleotide sequence encoding VH of C321

<400> SEQUENCE: 104
caggtgcagc tggtgcagtc tggggctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatggtaa cacaaactat 180
gcacagaagc tccagggcag agtcaccatg accacagaca catccacgag cacagcctac 240
atggagctga ggagcctgag atctgacgac acggccgtgt attactgtgc gagagactcc 300
catatttacg atattttgac tggttatgac tactggggcc agggaaccct ggtcaccgtc 360
tcctca 366

<210> SEQ ID NO 105
<211> LENGTH: 339
<212> TYPE: DNA
<213> ORGANISM: Artificial
<220> FEATURE:
<223> OTHER INFORMATION: nucleotide sequence encoding VL of C321

<400> SEQUENCE: 105
gatgttgtga tgacacagac tccactctcc tcacctgtca cccttggaca gccggcctcc 60
atctcctgcc actctagtca aagcctcgta cacagtgatg gaaacaccta cttgagttgg 120
cttcagcaga ggcccggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagatac acaatttcct 300
cagacgttcg gccaagggac caaggtggaa atcaaacgt 339

<210> SEQ ID NO 106
<211> LENGTH: 357
<212> TYPE: DNA
<213> ORGANISM: Artificial
<220> FEATURE:
<223> OTHER INFORMATION: nucleotide sequence encoding VH of C320

<400> SEQUENCE: 106
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgagtg gatgggatgg atgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgatacgg cctcctttga gtactggggc cagggaaccc tggtcaccgt ctcctca 357

<210> SEQ ID NO 107
<211> LENGTH: 333
<212> TYPE: DNA
<213> ORGANISM: Artificial
<220> FEATURE:
<223> OTHER INFORMATION: nucleotide sequence encoding VL of C320

<400> SEQUENCE: 107
cagtctgtgc tgacgcagcc gccctcagtg tctggggccc cagggcagag ggtcaccatc 60
tcctgcgctg ggagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctggccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 108
<211> LENGTH: 369
<212> TYPE: DNA
<213> ORGANISM: Artificial
<220> FEATURE:
<223> OTHER INFORMATION: nucleotide sequence encoding VH of C319

<400> SEQUENCE: 108
cagctgcagc tgcaggagtc gggcccagga ctggtgaagc cttcggggac cctgtccctc 60
acctgcgctg tctctggtgg ctccatcagc agtagaaact ggtggagttg ggtccgccag 120
tccccaggga aggggctgga gtggattggg gaaatctatc acagtgatat aaccaactat 180
aacccgtccc tcaagagtcg agtcaccatt tcagtagaca agtccaagaa ccagttctcc 240
ctgaagctga gctctgtgac cgccgcggac acggccgtgt attactgtgc gaaggacggg 300
gaggcgggcg ggacctacat tgatgctttt gatgtctggg gccaagggac aatggtcacc 360
gtctcttca 369

<210> SEQ ID NO 109
<211> LENGTH: 333
<212> TYPE: DNA
<213> ORGANISM: Artificial
<220> FEATURE:
<223> OTHER INFORMATION: nucleotide sequence encoding VL of C319

<400> SEQUENCE: 109
cagtctgccc tgactcagcc tcgctcagtg tccgggtctc ctggacagtc agtcaccatc 60
tcctgcactg gaaccagcag tgatgttggt atttataact atgtctcctg gtaccaacaa 120
cacccaggca aagcccccaa actcataatt tatgatgtca gtgagcggcc ctcaggggtc 180
cctgatcgct tctctggctc caagtctgac aacacggcct ccctgaccat ctctgggctc 240
caggctgagg atgaggctga ttattactgc tactcatatg caggcaccta cacttcctta 300
ttcggcggag ggaccaaggt caccgtccta ggt 333

<210> SEQ ID NO 110
<211> LENGTH: 357
<212> TYPE: DNA
<213> ORGANISM: artificial
<220> FEATURE:
<223> OTHER INFORMATION: nucleotide sequence encoding VH of C320-3

<400> SEQUENCE: 110
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg atgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgatacgg cctcctttga gtactggggc cagggaaccc tggtcaccgt ctcctca 357

<210> SEQ ID NO 111
<211> LENGTH: 333
<212> TYPE: DNA
<213> ORGANISM: artificial
<220> FEATURE:
<223> OTHER INFORMATION: nucleotide sequence encoding VL of C320-5

<400> SEQUENCE: 111
cagtctgtgc tgacgcagcc gccctcagtg tctggggccc cagggcagag ggtcaccatc 60
tcctgcgctg ggagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 112
<211> LENGTH: 357
<212> TYPE: DNA
<213> ORGANISM: artificial
<220> FEATURE:
<223> OTHER INFORMATION: nucleotide sequence encoding VH of C320-90

<400> SEQUENCE: 112
caggtgcagc tggtgcagtc tggcgccgaa gtgaagaaac ctggcgccag cgtgaaggtg 60
tcctgcaagg ccagcggcta caccttcacc agctacgaca tcaactgggt ccgacaggcc 120
accggccagg gcctggaatg gatgggctgg atgaacccca acagcggcaa caccggctac 180
gcccagaaat tccagggcag agtgaccatg acccggaaca ccagcatcag caccgcctac 240
atggaactga gcagcctgcg gagcgaggac accgccgtgt actactgcgc cagagaggtg 300
cccgacgacg ccagcttcga gtattggggc cagggcaccc tggtcaccgt gtctagc 357

<210> SEQ ID NO 113
<211> LENGTH: 357
<212> TYPE: DNA
<213> ORGANISM: artificial
<220> FEATURE:
<223> OTHER INFORMATION: nucleotide sequence encoding VH of C320-103

<400> SEQUENCE: 113
caggtgcagc tggtgcagtc tggcgccgaa gtgaagaaac ctggcgccag cgtgaaggtg 60
tcctgcaagg ccagcggcta caccttcacc agctacgaca tcaactgggt ccgacaggcc 120
accggccagg gcctggaatg gatgggctgg atgaacccca acagcggcaa caccggctac 180
gcccagaaat tccagggcag agtgaccatg acccggaaca ccagcatcag caccgcctac 240
atggaactga gcagcctgcg gagcgaggac accgccgtgt actactgcgc cagagaggtg 300
cccgacaccg ccgccttcga gtattggggc cagggcaccc tggtcaccgt gtctagc 357

<210> SEQ ID NO 114

<211> LENGTH: 357
<212> TYPE: DNA
<213> ORGANISM: artificial
<220> FEATURE:
<223> OTHER INFORMATION: nucleotide sequence encoding VH of C320-114

<400> SEQUENCE: 114
caggtgcagc tggtgcagtc tggcgccgaa gtgaagaaac ctggcgccag cgtgaaggtg 60
tcctgcaagg ccagcggcta caccttcacc agctacgaca tcaactgggt ccgacaggcc 120
accggccagg gcctggaatg gatgggctgg atgaacccca acagcggcaa caccggctac 180
gcccagaaat tccagggcag agtgaccatg acccggaaca ccagcatcag caccgcctac 240
atggaactga gcagcctgcg gagcgaggac accgccgtgt actactgcgc cagagaggtg 300
cccgacaccg ccagcttcct gtattggggc cagggcaccc tggtcaccgt gtctagc 357

<210> SEQ ID NO 115
<211> LENGTH: 357
<212> TYPE: DNA
<213> ORGANISM: artificial
<220> FEATURE:
<223> OTHER INFORMATION: nucleotide sequence encoding VH of C320-115

<400> SEQUENCE: 115
caggtgcagc tggtgcagtc tggcgccgaa gtgaagaaac ctggcgccag cgtgaaggtg 60
tcctgcaagg ccagcggcta caccttcacc agctacgaca tcaactgggt ccgacaggcc 120
accggccagg gcctggaatg gatgggctgg atgaacccca acagcggcaa caccggctac 180
gcccagaaat tccagggcag agtgaccatg acccggaaca ccagcatcag caccgcctac 240
atggaactga gcagcctgcg gagcgaggac accgccgtgt actactgcgc cagagaggtg 300
cccgacaccg ccagcttcga ctattggggc cagggcaccc tggtcaccgt gtctagc 357

<210> SEQ ID NO 116
<211> LENGTH: 333
<212> TYPE: DNA
<213> ORGANISM: artificial
<220> FEATURE:
<223> OTHER INFORMATION: nucleotide sequence encoding VL of C320-120

<400> SEQUENCE: 116
cagagcgtgc tgacacagcc ccctagcgtg tcaggcgccc ctggccagag agtgaccatc 60
tcttgcaccg gcagcagcag cgacatcgga gctggactgg gcgtgcactg gtatcagcag 120
ctgcctggca ccgcccccaa gctgctgatc tacggctact acaaccggcc cagcggcgtg 180
cccgacagat tcagcggcag caagagcggc accagcgcca gcctggccat cactggactg 240
ctgcccgagg acgagggcga ctactactgc cagagctacg acggcaccct gagcgccctg 300
tttggcggag gcaccaagct gaccgtccta ggt 333

<210> SEQ ID NO 117
<211> LENGTH: 357
<212> TYPE: DNA
<213> ORGANISM: artificial
<220> FEATURE:
<223> OTHER INFORMATION: nucleotide sequence encoding VH of C320-129

<400> SEQUENCE: 117
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgagtg gatgggatgg atgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgagacgg cctcctttga gtactggggc cagggaaccc tggtcaccgt ctcctca 357

<210> SEQ ID NO 118
<211> LENGTH: 357
<212> TYPE: DNA
<213> ORGANISM: artificial
<220> FEATURE:
<223> OTHER INFORMATION: nucleotide sequence encoding VH of C320-130

<400> SEQUENCE: 118
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgagtg gatgggatgg ctgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgatacgg cctcctttga gtactggggc cagggaaccc tggtcaccgt ctcctca 357

<210> SEQ ID NO 119
<211> LENGTH: 124
<212> TYPE: PRT
<213> ORGANISM: Artificial
<220> FEATURE:
<223> OTHER INFORMATION: amino acid sequence of VH of humanized antibody 1B4

<400> SEQUENCE: 119

Gln Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Asn Met Gly Val Val Trp Ile Arg Gln Pro Pro Gly Lys Ala Leu Glu
35 40 45

Trp Leu Ala His Ile Leu Trp Asp Asp Arg Glu Tyr Ser Asn Pro Ala
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Met Ser Arg Asn Tyr Tyr Gly Ser Ser Tyr Val Met Asp
100 105 110

Tyr Trp Gly Gln Gly Thr Leu Val Thr Val Ser Ser
115 120

<210> SEQ ID NO 120
<211> LENGTH: 106
<212> TYPE: PRT
<213> ORGANISM: Artificial
<220> FEATURE:
<223> OTHER INFORMATION: amino acid sequence of VL of humanized antibody 1B4

<400> SEQUENCE: 120

Asp Ile Gln Leu Thr Gln Ser Pro Ser Phe Leu Ser Ala Ser Val Gly
1 5 10 15

Asp Arg Val Thr Ile Thr Cys Ser Ala Ser Ser Ser Val Asn Tyr Met

-continued

```
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Asn Asn Tyr Gly Thr Phe
                85                  90                  95

Gly Gln Gly Thr Lys Val Glu Ile Lys Arg
            100                 105


<210> SEQ ID NO 121
<211> LENGTH: 372
<212> TYPE: DNA
<213> ORGANISM: Artificial
<220> FEATURE:
<223> OTHER INFORMATION: nucleotide sequence encoding VH of humanized
      antibody 1B4

<400> SEQUENCE: 121

caggtcacac tgaaagagtc cggccctgcc ctggtcaagc ccacccagac cctgaccctg      60

acatgcacct tcagcggctt cagcctgagc accagcaaca tgggcgtcgt gtggatcaga     120

cagccccctg gcaaggccct ggaatggctg gcccacatcc tgtgggacga cagagagtac     180

agcaaccccg ccctgaagtc ccggctgacc atcagcaagg acaccagcaa gaaccaggtg     240

gtgctgacca tgaccaacat ggaccccgtg gacaccgcca cctactactg cgcccggatg     300

agccggaact actacggcag cagctacgtg atggactact ggggccaggg caccctggtc     360

accgtgtcct ca                                                         372


<210> SEQ ID NO 122
<211> LENGTH: 318
<212> TYPE: DNA
<213> ORGANISM: Artificial
<220> FEATURE:
<223> OTHER INFORMATION: nucleotide sequence encoding VL of humanized
      antibody 1B4

<400> SEQUENCE: 122

gacatccagc tgacccagag ccccagcttc ctgagcgcca gcgtgggcga cagagtgacc      60

atcacctgta gcgccagcag cagcgtgaac tacatgcact ggtatcagca gaagcccggc     120

aaggccccca agctgctgat ctacagcacc agcaacctgg ccagcggcgt gcccagcaga     180

ttttctggca gcggcagcgg caccgagttc accctgacca tcagcagcct gcagcccgag     240

gacttcgcca cctactactg ccaccagtgg aacaactacg gcaccttcgg ccagggcacc     300

aaggtggaaa tcaagcgt                                                   318


<210> SEQ ID NO 123
<211> LENGTH: 251
<212> TYPE: PRT
<213> ORGANISM: Homo sapiens

<400> SEQUENCE: 123

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30
```

-continued

```
Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250


<210> SEQ ID NO 124
<211> LENGTH: 177
<212> TYPE: PRT
<213> ORGANISM: Mus musculus

<400> SEQUENCE: 124

Ile Thr Glu Glu Arg Ser Glu Pro Ser Pro Gln Gln Val Tyr Ser Pro
1               5                   10                  15

Pro Arg Gly Lys Pro Arg Ala His Leu Thr Ile Lys Lys Gln Thr Pro
            20                  25                  30

Ala Pro His Leu Lys Asn Gln Leu Ser Ala Leu His Trp Glu His Asp
        35                  40                  45

Leu Gly Met Ala Phe Thr Lys Asn Gly Met Lys Tyr Ile Asn Lys Ser
    50                  55                  60

Leu Val Ile Pro Glu Ser Gly Asp Tyr Phe Ile Tyr Ser Gln Ile Thr
65                  70                  75                  80

Phe Arg Gly Thr Thr Ser Val Cys Gly Asp Ile Ser Arg Gly Arg Arg
                85                  90                  95

Pro Asn Lys Pro Asp Ser Ile Thr Met Val Ile Thr Lys Val Ala Asp
            100                 105                 110

Ser Tyr Pro Glu Pro Ala Arg Leu Leu Thr Gly Ser Lys Ser Val Cys
        115                 120                 125

Glu Ile Ser Asn Asn Trp Phe Gln Ser Leu Tyr Leu Gly Ala Thr Phe
    130                 135                 140

Ser Leu Glu Glu Gly Asp Arg Leu Met Val Asn Val Ser Asp Ile Ser
145                 150                 155                 160
```

```
Leu Val Asp Tyr Thr Lys Glu Asp Lys Thr Phe Phe Gly Ala Phe Leu
                165                 170                 175

Leu


<210> SEQ ID NO 125
<211> LENGTH: 180
<212> TYPE: PRT
<213> ORGANISM: Macaca mulatta

<400> SEQUENCE: 125

Leu Lys Gly Gln Glu Phe Ala Pro Ser His Gln Gln Val Tyr Ala Pro
1               5                   10                  15

Leu Arg Ala Asp Gly Asp Lys Pro Arg Ala His Leu Thr Val Val Arg
            20                  25                  30

Gln Thr Pro Thr Gln His Leu Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Val Tyr Ser
65                  70                  75                  80

Gln Val Thr Phe Arg Gly Met Thr Ser Glu Cys Ser Glu Ile Arg Gln
                85                  90                  95

Ala Gly Arg Pro Asn Lys Pro Asp Ser Ile Thr Val Val Ile Thr Lys
            100                 105                 110

Val Thr Asp Ser Tyr Pro Glu Pro Thr Gln Leu Leu Met Gly Thr Lys
        115                 120                 125

Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180


<210> SEQ ID NO 126
<211> LENGTH: 177
<212> TYPE: PRT
<213> ORGANISM: Rattus rattus

<400> SEQUENCE: 126

Val Thr Glu Glu Arg Ser Ala Pro Ser Ala Gln Pro Val Tyr Thr Pro
1               5                   10                  15

Ser Arg Asp Lys Pro Lys Ala His Leu Thr Ile Met Arg Gln Thr Pro
            20                  25                  30

Val Pro His Leu Lys Asn Glu Leu Ala Ala Leu His Trp Glu Asn Asn
        35                  40                  45

Leu Gly Met Ala Phe Thr Lys Asn Arg Met Asn Tyr Thr Asn Lys Phe
    50                  55                  60

Leu Val Ile Pro Glu Ser Gly Asp Tyr Phe Ile Tyr Ser Gln Ile Thr
65                  70                  75                  80

Phe Arg Gly Thr Thr Ser Glu Cys Gly Asp Ile Ser Arg Val Arg Arg
                85                  90                  95

Pro Lys Lys Pro Asp Ser Ile Thr Val Val Ile Thr Lys Val Ala Asp
            100                 105                 110
```

-continued

```
Ser Tyr Pro Glu Pro Ala His Leu Leu Thr Gly Thr Lys Ser Val Cys
        115                 120                 125

Glu Ile Ser Ser Asn Trp Phe Gln Pro Ile Tyr Leu Gly Ala Met Phe
    130                 135                 140

Ser Leu Glu Glu Gly Asp Arg Leu Met Val Asn Val Ser Asp Ile Ser
145                 150                 155                 160

Leu Val Asp Tyr Thr Lys Glu Asp Lys Thr Phe Phe Gly Ala Phe Leu
                165                 170                 175

Ile


<210> SEQ ID NO 127
<211> LENGTH: 179
<212> TYPE: PRT
<213> ORGANISM: Oryctolagus cuniculus

<400> SEQUENCE: 127

Leu Lys Gly Arg Glu Phe Gly Pro Ser Gln Gln Arg Ala Tyr Met Pro
1               5                   10                  15

Leu Arg Ala Asp Gly Asn Lys Pro Arg Ala His Leu Thr Ala Val Lys
            20                  25                  30

Gln Thr Pro Thr Gln Pro Leu Arg Asn His Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Val Ile Pro Glu Ser Gly Asp Tyr Phe Val Tyr Ser
65                  70                  75                  80

Gln Val Thr Phe Arg Gly Thr Thr Ser Glu Cys Gly Val Ile Asn Gln
                85                  90                  95

Arg Arg Arg Gln Thr Lys Pro Asp Ser Ile Val Val Val Ile Thr Lys
            100                 105                 110

Val Thr Asp Asn Tyr Pro Glu Pro Ala Gln Leu Leu Thr Gly Thr Lys
        115                 120                 125

Ser Val Cys Glu Met Gly Asn Trp Phe Gln Pro Ile Tyr Leu Gly Ala
    130                 135                 140

Met Phe Ser Leu Glu Glu Gly Asp Lys Leu Met Val Asn Val Ser Asp
145                 150                 155                 160

Val Ser Leu Val Asp Tyr Thr Lys Glu Asp Lys Thr Phe Phe Gly Ala
                165                 170                 175

Phe Leu Leu


<210> SEQ ID NO 128
<211> LENGTH: 180
<212> TYPE: PRT
<213> ORGANISM: Cavia porcellus

<400> SEQUENCE: 128

Thr Ile Asn Glu Gln Arg Phe Gly Pro Ser Tyr Gln Arg Val Tyr Thr
1               5                   10                  15

Pro Leu Arg Asp Asp Arg Asp Lys Pro Arg Ala His Leu Thr Val Val
            20                  25                  30

Arg Gln Thr Pro Thr Gln His Leu Lys Asn Gln Phe Pro Ala Leu His
        35                  40                  45

Trp Glu His Glu Leu Gly Leu Ala Phe Thr Lys Asn Arg Met Asn Tyr
    50                  55                  60

Thr Asn Lys Phe Leu Val Ile Pro Glu Thr Gly Asp Tyr Phe Val Tyr
65                  70                  75                  80
```

Ser Gln Ile Thr Phe Arg Gly Thr Thr Ser Glu Cys Gly Ile Ser Pro
85 90 95

Gly Arg Gln Gln Asn Lys Pro Asp Ser Ile Phe Val Val Ile Thr Lys
100 105 110

Val Thr Asp Ser Tyr Pro Glu Pro Ser Gln Leu Leu Thr Gly Thr Lys
115 120 125

Ser Val Cys Glu Ile Ser Ser Asn Trp Phe Gln Pro Leu Tyr Leu Gly
130 135 140

Ala Met Phe Ser Leu Gln Glu Gly Asp Lys Leu Met Val Asn Val Ser
145 150 155 160

Asp Ile Ser Leu Val Asp Tyr Thr Lys Glu Asp Lys Thr Phe Phe Gly
165 170 175

Ala Phe Leu Leu
180

<210> SEQ ID NO 129
<211> LENGTH: 417
<212> TYPE: PRT
<213> ORGANISM: Homo sapiens

<400> SEQUENCE: 129

Met Glu Gln Arg Pro Arg Gly Cys Ala Ala Val Ala Ala Ala Leu Leu
1 5 10 15

Leu Val Leu Leu Gly Ala Arg Ala Gln Gly Gly Thr Arg Ser Pro Arg
20 25 30

Cys Asp Cys Ala Gly Asp Phe His Lys Lys Ile Gly Leu Phe Cys Cys
35 40 45

Arg Gly Cys Pro Ala Gly His Tyr Leu Lys Ala Pro Cys Thr Glu Pro
50 55 60

Cys Gly Asn Ser Thr Cys Leu Val Cys Pro Gln Asp Thr Phe Leu Ala
65 70 75 80

Trp Glu Asn His His Asn Ser Glu Cys Ala Arg Cys Gln Ala Cys Asp
85 90 95

Glu Gln Ala Ser Gln Val Ala Leu Glu Asn Cys Ser Ala Val Ala Asp
100 105 110

Thr Arg Cys Gly Cys Lys Pro Gly Trp Phe Val Glu Cys Gln Val Ser
115 120 125

Gln Cys Val Ser Ser Ser Pro Phe Tyr Cys Gln Pro Cys Leu Asp Cys
130 135 140

Gly Ala Leu His Arg His Thr Arg Leu Leu Cys Ser Arg Arg Gly Thr
145 150 155 160

Asp Cys Gly Thr Cys Leu Pro Gly Phe Tyr Glu His Gly Asp Gly Cys
165 170 175

Val Ser Cys Pro Thr Ser Thr Leu Gly Ser Cys Pro Glu Arg Cys Ala
180 185 190

Ala Val Cys Gly Trp Arg Gln Met Phe Trp Val Gln Val Leu Leu Ala
195 200 205

Gly Leu Val Val Pro Leu Leu Leu Gly Ala Thr Leu Thr Tyr Thr Tyr
210 215 220

Arg His Cys Trp Pro His Lys Pro Leu Val Thr Ala Asp Glu Ala Gly
225 230 235 240

Met Glu Ala Leu Thr Pro Pro Pro Ala Thr His Leu Ser Pro Leu Asp
245 250 255

Ser Ala His Thr Leu Leu Ala Pro Pro Asp Ser Ser Glu Lys Ile Cys

```
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365

Gly Arg Phe Arg Asp Gln Gln Tyr Glu Met Leu Lys Arg Trp Arg Gln
    370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro


<210> SEQ ID NO 130
<211> LENGTH: 300
<212> TYPE: PRT
<213> ORGANISM: Homo sapiens

<400> SEQUENCE: 130

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Cys Ala Gln Cys Pro Pro Gly Thr Phe Val Gln Arg Pro Cys Arg Arg
    50                  55                  60

Asp Ser Pro Thr Thr Cys Gly Pro Cys Pro Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
        115                 120                 125

His Ala Ser Cys Pro Pro Gly Ala Gly Val Ile Ala Pro Gly Thr Pro
    130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
```

```
    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

Leu Val Arg Leu Leu Gln Ala Leu Arg Val Ala Arg Met Pro Gly Leu
        275                 280                 285

Glu Arg Ser Val Arg Glu Arg Phe Leu Pro Val His
    290                 295                 300


<210> SEQ ID NO 131
<211> LENGTH: 2
<212> TYPE: PRT
<213> ORGANISM: Artificial
<220> FEATURE:
<223> OTHER INFORMATION: sequence from TL1a

<400> SEQUENCE: 131

Leu Ala
1


<210> SEQ ID NO 132
<211> LENGTH: 4
<212> TYPE: PRT
<213> ORGANISM: Artificial
<220> FEATURE:
<223> OTHER INFORMATION: sequence from TL1a

<400> SEQUENCE: 132

Gln Pro Ile Tyr
1


<210> SEQ ID NO 133
<211> LENGTH: 7
<212> TYPE: PRT
<213> ORGANISM: Artificial
<220> FEATURE:
<223> OTHER INFORMATION: sequence from TL1a

<400> SEQUENCE: 133

Asn Val Ser Asp Ile Ser Leu
1               5


<210> SEQ ID NO 134
<211> LENGTH: 330
<212> TYPE: PRT
<213> ORGANISM: Homo sapiens

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 135
<211> LENGTH: 106
<212> TYPE: PRT
<213> ORGANISM: Homo sapiens

<400> SEQUENCE: 135

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 136
```

<211> LENGTH: 105
<212> TYPE: PRT
<213> ORGANISM: Homo sapiens

<400> SEQUENCE: 136

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 137
<211> LENGTH: 120
<212> TYPE: PRT
<213> ORGANISM: Artificial Sequence
<220> FEATURE:
<223> OTHER INFORMATION: VH consensus sequence of C320 and derivatives
<220> FEATURE:
<221> NAME/KEY: VARIANT
<222> LOCATION: (1)..(1)
<220> FEATURE:
<221> NAME/KEY: VARIANT
<222> LOCATION: (4)..(4)
<223> OTHER INFORMATION: X=L or V
<220> FEATURE:
<221> NAME/KEY: VARIANT
<222> LOCATION: (5)..(5)
<223> OTHER INFORMATION: X=V or L or Q
<220> FEATURE:
<221> NAME/KEY: VARIANT
<222> LOCATION: (6)..(6)
<223> OTHER INFORMATION: X=L or absent
<220> FEATURE:
<221> NAME/KEY: VARIANT
<222> LOCATION: (7)..(7)
<223> OTHER INFORMATION: X=Q or E
<220> FEATURE:
<221> NAME/KEY: VARIANT
<222> LOCATION: (13)..(13)
<223> OTHER INFORMATION: X=K or R
<220> FEATURE:
<221> NAME/KEY: VARIANT
<222> LOCATION: (14)..(14)
<223> OTHER INFORMATION: X=K or R or A
<220> FEATURE:
<221> NAME/KEY: VARIANT
<222> LOCATION: (17)..(17)
<223> OTHER INFORMATION: X=A or S
<220> FEATURE:
<221> NAME/KEY: VARIANT
<222> LOCATION: (20)..(20)
<223> OTHER INFORMATION: X=K or T or Q or R
<220> FEATURE:
<221> NAME/KEY: VARIANT
<222> LOCATION: (24)..(24)
<223> OTHER INFORMATION: X=K or T
<220> FEATURE:
<221> NAME/KEY: VARIANT
<222> LOCATION: (25)..(25)
<223> OTHER INFORMATION: X=A or S or V
<220> FEATURE:
<221> NAME/KEY: VARIANT
<222> LOCATION: (42)..(42)
<223> OTHER INFORMATION: X=T or P
<220> FEATURE:
<221> NAME/KEY: VARIANT
<222> LOCATION: (44)..(44)
<223> OTHER INFORMATION: X=Q or R or H or K
<220> FEATURE:
<221> NAME/KEY: VARIANT
<222> LOCATION: (46)..(46)
<223> OTHER INFORMATION: X=L or P
<220> FEATURE:
<221> NAME/KEY: VARIANT
<222> LOCATION: (47)..(47)
<223> OTHER INFORMATION: X=E or Q
<220> FEATURE:
<221> NAME/KEY: VARIANT
<222> LOCATION: (49)..(49)
<223> OTHER INFORMATION: X=M or L
<220> FEATURE:
<221> NAME/KEY: VARIANT
<222> LOCATION: (52)..(52)
<223> OTHER INFORMATION: X=M or L
<220> FEATURE:
<221> NAME/KEY: VARIANT
<222> LOCATION: (69)..(69)
<223> OTHER INFORMATION: X=V or I or L
<220> FEATURE:
<221> NAME/KEY: VARIANT
<222> LOCATION: (70)..(70)
<223> OTHER INFORMATION: X=T or S
<220> FEATURE:
<221> NAME/KEY: VARIANT
<222> LOCATION: (71)..(71)
<223> OTHER INFORMATION: X=M or I or F
<220> FEATURE:
<221> NAME/KEY: VARIANT
<222> LOCATION: (73)..(73)
<223> OTHER INFORMATION: X=R or A or T or E
<220> FEATURE:
<221> NAME/KEY: VARIANT
<222> LOCATION: (74)..(74)
<223> OTHER INFORMATION: X=N or D
<220> FEATURE:
<221> NAME/KEY: VARIANT
<222> LOCATION: (75)..(75)
<223> OTHER INFORMATION: X=T or R or Q or E or D
<220> FEATURE:
<221> NAME/KEY: VARIANT
<222> LOCATION: (76)..(76)
<223> OTHER INFORMATION: X=S or A or F
<220> FEATURE:
<221> NAME/KEY: VARIANT
<222> LOCATION: (77)..(77)
<223> OTHER INFORMATION: X=I ot T or A
<220> FEATURE:
<221> NAME/KEY: VARIANT
<222> LOCATION: (78)..(78)
<223> OTHER INFORMATION: X=S or R or G or N
<220> FEATURE:
<221> NAME/KEY: VARIANT
<222> LOCATION: (80)..(80)
<223> OTHER INFORMATION: X=A or V
<220> FEATURE:
<221> NAME/KEY: VARIANT
<222> LOCATION: (82)..(82)
<223> OTHER INFORMATION: X=M or L
<220> FEATURE:
<221> NAME/KEY: VARIANT
<222> LOCATION: (83)..(83)
<223> OTHER INFORMATION: X=E or D
<220> FEATURE:
<221> NAME/KEY: VARIANT
<222> LOCATION: (85)..(85)
<223> OTHER INFORMATION: X=S or N or T or R
<220> FEATURE:
<221> NAME/KEY: VARIANT
<222> LOCATION: (86)..(86)
<223> OTHER INFORMATION: X=S or N
<220> FEATURE:

```
<221> NAME/KEY: VARIANT
<222> LOCATION: (89)..(89)
<223> OTHER INFORMATION: X=S or P or Y
<220> FEATURE:
<221> NAME/KEY: VARIANT
<222> LOCATION: (90)..(90)
<223> OTHER INFORMATION: X=E or D
<220> FEATURE:
<221> NAME/KEY: VARIANT
<222> LOCATION: (94)..(94)
<223> OTHER INFORMATION: X=V or M
<220> FEATURE:
<221> NAME/KEY: VARIANT
<222> LOCATION: (98)..(98)
<223> OTHER INFORMATION: X=A or T
<220> FEATURE:
<221> NAME/KEY: VARIANT
<222> LOCATION: (99)..(99)
<223> OTHER INFORMATION: X=R or K or T
<220> FEATURE:
<221> NAME/KEY: VARIANT
<222> LOCATION: (101)..(101)
<223> OTHER INFORMATION: X=V or A or S or H or L or D or Y or P or Q or
      K
<220> FEATURE:
<221> NAME/KEY: VARIANT
<222> LOCATION: (103)..(103)
<223> OTHER INFORMATION: X=E or D or A or S or H or K
<220> FEATURE:
<221> NAME/KEY: VARIANT
<222> LOCATION: (104)..(104)
<223> OTHER INFORMATION: X=T or D or A or S or D or Y
<220> FEATURE:
<221> NAME/KEY: VARIANT
<222> LOCATION: (106)..(106)
<223> OTHER INFORMATION: X=S or A or H or L or D or Y
<220> FEATURE:
<221> NAME/KEY: VARIANT
<222> LOCATION: (108)..(108)
<223> OTHER INFORMATION: X=L or D or E or A or S or H or P or Q or K
<220> FEATURE:
<221> NAME/KEY: VARIANT
<222> LOCATION: (112)..(112)
<223> OTHER INFORMATION: X=Q or K
<220> FEATURE:
<221> NAME/KEY: VARIANT
<222> LOCATION: (115)..(115)
<223> OTHER INFORMATION: X=L or T

<400> SEQUENCE: 137

Xaa Val Gln Xaa Xaa Xaa Xaa Ser Gly Ala Glu Val Xaa Xaa Pro Gly
1               5                   10                  15

Xaa Ser Val Xaa Val Ser Cys Xaa Xaa Ser Gly Tyr Thr Phe Thr Ser
            20                  25                  30

Tyr Asp Ile Asn Trp Val Arg Gln Ala Xaa Gly Xaa Gly Xaa Xaa Trp
        35                  40                  45

Xaa Gly Trp Xaa Asn Pro Asn Ser Gly Asn Thr Gly Tyr Ala Gln Lys
    50                  55                  60

Phe Gln Gly Arg Xaa Xaa Xaa Thr Xaa Xaa Xaa Xaa Xaa Xaa Thr Xaa
65                  70                  75                  80

Tyr Xaa Xaa Leu Xaa Xaa Leu Arg Xaa Xaa Asp Thr Ala Xaa Tyr Tyr
                85                  90                  95

Cys Xaa Xaa Glu Xaa Pro Xaa Xaa Ala Xaa Phe Xaa Tyr Trp Gly Xaa
            100                 105                 110

Gly Thr Xaa Val Thr Val Ser Ser
        115                 120


<210> SEQ ID NO 138
<211> LENGTH: 112
<212> TYPE: PRT
```

```
<213> ORGANISM: Artificial Sequence
<220> FEATURE:
<223> OTHER INFORMATION: consensus sequence of C320 and derivatives
<220> FEATURE:
<221> NAME/KEY: VARIANT
<222> LOCATION: (1)..(1)
<223> OTHER INFORMATION: X=Q or S or D or E
<220> FEATURE:
<221> NAME/KEY: VARIANT
<222> LOCATION: (2)..(2)
<223> OTHER INFORMATION: X=S or I or Y or P or L
<220> FEATURE:
<221> NAME/KEY: VARIANT
<222> LOCATION: (3)..(3)
<223> OTHER INFORMATION: X=V or A or G
<220> FEATURE:
<221> NAME/KEY: VARIANT
<222> LOCATION: (7)..(7)
<223> OTHER INFORMATION: X=P or S
<220> FEATURE:
<221> NAME/KEY: VARIANT
<222> LOCATION: (8)..(8)
<223> OTHER INFORMATION: X=P or S or A
<220> FEATURE:
<221> NAME/KEY: VARIANT
<222> LOCATION: (9)..(9)
<223> OTHER INFORMATION: X=absent or G
<220> FEATURE:
<221> NAME/KEY: VARIANT
<222> LOCATION: (10)..(10)
<223> OTHER INFORMATION: X=S or T
<220> FEATURE:
<221> NAME/KEY: VARIANT
<222> LOCATION: (11)..(11)
<223> OTHER INFORMATION: X=V or Q or L
<220> FEATURE:
<221> NAME/KEY: VARIANT
<222> LOCATION: (13)..(13)
<223> OTHER INFORMATION: X=G or V or K or A or L
<220> FEATURE:
<221> NAME/KEY: VARIANT
<222> LOCATION: (14)..(14)
<223> OTHER INFORMATION: X=A or G or T or S
<220> FEATURE:
<221> NAME/KEY: VARIANT
<222> LOCATION: (15)..(15)
<223> OTHER INFORMATION: X=P or L or A
<220> FEATURE:
<221> NAME/KEY: VARIANT
<222> LOCATION: (16)..(16)
<223> OTHER INFORMATION: X=G or R
<220> FEATURE:
<221> NAME/KEY: VARIANT
<222> LOCATION: (17)..(17)
<223> OTHER INFORMATION: X=Q or K or E
<220> FEATURE:
<221> NAME/KEY: VARIANT
<222> LOCATION: (18)..(18)
<223> OTHER INFORMATION: X=R or S or K or T
<220> FEATURE:
<221> NAME/KEY: VARIANT
<222> LOCATION: (19)..(19)
<223> OTHER INFORMATION: X=V or I or A
<220> FEATURE:
<221> NAME/KEY: VARIANT
<222> LOCATION: (20)..(20)
<223> OTHER INFORMATION: X=T or R
<220> FEATURE:
<221> NAME/KEY: VARIANT
<222> LOCATION: (21)..(21)
<223> OTHER INFORMATION: X=I or S
<220> FEATURE:
<221> NAME/KEY: VARIANT
<222> LOCATION: (22)..(22)
<223> OTHER INFORMATION: X=S
<220> FEATURE:
<221> NAME/KEY: VARIANT
<222> LOCATION: (24)..(24)
<223> OTHER INFORMATION: X=A or T
```

<220> FEATURE:
<221> NAME/KEY: VARIANT
<222> LOCATION: (25)..(25)
<223> OTHER INFORMATION: X=G or S
<220> FEATURE:
<221> NAME/KEY: VARIANT
<222> LOCATION: (39)..(39)
<223> OTHER INFORMATION: X=Y or L
<220> FEATURE:
<221> NAME/KEY: VARIANT
<222> LOCATION: (42)..(42)
<223> OTHER INFORMATION: X=L or K or R or H
<220> FEATURE:
<221> NAME/KEY: VARIANT
<222> LOCATION: (43)..(43)
<223> OTHER INFORMATION: X=P or Q
<220> FEATURE:
<221> NAME/KEY: VARIANT
<222> LOCATION: (45)..(45)
<223> OTHER INFORMATION: X=T or Q or K or H
<220> FEATURE:
<221> NAME/KEY: VARIANT
<222> LOCATION: (46)..(46)
<223> OTHER INFORMATION: X=A or P
<220> FEATURE:
<221> NAME/KEY: VARIANT
<222> LOCATION: (48)..(48)
<223> OTHER INFORMATION: X=K or R or V
<220> FEATURE:
<221> NAME/KEY: VARIANT
<222> LOCATION: (50)..(50)
<223> OTHER INFORMATION: X=L or V or M
<220> FEATURE:
<221> NAME/KEY: VARIANT
<222> LOCATION: (51)..(51)
<223> OTHER INFORMATION: X=I or V or S
<220> FEATURE:
<221> NAME/KEY: VARIANT
<222> LOCATION: (52)..(52)
<223> OTHER INFORMATION: X=P or E or G or Y
<220> FEATURE:
<221> NAME/KEY: VARIANT
<222> LOCATION: (54)..(54)
<223> OTHER INFORMATION: X=Y
<220> FEATURE:
<221> NAME/KEY: VARIANT
<222> LOCATION: (55)..(55)
<223> OTHER INFORMATION: X=Y
<220> FEATURE:
<221> NAME/KEY: VARIANT
<222> LOCATION: (60)..(60)
<223> OTHER INFORMATION: X=G or I
<220> FEATURE:
<221> NAME/KEY: VARIANT
<222> LOCATION: (61)..(61)
<223> OTHER INFORMATION: X=V or A or S
<220> FEATURE:
<221> NAME/KEY: VARIANT
<222> LOCATION: (62)..(62)
<223> OTHER INFORMATION: X=P or E or N
<220> FEATURE:
<221> NAME/KEY: VARIANT
<222> LOCATION: (66)..(66)
<223> OTHER INFORMATION: X=S or A
<220> FEATURE:
<221> NAME/KEY: VARIANT
<222> LOCATION: (68)..(68)
<223> OTHER INFORMATION: X=S or G or N or R
<220> FEATURE:
<221> NAME/KEY: VARIANT
<222> LOCATION: (71)..(71)
<223> OTHER INFORMATION: X=G or N
<220> FEATURE:
<221> NAME/KEY: VARIANT
<222> LOCATION: (72)..(72)
<223> OTHER INFORMATION: X=T or D
<220> FEATURE:
<221> NAME/KEY: VARIANT
<222> LOCATION: (73)..(73)

```
<223> OTHER INFORMATION: X=S or F
<220> FEATURE:
<221> NAME/KEY: VARIANT
<222> LOCATION: (74)..(74)
<223> OTHER INFORMATION: X=A or T
<220> FEATURE:
<221> NAME/KEY: VARIANT
<222> LOCATION: (76)..(76)
<223> OTHER INFORMATION: X=L or T or G
<220> FEATURE:
<221> NAME/KEY: VARIANT
<222> LOCATION: (77)..(77)
<223> OTHER INFORMATION: X=A or T
<220> FEATURE:
<221> NAME/KEY: VARIANT
<222> LOCATION: (78)..(78)
<223> OTHER INFORMATION: X=I or G or S
<220> FEATURE:
<221> NAME/KEY: VARIANT
<222> LOCATION: (79)..(79)
<223> OTHER INFORMATION: X=T or R
<220> FEATURE:
<221> NAME/KEY: VARIANT
<222> LOCATION: (80)..(80)
<223> OTHER INFORMATION: X=G or V
<220> FEATURE:
<221> NAME/KEY: VARIANT
<222> LOCATION: (81)..(81)
<223> OTHER INFORMATION: X=L or E or Q or R
<220> FEATURE:
<221> NAME/KEY: VARIANT
<222> LOCATION: (82)..(82)
<223> OTHER INFORMATION: X=L or A or T or S or Q
<220> FEATURE:
<221> NAME/KEY: VARIANT
<222> LOCATION: (83)..(83)
<223> OTHER INFORMATION: X=P or G or A
<220> FEATURE:
<221> NAME/KEY: VARIANT
<222> LOCATION: (85)..(85)
<223> OTHER INFORMATION: X=D or L or F
<220> FEATURE:
<221> NAME/KEY: VARIANT
<222> LOCATION: (86)..(86)
<223> OTHER INFORMATION: X=E or A
<220> FEATURE:
<221> NAME/KEY: VARIANT
<222> LOCATION: (87)..(87)
<223> OTHER INFORMATION: X=G or V or N or A
<220> FEATURE:
<221> NAME/KEY: VARIANT
<222> LOCATION: (96)..(96)
<223> OTHER INFORMATION: X=G
<220> FEATURE:
<221> NAME/KEY: VARIANT
<222> LOCATION: (97)..(97)
<223> OTHER INFORMATION: X=T
<220> FEATURE:
<221> NAME/KEY: VARIANT
<222> LOCATION: (103)..(103)
<223> OTHER INFORMATION: X=G or Q or T or A
<220> FEATURE:
<221> NAME/KEY: VARIANT
<222> LOCATION: (107)..(107)
<223> OTHER INFORMATION: X=K or V
<220> FEATURE:
<221> NAME/KEY: VARIANT
<222> LOCATION: (108)..(108)
<223> OTHER INFORMATION: X=L or E
<220> FEATURE:
<221> NAME/KEY: VARIANT
<222> LOCATION: (109)..(109)
<223> OTHER INFORMATION: X=T or I
<220> FEATURE:
<221> NAME/KEY: VARIANT
<222> LOCATION: (110)..(110)
<223> OTHER INFORMATION: X=V or K
<220> FEATURE:
<221> NAME/KEY: VARIANT
```

<222> LOCATION: (111)..(111)
<223> OTHER INFORMATION: X=L or R

<400> SEQUENCE: 138

Xaa Xaa Xaa Leu Thr Gln Xaa Xaa Xaa Xaa Xaa Ser Xaa Xaa Xaa Xaa
1               5                   10                  15

Xaa Xaa Xaa Xaa Xaa Xaa Cys Xaa Xaa Ser Ser Ser Asp Ile Gly Ala
            20                  25                  30

Gly Leu Gly Val His Trp Xaa Gln Gln Xaa Xaa Gly Xaa Xaa Pro Xaa
        35                  40                  45

Leu Xaa Xaa Xaa Gly Xaa Xaa Asn Arg Pro Ser Xaa Xaa Xaa Asp Arg
    50                  55                  60

Phe Xaa Gly Xaa Lys Ser Xaa Xaa Xaa Xaa Ser Xaa Xaa Xaa Xaa Xaa
65                  70                  75                  80

Xaa Xaa Xaa Glu Xaa Xaa Xaa Asp Tyr Tyr Cys Gln Ser Tyr Asp Xaa
                85                  90                  95

Xaa Leu Ser Ala Leu Phe Xaa Gly Gly Thr Xaa Xaa Xaa Xaa Xaa Gly
            100                 105                 110

<210> SEQ ID NO 139
<211> LENGTH: 14
<212> TYPE: PRT
<213> ORGANISM: artificial
<220> FEATURE:
<223> OTHER INFORMATION: LCDR1 consensus sequence of C320 and derivatives
<220> FEATURE:
<221> NAME/KEY: VARIANT
<222> LOCATION: (1)..(1)
<220> FEATURE:
<221> NAME/KEY: VARIANT
<222> LOCATION: (2)..(2)
<223> OTHER INFORMATION: X at position 2 is G or S

<400> SEQUENCE: 139

Xaa Xaa Ser Ser Ser Asp Ile Gly Ala Gly Leu Gly Val His
1               5                   10

<210> SEQ ID NO 140
<211> LENGTH: 7
<212> TYPE: PRT
<213> ORGANISM: artificial
<220> FEATURE:
<223> OTHER INFORMATION: LCDR2 consensus sequence of C320 and derivatives

<400> SEQUENCE: 140

Gly Tyr Tyr Asn Arg Pro Ser
1               5

<210> SEQ ID NO 141
<211> LENGTH: 10
<212> TYPE: PRT
<213> ORGANISM: artificial
<220> FEATURE:
<223> OTHER INFORMATION: LCDR3 consensus sequence of C320 and derivatives

<400> SEQUENCE: 141

Gln Ser Tyr Asp Gly Thr Leu Ser Ala Leu
1               5                   10

<210> SEQ ID NO 142
<211> LENGTH: 17
<212> TYPE: PRT

```
<213> ORGANISM: artificial
<220> FEATURE:
<223> OTHER INFORMATION: HCDR2 consensus sequence of C320 and
      derivatives
<220> FEATURE:
<221> NAME/KEY: VARIANT
<222> LOCATION: (2)..(2)
<223> OTHER INFORMATION: X at position 2 is methionine or leucine

<400> SEQUENCE: 142

Trp Xaa Asn Pro Asn Ser Gly Asn Thr Gly Tyr Ala Gln Lys Phe Gln
1               5                   10                  15

Gly


<210> SEQ ID NO 143
<211> LENGTH: 10
<212> TYPE: PRT
<213> ORGANISM: artificial
<220> FEATURE:
<223> OTHER INFORMATION: HCDR3 consensus sequence of C320 and
      derivatives
<220> FEATURE:
<221> NAME/KEY: MISC_FEATURE
<222> LOCATION: (4)..(4)
<223> OTHER INFORMATION: X = A or T
<220> FEATURE:
<221> NAME/KEY: MISC_FEATURE
<222> LOCATION: (7)..(7)
<223> OTHER INFORMATION: X = G or S

<400> SEQUENCE: 143

Glu Val Pro Xaa Thr Ala Xaa Phe Glu Tyr
1               5                   10


<210> SEQ ID NO 144
<211> LENGTH: 30
<212> TYPE: PRT
<213> ORGANISM: Artificial Sequence
<220> FEATURE:
<223> OTHER INFORMATION: amino acid sequence of HFR1 consesnys seq od
      C320 and der

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 145
<211> LENGTH: 14
<212> TYPE: PRT
<213> ORGANISM: Artificial Sequence
<220> FEATURE:
<223> OTHER INFORMATION: HFR2 consensus sequence of C320 and derivatives
<220> FEATURE:
<221> NAME/KEY: VARIANT
<222> LOCATION: (6)..(6)
<223> OTHER INFORMATION: X= T or P

<400> SEQUENCE: 145

Trp Val Arg Gln Ala Xaa Gly Gln Gly Leu Glu Trp Met Gly
1               5                   10


<210> SEQ ID NO 146
<211> LENGTH: 32
<212> TYPE: PRT
<213> ORGANISM: Artificial Sequence
<220> FEATURE:
<223> OTHER INFORMATION: HFR3 consensus sequence of C320 and derivatives
```

```
<220> FEATURE:
<221> NAME/KEY: VARIANT
<222> LOCATION: (6)..(6)
<223> OTHER INFORMATION: X = R or A
<220> FEATURE:
<221> NAME/KEY: VARIANT
<222> LOCATION: (7)..(7)
<223> OTHER INFORMATION: X = N or D
<220> FEATURE:
<221> NAME/KEY: VARIANT
<222> LOCATION: (8)..(8)
<223> OTHER INFORMATION: X = T or R
<220> FEATURE:
<221> NAME/KEY: VARIANT
<222> LOCATION: (9)..(9)
<223> OTHER INFORMATION: X = S or A
<220> FEATURE:
<221> NAME/KEY: VARIANT
<222> LOCATION: (10)..(10)
<223> OTHER INFORMATION: X = I or T

<400> SEQUENCE: 146

Arg Val Thr Met Thr Xaa Xaa Xaa Xaa Xaa Ser Thr Ala Tyr Met Glu
1               5                   10                  15

Leu Ser Ser Leu Arg Ser Glu Asp Thr Ala Val Tyr Tyr Cys Ala Arg
            20                  25                  30


<210> SEQ ID NO 147
<211> LENGTH: 11
<212> TYPE: PRT
<213> ORGANISM: Artificial Sequence
<220> FEATURE:
<223> OTHER INFORMATION: HFR4 consensus sequence of C320 and derivatives

<400> SEQUENCE: 147

Trp Gly Gln Gly Thr Leu Val Thr Val Ser Ser
1               5                   10


<210> SEQ ID NO 148
<211> LENGTH: 22
<212> TYPE: PRT
<213> ORGANISM: Artificial Sequence
<220> FEATURE:
<223> OTHER INFORMATION: LFR1 consensus sequence of C320 and derivatives

<400> SEQUENCE: 148

Gln Ser Val Leu Thr Gln Pro Pro Ser Val Ser Gly Ala Pro Gly Gln
1               5                   10                  15

Arg Val Thr Ile Ser Cys
            20


<210> SEQ ID NO 149
<211> LENGTH: 15
<212> TYPE: PRT
<213> ORGANISM: Artificial Sequence
<220> FEATURE:
<223> OTHER INFORMATION: LFR2 consensus sequence of C320 and derivatives
<220> FEATURE:
<221> NAME/KEY: VARIANT
<222> LOCATION: (15)..(15)
<223> OTHER INFORMATION: X = Y or E or G

<400> SEQUENCE: 149

Trp Tyr Gln Gln Leu Pro Gly Thr Ala Pro Lys Leu Leu Ile Xaa
1               5                   10                  15


<210> SEQ ID NO 150
<211> LENGTH: 32
<212> TYPE: PRT
```

```
<213> ORGANISM: Artificial Sequence
<220> FEATURE:
<223> OTHER INFORMATION: LFR3 consensus sequence of C320 and derivatives
<220> FEATURE:
<221> NAME/KEY: VARIANT
<222> LOCATION: (18)..(18)
<223> OTHER INFORMATION: X=A or T

<400> SEQUENCE: 150

Gly Val Pro Asp Arg Phe Ser Gly Ser Lys Ser Gly Thr Ser Ala Ser
1               5                   10                  15

Leu Xaa Ile Thr Gly Leu Leu Pro Glu Asp Glu Gly Asp Tyr Tyr Cys
            20                  25                  30


<210> SEQ ID NO 151
<211> LENGTH: 11
<212> TYPE: PRT
<213> ORGANISM: Artificial Sequence
<220> FEATURE:
<223> OTHER INFORMATION: LFR4 consensus sequence of C320 and derivatives
<220> FEATURE:
<221> NAME/KEY: VARIANT
<222> LOCATION: (3)..(3)
<223> OTHER INFORMATION: X=Q or K
<220> FEATURE:
<221> NAME/KEY: VARIANT
<222> LOCATION: (3)..(3)
<223> OTHER INFORMATION: X=L or T

<400> SEQUENCE: 151

Phe Gly Gly Gly Thr Lys Leu Thr Val Leu Gly
1               5                   10


<210> SEQ ID NO 152
<211> LENGTH: 119
<212> TYPE: PRT
<213> ORGANISM: Artificial Sequence
<220> FEATURE:
<223> OTHER INFORMATION: VH consensus sequence of C320 and derivatives
<220> FEATURE:
<221> NAME/KEY: VARIANT
<222> LOCATION: (41)..(41)
<223> OTHER INFORMATION: X=T or P
<220> FEATURE:
<221> NAME/KEY: VARIANT
<222> LOCATION: (51)..(51)
<223> OTHER INFORMATION: X=M or L
<220> FEATURE:
<221> NAME/KEY: VARIANT
<222> LOCATION: (102)..(102)
<223> OTHER INFORMATION: X=E or D
<220> FEATURE:
<221> NAME/KEY: VARIANT
<222> LOCATION: (103)..(103)
<223> OTHER INFORMATION: X=T or D
<220> FEATURE:
<221> NAME/KEY: VARIANT
<222> LOCATION: (105)..(105)
<223> OTHER INFORMATION: X=S or A
<220> FEATURE:
<221> NAME/KEY: VARIANT
<222> LOCATION: (107)..(107)
<223> OTHER INFORMATION: X=L or D or E

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Xaa Gly Gln Gly Leu Glu Trp Met
        35                  40                  45
```

```
Gly Trp Xaa Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Xaa Xaa Ala Xaa Phe Xaa Tyr Trp Gly Gln Gly
            100                 105                 110

Thr Leu Val Thr Val Ser Ser
        115


<210> SEQ ID NO 153
<211> LENGTH: 111
<212> TYPE: PRT
<213> ORGANISM: Artificial Sequence
<220> FEATURE:
<223> OTHER INFORMATION: Vl consensus sequence of C320 and derivatives
<220> FEATURE:
<221> NAME/KEY: VARIANT
<222> LOCATION: (23)..(23)
<223> OTHER INFORMATION: X=A or T
<220> FEATURE:
<221> NAME/KEY: VARIANT
<222> LOCATION: (76)..(76)
<223> OTHER INFORMATION: X=A or T

<400> SEQUENCE: 153

Gln Ser Val Leu Thr Gln Pro Pro Ser Val Ser Gly Ala Pro Gly Gln
1               5                   10                  15

Arg Val Thr Ile Ser Cys Xaa Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Xaa Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 154
<211> LENGTH: 119
<212> TYPE: PRT
<213> ORGANISM: Artificial Sequence
<220> FEATURE:
<223> OTHER INFORMATION: VH comprising CDRs from C320 grafted onto FRs
      of antibody 1TZG

<400> SEQUENCE: 154

Gln Val Gln Leu Val Gln Ser Gly Ala Glu Val Lys Arg Pro Gly Ser
1               5                   10                  15

Ser Val Thr Val Ser Cys Lys Ala Ser Gly Tyr Thr Phe Thr Ser Tyr
            20                  25                  30

Asp Ile Asn Trp Val Arg Gln Ala Pro Gly Arg Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Ile Thr Ile Thr Ala Asp Arg Ser Thr Ser Thr Ala Tyr
```

```
65                  70                  75                  80

Leu Glu Leu Asn Ser Leu Arg Pro Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115


<210> SEQ ID NO 155
<211> LENGTH: 120
<212> TYPE: PRT
<213> ORGANISM: Artificial Sequence
<220> FEATURE:
<223> OTHER INFORMATION: VH comprising CDRs from C320 grafted onto FRs
      of antibody 1RHH

<400> SEQUENCE: 155

Glu Val Gln Leu Leu Glu Gln Ser Gly Ala Glu Val Lys Lys Pro Gly
1               5                   10                  15

Ser Ser Val Gln Val Ser Cys Lys Ala Ser Gly Tyr Thr Phe Thr Ser
            20                  25                  30

Tyr Asp Ile Asn Trp Val Arg Gln Ala Pro Gly His Gly Leu Glu Trp
        35                  40                  45

Met Gly Trp Met Asn Pro Asn Ser Gly Asn Thr Gly Tyr Ala Gln Lys
    50                  55                  60

Phe Gln Gly Arg Val Thr Phe Thr Ala Asp Gln Ala Thr Ser Thr Ala
65                  70                  75                  80

Tyr Met Glu Leu Thr Asn Leu Arg Ser Asp Asp Thr Ala Val Tyr Tyr
                85                  90                  95

Cys Ala Arg Glu Val Pro Asp Thr Ala Ser Phe Glu Tyr Trp Gly Gln
            100                 105                 110

Gly Thr Leu Val Thr Val Ser Ser
        115                 120


<210> SEQ ID NO 156
<211> LENGTH: 119
<212> TYPE: PRT
<213> ORGANISM: Artificial Sequence
<220> FEATURE:
<223> OTHER INFORMATION: VH comprising CDRs from C320 grafted onto FRs
      of antibody 2DD8

<400> SEQUENCE: 156

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Thr Val Thr Val Ser Ser
```

115

<210> SEQ ID NO 157
<211> LENGTH: 119
<212> TYPE: PRT
<213> ORGANISM: Artificial Sequence
<220> FEATURE:
<223> OTHER INFORMATION: VH comprising CDRs from C320 grafted onto FRs of antibody 2JB5

<400> SEQUENCE: 157

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115
```

<210> SEQ ID NO 158
<211> LENGTH: 119
<212> TYPE: PRT
<213> ORGANISM: Artificial Sequence
<220> FEATURE:
<223> OTHER INFORMATION: VH comprising CDRs from C320 grafted onto FRs of antibody 3FKU

<400> SEQUENCE: 158

```
Gln Val Gln Leu Val Gln Ser Gly Ala Glu Val Lys Lys Pro Gly Ser
1               5                   10                  15

Ser Val Lys Val Ser Cys Thr Ser Ser Gly Tyr Thr Phe Thr Ser Tyr
            20                  25                  30

Asp Ile Asn Trp Val Arg Gln Ala Pro Gly Gln Gly Leu Glu Trp Leu
        35                  40                  45

Gly Trp Met Asn Pro Asn Ser Gly Asn Thr Gly Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115
```

<210> SEQ ID NO 159
<211> LENGTH: 119
<212> TYPE: PRT
<213> ORGANISM: Artificial Sequence
<220> FEATURE:
<223> OTHER INFORMATION: VH comprising CDRs from C320 grafted onto FRs of antibody 3GBM

<400> SEQUENCE: 159

Glu Val Gln Leu Val Glu Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Pro Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys Glu Val Pro Asp Thr Ala Ser Phe Glu Tyr Trp Gly Lys Gly
            100                 105                 110

Thr Thr Val Thr Val Ser Ser
        115

<210> SEQ ID NO 160
<211> LENGTH: 119
<212> TYPE: PRT
<213> ORGANISM: Artificial Sequence
<220> FEATURE:
<223> OTHER INFORMATION: VH comprising CDRs from C320 grafted onto FRs
      of antibody 3LMJ

<400> SEQUENCE: 160

Gln Val Gln Val Val Gln Ser Gly Ala Glu Val Arg Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Met
        35                  40                  45

Gly Trp Met Asn Pro Asn Ser Gly Asn Thr Gly Tyr Ala Gln Lys Phe
    50                  55                  60

Gln Lys Arg Val Ser Met Thr Glu Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Val Pro Asp Thr Ala Ser Phe Glu Tyr Trp Gly Gln Gly
            100                 105                 110

Thr Leu Val Thr Val Ser Ser
        115

<210> SEQ ID NO 161
<211> LENGTH: 119
<212> TYPE: PRT
<213> ORGANISM: Artificial Sequence
<220> FEATURE:
<223> OTHER INFORMATION: VH comprising CDRs from C320 grafted onto FRs
      of antibody 3P30

<400> SEQUENCE: 161

Gln Val Gln Leu Val Gln Ser Gly Ala Glu Val Lys Lys Ala Gly Ser
1               5                   10                  15

Ser Val Arg Val Ser Cys Lys Ala Ser Gly Tyr Thr Phe Thr Ser Tyr
            20                  25                  30

```
Asp Ile Asn Trp Val Arg Gln Ala Pro Gly Gln Gly Pro Gln Trp Met
        35                  40                  45

Gly Trp Met Asn Pro Asn Ser Gly Asn Thr Gly Tyr Ala Gln Lys Phe
    50                  55                  60

Gln Gly Arg Leu Thr Ile Thr Ala Asp Thr Ser Thr Asn Thr Ala Tyr
65                  70                  75                  80

Leu Glu Leu Ser Ser Leu Arg Tyr Asp Asp Thr Ala Val Tyr Tyr Cys
                85                  90                  95

Thr Arg Glu Val Pro Asp Thr Ala Ser Phe Glu Tyr Trp Gly Gln Gly
            100                 105                 110

Thr Leu Val Thr Val Ser Ser
        115
```

<210> SEQ ID NO 162
<211> LENGTH: 120
<212> TYPE: PRT
<213> ORGANISM: Artificial Sequence
<220> FEATURE:
<223> OTHER INFORMATION: amino acid sequence of VH consensus sequence of
      C320 and derivatives
<220> FEATURE:
<221> NAME/KEY: VARIANT
<222> LOCATION: (1)..(1)
<223> OTHER INFORMATION: X=Q or E
<220> FEATURE:
<221> NAME/KEY: VARIANT
<222> LOCATION: (4)..(4)
<223> OTHER INFORMATION: X=L or V
<220> FEATURE:
<221> NAME/KEY: VARIANT
<222> LOCATION: (5)..(5)
<223> OTHER INFORMATION: X=V or L or Q
<220> FEATURE:
<221> NAME/KEY: VARIANT
<222> LOCATION: (6)..(6)
<223> OTHER INFORMATION: X=L or absent
<220> FEATURE:
<221> NAME/KEY: VARIANT
<222> LOCATION: (7)..(7)
<223> OTHER INFORMATION: X=Q or E
<220> FEATURE:
<221> NAME/KEY: VARIANT
<222> LOCATION: (13)..(13)
<223> OTHER INFORMATION: X=K or R
<220> FEATURE:
<221> NAME/KEY: VARIANT
<222> LOCATION: (14)..(14)
<223> OTHER INFORMATION: X=K or R or A
<220> FEATURE:
<221> NAME/KEY: VARIANT
<222> LOCATION: (17)..(17)
<223> OTHER INFORMATION: X=A or S
<220> FEATURE:
<221> NAME/KEY: VARIANT
<222> LOCATION: (20)..(20)
<223> OTHER INFORMATION: X=K or T or Q or R
<220> FEATURE:
<221> NAME/KEY: VARIANT
<222> LOCATION: (24)..(24)
<223> OTHER INFORMATION: X=K or T
<220> FEATURE:
<221> NAME/KEY: VARIANT
<222> LOCATION: (25)..(25)
<223> OTHER INFORMATION: X=A or S or V
<220> FEATURE:
<221> NAME/KEY: VARIANT
<222> LOCATION: (42)..(42)
<223> OTHER INFORMATION: X=T or P
<220> FEATURE:
<221> NAME/KEY: VARIANT
<222> LOCATION: (44)..(44)
<223> OTHER INFORMATION: X=Q or R or H or K
<220> FEATURE:
<221> NAME/KEY: VARIANT
<222> LOCATION: (46)..(46)
<223> OTHER INFORMATION: X=L or P
<220> FEATURE:
<221> NAME/KEY: VARIANT
<222> LOCATION: (47)..(47)
<223> OTHER INFORMATION: X=E or Q
<220> FEATURE:
<221> NAME/KEY: VARIANT
<222> LOCATION: (49)..(49)
<223> OTHER INFORMATION: X=M or L
<220> FEATURE:
<221> NAME/KEY: VARIANT
<222> LOCATION: (69)..(69)
<223> OTHER INFORMATION: X=V or I or L
<220> FEATURE:
<221> NAME/KEY: VARIANT
<222> LOCATION: (70)..(70)
<223> OTHER INFORMATION: X=T or S
<220> FEATURE:
<221> NAME/KEY: VARIANT
<222> LOCATION: (71)..(71)
<223> OTHER INFORMATION: X=M or I or F
<220> FEATURE:
<221> NAME/KEY: VARIANT
<222> LOCATION: (73)..(73)
<223> OTHER INFORMATION: X=R or A or T or E
<220> FEATURE:
<221> NAME/KEY: VARIANT
<222> LOCATION: (74)..(74)
<223> OTHER INFORMATION: X=N or D
<220> FEATURE:
<221> NAME/KEY: VARIANT
<222> LOCATION: (75)..(75)
<223> OTHER INFORMATION: X=T or R or Q or E or D
<220> FEATURE:
<221> NAME/KEY: VARIANT
<222> LOCATION: (76)..(76)
<223> OTHER INFORMATION: X=S or A or F
<220> FEATURE:
<221> NAME/KEY: VARIANT
<222> LOCATION: (77)..(77)
<223> OTHER INFORMATION: X=I or T or A
<220> FEATURE:
<221> NAME/KEY: VARIANT
<222> LOCATION: (78)..(78)
<223> OTHER INFORMATION: X=S or R or G or N
<220> FEATURE:
<221> NAME/KEY: VARIANT
<222> LOCATION: (80)..(80)
<223> OTHER INFORMATION: X=A or V
<220> FEATURE:
<221> NAME/KEY: VARIANT
<222> LOCATION: (82)..(82)
<223> OTHER INFORMATION: X=M or L
<220> FEATURE:
<221> NAME/KEY: VARIANT
<222> LOCATION: (83)..(83)
<223> OTHER INFORMATION: X=E or D
<220> FEATURE:
<221> NAME/KEY: VARIANT
<222> LOCATION: (85)..(85)
<223> OTHER INFORMATION: X=S or N or T or R
<220> FEATURE:
<221> NAME/KEY: VARIANT
<222> LOCATION: (86)..(86)
<223> OTHER INFORMATION: X=S or N
<220> FEATURE:
<221> NAME/KEY: VARIANT
<222> LOCATION: (89)..(89)
<223> OTHER INFORMATION: X=S or P or Y
<220> FEATURE:
<221> NAME/KEY: VARIANT
<222> LOCATION: (90)..(90)
<223> OTHER INFORMATION: X=E or D
<220> FEATURE:
<221> NAME/KEY: VARIANT
<222> LOCATION: (94)..(94)

<223> OTHER INFORMATION: X=V or M
<220> FEATURE:
<221> NAME/KEY: VARIANT
<222> LOCATION: (98)..(98)
<223> OTHER INFORMATION: X=A or T
<220> FEATURE:
<221> NAME/KEY: VARIANT
<222> LOCATION: (99)..(99)
<223> OTHER INFORMATION: X=R or K or T
<220> FEATURE:
<221> NAME/KEY: VARIANT
<222> LOCATION: (112)..(112)
<223> OTHER INFORMATION: X=Q or K
<220> FEATURE:
<221> NAME/KEY: VARIANT
<222> LOCATION: (115)..(115)
<223> OTHER INFORMATION: X=L or T

<400> SEQUENCE: 162

```
Xaa Val Gln Xaa Xaa Xaa Xaa Ser Gly Ala Glu Val Xaa Xaa Pro Gly
1               5                   10                  15

Xaa Ser Val Xaa Val Ser Cys Xaa Xaa Ser Gly Tyr Thr Phe Thr Ser
            20                  25                  30

Tyr Asp Ile Asn Trp Val Arg Gln Ala Xaa Gly Xaa Gly Xaa Xaa Trp
        35                  40                  45

Xaa Gly Trp Met Asn Pro Asn Ser Gly Asn Thr Gly Tyr Ala Gln Lys
    50                  55                  60

Phe Gln Gly Arg Xaa Xaa Xaa Thr Xaa Xaa Xaa Xaa Xaa Xaa Thr Xaa
65                  70                  75                  80

Tyr Xaa Xaa Leu Xaa Xaa Leu Arg Xaa Xaa Asp Thr Ala Xaa Tyr Tyr
                85                  90                  95

Cys Xaa Xaa Glu Val Pro Asp Thr Ala Ser Phe Glu Tyr Trp Gly Xaa
            100                 105                 110

Gly Thr Xaa Val Thr Val Ser Ser
        115                 120
```

<210> SEQ ID NO 163
<211> LENGTH: 112
<212> TYPE: PRT
<213> ORGANISM: Artificial Sequence
<220> FEATURE:
<223> OTHER INFORMATION: VL comprising CDRs from C320 grafted onto FRs
      of antibody 1RHH

<400> SEQUENCE: 163

```
Glu Leu Val Leu Thr Gln Ser Pro Gly Thr Leu Ser Leu Ser Ala Gly
1               5                   10                  15

Glu Arg Ala Thr Leu Ser Cys Ala Gly Ser Ser Ser Asp Ile Gly Ala
            20                  25                  30

Gly Leu Gly Val His Trp Tyr Gln Gln Lys Pro Gly Gln Ala Pro Arg
        35                  40                  45

Leu Leu Ile Tyr Gly Tyr Tyr Asn Arg Pro Ser Gly Ile Pro Asp Arg
    50                  55                  60

Phe Ser Gly Ser Gly Ser Gly Thr Asp Phe Thr Leu Thr Ile Gly Arg
65                  70                  75                  80

Leu Glu Pro Glu Asp Leu Ala Val Tyr Tyr Cys Gln Ser Tyr Asp Gly
                85                  90                  95

Thr Leu Ser Ala Leu Phe Gly Gln Gly Thr Lys Leu Glu Ile Lys Arg
            100                 105                 110
```

<210> SEQ ID NO 164
<211> LENGTH: 112

```
<212> TYPE: PRT
<213> ORGANISM: Artificial Sequence
<220> FEATURE:
<223> OTHER INFORMATION: VL comprising CDRs from C320 grafted onto FRs
      of antibody 1TZGL

<400> SEQUENCE: 164

Glu Ile Val Leu Thr Gln Ser Pro Gly Thr Gln Ser Leu Ser Pro Gly
1               5                   10                  15

Glu Arg Ala Thr Leu Ser Cys Ala Gly Ser Ser Ser Asp Ile Gly Ala
            20                  25                  30

Gly Leu Gly Val His Trp Tyr Gln Gln Arg Pro Gly Gln Ala Pro Arg
        35                  40                  45

Leu Leu Ile Tyr Gly Tyr Tyr Asn Arg Pro Ser Gly Val Ala Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Ser Tyr Asp Gly
                85                  90                  95

Thr Leu Ser Ala Leu Phe Gly Gln Gly Thr Lys Val Glu Val Lys Arg
            100                 105                 110


<210> SEQ ID NO 165
<211> LENGTH: 111
<212> TYPE: PRT
<213> ORGANISM: Artificial Sequence
<220> FEATURE:
<223> OTHER INFORMATION: VL comprising CDRs from C320 grafted onto FRs
      of antibody 2DD8

<400> SEQUENCE: 165

Ser Tyr Glu Leu Thr Gln Pro Pro Ser Val Ser Val Ala Pro Gly Lys
1               5                   10                  15

Thr Ala Arg Ile Thr Cys Ala Gly Ser Ser Ser Asp Ile Gly Ala Gly
            20                  25                  30

Leu Gly Val His Trp Tyr Gln Gln Lys Pro Gly Gln Ala Pro Val Leu
        35                  40                  45

Val Val Tyr Gly Tyr Tyr Asn Arg Pro Ser Gly Ile Pro Glu Arg Phe
    50                  55                  60

Ser Gly Ser Asn Ser Gly Asn Thr Ala Thr Leu Thr Ile Ser Arg Val
65                  70                  75                  80

Glu Ala Gly Asp Glu Ala Asp Tyr Tyr Cys Gln Ser Tyr Asp Gly Thr
                85                  90                  95

Leu Ser Ala Leu Phe Gly Thr Gly Thr Lys Val Thr Val Leu Gly
            100                 105                 110


<210> SEQ ID NO 166
<211> LENGTH: 111
<212> TYPE: PRT
<213> ORGANISM: Artificial Sequence
<220> FEATURE:
<223> OTHER INFORMATION: VL comprising CDRs from C320 grafted onto FRs
      of antibody 2JB5

<400> SEQUENCE: 166

Asp Ile Ala Leu Thr Gln Pro Ala Ser Val Ser Gly Ser Pro Gly Gln
1               5                   10                  15

Ser Ile Thr Ile Ser Cys Ala Gly Ser Ser Ser Asp Ile Gly Ala Gly
            20                  25                  30

Leu Gly Val His Trp Tyr Gln Gln His Pro Gly Lys Ala Pro Lys Leu
```

```
        35                  40                  45

Met Ile Tyr Gly Tyr Tyr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 167
<211> LENGTH: 111
<212> TYPE: PRT
<213> ORGANISM: Artificial Sequence
<220> FEATURE:
<223> OTHER INFORMATION: VL comprising CDRs from C320 grafted onto FRs
      of antibody 3FKU

<400> SEQUENCE: 167

Gln Pro Gly Leu Thr Gln Pro Pro Ser Val Ser Lys Gly Leu Arg Gln
1               5                   10                  15

Thr Ala Thr Leu Thr Cys Ala Gly Ser Ser Ser Asp Ile Gly Ala Gly
            20                  25                  30

Leu Gly Val His Trp Leu Gln Gln His Gln Gly His Pro Pro Lys Leu
        35                  40                  45

Leu Ser Tyr Gly Tyr Tyr Asn Arg Pro Ser Gly Ile Ser Glu Arg Phe
    50                  55                  60

Ser Ala Ser Arg Ser Gly Asn Thr Ala Ser Leu Thr Ile Thr Gly Leu
65                  70                  75                  80

Gln Pro Glu Asp Glu Ala Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 168
<211> LENGTH: 111
<212> TYPE: PRT
<213> ORGANISM: Artificial Sequence
<220> FEATURE:
<223> OTHER INFORMATION: VL comprising CDRs from C320 grafted onto FRs
      of antibody 3GBM

<400> SEQUENCE: 168

Gln Ser Val Leu Thr Gln Pro Pro Ser Val Ser Ala Ala Pro Gly Gln
1               5                   10                  15

Lys Val Thr Ile Ser Cys Ala Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asn Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 169
<211> LENGTH: 111
<212> TYPE: PRT
<213> ORGANISM: Artificial Sequence
<220> FEATURE:
<223> OTHER INFORMATION: VL comprising CDRs from C320 grafted onto FRs of antibody 3LMJ

<400> SEQUENCE: 169

Gln Ser Val Leu Thr Gln Pro Pro Ser Val Ser Ala Ala Pro Gly Gln
1 5 10 15

Lys Val Thr Ile Ser Cys Ala Gly Ser Ser Ser Asp Ile Gly Ala Gly
20 25 30

Leu Gly Val His Trp Tyr Gln Gln Leu Pro Gly Ala Ala Pro Lys Leu
35 40 45

Leu Ile Phe Gly Tyr Tyr Asn Arg Pro Ser Gly Ile Pro Asp Arg Phe
50 55 60

Ser Gly Ser Lys Ser Gly Thr Ser Ala Thr Leu Ala Ile Thr Gly Leu
65 70 75 80

Gln Thr Gly Asp Glu Ala Asp Tyr Tyr Cys Gln Ser Tyr Asp Gly Thr
85 90 95

Leu Ser Ala Leu Phe Gly Gly Gly Thr Lys Leu Thr Val Leu Gly
100 105 110

<210> SEQ ID NO 170
<211> LENGTH: 111
<212> TYPE: PRT
<213> ORGANISM: Artificial Sequence
<220> FEATURE:
<223> OTHER INFORMATION: VL comprising CDRs from C320 grafted onto FRs of antibody 3P30

<400> SEQUENCE: 170

Gln Ser Val Leu Thr Gln Pro Pro Ser Val Ser Gly Thr Pro Gly Gln
1 5 10 15

Arg Val Thr Ile Ser Cys Ala Gly Ser Ser Ser Asp Ile Gly Ala Gly
20 25 30

Leu Gly Val His Trp Tyr Gln Gln Leu Pro Gly Thr Ala Pro Lys Leu
35 40 45

Leu Ile Tyr Gly Tyr Tyr Asn Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Ser Tyr Asp Gly Thr
85 90 95

Leu Ser Ala Leu Phe Gly Ala Gly Thr Lys Leu Thr Val Leu Gly
100 105 110

<210> SEQ ID NO 171
<211> LENGTH: 111
<212> TYPE: PRT
<213> ORGANISM: Artificial Sequence
<220> FEATURE:
<223> OTHER INFORMATION: VL comprising CDRs from C320 grafted onto FRs of antibody 3IYW

<400> SEQUENCE: 171

Gln Ser Val Leu Thr Gln Pro Ser Ser Val Ser Gly Thr Pro Gly Gln
1 5 10 15

Arg Val Thr Ile Ser Cys Ala Gly Ser Ser Ser Asp Ile Gly Ala Gly
20 25 30

```
Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 172
<211> LENGTH: 112
<212> TYPE: PRT
<213> ORGANISM: Artificial Sequence
<220> FEATURE:
<223> OTHER INFORMATION: VL consensus sequence of C320 and derivatives
<220> FEATURE:
<221> NAME/KEY: VARIANT
<222> LOCATION: (1)..(1)
<223> OTHER INFORMATION: X=Q or E or S or D
<220> FEATURE:
<221> NAME/KEY: VARIANT
<222> LOCATION: (2)..(2)
<223> OTHER INFORMATION: X=S or L or I or Y
<220> FEATURE:
<221> NAME/KEY: VARIANT
<222> LOCATION: (3)..(3)
<223> OTHER INFORMATION: X=V or E or A or G
<220> FEATURE:
<221> NAME/KEY: VARIANT
<222> LOCATION: (7)..(7)
<223> OTHER INFORMATION: X=P or S
<220> FEATURE:
<221> NAME/KEY: VARIANT
<222> LOCATION: (8)..(8)
<223> OTHER INFORMATION: X=P or A or S
<220> FEATURE:
<221> NAME/KEY: VARIANT
<222> LOCATION: (9)..(9)
<223> OTHER INFORMATION: X=G or absent
<220> FEATURE:
<221> NAME/KEY: VARIANT
<222> LOCATION: (10)..(10)
<223> OTHER INFORMATION: X=S or T
<220> FEATURE:
<221> NAME/KEY: VARIANT
<222> LOCATION: (11)..(11)
<223> OTHER INFORMATION: X=V or L or Q
<220> FEATURE:
<221> NAME/KEY: VARIANT
<222> LOCATION: (13)..(13)
<223> OTHER INFORMATION: X=G or L or V or K or A
<220> FEATURE:
<221> NAME/KEY: VARIANT
<222> LOCATION: (14)..(14)
<223> OTHER INFORMATION: X=A or S or G or T
<220> FEATURE:
<221> NAME/KEY: VARIANT
<222> LOCATION: (15)..(15)
<223> OTHER INFORMATION: X=P or A or L
<220> FEATURE:
<221> NAME/KEY: VARIANT
<222> LOCATION: (16)..(16)
<223> OTHER INFORMATION: X=G or R
<220> FEATURE:
<221> NAME/KEY: VARIANT
<222> LOCATION: (17)..(17)
<223> OTHER INFORMATION: X=Q or E or K
<220> FEATURE:
<221> NAME/KEY: VARIANT
<222> LOCATION: (18)..(18)
<223> OTHER INFORMATION: X=R or T or S or K
<220> FEATURE:
<221> NAME/KEY: VARIANT
<222> LOCATION: (19)..(19)
<223> OTHER INFORMATION: X=V or A or I
<220> FEATURE:
<221> NAME/KEY: VARIANT
<222> LOCATION: (20)..(20)
<223> OTHER INFORMATION: X=T or R
<220> FEATURE:
<221> NAME/KEY: VARIANT
<222> LOCATION: (21)..(21)
<223> OTHER INFORMATION: X=I or L
<220> FEATURE:
<221> NAME/KEY: VARIANT
<222> LOCATION: (22)..(22)
<223> OTHER INFORMATION: X=S or T
<220> FEATURE:
<221> NAME/KEY: VARIANT
<222> LOCATION: (39)..(39)
<223> OTHER INFORMATION: X=Y or L
<220> FEATURE:
<221> NAME/KEY: VARIANT
<222> LOCATION: (42)..(42)
<223> OTHER INFORMATION: X=L or K or R or H
<220> FEATURE:
<221> NAME/KEY: VARIANT
<222> LOCATION: (43)..(43)
<223> OTHER INFORMATION: X=P or Q
<220> FEATURE:
<221> NAME/KEY: VARIANT
<222> LOCATION: (45)..(45)
<223> OTHER INFORMATION: X=T or Q or K or H
<220> FEATURE:
<221> NAME/KEY: VARIANT
<222> LOCATION: (46)..(46)
<223> OTHER INFORMATION: X=A or P
<220> FEATURE:
<221> NAME/KEY: VARIANT
<222> LOCATION: (48)..(48)
<223> OTHER INFORMATION: X=K or R or V
<220> FEATURE:
<221> NAME/KEY: VARIANT
<222> LOCATION: (50)..(50)
<223> OTHER INFORMATION: X=L or V or M
<220> FEATURE:
<221> NAME/KEY: VARIANT
<222> LOCATION: (51)..(51)
<223> OTHER INFORMATION: X=I or V or S
<220> FEATURE:
<221> NAME/KEY: VARIANT
<222> LOCATION: (60)..(60)
<223> OTHER INFORMATION: X=G or I
<220> FEATURE:
<221> NAME/KEY: VARIANT
<222> LOCATION: (61)..(61)
<223> OTHER INFORMATION: X=V or A or S
<220> FEATURE:
<221> NAME/KEY: VARIANT
<222> LOCATION: (62)..(62)
<223> OTHER INFORMATION: X=P or E or N
<220> FEATURE:
<221> NAME/KEY: VARIANT
<222> LOCATION: (66)..(66)
<223> OTHER INFORMATION: X=S or A
<220> FEATURE:
<221> NAME/KEY: VARIANT
<222> LOCATION: (68)..(68)
<223> OTHER INFORMATION: X=S or G or N or R
<220> FEATURE:
<221> NAME/KEY: VARIANT
<222> LOCATION: (71)..(71)
<223> OTHER INFORMATION: X=G or N
<220> FEATURE:
<221> NAME/KEY: VARIANT
<222> LOCATION: (72)..(72)
<223> OTHER INFORMATION: X=T or D
<220> FEATURE:
<221> NAME/KEY: VARIANT
<222> LOCATION: (73)..(73)

<223> OTHER INFORMATION: X=S or F
<220> FEATURE:
<221> NAME/KEY: VARIANT
<222> LOCATION: (74)..(74)
<223> OTHER INFORMATION: X=A or T
<220> FEATURE:
<221> NAME/KEY: VARIANT
<222> LOCATION: (76)..(76)
<223> OTHER INFORMATION: X=L or T or G
<220> FEATURE:
<221> NAME/KEY: VARIANT
<222> LOCATION: (78)..(78)
<223> OTHER INFORMATION: X=I or G or S
<220> FEATURE:
<221> NAME/KEY: VARIANT
<222> LOCATION: (79)..(79)
<223> OTHER INFORMATION: X=T or R
<220> FEATURE:
<221> NAME/KEY: VARIANT
<222> LOCATION: (80)..(80)
<223> OTHER INFORMATION: X=G or V
<220> FEATURE:
<221> NAME/KEY: VARIANT
<222> LOCATION: (81)..(81)
<223> OTHER INFORMATION: X=L or E or Q or R
<220> FEATURE:
<221> NAME/KEY: VARIANT
<222> LOCATION: (82)..(82)
<223> OTHER INFORMATION: X=L or A or T or S
<220> FEATURE:
<221> NAME/KEY: VARIANT
<222> LOCATION: (83)..(83)
<223> OTHER INFORMATION: X=P or G
<220> FEATURE:
<221> NAME/KEY: VARIANT
<222> LOCATION: (85)..(85)
<223> OTHER INFORMATION: X=D or L or F
<220> FEATURE:
<221> NAME/KEY: VARIANT
<222> LOCATION: (86)..(86)
<223> OTHER INFORMATION: X=E or A
<220> FEATURE:
<221> NAME/KEY: VARIANT
<222> LOCATION: (87)..(87)
<223> OTHER INFORMATION: X=G or V or N
<220> FEATURE:
<221> NAME/KEY: VARIANT
<222> LOCATION: (103)..(103)
<223> OTHER INFORMATION: X=G or Q or T or A
<220> FEATURE:
<221> NAME/KEY: VARIANT
<222> LOCATION: (107)..(107)
<223> OTHER INFORMATION: X=K or V
<220> FEATURE:
<221> NAME/KEY: VARIANT
<222> LOCATION: (108)..(108)
<223> OTHER INFORMATION: X=L or E
<220> FEATURE:
<221> NAME/KEY: VARIANT
<222> LOCATION: (109)..(109)
<223> OTHER INFORMATION: X=T or I
<220> FEATURE:
<221> NAME/KEY: VARIANT
<222> LOCATION: (110)..(110)
<223> OTHER INFORMATION: X=V or K
<220> FEATURE:
<221> NAME/KEY: VARIANT
<222> LOCATION: (111)..(111)
<223> OTHER INFORMATION: X=L or R

<400> SEQUENCE: 172

```
Xaa Xaa Xaa Leu Thr Gln Xaa Xaa Xaa Xaa Xaa Ser Xaa Xaa Xaa Xaa
1               5                   10                  15

Xaa Xaa Xaa Xaa Xaa Xaa Cys Ala Gly Ser Ser Ser Asp Ile Gly Ala
            20                  25                  30

Gly Leu Gly Val His Trp Xaa Gln Gln Xaa Xaa Gly Xaa Xaa Pro Xaa
```

```
        35                  40                  45

Leu Xaa Xaa Tyr Gly Tyr Tyr Asn Arg Pro Ser Xaa Xaa Pro Asp Arg
    50                  55                  60

Phe Xaa Gly Xaa Lys Ser Xaa Xaa Xaa Xaa Ser Xaa Ala Xaa Xaa Xaa
65                  70                  75                  80

Xaa Xaa Xaa Glu Xaa Xaa Xaa Asp Tyr Tyr Cys Gln Ser Tyr Asp Gly
                85                  90                  95

Thr Leu Ser Ala Leu Phe Xaa Gly Gly Thr Xaa Xaa Xaa Xaa Xaa Gly
            100                 105                 110


<210> SEQ ID NO 173
<211> LENGTH: 119
<212> TYPE: PRT
<213> ORGANISM: Artificial Sequence
<220> FEATURE:
<223> OTHER INFORMATION: VH consensus sequence of C320 and derivatives
<220> FEATURE:
<221> NAME/KEY: VARIANT
<222> LOCATION: (41)..(41)
<223> OTHER INFORMATION: X= T or P
<220> FEATURE:
<221> NAME/KEY: VARIANT
<222> LOCATION: (51)..(51)
<223> OTHER INFORMATION: X= M or L
<220> FEATURE:
<221> NAME/KEY: VARIANT
<222> LOCATION: (72)..(72)
<223> OTHER INFORMATION: X= R or A
<220> FEATURE:
<221> NAME/KEY: VARIANT
<222> LOCATION: (73)..(73)
<223> OTHER INFORMATION: X= N or D
<220> FEATURE:
<221> NAME/KEY: VARIANT
<222> LOCATION: (74)..(74)
<223> OTHER INFORMATION: X= T or R
<220> FEATURE:
<221> NAME/KEY: VARIANT
<222> LOCATION: (75)..(75)
<223> OTHER INFORMATION: X= S or A
<220> FEATURE:
<221> NAME/KEY: VARIANT
<222> LOCATION: (76)..(76)
<223> OTHER INFORMATION: X=I or T
<220> FEATURE:
<221> NAME/KEY: VARIANT
<222> LOCATION: (102)..(102)
<223> OTHER INFORMATION: X= D or E
<220> FEATURE:
<221> NAME/KEY: VARIANT
<222> LOCATION: (105)..(105)
<223> OTHER INFORMATION: X= S or A

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Xaa Gly Gln Gly Leu Glu Trp Met
        35                  40                  45

Gly Trp Xaa Asn Pro Asn Ser Gly Asn Thr Gly Tyr Ala Gln Lys Phe
    50                  55                  60

Gln Gly Arg Val Thr Met Thr Xaa Xaa Xaa Xaa Xaa Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Xaa Thr Ala Xaa Phe Glu Tyr Trp Gly Gln Gly
```

```
            100                 105                 110

Thr Leu Val Thr Val Ser Ser
        115


<210> SEQ ID NO 174
<211> LENGTH: 111
<212> TYPE: PRT
<213> ORGANISM: Artificial Sequence
<220> FEATURE:
<223> OTHER INFORMATION: VL consensus sequence of C320 and derivatives
<220> FEATURE:
<221> NAME/KEY: MISC_FEATURE
<222> LOCATION: (23)..(23)
<223> OTHER INFORMATION: X = A or T
<220> FEATURE:
<221> NAME/KEY: MISC_FEATURE
<222> LOCATION: (24)..(24)
<223> OTHER INFORMATION: X = G or S
<220> FEATURE:
<221> NAME/KEY: MISC_FEATURE
<222> LOCATION: (51)..(51)
<223> OTHER INFORMATION: X = Y or P or E or G
<220> FEATURE:
<221> NAME/KEY: MISC_FEATURE
<222> LOCATION: (76)..(76)
<223> OTHER INFORMATION: X = A or T

<400> SEQUENCE: 174

Gln Ser Val Leu Thr Gln Pro Pro Ser Val Ser Gly Ala Pro Gly Gln
1               5                   10                  15

Arg Val Thr Ile Ser Cys Xaa Xaa Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Xaa Gly Tyr Tyr Asn Arg Pro Ser Gly Val Pro Asp Arg Phe
    50                  55                  60

Ser Gly Ser Lys Ser Gly Thr Ser Ala Ser Leu Xaa Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 175
<211> LENGTH: 119
<212> TYPE: PRT
<213> ORGANISM: Artificial Sequence
<220> FEATURE:
<223> OTHER INFORMATION: amino acid sequence of VH of antibody C320-162

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ala Ile Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 176
<211> LENGTH: 119
<212> TYPE: PRT
<213> ORGANISM: Artificial Sequence
<220> FEATURE:
<223> OTHER INFORMATION: amino acid sequence of VH of antibody C320-163

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115


<210> SEQ ID NO 177
<211> LENGTH: 119
<212> TYPE: PRT
<213> ORGANISM: Artificial Sequence
<220> FEATURE:
<223> OTHER INFORMATION: amino acid sequence of VH of antibody C320-164

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 178
<211> LENGTH: 119
<212> TYPE: PRT
```

```
<213> ORGANISM: Artificial Sequence
<220> FEATURE:
<223> OTHER INFORMATION: amino acid sequence of VH of antibody C320-165

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 179
<211> LENGTH: 119
<212> TYPE: PRT
<213> ORGANISM: Artificial Sequence
<220> FEATURE:
<223> OTHER INFORMATION: amino acid sequence of VH of antibody C320-166

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 180
<211> LENGTH: 119
<212> TYPE: PRT
<213> ORGANISM: Artificial Sequence
<220> FEATURE:
<223> OTHER INFORMATION: amino acid sequence of VH of antibody C320-167

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ser Phe Glu Tyr Trp Gly Gln Gly
            100                 105                 110

Thr Leu Val Thr Val Ser Ser
        115


<210> SEQ ID NO 181
<211> LENGTH: 119
<212> TYPE: PRT
<213> ORGANISM: Artificial Sequence
<220> FEATURE:
<223> OTHER INFORMATION: amino acid sequence of VH of antibody C320-168

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115


<210> SEQ ID NO 182
<211> LENGTH: 119
<212> TYPE: PRT
<213> ORGANISM: Artificial Sequence
<220> FEATURE:
<223> OTHER INFORMATION: amino acid sequence of VH of antibody C320-169

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115


<210> SEQ ID NO 183
<211> LENGTH: 119
<212> TYPE: PRT
<213> ORGANISM: Artificial Sequence
<220> FEATURE:
<223> OTHER INFORMATION: amino acid sequence of VH of antibody C320-170

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115


<210> SEQ ID NO 184
<211> LENGTH: 119
<212> TYPE: PRT
<213> ORGANISM: Artificial Sequence
<220> FEATURE:
<223> OTHER INFORMATION: amino acid sequence of VH of antibody C320-171

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115


<210> SEQ ID NO 185
<211> LENGTH: 119
```

<212> TYPE: PRT
<213> ORGANISM: Artificial Sequence
<220> FEATURE:
<223> OTHER INFORMATION: amino acid sequence of VH of antibody C320-172

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115
```

<210> SEQ ID NO 186
<211> LENGTH: 119
<212> TYPE: PRT
<213> ORGANISM: Artificial Sequence
<220> FEATURE:
<223> OTHER INFORMATION: amino acid sequence of VH of antibody C320-179

<400> SEQUENCE: 186

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115
```

<210> SEQ ID NO 187
<211> LENGTH: 119
<212> TYPE: PRT
<213> ORGANISM: Artificial Sequence
<220> FEATURE:
<223> OTHER INFORMATION: amino acid sequence of VH of antibody C320-183

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115
```

<210> SEQ ID NO 188
<211> LENGTH: 111
<212> TYPE: PRT
<213> ORGANISM: Artificial Sequence
<220> FEATURE:
<223> OTHER INFORMATION: amino acid sequence of VL of antibody C320-162

<400> SEQUENCE: 188

```
Gln Ser Val Leu Thr Gln Pro Pro Ser Val Ser Gly Ala Pro Gly Gln
1               5                   10                  15

Arg Val Thr Ile Ser Cys Ala Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 189
<211> LENGTH: 111
<212> TYPE: PRT
<213> ORGANISM: Artificial Sequence
<220> FEATURE:
<223> OTHER INFORMATION: amino acid sequence of VL of antibody C320-163

<400> SEQUENCE: 189

```
Gln Ser Val Leu Thr Gln Pro Pro Ser Val Ser Gly Ala Pro Gly Gln
1               5                   10                  15

Arg Val Thr Ile Ser Cys Ala Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95
```

```
Leu Ser Ala Leu Phe Gly Gly Gly Thr Lys Leu Thr Val Leu Gly
            100                 105                 110


<210> SEQ ID NO 190
<211> LENGTH: 111
<212> TYPE: PRT
<213> ORGANISM: Artificial Sequence
<220> FEATURE:
<223> OTHER INFORMATION: amino acid sequence of VL of antibody C320-164

<400> SEQUENCE: 190

Gln Ser Val Leu Thr Gln Pro Pro Ser Val Ser Gly Ala Pro Gly Gln
1               5                   10                  15

Arg Val Thr Ile Ser Cys Ala Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 191
<211> LENGTH: 111
<212> TYPE: PRT
<213> ORGANISM: Artificial Sequence
<220> FEATURE:
<223> OTHER INFORMATION: amino acid sequence of VL of antibody C320-165

<400> SEQUENCE: 191

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 192
<211> LENGTH: 111
<212> TYPE: PRT
<213> ORGANISM: Artificial Sequence
<220> FEATURE:
<223> OTHER INFORMATION: amino acid sequence of VL of antibody C320-166

<400> SEQUENCE: 192

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
```

```
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 193
<211> LENGTH: 111
<212> TYPE: PRT
<213> ORGANISM: Artificial Sequence
<220> FEATURE:
<223> OTHER INFORMATION: amino acid sequence of VL of antibody C320-167

<400> SEQUENCE: 193

Gln Ser Val Leu Thr Gln Pro Pro Ser Val Ser Gly Ala Pro Gly Gln
1               5                   10                  15

Arg Val Thr Ile Ser Cys Ala Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 194
<211> LENGTH: 111
<212> TYPE: PRT
<213> ORGANISM: Artificial Sequence
<220> FEATURE:
<223> OTHER INFORMATION: amino acid sequence of VL of antibody C320-168

<400> SEQUENCE: 194

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 195
<211> LENGTH: 111
<212> TYPE: PRT
<213> ORGANISM: Artificial Sequence
<220> FEATURE:
<223> OTHER INFORMATION: amino acid sequence of VL of antibody C320-169

<400> SEQUENCE: 195

```
Gln Ser Val Leu Thr Gln Pro Pro Ser Val Ser Gly Ala Pro Gly Gln
1               5                   10                  15

Arg Val Thr Ile Ser Cys Ala Gly Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 196
<211> LENGTH: 111
<212> TYPE: PRT
<213> ORGANISM: Artificial Sequence
<220> FEATURE:
<223> OTHER INFORMATION: amino acid sequence of VL of antibody C320-170

<400> SEQUENCE: 196

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Tyr Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 197
<211> LENGTH: 111
<212> TYPE: PRT
<213> ORGANISM: Artificial Sequence
<220> FEATURE:
<223> OTHER INFORMATION: amino acid sequence of VL of antibody C320-171

<400> SEQUENCE: 197

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
```

```
        35                  40                  45

Leu Ile Pro Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 198
<211> LENGTH: 111
<212> TYPE: PRT
<213> ORGANISM: Artificial Sequence
<220> FEATURE:
<223> OTHER INFORMATION: amino acid sequence of VL of antibody C320-172

<400> SEQUENCE: 198

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 199
<211> LENGTH: 111
<212> TYPE: PRT
<213> ORGANISM: Artificial Sequence
<220> FEATURE:
<223> OTHER INFORMATION: amino acid sequence of VL of antibody C320-179

<400> SEQUENCE: 199

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 200
<211> LENGTH: 111
```

<212> TYPE: PRT
<213> ORGANISM: Artificial Sequence
<220> FEATURE:
<223> OTHER INFORMATION: amino acid sequence of VL of antibody C320-183

<400> SEQUENCE: 200

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Gly Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110
```

<210> SEQ ID NO 201
<211> LENGTH: 111
<212> TYPE: PRT
<213> ORGANISM: Artificial Sequence
<220> FEATURE:
<223> OTHER INFORMATION: amino acid sequence of VL of germline sequence
      IGLV1-40*1
<220> FEATURE:
<221> NAME/KEY: misc_feature
<222> LOCATION: (100)..(111)
<223> OTHER INFORMATION: Xaa can be any naturally occurring amino acid

<400> SEQUENCE: 201

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Xaa Xaa Xaa Xaa Xaa Xaa Xaa Xaa Xaa Xaa Xaa Xaa
            100                 105                 110
```

<210> SEQ ID NO 202
<211> LENGTH: 180
<212> TYPE: PRT
<213> ORGANISM: Artificial Sequence
<220> FEATURE:
<223> OTHER INFORMATION: amino acid sequence of soluble hTL1a

<400> SEQUENCE: 202

```
Leu Lys Gly Gln Glu Phe Ala Pro Ser His Gln Gln Val Tyr Ala Pro
1               5                   10                  15

Leu Arg Ala Asp Gly Asp Lys Pro Arg Ala His Leu Thr Val Val Arg
            20                  25                  30
```

```
Gln Thr Pro Thr Gln His Phe Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Ile Tyr Ser
65                  70                  75                  80

Gln Val Thr Phe Arg Gly Met Thr Ser Glu Cys Ser Glu Ile Arg Gln
                85                  90                  95

Ala Gly Arg Pro Asn Lys Pro Asp Ser Ile Thr Val Val Ile Thr Lys
            100                 105                 110

Val Thr Asp Ser Tyr Pro Glu Pro Thr Gln Leu Leu Met Gly Thr Lys
        115                 120                 125

Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180


<210> SEQ ID NO 203
<211> LENGTH: 5
<212> TYPE: PRT
<213> ORGANISM: Artificial Sequence
<220> FEATURE:
<223> OTHER INFORMATION: amino acid sequence of N-linked glycosylation
      site in VH of C320

<400> SEQUENCE: 203

Arg Asn Thr Ser Ile
1               5


<210> SEQ ID NO 204
<211> LENGTH: 5
<212> TYPE: PRT
<213> ORGANISM: Artificial Sequence
<220> FEATURE:
<223> OTHER INFORMATION: amino acid sequence from VH of 1TZG
      corresponding to N-linked
      glycosylation site in VH of C320

<400> SEQUENCE: 204

Ala Asp Arg Ser Thr
1               5


<210> SEQ ID NO 205
<211> LENGTH: 15
<212> TYPE: PRT
<213> ORGANISM: Artificial Sequence
<220> FEATURE:
<223> OTHER INFORMATION: amino acid sequence of peptide from VH of
      C320-168

<400> SEQUENCE: 205

Gly Leu Glu Trp Met Gly Trp Leu Asn Pro Asn Ser Gly Asn Thr
1               5                   10                  15


<210> SEQ ID NO 206
<211> LENGTH: 15
<212> TYPE: PRT
<213> ORGANISM: Artificial Sequence
```

<220> FEATURE:
<223> OTHER INFORMATION: amino acid sequence of peptide from VL of C320-168

<400> SEQUENCE: 206

Leu Leu Ile Tyr Gly Tyr Tyr Asn Arg Pro Ser Gly Val Pro Asp
1 5 10 15

<210> SEQ ID NO 207
<211> LENGTH: 13
<212> TYPE: PRT
<213> ORGANISM: Artificial Sequence
<220> FEATURE:
<223> OTHER INFORMATION: amino acid sequence of influenza peptide

<400> SEQUENCE: 207

Pro Lys Tyr Val Lys Gln Asn Thr Leu Lys Leu Ala Thr
1 5 10

<210> SEQ ID NO 208
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 208

Leu Leu Ile Glu Gly Tyr Tyr Asn Arg Pro Ser Gly Val Pro Asp
1 5 10 15

<210> SEQ ID NO 209
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 209

Leu Leu Ile Gly Gly Tyr Tyr Asn Arg Pro Ser Gly Val Pro Asp
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 210

Leu Leu Ile Pro Gly Tyr Tyr Asn Arg Pro Ser Gly Val Pro Asp
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 211

Leu Leu Ile Lys Gly Tyr Tyr Asn Arg Pro Ser Gly Val Pro Asp
1 5 10 15

<210> SEQ ID NO 212
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 212

Leu Leu Ile Tyr Gly Tyr Tyr Asn Arg Pro Ser Gly Val Pro Asp
1 5 10 15

<210> SEQ ID NO 213
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 213

Leu Leu Ile Glu Gly Tyr Tyr Asn Arg Pro Ser Gly Val Pro Asp
1 5 10 15

<210> SEQ ID NO 214
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 214

Leu Leu Ile Gly Gly Tyr Tyr Asn Arg Pro Ser Gly Val Pro Asp
1 5 10 15

<210> SEQ ID NO 215
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 215

Leu Leu Ile Pro Gly Tyr Tyr Asn Arg Pro Ser Gly Val Pro Asp
1 5 10 15

<210> SEQ ID NO 216
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 216

Leu Leu Ile Lys Gly Tyr Tyr Asn Arg Pro Ser Gly Val Pro Asp
1 5 10 15

<210> SEQ ID NO 217
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 217

Leu Leu Ile Tyr Gly Tyr Tyr Asn Arg Pro Ser Gly Val Pro Asp
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 218

Leu Leu Ile Glu Gly Tyr Tyr Asn Arg Pro Ser Gly Val Pro Asp
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 219

Leu Leu Ile Gly Gly Tyr Tyr Asn Arg Pro Ser Gly Val Pro Asp
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 220

Leu Leu Ile Pro Gly Tyr Tyr Asn Arg Pro Ser Gly Val Pro Asp
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: amino acid sequence of mutant peptide from VL of C320-168

<400> SEQUENCE: 221

Leu Leu Ile Lys Gly Tyr Tyr Asn Arg Pro Ser Gly Val Pro Asp
1 5 10 15

<210> SEQ ID NO 222
<211> LENGTH: 357
<212> TYPE: DNA
<213> ORGANISM: Artificial Sequence
<220> FEATURE:
<223> OTHER INFORMATION: nucleotide sequence encoding VH of antibody C320-162

<400> SEQUENCE: 222
caggtgcagc tggtgcagtc tggggccgag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg ctgaacccta acagtggtaa cacaggctat 180
gcacagaagt tccagggcag agtcaccatg accaggaaca ccgccataag cacagcctac 240
atggagctga gcagcctgag atctgaggac acggccgtgt attactgtgc gagagaagtg 300
cctgagacgg cctcctttga gtactggggc cagggaaccc tggtgacagt gtcctca 357

<210> SEQ ID NO 223
<211> LENGTH: 357
<212> TYPE: DNA
<213> ORGANISM: Artificial Sequence
<220> FEATURE:
<223> OTHER INFORMATION: nucleotide sequence encoding VH of antibody C320-163

<400> SEQUENCE: 223
caggtgcagc tggtgcagtc tggggcggag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg atgaacccta acagtggtaa cacaggctat 180
gcacagaagt tccagggcag agtcaccatg accgcagatc gttccaccag cacagcctac 240
atggagctga gcagcctgag atctgaggac acggccgtgt attactgtgc gagagaagtg 300
cctgatacgg cctcctttga gtactggggc cagggaaccc tggtcaccgt ctcctca 357

<210> SEQ ID NO 224
<211> LENGTH: 357
<212> TYPE: DNA
<213> ORGANISM: Artificial Sequence
<220> FEATURE:
<223> OTHER INFORMATION: nucleotide sequence encoding VH of antibodies C320-164, C320-165, C320-166 and C320-167

<400> SEQUENCE: 224
caggtgcagc tggtgcagtc tggggccgag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg ctgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgagacgg cctcctttga gtactggggc cagggaaccc tggtgacagt gtcctca 357

<210> SEQ ID NO 225
<211> LENGTH: 357
<212> TYPE: DNA
<213> ORGANISM: Artificial Sequence
<220> FEATURE:
<223> OTHER INFORMATION: nucleotide sequence encoding VH of antibodies C320-168 and C320-169

<400> SEQUENCE: 225
caggtgcagc tggtgcagtc tggggccgag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg ctgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagaagtg 300
cctgagacgg ccgcctttga gtactggggc cagggaaccc tggtgacagt gtcctca 357

<210> SEQ ID NO 226
<211> LENGTH: 357
<212> TYPE: DNA
<213> ORGANISM: Artificial Sequence
<220> FEATURE:

<223> OTHER INFORMATION: nucleotide sequence encoding VH of antibodies
C320-170 and C320-172

<400> SEQUENCE: 226
caggtgcagc tggtgcagtc tggggcggag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg atgaacccta acagtggtaa cacaggctat 180
gcacagaagt tccagggcag agtcaccatg accgcagatc gttccaccag cacagcctac 240
atggagctga gcagcctgag atctgaggac acggccgtgt attactgtgc gagagaagtg 300
cctgatacgg cctcctttga gtactggggc cagggaaccc tggtcaccgt ctcctca 357

<210> SEQ ID NO 227
<211> LENGTH: 357
<212> TYPE: DNA
<213> ORGANISM: Artificial Sequence
<220> FEATURE:
<223> OTHER INFORMATION: nucleotide sequence encoding VH of antibodies
C320-179 and C320-183

<400> SEQUENCE: 227
caggtgcagc tggtgcagtc tggggcggag gtgaagaagc ctggggcctc agtgaaggtc 60
tcctgcaagg cttctggata caccttcacc agttatgata tcaactgggt gcgacaggcc 120
cccggacaag ggcttgagtg gatgggatgg ctgaacccta acagtggtaa cacaggctat 180
gcacagaagt tccagggcag agtcaccatg accgcagatc gttccaccag cacagcctac 240
atggagctga gcagcctgag atctgaggac acggccgtgt attactgtgc gagagaagtg 300
cctgagacgg ccgcctttga gtactggggc cagggaaccc tggtcaccgt ctcctca 357

<210> SEQ ID NO 228
<211> LENGTH: 333
<212> TYPE: DNA
<213> ORGANISM: Artificial Sequence
<220> FEATURE:
<223> OTHER INFORMATION: nucleotide sequence encoding VL of antibodies
C320-162, C320-163, C320-167 and C320-169

<400> SEQUENCE: 228
cagtctgtgc tgacgcagcc gccctcagtg tctggggccc cagggcagag ggtcaccatc 60
tcctgcgctg ggagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 229
<211> LENGTH: 333
<212> TYPE: DNA
<213> ORGANISM: Artificial Sequence
<220> FEATURE:
<223> OTHER INFORMATION: nucleotide sequence encoding VL of antibody
C320-164

<400> SEQUENCE: 229
cagtctgtgc tgacgcagcc gccctcagtg tctggggccc cagggcagag ggtcaccatc 60
tcctgcgcta gcagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 230
<211> LENGTH: 333
<212> TYPE: DNA
<213> ORGANISM: Artificial Sequence
<220> FEATURE:
<223> OTHER INFORMATION: nucleotide sequence encoding VL of antibodies C320-165, C320-168 and C320-170

<400> SEQUENCE: 230
cagtctgtgc tgacgcagcc gccctcagtg tctggggccc cagggcagag ggtcaccatc 60
tcctgcacta gcagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 231
<211> LENGTH: 333
<212> TYPE: DNA
<213> ORGANISM: Artificial Sequence
<220> FEATURE:
<223> OTHER INFORMATION: nucleotide sequence encoding VL of antibody C320-166

<400> SEQUENCE: 231
cagtctgtgc tgacgcagcc gccctcagtg tctggggccc cagggcagag ggtcaccatc 60
tcctgcactg ggagtagttc cgacatcggg gcaggtcttg gcgtgcactg gtatcagcag 120
cttccaggaa cagcccccaa actcctcatc tatggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 232
<211> LENGTH: 333
<212> TYPE: DNA
<213> ORGANISM: Artificial Sequence
<220> FEATURE:
<223> OTHER INFORMATION: nucleotide sequence encoding VL of antibodies C320-172 and C320-179

<400> SEQUENCE: 232
cagtctgtgc tgacgcagcc gccctcagtg tctggggccc cagggcagag ggtcaccatc 60
tcctgcacta gcagtagttc cgacatcggg gcaggtcttg gcgtgcactg gtatcagcag 120
cttccaggaa cagcccccaa actcctcatc gaaggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 233
<211> LENGTH: 333

<212> TYPE: DNA
<213> ORGANISM: Artificial Sequence
<220> FEATURE:
<223> OTHER INFORMATION: nucleotide sequence encoding VL of antibody C320-183

<400> SEQUENCE: 233
cagtctgtgc tgacgcagcc gccctcagtg tctggggccc cagggcagag ggtcaccatc 60
tcctgcacta gcagtagttc cgacatcggg gcaggtcttg gcgtgcactg gtatcagcag 120
cttccaggaa cagcccccaa actcctcatc ggaggttact acaatcggcc ctcaggggtc 180
cctgaccgat tctctggctc caagtctggc acctcagcct ccctgaccat cactgggctc 240
ctgcctgagg atgagggtga ttattactgc cagtcctatg acggcactct gagtgcccta 300
ttcggcggag ggaccaagct gaccgtccta ggt 333

<210> SEQ ID NO 234
<211> LENGTH: 119
<212> TYPE: PRT
<213> ORGANISM: artificial
<220> FEATURE:
<223> OTHER INFORMATION: amino acid sequence of VH of antibody C320-12 and C320-22

<400> SEQUENCE: 234

Glu Val Gln Leu Val Gln Ser Gly Ala Glu Val Arg Lys Pro Gly Ala
1               5                   10                  15

Ser Thr Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Val Pro Asp Thr Ala Ser Phe Glu Tyr Trp Gly Gln Gly
            100                 105                 110

Thr Leu Val Thr Val Ser Ser
        115

<210> SEQ ID NO 235
<211> LENGTH: 10
<212> TYPE: PRT
<213> ORGANISM: artificial
<220> FEATURE:
<223> OTHER INFORMATION: consensus of HCDR3 of C320 and derivatives
<220> FEATURE:
<221> NAME/KEY: VARIANT
<222> LOCATION: (2)..(2)
<223> OTHER INFORMATION: X = V or A or S or H or D or L or Y or P or Q or K
<220> FEATURE:
<221> NAME/KEY: VARIANT
<222> LOCATION: (4)..(4)
<223> OTHER INFORMATION: X = A or S or H or K or E or D
<220> FEATURE:
<221> NAME/KEY: VARIANT
<222> LOCATION: (5)..(5)
<223> OTHER INFORMATION: X = A or S or D or Y or T
<220> FEATURE:
<221> NAME/KEY: VARIANT
<222> LOCATION: (7)..(7)
<223> OTHER INFORMATION: X = A or S or H or L or D or Y -continued

```
<220> FEATURE:
<221> NAME/KEY: VARIANT
<222> LOCATION: (9)..(9)
<223> OTHER INFORMATION: X = A or S or H or L or D or P or Q or E or K

<400> SEQUENCE: 235

Glu Xaa Pro Xaa Xaa Ala Xaa Phe Xaa Tyr
1               5                   10
```